United States Patent [19]

Christensen et al.

[11] Patent Number: 4,992,542
[45] Date of Patent: Feb. 12, 1991

[54] 2-SUBSTITUTED-6-CARBADETHIAPEN-2-EM-3-CARBOXYLIC ACIDS

[75] Inventors: Burton G. Christensen, Scotch Plains; David B. R. Johnston, Warren; Susan M. Schmitt, Scotch Plains, all of N.J.

[73] Assignee: Merck & Co., Inc., Rahway, N.J.

[21] Appl. No.: 20,189

[22] Filed: Feb. 26, 1987

Related U.S. Application Data

[63] Continuation of Ser. No. 573,527, Jan. 24, 1984, abandoned, which is a continuation of Ser. No. 197,856, Oct. 17, 1980, which is a continuation-in-part of Ser. No. 129,851, Mar. 27, 1980, abandoned, which is a continuation-in-part of Ser. No. 31,694, Apr. 19, 1979, which is a continuation-in-part of Ser. No. 134,381, Mar. 27, 1980, abandoned, which is a continuation-in-part of Ser. No. 933,681, Aug. 17, 1978, abandoned, which is a continuation-in-part of Ser. No. 843,378, Oct. 19, 1977, abandoned, which is a continuation-in-part of Ser. No. 134,604, Mar. 27, 1980, abandoned, which is a continuation-in-part of Ser. No. 843,375, Oct. 19, 1977, abandoned.

[51] Int. Cl.⁵ .................. C07D 487/04; A61K 31/40
[52] U.S. Cl. .................................................. 540/350
[58] Field of Search ........................................ 540/350

[56] References Cited

U.S. PATENT DOCUMENTS

| | | | |
|---|---|---|---|
| 4,150,145 | 4/1979 | Christensen et al. | 260/245.2 T |
| 4,172,144 | 10/1979 | Bouffard et al. | 260/245.2 T |
| 4,194,047 | 3/1980 | Christensen et al. | 546/272 |
| 4,223,038 | 9/1980 | Smale | 540/350 |
| 4,226,870 | 10/1980 | Christensen et al. | 424/274 T |
| 4,235,917 | 11/1980 | Christensen et al. | 260/245.2 T |
| 4,235,920 | 11/1980 | Christensen et al. | 424/274 T |
| 4,235,922 | 11/1980 | Ratcliffe et al. | 260/245.2 T |
| 4,289,696 | 9/1981 | Smale | 260/245.2 T |
| 4,309,438 | 1/1982 | Christensen et al. | 424/274 T |
| 4,335,043 | 6/1982 | Christensen et al. | 260/245.2 T |
| 4,347,367 | 8/1982 | Christensen et al. | 546/272 |
| 4,347,368 | 8/1982 | Christensen et al. | 546/272 |
| 4,397,861 | 8/1983 | Christensen et al. | 424/274 T |
| 4,413,000 | 11/1983 | Eglingten et al. | 540/350 |
| 4,552,873 | 11/1985 | Mujadea et al. | 540/350 |
| 4,640,915 | 2/1987 | Hashimoto et al. | 540/350 |

FOREIGN PATENT DOCUMENTS 0000828 2/1979 European Pat. Off. .
1593524 5/1978 United Kingdom .

Primary Examiner—Nicholas S. Rizzo
Attorney, Agent, or Firm—Raymond M. Speer; Hesna J. Pfeiffer

[57] ABSTRACT

Disclosed are 2- and 6-substituted-1-carbadethiapen-2-em-3-carboxylic acids having the structure:

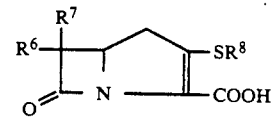

wherein $R^6$, $R^7$ and $R^8$ are inter alia, independently selected from the group consisting of hydrogen, alkyl, alkenyl, aryl and aralkyl. Such compounds as well as their pharmaceutically acceptable salt, ester and amide derivatives are useful as antibiotics. Also disclosed are processes for the preparation of such compounds, pharmaceutical compositions comprising such compounds and methods of treatment comprising administering such compounds and compositions when an antibiotic effect is indicated.

2 Claims, No Drawings

2-SUBSTITUTED-6-CARBADETHIAPEN-2-EM-3-CARBOXYLIC ACIDS

This is a continuation, of application Ser. No. 573,525, filed Jan. 24, 1984 now abandoned, which is a continuation of application Ser. No. 197,856, filed Oct. 17, 1980 which in turn is a continuation-in-part of U.S. patent application 129,851 filed Mar. 27, 1980, now abandoned, which in turn is a continuation in part of U.S patent application Ser. No. 31,694 filed Apr. 19, 1979, it is also a continuation-in-part of U.S. patent application Ser. No. 134,381 filed Mar. 27, 1980, now abandoned, which is a continuation-in-part of U.S. patent application Ser. No. 933,681, filed Aug. 17, 1978, now abandoned, which in turn is a continuation-in-part of U.S. patent application Ser. No. 843,378, filed Oct. 19, 1977, now abandoned, and U.S. patent application Ser. No. 134,604, now abandoned, filed Mar. 27, 1980, which is a continuation-in-part of U.S. Ser. No. 843,375, filed Oct. 19, 1977, now abandoned.

BACKGROUND OF THE INVENTION

This invention relates to 2- and 6-substituted-1-carbadethiapen-2-em-3-carboxylic acids (I) and the pharmaceutically acceptable salt, ester and amide derivatives thereof which are useful as antibiotics:

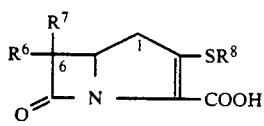

wherein $R^6$, $R^7$, and $R^8$ are independently selected from the group consisting of hydrogen, substituted and unsubstituted: alkyl, alkenyl, and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and the aliphatic portion has 1-6 carbon atoms; heteroaryl, heteroaralkyl, heterocyclyl and heterocyclylalkyl; wherein the substituent or substituents relative to the above-named radicals are selected from the group consisting of:

—X· halo (chloro, bromo, fluoro)

—OH hydroxy

—$OR^1$ alkoxy, aryloxy

—$ONR^1R^2$ aminoxy

—$OCNR^1R^2$ carbamoyloxy (with C=O)

—$CNR^1R^2$ carbamoyl (with C=O)

—$NR^1R^2$ amino

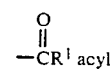
—N—$NR^1R^2$ hydrazino (with $R^1$ on N)

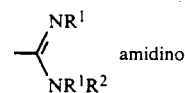
amidino

—$SO_2NR^1R^2$ sulfonamido

—$NHCNR^1R^2$ ureido (with C=O)

—$R^1CNR^2$ amido (with C=O)

—$CO_2H$ carboxy

—$OSO_2R^1$ sulphate

—$NO_2$ nitro

—$\overset{\oplus}{N}(R^1)_3$ tri-substituted amino ($R^1$ group independently chosen)

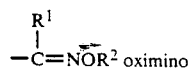
—C=$\overset{\_}{N}OR^2$ oximino (with $R^1$ on C)

—$CO_2R^1$ carboxylate

—$CR^1$ acyl (with C=O)

—$OCR^1$ acyloxy (with C=O)

—SH mercapto

—$SR^1$ alkyl and aryl sulfinyl (with S=O)

—$SR^1$ alkyl and aryl sulfonyl (with two S=O)

—CN cyano

—$N_3$ azido

—$SR^1$ alkyl- and arylthio wherein, relative to the above listed substituents on $R^6$, $R^7$, and $R^8$, the groups $R^1$ and $R^2$ are independently selected from: $R^6$, $R^7$ and $R^8$ and include inter alia: hydrogen, —$OR^1$ and —$SR^1$ (wherein $R^1$ is broadly defined here; for example, alkoxy and alkylthiol having 1-6 carbon atoms), —$NR^1R^2$ ($R^1$ and $R^2$ are defined here), alkyl, alkenyl and alkynyl, having from 1-10 carbon atoms; cycloalkyl, cycloalkylalkyl, and alkylcycloalkyl, having 3-6 carbon atoms in the cycloalkyl ring and 1-6 carbon atoms in the alkyl moieties; aryl, such as phenyl; aralkyl, aralkenyl, and aralkynyl wherein the aryl moiety is phenyl and phenyl substituted by alkyl, OH, $NR^1R^2$, and the aliphatic portion has 1-6 carbon atoms; heteroalkyl, heteroaralkyl, heterocyclyl and heterocyclylalkyl and wherein the hetero atom or atoms in the above-named heterocyclic moieties are selected from the group consisting of 1-4 oxygen, nitrogen or sulphur atoms and wherein the alkyl moieties associated with said heterocyclic moieties have 1-6 carbon atoms.

Further, relative to the 2-substituent —SR⁸ of I and in particular to R⁸ radicals which carry an amino group (—NH₂) or an N-substituted amino group (—NR¹H), and which can be represented conveniently as: —R⁸—NH₂, and —R⁸—NR¹H, respectively, there exists the following groups classed under previously defined R⁸:

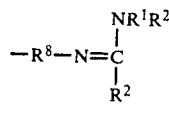 and 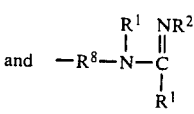  amidino
(A) (B)

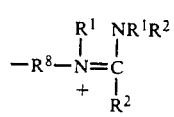  amidinium
(C)

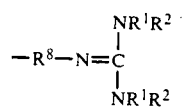 and 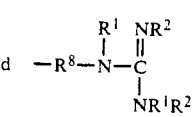  guanidino
(D) (E)

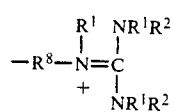  guanidinium
(F)

wherein: R⁸, R¹ and R² are as defined above; the methylene carbon atom, which is joined to R⁸ via nitrogen, may be a member of a ring formed on joinder of its substituents. With regard to the above-defined groups A-F, it will be appreciated that, while they represent distinct entities, subsequent reference to "amidino" and "guanidino" embodiments of I will be intended to speak generically of all such forms—including all canonical tautomeric forms. Also embraced, but not depicted above for clarity, are all remaining N-quaternized forms which nevertheless are fairly suggested by structures A-F. It will also be appreciated that such amidino and quanidino embodiments of I are capable of zwitterionic behavior. This feature to the extent that it is helpful in appreciating the nature of such embodiments of I, is discussed below.

A particularly preferred subclass of such "amidine" and "guanidine" values for R⁸ may be represented by

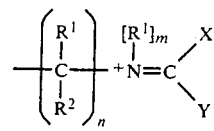

wherein: n=2, 3, 4, 5, or 6; m=0 or 1; X and Y are selected from R¹ and —NR¹R²; the methylene carbon may become a member of a ring caused by the joinder of its substituents X and Y; wherein R¹ and R² are as defined above.

Further relative to R⁸ there exists the following groups classed under previously defined R⁸:

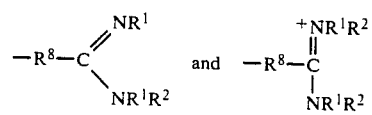

such groups give rise to embodiments of I which will be referred to herein as "carbamimidoyls"; R⁸, R¹ and R² are as defined above. A particularly preferred subclass of such carbamimidoyls may be represented by:

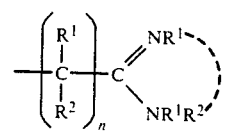

wherein: n=0, 1, 2, 3, 4, 5 or 6; and R¹ and R² are as previously defined; the two nitrogen atoms demonstrated in the above structure, may be joined, via their substituents, to form a ring which is indicated by the dotted lines.

Specific examples of representative and preferred values for R⁶, R⁷ and R⁸ in the definition of antibiotics I are given below.

It should be noted that the final products of this invention (I) wherein R⁸ contains a basic functionally such as amino, amidino, guanidino, or carbamimidoyl can exist in either neutral or zwitterionic (internal salt) forms. In the zwitterionic form, the basic function is protonated and positively charged and the carboxyl group is deprotonated and negatively charged. The zwitterionic (or internal salt) form is the predominant species under most conditions and is in equilibrium with a minor amount of the uncharged, neutral species. The equilibrium process is conveniently visualized as an internal acid-base neutralization. The neutral and zwitterionic forms are shown below.

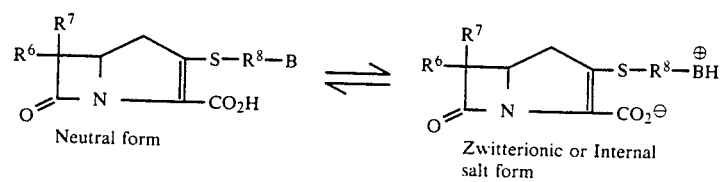

Neutral form    Zwitterionic or Internal salt form wherein B is a basic group such as $NH_2$, $NHR^1$, $NR^1R^2$, amidino, guanidino, carbamimidoyl, and $B^{\oplus}H$ is a protonated basic group such as $N^{\oplus}H_3$, $N^{\oplus}H_2R^1$,

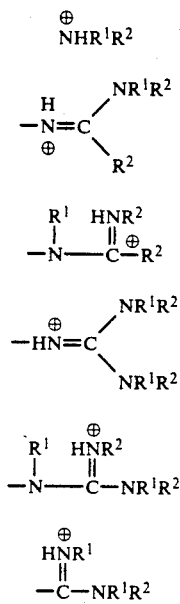

Further, the final products of this invention I wherein $R^8$ contains a positively charged, quaternary nitrogen function such as ammonium, amidinium, guanidinium, or carbamimidinium can exist as zwitterionic (internal salt) forms or as external salt forms. The preferred form of this product group is the zwitterionic or internal salt form. These forms are shown below:

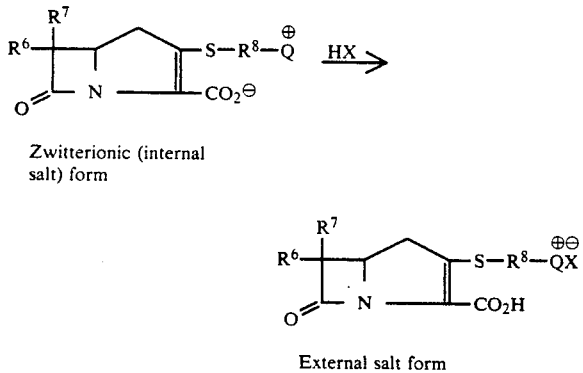

Zwitterionic (internal salt) form

External salt form wherein $Q^{\oplus}$ is a quaterized nitrogen group such as $-N^{\oplus}(R^1)_3$

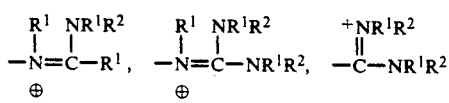

and HX is an acid; wherein X is a pharmaceutically acceptable anion such as those listed in U.S. Pat. No. 4,194,047, issued 3/18/80 which is incorporated herein by reference.

This invention also relates to the carboxyl derivatives of I which are antibiotics and which may be represented by the following generic structure (I):

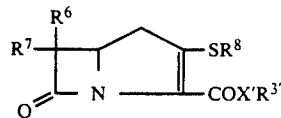

wherein X' is oxygen, sulphur or NR' (R'=H or lower alkyl having 1-6 carbon atoms); and $R^{3'}$ is, inter alia, representatively selected from the group consisting of hydrogen, conventional blocking groups such as trialkylsilyl, acyl and the pharmaceutically acceptable salt, ester and amide moieties known in bicyclic β-lactam antibiotic art; the definition of $R^{3'}$ is given in greater detail below.

This invention also relates to process for the preparation of such compounds (I); pharmaceutical compositions comprising such compounds; and to methods of treatment comprising administering such compounds and compositions when an antibiotic effect is indicated.

There is a continuing need for new antibiotics. For unfortunately, there is no static effectiveness of any given antibiotic because continued wide scale usage selectively gives rise to resistant strains of pathogens. In addition, the known antibiotics suffer from the disadvantage of being effective only against certain types of microorganisms. Accordingly, the search for new antibiotics continues.

Thus, it is an object of the present invention to provide a novel class of antibiotics which are useful in animal and human therapy and in inaminate systems. These antibiotics are active against a broad range of pathogens which representatively include both gram positive bacteria such as *S. aureus, Strep. pyogenes,* and *B. subtilis,* and gram negative bacteria such as *E. coli,* Pseudomonas, *Proteus morganii,* Serratia, and Klebsiella. Further objects of this invention are to provide chemical processes for the preparation of such antibiotics and their non-toxic pharmaceutically acceptable salts; pharmaceutical compositions comprising such antibiotics; and to provide methods of treatment comprising administering such antibiotics and compositions when an antibiotic effect is indicated.

DETAILED DESCRIPTION OF THE INVENTION

The compounds of the present invention (I, above) are conveniently prepared by the following scheme:

DIAGRAM I

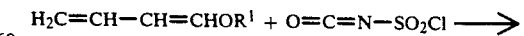

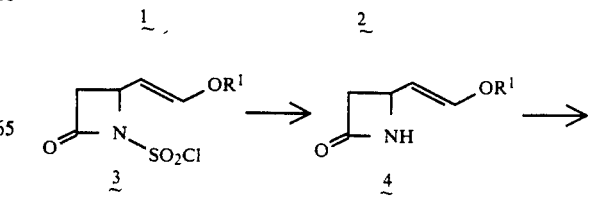

-continued
DIAGRAM I

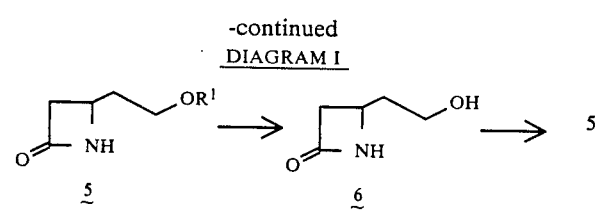
5

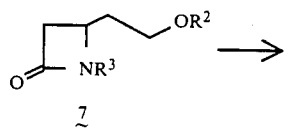
10

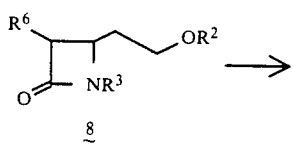

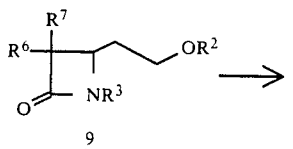
20

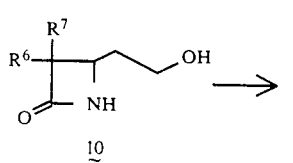
25

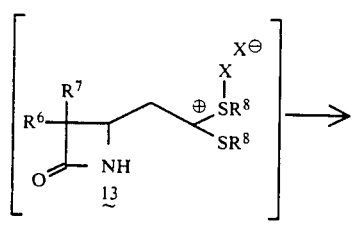

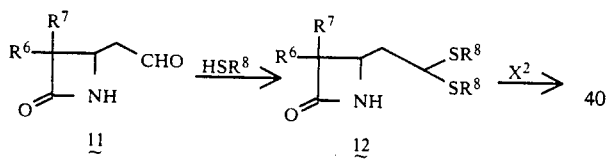
40

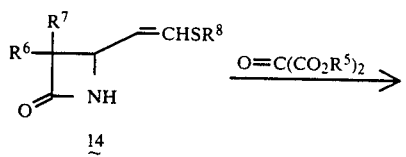

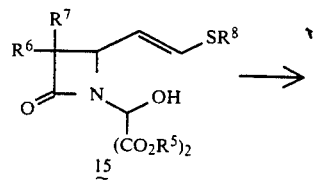

-continued
DIAGRAM I

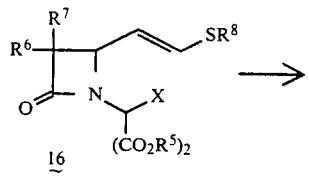

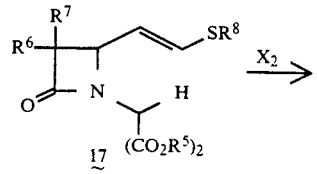

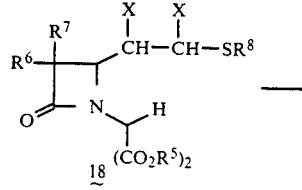

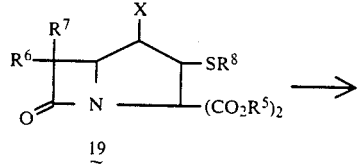

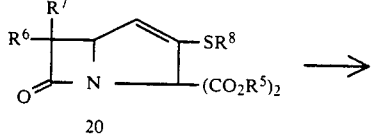

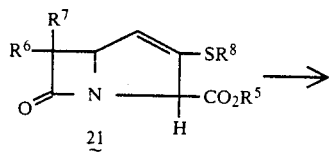

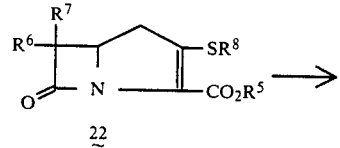

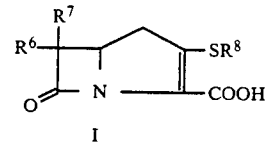

In words relative to the above diagram, the 4-(2-substituted-vinyl)azetidine-2-one, 4, starting material is prepared by reacting an $R^1$-oxybutadiene, 1, with chlorosulfonylisocyanate 2. The reaction is conducted without solvent or may be run in solvent such as diethyl ether, ethyl acetate, chloroform, methylene chloride, or the like, at a temperature of from −78° C. to 25° C. for from a few minutes to 1 hour to provide 3. The radical R[1] is an easily removable acyl blocking group such as alkanoyl or aralkanoyl which bears no functional group or groups which might interfere with the desired course of reaction (1+2→3→4). Intermediate species 3 is converted to the sulfinamide by reduction which is then hydrolyzed to 4 at pH 6-8. Typically the reaction solution comprising 3 is contacted (5-30 minutes) with an aqueous solution (at 0°-25° C.) of a reducing agent such as sodium sulfite, thiophenol, or the like, at pH 6-8 to provide 4.

The reaction 4→5 is a reduction, and is preferably achieved by hydrogenation in a solvent such as ethyl acetate, ether, dioxane, tetrahydrofuran (THF), ethanol or the like at 0° to 25° C. for from 5 minutes to 2 hours under 1 to 10 atmospheres of hydrogen in the presence of a hydrogenation catalyst such as a platinum metal or oxide thereof such as 10% Pd/C or the like.

The de-blocking reaction 5→6 is usually desirable when R[1] is acyl to permit the later alkylation, 7→8. The preferred de-blocking procedure is by alcoholysis wherein the solvent is a lower alkanol such as methanol, ethanol or the like in the presence of the corresponding alkali metal alkoxide, such as sodium methodxide. Typically, the reaction is conducted for from 5 minutes to 1 hour at a temperature of from −10° to 25° C.

Blocking groups R[3] and R[2] are established (6→7) to provide a suitably protected species for alkylation (7→8→9). There is no criticality in the choice of blocking groups, provided only that they do not interfere with the intended alkylation. R[3] may be hydrogen, a triorganosilyl group such as trimethylsilyl or the like, or a cyclic ether such as 2-tetrahydrophyranyl. R[2] may also be cyclic ether such as 2-tetrahydropyranyl; alternatively R[3] and R[2] may be joined together to form protected species such as 7a:

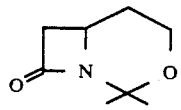

7a

For example, species such as 7a are conveniently prepared by treating 6 with 2,2-dimethoxypropane in the presence of a catalyst such as boron trifluoride etherate, toluene sulphonic acid, or the like in a solvent such as methylene chloride, ether, chloroform, dioxane or the like at a temperature of from −10° C. to 35° C. for from a few minutes to 1 hour. Species 7 can be mono- or dialkylated at ring position 6. Alkylation of 7 provides 8. Typically, 7 is treated with a strong base such as lithium diisopropyl amide, sodium hydride, phenyl lithium or butyl lithium and the like in a solvent such as tetrahydrofuran (THF), ether, dimethoxyethane and the like at a temperature of form −80° C. to 0° C., whereupon the alkylating agent of choice, R[6]X, is added (R[6] is as described above and X is chloro, iodo or bromo; alternatively the alkylating agent may be R[6]-tosylate, R[6]-mesylate or an aldehyde or ketone such as acetaldehyde and the like) to provide monoalkylated species 8. When desired, dialkylated species 9 may be obtained from 8 by repeating the alkylating procedure, 7→8.

The de-blocking reaction 9→10 is typically conducted by acid hydrolysis such as aqueous acetic acid at a temperature of from 25° C. to 75° C. for from 5 minutes to 3 hours.

The aldehyde intermediate 11 is prepared by treating 10 with an oxidizing agent such as $CrO_3.2$ (pyridine) in $CH_3CN$, 1:1 mixture of dimethylsulfoxide and acetic anhydride, cyclohexylcarbodiimide in DMSO or the like at a temperature of from 0°-25° C. for from 5 minutes to 1 hour. The resulting species 11 in a solvent such acetonitrile, methylene chloride, chloroform or the like at a temperature of from −10° to 25° C. is treated with an excess of the reagent HSR[8] in the presence of an acid catalyst such as boron trifluoride etherate, toluene sulphonic acid or the like to provide 12. Typically, the reaction requires from 1 to 60 minutes.

The vinyl sulphide 14 is obtained via intermediate 13 by treating 12 with a halogen such as chlorine or bromine (X=Cl or Br) in a solvent such as ether, methylene chloride, tetrahydrofuran, glyme or the like at a temperature of from −78° to 30° C. for from 1 to 30 minutes, followed immediately by treating with an olefin such as cyclohexene, isobutylene, or the like in the presence of base such as triethylamine. DBU, sodium hydride, or the like in a solvent such as DMF, glyme, THF, HMPA. The solution is held at −20° to 25° C. for from 1 to 8 hours to yield 14.

The vinyl sulphide species 14 is reacted with a diester of oxomalonic acid (or its monohydrate) to provide 15. There is no criticality as to the identity of the ester moiety, R[5], of the oxomalonic acid. R[5] may be a conventional, easily removable blocking group or it may be a pharmaceutically acceptable ester moiety. Suitable ester radicals R[5] are p-nitrobenzyl, benzyl, o-nitrobenzyl, t-butyl, 2,2,2-trichloroethyl. The reaction 14→15 is typically conducted in a high boiling organic solvent such as benzene, toluene, cyclohexane, halo aromatic or the like at a temperature of from about 50° C. to reflux for from 0.5 to 6 hours.

The halogenation reaction 15→16 is typically conducted in a solvent such as THF, glyme, ether, methylene chloride, chloroform or the like in the presence of a halogenating agent such as thionyl chloride, phosphorous pentachloride or the like in the presence of base such as pyridine at a temperature of from −20° to 25° C. for from 5 minutes to 3 hours. The selective reduction of 15→17 via 16 is completed by treating 16 with tributylphosphine, triphenylphosphine or the like in aqueous DMF or similar aqueous systems involving dioxane, THF, glyme, DMSO, or acetone at a temperature of from about 0°-50° C. for from 10 minutes to 5 hours.

Species 17 is halogenated by the previous procedure (12→13), but omitting the addition of the cyclohexene or other olefin, to provide the dihalo species 18. Species 18 is treated with a base such as triethylamine, sodium hydride or potassium hydride in a solvent such as DMF, acetonitrile, methylene chloride, chloroform, glyme or the like at a temperature of from about −78° to 25° C.

for 1 to 5 hours to provide 19. Species 19 is converted to 20 on treatment with a strong base such as 1,5-diazabicyclo [5.4.0]-undec-5-ene(DBU),1,5-diazabicyclo[3.4.0]non-5-ene(DBN), or the like in a solvent such as DMSO, acetone, chloroform, DMF, THF, glyme or the like or on treatment with AgF in pyridine at a temperature of from 0°–40° C. for from ¼ to 24 hours. The reaction 20→21 is conducted by treating 20 with an aromatic base such as pyridine, aqueous dimethylsulfoxide, s-collidine or lutidine, in the presence of a displacing agent such as lithium iodide, sodium chloride, lithium bromide, sodium bromide, or the like at a temperature of from about 80°–150° C. for from 15 minutes to 2 hours. An aqueous work up of the resulting reaction mixture provides 21. Isomerization of the double bond 21→22 is accomplished by treating 21 in a solvent such as DMF, DMSO, ethyl ether, THF, glyme, methylene chloride with a strong base such as diisopropylamine, DBU, DBN, or the like at a temperature of from 0° to about 25° C. for from a few minutes to 2 hours or until equilibrium has been established as determined by examination of sample aliquots by ultraviolet absorption or by thin layer chromatogrpahy. The final reaction 22→I (hydrogenolysis of the blocking group) is accomplished by treating 22 in a solvent such as dioxane, ethanol, THF or the like or an aqueous mixture thereof in the presence of a platinum metal catalyst such as Pd/C under a hydrogen pressure of from 1–4 atmospheres for from 0.5 to 8 hours at a temperature of from about 0°–25° C.

The above-described total synthesis may also advantageously start with 4-vinyl azetidinone [(23), below; E. J. Moriconi, W. C. Meyer, *J. Org. Chem.*, 36, 2841 (1971)]rather than the enol acylate azetidinone (4, above). This variation in the total synthesis has the advantage of conveniently imparting stereoselectivity to the process at an early stage. The following scheme illustrates this 4-vinyl azetidinone embodiment of the present invention; notice that it ties into the above scheme at species 14.

DIAGRAM II

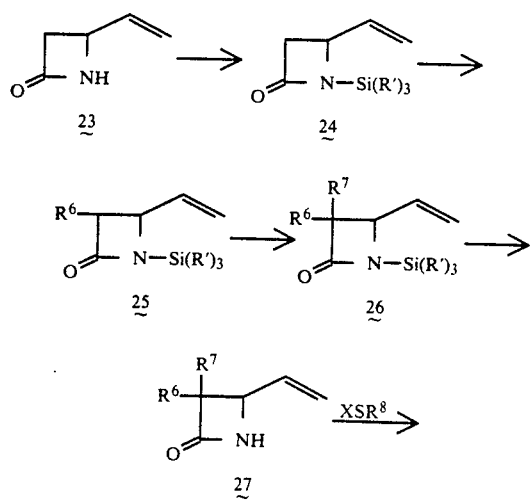

-continued
DIAGRAM II

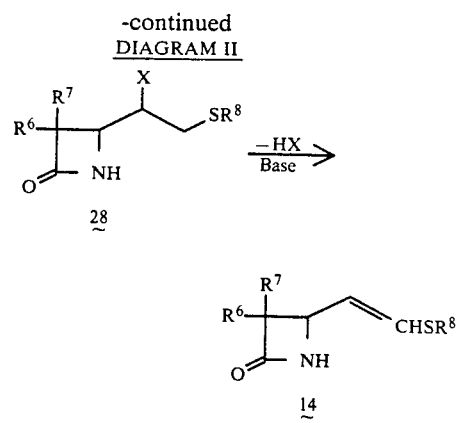

In words relative to the above reaction diagram, 4-vinyl azetidinone 23 is silylated to provide the N-silyl species 24. The groups R' on the silyl radical are lower alkyl having from 1–6 carbon atoms especially preferred triorganosilyl groups are trimethylsilyl and t-butyl-dimethylsilyl. Typically, the silylation (23→24) is achieved by treating 23 in a solvent such as DMF, DMSO, HMPA or the like with the silylating agent of choice, dimethyl t-butylsilyl chloride, and a base such as Et₃N, pyridine, N,N-dimethylaniline and the like at a temperature of from −10° to 30° C. for from 1 to 8 hours. Species 24 is alkylated to form 25 or 26 and this alkylation is conducted exactly as described above for the alkylation 7→8→9. It should be noted here that the reactions (24→25) and (25→26) represent convenient opportunities to separate species 25 and 26 into their racemic diastereoisomers if desired. The removal of the N-triorganosilyl group is accomplished in reaction 26→27 my mild acid catalyzed solvolysis. The halo sulfide species 28 is obtained from 27 by treating 27 in a solvent such as methylene chloride, THF, glyme, or the like with the reagent XSR⁸ wherein R⁸ has previously been defined and X is halogen such as chloro or bromo at a temperature of from −50° to 50° C. for from 1 to 16 hours. The vinyl sulfide intermediate 14, which is common to the above illustrated scheme of total synthesis is obtained from 28 by elimination of HX on treatment of 28 with a base such as 1,5-diazabicyclo[5.4.0]undec-5-ene (DBU), 1,5-diazabicyclo[4.3.0]non-5-ene, (DBN), 1,4-diazabicyclo[2.2.2]octane, (DABCO), or silver fluoride in a solvent such as DMSO, pyridine, DMF, HMPA or the like at a temperature of from −20° to 50° C. for from ¼ to 16 hours.

The compounds of the present invention may also be prepared by the following scheme:

DIAGRAM III

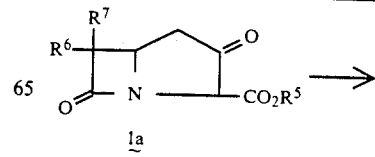

-continued
DIAGRAM III

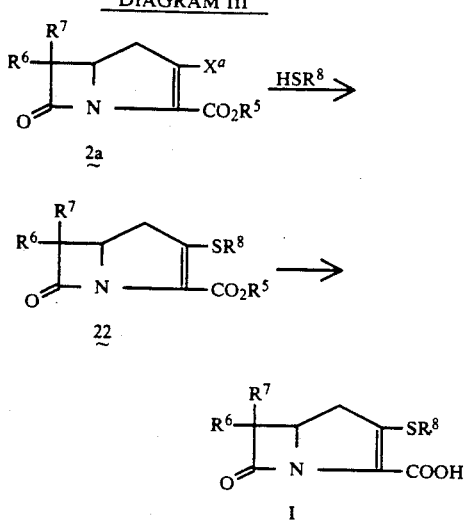

In words relative to the above reaction scheme, Diagram III, the step 1a→2a to establish leaving group $X^a$ is accomplished by acylating the bicyclic keto ester 1a with an acylating agent $R°X^a$ such as p-toluenesulfonic acid anhydride, p-nitrophenylsulfonic acid anhydride, 2,4,6-triisopropylphenylsulfonic acid anhydride, methanesulfonic acid anhydride, trifluoromethane sulfonic acid anhydride, diphenyl chlorophosphate, toluenesulfonyl chloride, p-bromophenylsulfonyl chloride, or the like wherein $X^a$ is the corresponding leaving group such as toluene sulfonyloxy, p-nitrophenylsulfonyloxy, diphenylphosphoryl, and other leaving groups which are established by conventional procedures and are well known in the art. Typically, the above acylation to establish leaving groups $X^a$ is conducted in a solvent such as methylene chloride, acetonitrile or dimethylformamide, in the presence of a base such as diisopropylethylamine, triethylamine, 4-dimethylaminopyridine or the like at a temperature of from −20° to 40° C. for from 0.1 to 5 hours. The leaving group $X^a$ is intermediate 2a can also be halogen. The halogen leaving group is established by treating 1a with a halogenating agent such as $\phi_3PCl_2$, $\phi_3PBr_2$, $(\phi O)_3PBr_2$, oxalyl chloride or the like in a solvent such as $CH_2Cl_2$, $CH_3CN$, THF, or the like in the presence of a base such as diisopropylethylamine, triethylamine, or 4-dimethylaminopyridine or the like. [$\phi$=phenyl.]

The reaction 2a→22 is accomplished by treating 2a in a solvent such as dioxane, dimethylformamide, dimethylsulfoxide, acetonitrile, hexamethylphosphoramide, or the like in the presence of an approximately equivalent to excess of the mercaptan reagent $HSR^8$, wherein $R^8$ is as defined above, in the presence of a base such as sodium hydrogen carbonate, potassium carbonate, triethylamine, diisopropylethylamine, or the like at a temperature of from −40° to 25° C. for from 1 min. to 72 hours. When $R^8$ is substituted by a primary or secondary amino group, for example $-CH_2CH_2NH_2$, the mercaptan reagent may be represented as $HSCH_2CH_2NHR°$, for example; wherein $R°$ is a readily removable N-protecting group such as p-nitrobenzyloxycarbonyl, ($-CO_2PNB$), o-nitrobenzyloxycarbonyl, or the like. The specifically illustrated mercaptan reagent, $HSCH_2CH_2NHR°$, is typically prepared by treating aminoethylmercaptan in the presence of the desired acid chloride in the presence of a base such as sodium bicarbonate, sodium hydroxide, or the like in a solvent such as aqueous diethylether, aqueous dioxane, aqueous acetone, or the like at a temperature of from 0° to 25° C. for from 0.5 to 4 hours. The foregoing mercaptan reagent, $HSR^8$, and means for its protection, is simply illustrative. The class of suitable $HSR^8$ reagents is representatively described below and in the Examples.

The final deblocking step 22→I is accomplished by conventional procedures such as solvolysis or hydrogenation. The conditions of deblocking 22→I were given above, but to repeat and to additionally describe: typically 22 in a solvent such as tetrahydrofuran-water, tetrahydrofuran-ethanol-water, dioxane-water, dioxane-ethanol-water, or the like containing pH 7 morpholinopropanesulfonic acid buffer, pH 7 phosphate buffer, dipotassium hydrogen phosphate, sodium bicarbonate, or the like is treated under a hydrogen pressure of from 1 to 4 atmospheres in the presence of a catalyst such as platinum oxide, palladium on charcoal, or palladium hydroxide, or the like at a temperature of from 0° to 50° C. for from 0.25 to 4 hours to provide I. Photolysis, when $R^5$ is a group such as o-nitrobenzyl, for example, may also be used for deblocking.

Relative to Diagram III, the bicyclic keto ester 1a may be obtained by a variety of schemes of total schemes. One of these schemes wherein $R^7$ is hydrogen and $R^6$ is hydroxyethyl (1a)

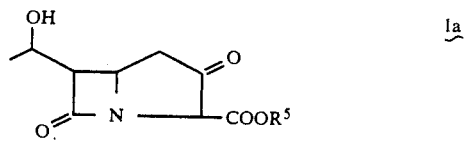

is disclosed in European Patent Application Number 79101307.1 filed May 1, 1979, publication number 0007973 (Feb. 20, 1980).

This application is incorporated herein by reference to the extent that it describes the preparation of this embodiment of starting material 1a and the subsequent reactive schemes: 1a→2a→22→I.

The bicyclic keto ester 1a, in the general case, may be prepared by the processes disclosed and claimed in the three following, co-pending, commonly assigned U.S. patent applications of Christensen, Ratcliffe and Salzmann. To the extent that these applications disclose processes for the preparation of 1a, in its general expression,

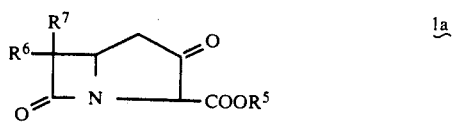

and the process scheme for the preparation of antibiotics I of the present invention according to reactive scheme $\underline{1a} \rightarrow \underline{2a} \rightarrow \underline{22} \rightarrow I$, they are hereby incorporated by reference. The three applications are:
1. Process for the Preparation of 1-Carbapenems and Intermediates via 4-Allylazetidinone; U.S. patent application Ser. No. 134,408 filed Mar. 27, 1980, now abandoned
2. Process for the Preparation of 1-Carbapenems and Intermediates via Trithioorthoacetates; U.S. patent application Ser. No. 134,396 filed Mar. 27, 1980, U.S. Pat. No. 4,309,346.
3. Process for the Preparation of 1-Carbapenems and Intermediates via Silyl-Substituted Dithioacetals; U.S. patent application Ser. No. 134,397 filed Mar. 27, 1980, now abandoned.

$HSR^8$ and $XSR^8$ REAGENTS

Relative to the foregoing description of the invention, suitable reagents, $HSR^8$, which are utilized in the transformations $\underline{11} \rightarrow \underline{12}$ (Diagram I) and $\underline{2a} \rightarrow \underline{22}$ (Diagram III), and $XSR^8$, which are utilized in the transformation $\underline{27} \rightarrow \underline{28}$ (Diagram III) are listed below. The list is arranged according to structural and functional characteristics of the thia side chain $-SR^8$; annotation is provided where necessary. [It should be noted that only $HSR^8$ reagents are expressly shown. The reagents $XSR^8$ (X=Cl or Br) are shown implicitly for each entry on permissible substitution of Cl or Br for "H" in $HSR^8$.] The thia side chain of choice $-SR^8$ is derived from the corresponding mercaptan reagent $HSR^8$, and thus the following list serves to further, specifically disclose $-SR^8$ side chains of I which are of special interest. When the mercaptan contains a functional group which might interfere with the intended course of reaction, the offending group is covered. For example, when a basic nitrogen group is encountered ($-NHR$ or $-NH_2$, for example) it is usually protected by acylation (e.g., $-CO_2PNB$) and when a carboxyl group ($-CO_2H$) is present, it is usually protected by esterification (e.g., PNB ester). Such protection also facilitates in the purification of products by chromatographic means. (PNB is p-nitrobenzyl). Such protection is, however, not a necessary requirement for introduction of the $-SR^8$ side chain. The transformation $\underline{2a} \rightarrow \underline{22}$ (Diagram III) is conveniently carried out using both protected and unprotected $HSR^8$ forms. It should be noted that the processes incorporated by reference above [1.) Process for the Preparation of 1-Carbapenems and Intermediates via 4-Allylazetidinone, U.S. Ser. No. 134,408 filed 3-27-80; 2.) Process for the Preparation of 1-Carbapenems and Intermediates via Trithioorthoacetates, U.S. Ser. No. 134,396, filed 3-27-80; and 3.) Process for the Preparation of 1-Carbapenems and Intermediates via Silyl-Substituted Dithioacetals, U.S. Ser. No. 134,397, filed Mar. 27, 1980] are preferred when $R^8$ contains a nucleophilic functionality such as alkenyl, alkynyl, imino, and the like. It is recognized that $SR^8$ side chains in which the $R^8$ group contains one or more chiral centers can be added as racemic or diastereomeric mixtures to provide mixtures of diastereomeric products or can be added as resolved, isomerically pure reagents to provide diastereomerically pure products. Since antibacterial activity and other pharmacological properties vary among isomers, it is frequently advantageous to prepare isomerically pure products by the introduction of resolved $-SR^8$ side chains.

1. Aliphatic Mercaptans: $HSR^8$ wherein $R^8$ is 1-10 carbon alkyl, cycloalkyl, alkenyl, cycloalkenyl, or alkynyl; $R^8$ may be branched or unbranched, Examples
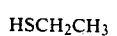
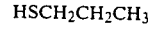
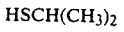
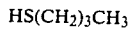
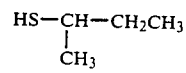
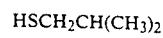
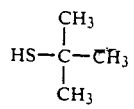
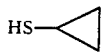
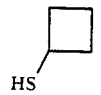
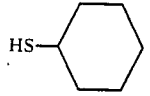
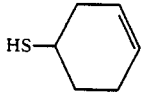
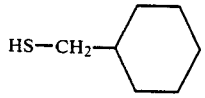
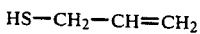
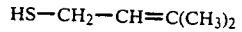
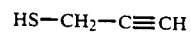
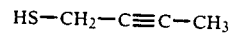

2. Substituted Aliphatic Mercaptans: $HSR^8$ wherein $R^8$ is a 1-10 carbon branched or unbranched alkyl, cycloalkyl, alkenyl, cycloalkenyl, or alkynyl group substituted by one or more halo,

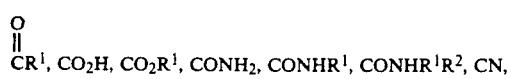
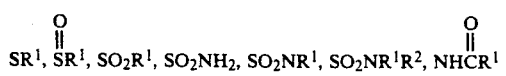
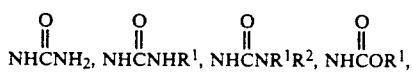
wherein $R^1$ and $R^2$ are as previously defined relative to substituents on $R^8$. Preferred substituents are basic nitrogen-containing groups.
EXAMPLES
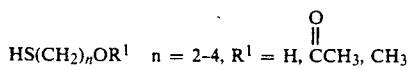
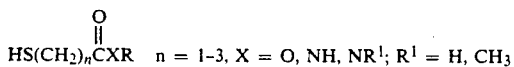
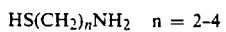
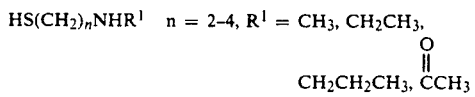
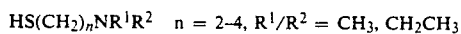
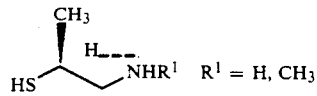
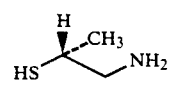
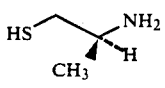
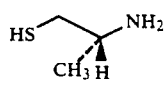
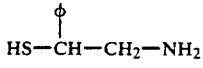
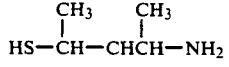
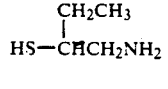
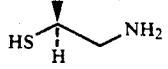
-continued
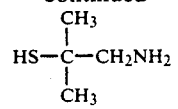
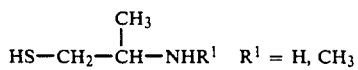
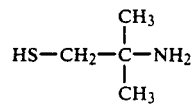
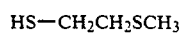
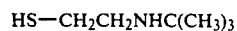
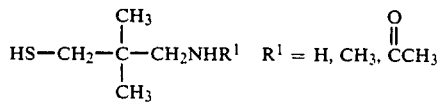
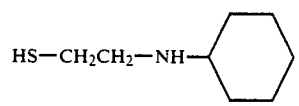
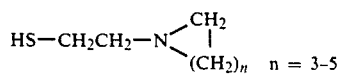
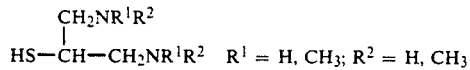
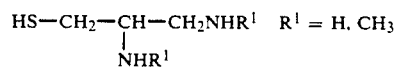
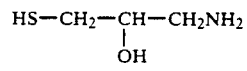
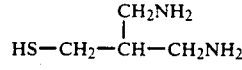
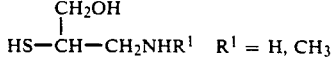
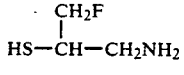
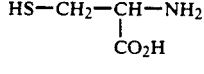
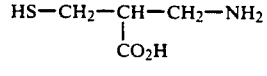
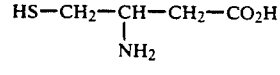
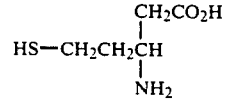
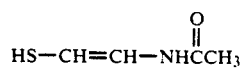

-continued

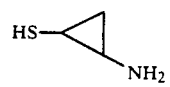
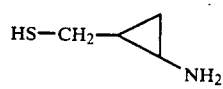
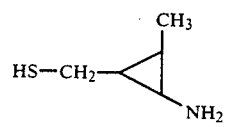
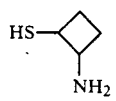
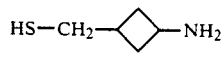
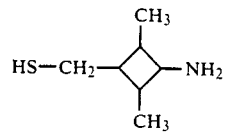

HS—CH₂—CH—CH₂OH
         |
         OH 5-thio-D-glucose

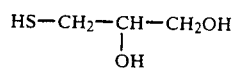
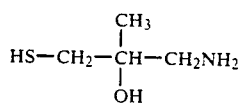
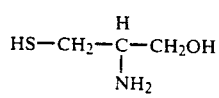
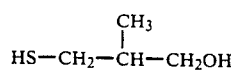
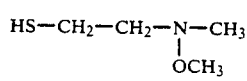

HS—CH₂—CH=CH—CH₂NH₂

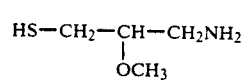
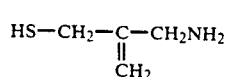
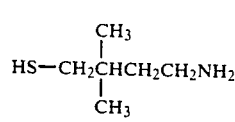

-continued

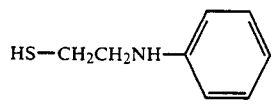
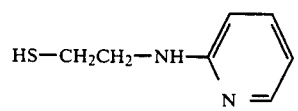
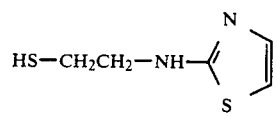
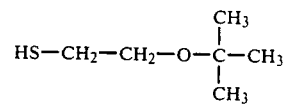

3. Aryl Mercaptans: HSR⁸ wherein R⁸ is phenyl or substituted phenyl. The substituents are independently selected from those previously defined for R⁸. Especially preferred substituents include alkyl, halo, hydroxy, alkoxy, acyloxy, acyl, carboxy, mercapto, sulfinyl, sulfonyl, amino, substituted amino, aminoalkyl, substituted aminoalkyl, amido, and ureido.

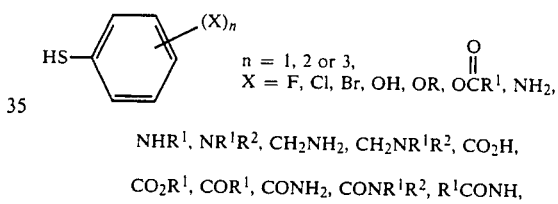

n = 1, 2 or 3,
X = F, Cl, Br, OH, OR, OCR¹, NH₂,
    ||
    O

NHR¹, NR¹R², CH₂NH₂, CH₂NR¹R², CO₂H,

CO₂R¹, COR¹, CONH₂, CONR¹R², R¹CONH,

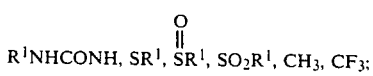

R¹NHCONH, SR¹, SR¹, SO₂R¹, CH₃, CF₃;
                ||
                O

R¹ and R² are as previously defined under R⁸.

EXAMPLES

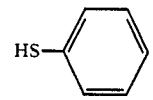
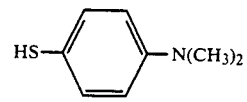
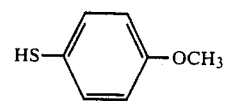
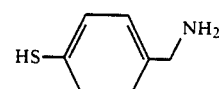

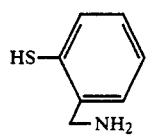

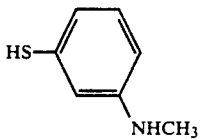

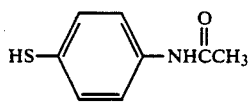

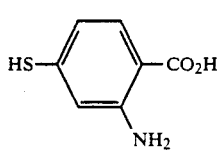

4. Heteroaryl Mercaptans: HSR⁸ wherein R⁸ is a substituted or unsubstituted heteroaryl group containing 1-4 O, N or S atoms. Typical substituents include those mentioned above under "Aryl Mercaptans".

EXAMPLES

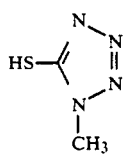

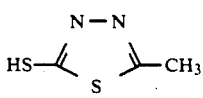

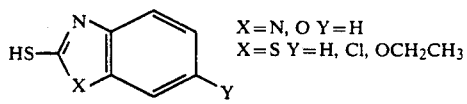

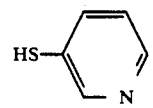

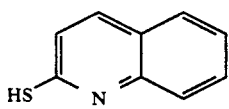

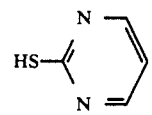

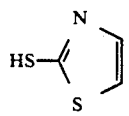

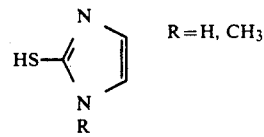

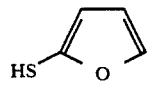

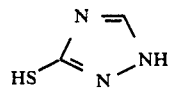

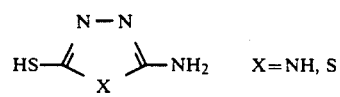

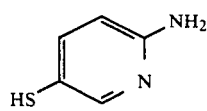

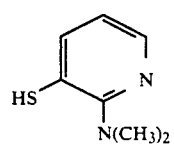

5. Arylaliphatic Mercaptans: HSR⁸ where R⁸ is a 1-6 carbon branched or unbranched alkyl, cycloalkyl, alkenyl, or alkynyl group substituted by a phenyl or substituted phenyl group. Typical phenyl substituents include those mentioned under "Aryl Mercaptans".

EXAMPLES

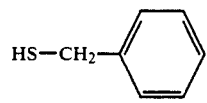

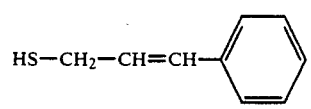

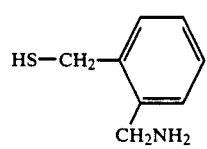

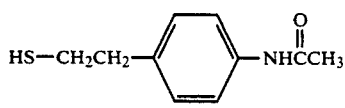

6. Heteroarylaliphatic and Heterocyclylaliphatic, and heterocyclic Mercaptans

HSR⁸ wherein R⁸ is a 1-6 carbon branched or unbranched alkyl, cycloalkyl, alkenyl, or alkynyl group substituted by a heteroaryl or heterocyclyl group containing 1-4, O, N, or S atoms. The heteroaryl or heterocyclic group is unsubstituted or substituted by those substituents mentioned under "Aryl Mercaptans", (No. 3 above).
EXAMPLES
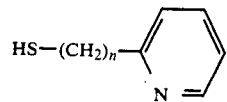
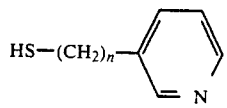
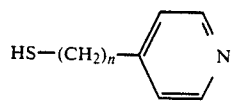
n = 1,2
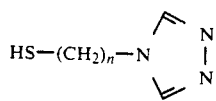
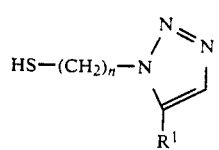
R¹ = OCH₂CH₃
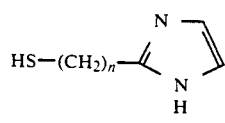
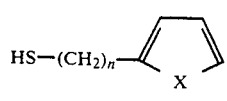
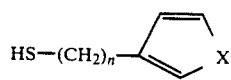
X = O, S, NH
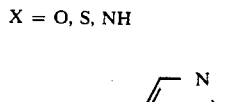
X = O, S, NH
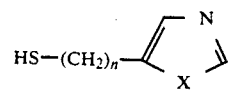
X = O, S, NH
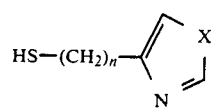
X = O, S, NH
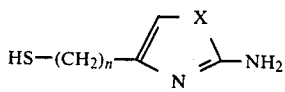
X = O, S, NH
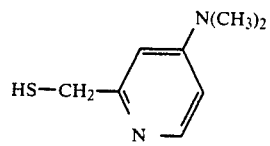
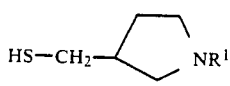
R¹ = H, CH₃
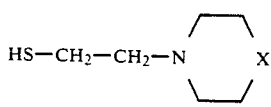
R¹ = H, CH₃
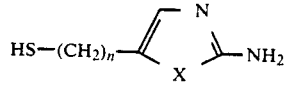
X = O, NH, NCH₃
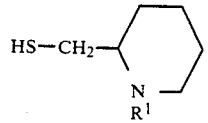
R¹ = H, CH₃
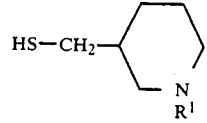
R¹ = H, CH₃
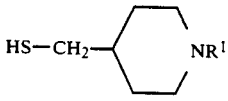
R¹ = H, CH₃
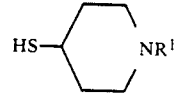
R¹ = H, CH₃

-continued

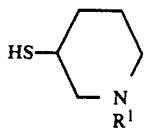

R¹ = H, CH₃

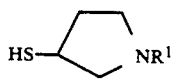

R¹ = H, CH₃

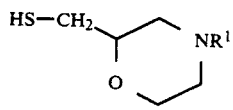

R¹ = H, CH₃

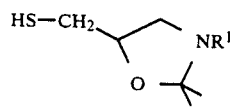

R¹ = H, CH₃

7. Alkyl-Heteroatom-Alkyl Mercaptans, HSR⁸ Wherein R⁸ is —(CH₂)$_n$X(CH₂)$_m$R⁹ wherein n=2 to 4, m=2 to 4; X is NRº, O or S; and wherein Rº is H, CH₃, CH₂CH₃, CH₂CH₂OH, or CH₂CH₂NH₂ and

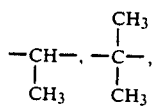

Note, in the above representation, the methylene carbons may be branched; for example:

$$-CH-, -C-$$
$$\phantom{xx}|\phantom{xxx}|$$
$$\phantom{xx}CH_3\phantom{x}CH_3$$
$$\phantom{xxxxxxx}|$$
$$\phantom{xxxxxxx}CH_3$$

and the like.

The following HSR⁸ are representative of this class:

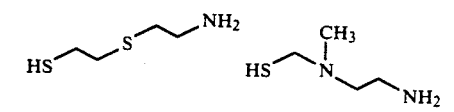

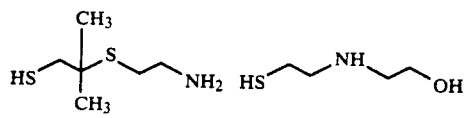

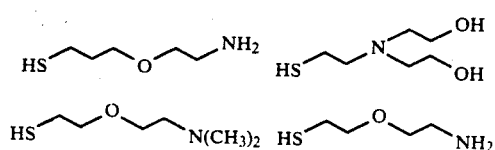

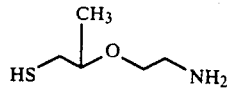

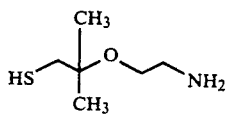

8. Amidino and Amidinium Mercaptans HSR⁸ Wherein R⁸ is:

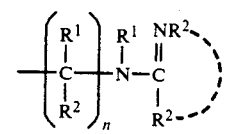

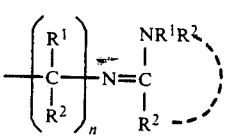

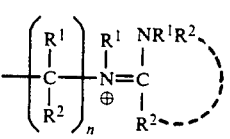

and wherein n=2–6; R¹ and R² are as initially defined under R⁸; and the dotted line indicates provision for the ring formed by the joinder of substituents carried by the imino carbon atoms. Such amidino and amidinium embodiments of final products I are also conveniently obtained by N-derivatization of the corresponding amino embodiment Ia according to the procedure disclosed in U.S. Pat. No. 4,194,047 which patent is incoproated herein by reference since the N-derivatization of thienamycin disclosed in the incorporated by reference patent is strictly analogous to the N-derivatization contemplated to achieve the amidino embodiments characterized herein.

The following reaction summarizes such N-derivatization;

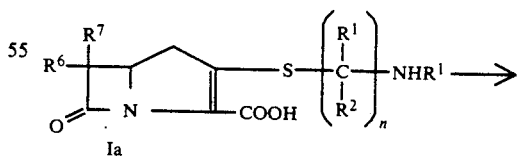

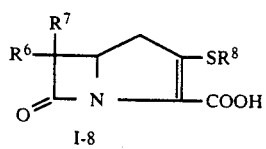

wherein: relative to I-8, R⁸ is defined above in this category No. 8.

Relative to the amidino embodiments characterized under this heading, representatively preferred values for $R^1$ and $R^2$ attached to the carbon atom include: H, $CH_3$, $CH_2CH_3$, $CH_2OH$, $OCH_3$, $CH_2NH_2$, F, PHENYL, $CF_3$, $CH(CH_3)_2$, $CH_2CH_2CH_3$, $CH_2F$ benzyl, $SCH_3$, $N(CH_3)_2$, $N^+(CH_3)_3X^-$ ($X^-$ defined above)

Representatively preferred values for $R^1$ and $R^2$ attached to the nitrogen atoms include: H, phenyl, $CH(CH_3)_2$, $C(CH_3)_3$, $NH_2$, $CH_3$, $NHCH_3$, $N(CH_3)_2$, $CH_2CH_3$, $CH_2CH_2OH$, $-CH_2)_4-$, $-CH_2CH_2-O-CH_2CH_2$, $OCH_3$ Representatively preferred values for $R^2$ attached to the imino carbon atom include: H, $CH_3$, $CH_2$, $CH_3$, phenyl The following values for $HSR^8$ are also classified under the amidino mercaptans, giving rise to amidino embodiments of I:

$R^8$ is:

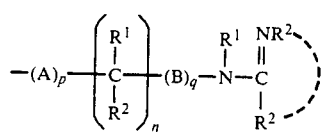

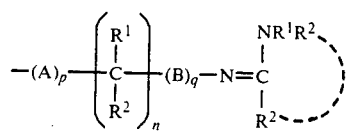

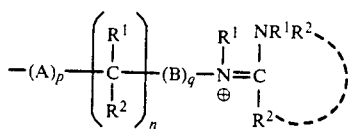

wherein $R^1$, $R^2$ and n are as defined immediately above; p and q are 0 or 1; A and B are selected from: the aforementioned values for $R^8$ expressed in bivalent form ($-R^8-$) from categories Nos. 1–7; thus, A and B (or $-R^8-$) are selected from: cycloalkyl, alkenyl, cycloalkenyl, alkynyl (see Class No. 1, above); substituted: cycloalkyl, alkenyl, cycloalkenyl, alkynyl (see Class No. 2, above); phenyl and substituted phenyl (see Class No. 3, above); substituted and unsubstituted heteroaryl (see Class No.4, above); aryl aliphatic (see Class No. 5, above); heteroarylaliphatic, heterocyclylaliphatic, and heterocyclic (see Class No. 6, above); and alkylheteroatom-alkyl (see Class No. 7, above); and B can also be selected from $-O-$ and $-NR^1-$.

EXAMPLES

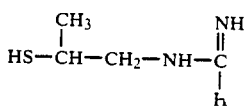

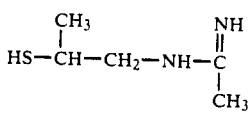

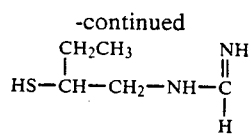

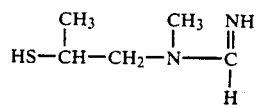

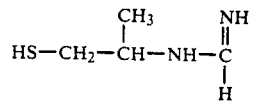

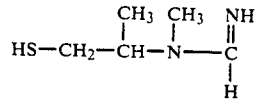

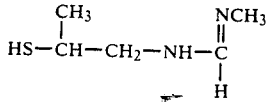

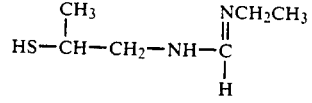

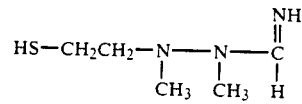

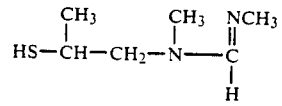

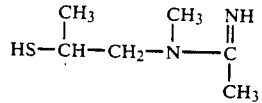

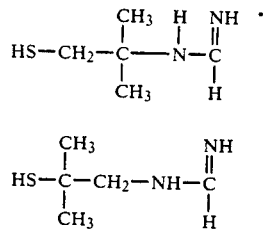

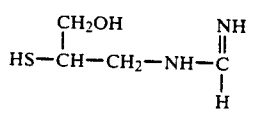

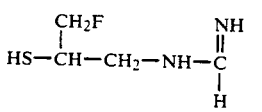

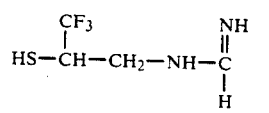

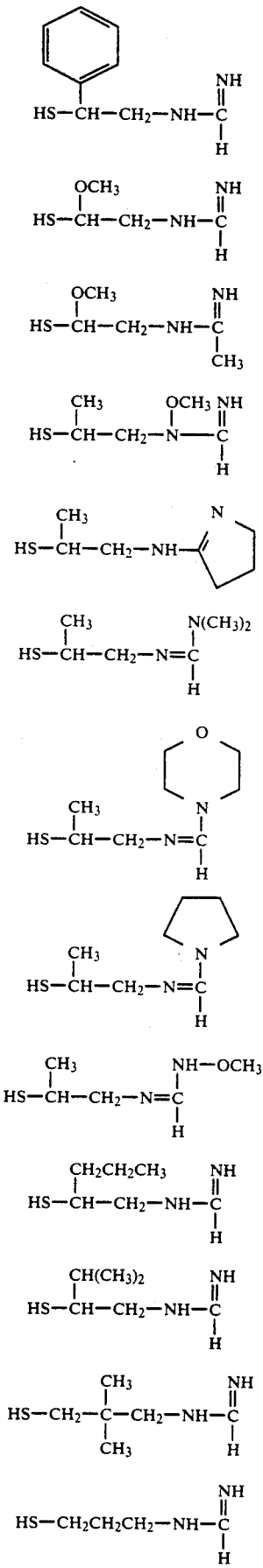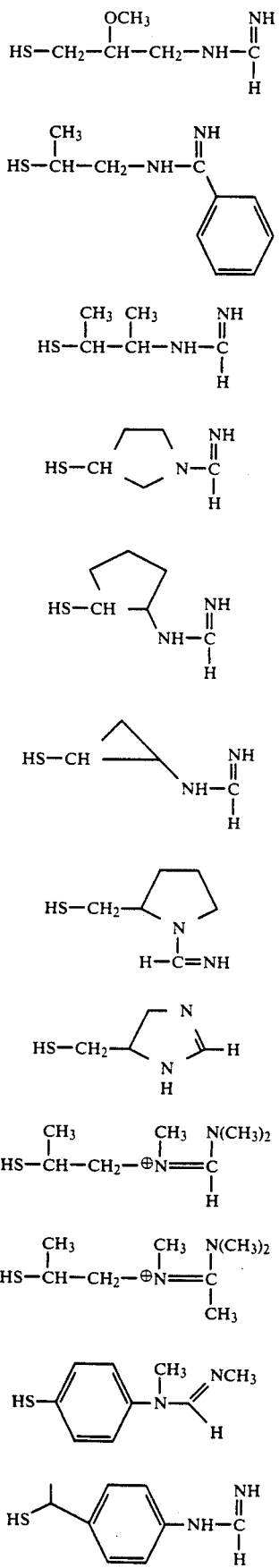

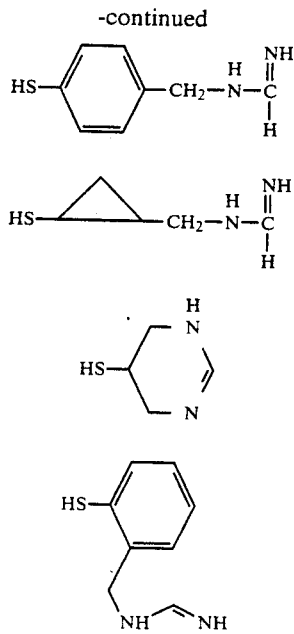

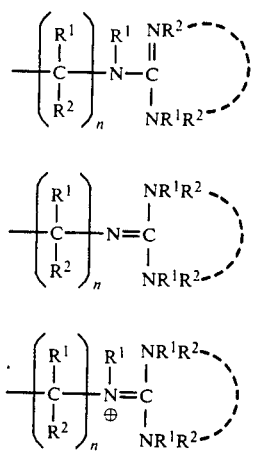

9. Guanidino and Guanidinium Mercaptans HSR$^8$
Wherein R$^8$ is:

and wherein n=2–6; R$^1$ and R$^2$ are as initially defined under R$^8$; and the dotted line indicates provision for the ring formed by the joinder of substituents carried by the imino carbon atom. Such guanidino and guanidinium embodiments of the final products I are conveniently obtained by N-derivatization of the corresponding amino embodiments according to procedures disclosed in U.S. Pat. No. 4,194,047 as was explained under 8. above.

Such guanidino embodiments are also conveniently prepared directly following the procedure described in Diagram III, above. Such procedure is also disclosed in co-pending, concurrently filed, commonly assigned U.S. patent application Ser. No. 197,865 filed Oct. 17, 1980 of W. J. Leanza now abandoned which application is incorporated herein by reference.

Representatively preferred values for R$^1$ and R$^2$ attached to the carobn atom include: H, CH$_3$, CH$_2$CH$_3$, CH$_2$OH, OCH$_3$, CH$_2$NH$_2$, F, phenyl, CF$_3$, CH(CH$_3$)$_2$, CH$_2$CH$_2$CH$_3$, CH$_2$F, benzyl, N(CH$_3$)$_2$ Representatively preferred values for R$^1$ and R$^2$ attached to nitrogen atoms include: H, CH$_3$, CH$_2$CH$_3$, CH$_2$CH$_2$OH, —(CH$_2$)$_2$— —(CH$_2$)$_3$— CH(CH$_3$)$_2$ —(CH$_2$)$_4$—, phenyl, CH(CH$_3$)$_2$, C(CH$_3$)$_3$, —CH$_2$CH$_2$OCH$_2$CH$_2$— OCH$_3$, NH$_2$, NHCH$_3$, N(CH$_3$)$_2$ The following values for HSR$^8$ are also classified under the guanidino mercaptans, giving rise to the guanidino embodiments of I:

R$^8$ is:

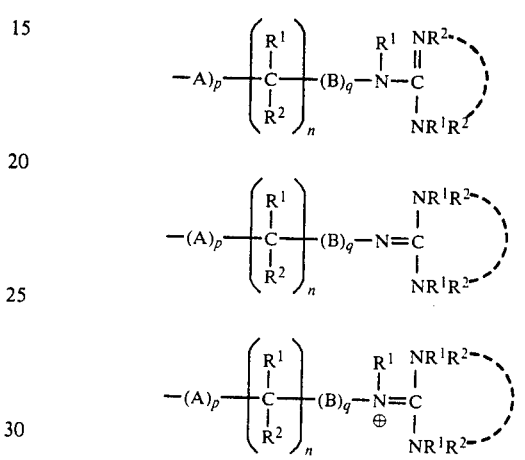

wherein R$^1$ and R$^2$ and n are as defined immediately above; p and q are 0 or 1; A and B are selected from: the aforementioned values for R$^8$ expressed in bivalent form from categories Nos. 1–7.

Thus, A and B (or —R$^8$— are selected from: cycloalkyl, alkenyl, cycloalkenyl, alkynyl (see Class No. 1, above); substituted: cycloalkyl, alkenyl, cycloalkenyl, alkynyl (see Class No. 2 above); phenyl and substituted phenyl (see Class No. 3, above); substituted and unsubstituted heteroaryl (see Class No. 4, above); aryl aliphatic (see Class No. 5, above); heteroarylaliphatic, heterocyclylaliphatic, and heterocyclic (see Class No. 6, above); and alkyl-heteroatom-alkyl (see Class No. 7, above); B is also selected from —O— and —NR'—.

EXAMPLES $$HS-CH_2-CH_2-\underset{\underset{CH_3}{|}}{N}-C\underset{\diagdown N(CH_3)_2}{\diagup^{NCH_3}}$$

$$HS-CH_2-CH_2-\overset{+}{\underset{\underset{CH_3}{|}}{N}}=C\underset{\diagdown N(CH_3)_2}{\diagup^{N(CH_3)_2}}$$

$$HS-\underset{\underset{CH_3}{|}}{CH}-CH_2-\underset{\underset{CH_3}{|}}{N}-C\underset{\diagdown NH_2}{\diagup^{NH}}$$

$$HS-CH_2-CH_2-NH-\overset{NH}{\overset{\|}{C}}-N(CH_3)_2$$

-continued

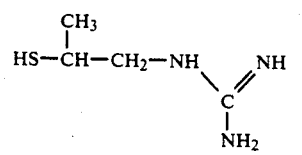

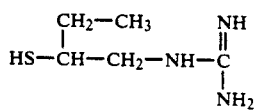

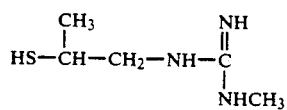

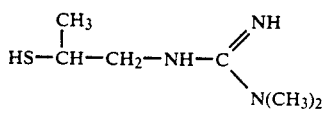

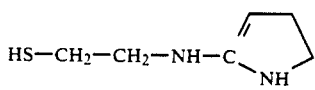

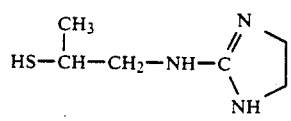

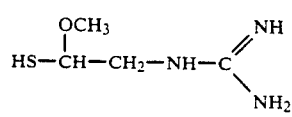

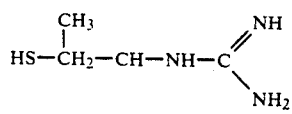

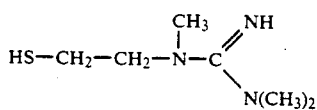

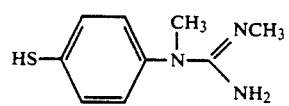

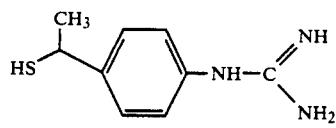

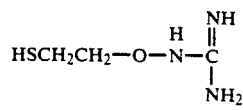

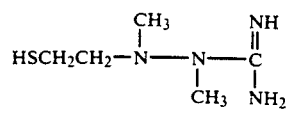

-continued

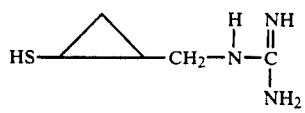

10. Carbamimidoyl and carbamimidinium Mercaptans $HSR^8$

Wherein $R^8$ is:

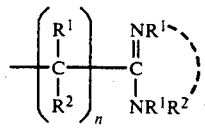

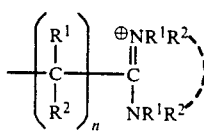

and wherein n is 0-6, and $R^1$ and $R^2$ are as initially defined under $R^8$; the two nitrogen atoms demonstrated in the above structure may be joined via their substituents to form a ring which is indicated by the dotted line.

Representatively preferred values for $R^1$ and $R^2$ attached to the carbon atom include: hydrogen, methyl, ethyl, propyl, isopropyl, phenyl, benzyl, amino, methylamino, dimethylamino, trimethyl ammonium, ethylthio, methoxy, methoximino, methylene, vinyl, hydroxy, fluoro, trifluoromethyl, hydroxymethyl, fluoromethyl.

Representatively preferred values of $R^1$ and $R^2$ attached to nitrogen atoms include: hydrogen, ethyl, methyl, phenyl, benzyl, isopropyl, t-butyl, methoxy, amino, methylamino, dimethylamino, $-(CH_2)_4-$, $-(CH_2)_3-$, $-(CH_2)_2-$.

The following values for $HSR^8$ are also classified under the carbamimidoyl mercaptans, giving rise to carbamimidoyl embodiments of I; $R^8$ is:

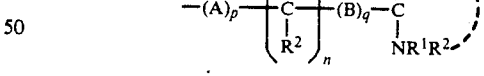

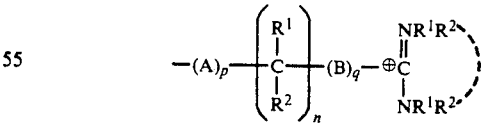

wherein $R^1$, $R^2$ and n are as defined immediately above; p and q are 0 or 1; and A and B are selected from the aforementioned values of $R^8$ expressed in bivalent form (e.g., $-R^8-$) from categories Nos. 1-7; thus, A and B (or $-R^8-$) are selected from: cycloalkyl, alkenyl, cycloalkenyl, alkynyl (see Class No. 1, above); substituted: cycloalkyl, alkenyl, cycloalkenyl, alkynyl (see Class No. 2, above); phenyl and substituted phenyl (see Class No. 3, above); substituted and unsubstituted heteroaryl (see Class No. 4, above); arylaliphatic (see Class No. 5, above); heteroarylaliphatic heterocyclylaliphatic, and heterocyclic (see Class No. 6, above); and alkylheteroatom-alkyl (see Class No. 7, above).
EXAMPLES
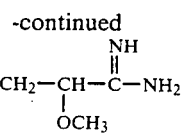
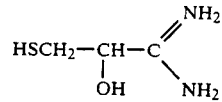
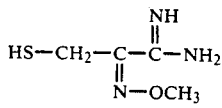
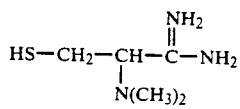
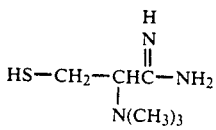
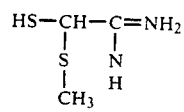
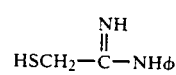
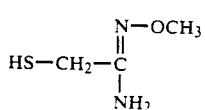
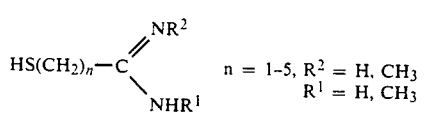
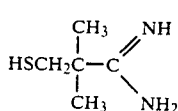
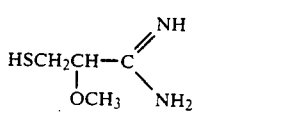
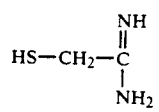
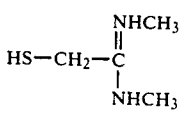
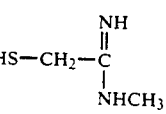
-continued -continued
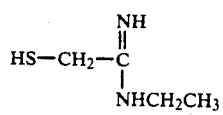
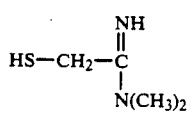
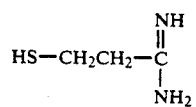
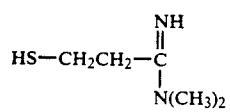
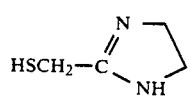
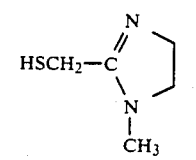
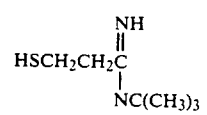
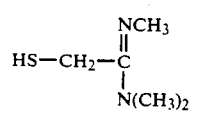
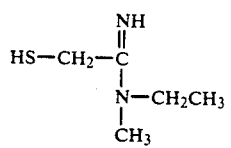
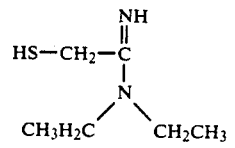
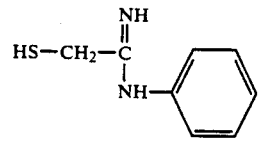
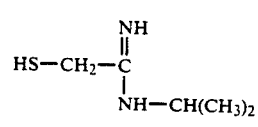
-continued
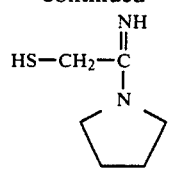
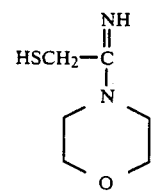
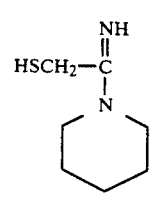
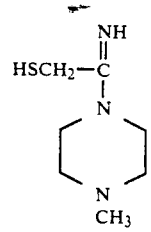
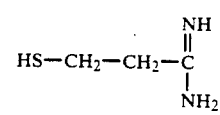
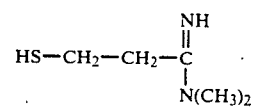
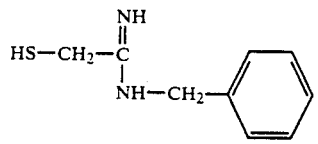
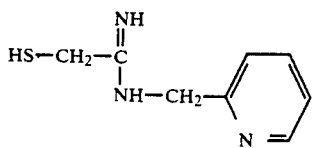
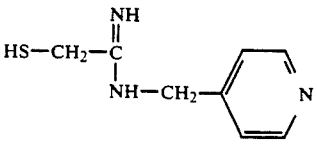
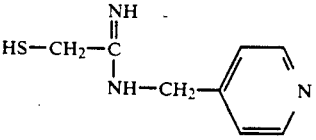

-continued
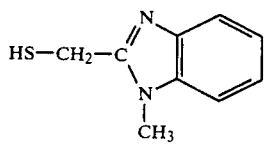
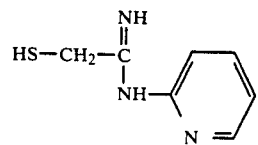
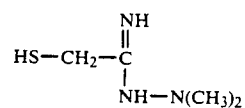
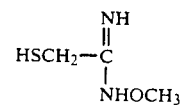
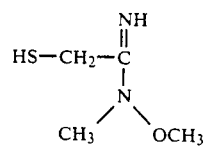
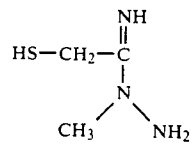
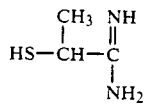
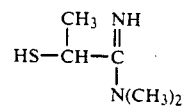
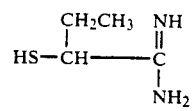
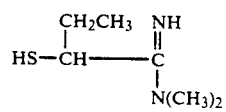
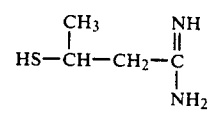
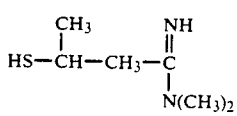
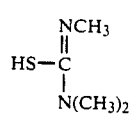
-continued
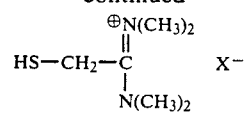
(11) Multiple Iminomethyl Mercaptans $HSR^8$
Wherein $R^8$ is:
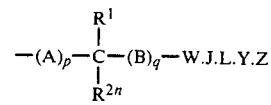
wherein W, J, L, Y and Z are chosen from $-NR^1-$, $NR^1R^2$,
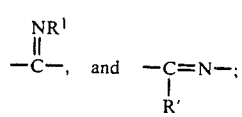
and $R^1$ is as previously initially defined.
Representative combination of radicals W, J, L, Y & Z are:
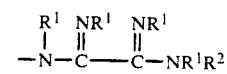
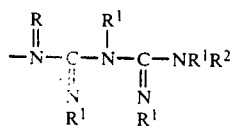
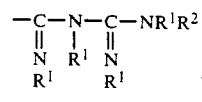
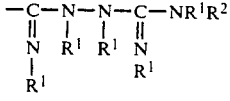
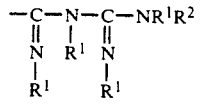
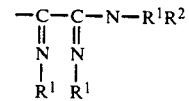
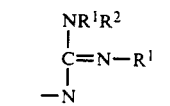
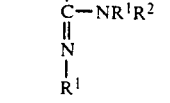

-continued
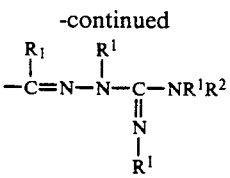
wherein R¹ and R² are as previously defined.
EXAMPLES
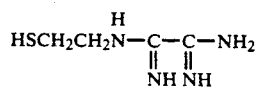
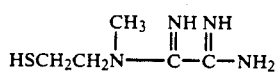
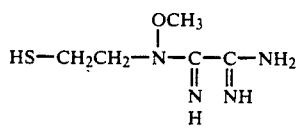
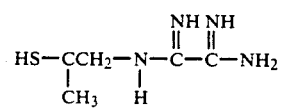
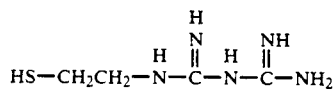
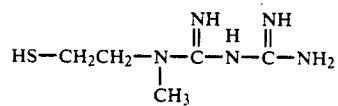
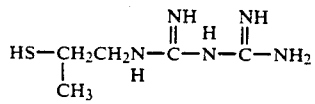
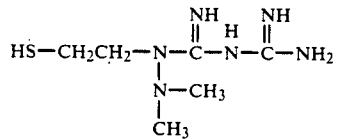
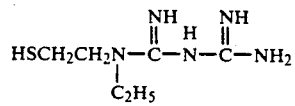
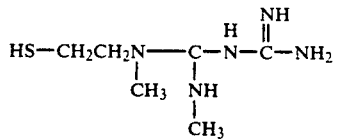
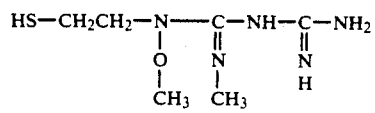
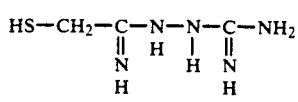
-continued
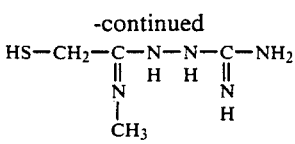
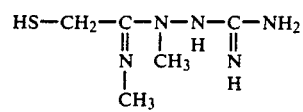
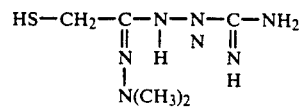
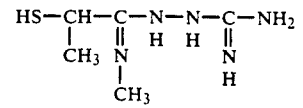
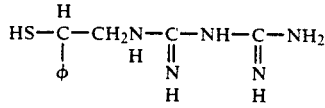
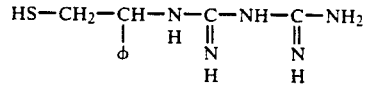
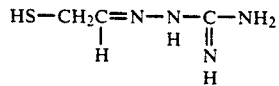
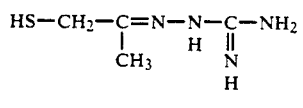
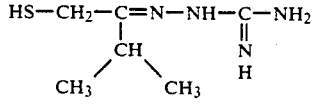
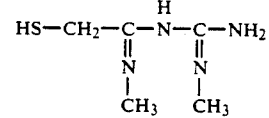
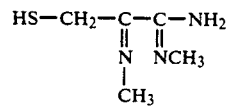
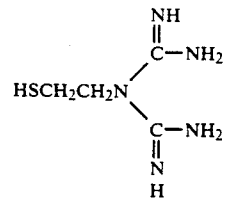
ALKYLATING AND ACYLATING REAGENTS FOR ESTABLISHING $R^6$ and $R^7$
Relative to Diagrams I, II and III, above, the establishment of $R^6$ and $R^7$ by alkylation has been shown (7→8→9, Diagram I; and analogously 24→25→26, Diagram II). There is yet a third scheme for establishing $R^6$ and R[7]. It involves direct acylation followed by reduction. The schemes are conveniently compared below (Diagram IV) and, there following, is a representative list of suitable alkylating and acylating reagents for establishing R[6] and R[7].

DIAGRAM IV
(Scheme I)

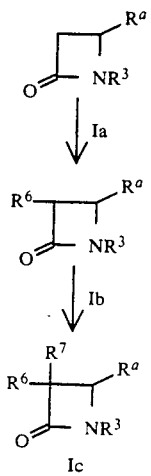

wherein: $R^a$ is $CH_2CH_2OR^2$; $R^3$ and $R^2$ are as defined above;
Diagram I;

$R^a$ is $CH=CH_2$, Diagram II, above;

$R^a$ is $CH_2CH=CH_2$, Diagram III, see previously incorporated by reference U.S. Ser. No. 134,408, filed Mar. 27, 1980;

$R^a$ is $C(SR°)_3$, Diagram III, R° values are selected from alkyl, aryl, and aralkyl; see previously incorporated by reference U.S. Ser. No. 154,190, filed May 29, 1980; and U.S. Ser. No. 134,396, filed Mar. 27, 1980; and $R^a$ is $C(SR°)_2SiR°_3$, Diagram III, R° values are selected from alkyl, aryl and aralkyl; see previously incorporated by reference U.S. Ser. No. 134,397, filed Mar. 27, 1980.

In words relative to the above reaction diagram, and as described above, starting material Ia can be mono-, or dialkylated at ring position 3. Alkylation of Ia provides Ic. Typically, Ia is treated with a strong base such as lithium diisopropylamide, lithium 2,2,6,6-tetramethylpiperidide, potassium hyride, lithium hexamethyldisilazane, phenyllithium or the like in a solvent such as tetrahydrofuran (THF), hexamethylphosphoramide, ether, dimethoxyethane, and the like at a temperature of from −80° C. to 0° C. whereupon the alkylating agent of choice, R[6]X° is added (X° is chloro, iodo or bromo); alternatively the alkylating agent may be R[6]-tosylate, R[6]-mesylate or an aldehyde or ketone such as acetaldehyde to provide monoalkylated species Ib. When desired, dialkylated species Ic may be obtained from Ib by repeating the alkylating procedures Ia→Ib.

The eventual 6-substituents (nomenclature relative to final, bicyclic structure) can also be established by direct acylation using an acylating agent such as N-acyl imidazole or the like. Such N-acyl imidazole acylating reagents are listed below. Also given below is a detailed description of this second approach for establishing, R[6] and R[7].

The following list is representative of useful alkylating agents for establishing R[6] and R[7], according to the above scheme Ia→Ib→Ic (this will be referred to as Scheme I, to be distinguished from Scheme II, below, which involves acylation):

Alkylating Agents
$CH_3CHO$
$\phi CH_2CHO$    $\phi$ = phenyl
$\phi CH_2CH_2CHO$
$CH_2O$
$CH_3I$
$\phi CH_2Br$
$CH_3COCH_3$

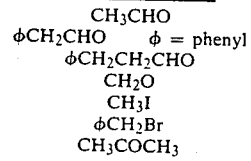

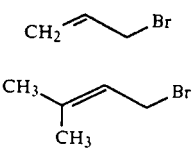

$CH_3OCH_2CHO$
$CH_3CH_2I$
$(CH_3)_2CHI$
$N_3CH_2CHO$
$(CH_3)_2NCH_2CHO$
$RO_2CCH_2Br$    R = $CH_3$, benzyl, p-nitrobenzyl
$CF_3CF_2CHO$
$RO_2CCH_2CHO$    R = $CH_3$, benzyl, p-nitrobenzyl
$CH_3CH(CH_3)CHO$,
$CH_3(CH_3)CHCH_2CHO$,
$CH_3CH_2CHO$,

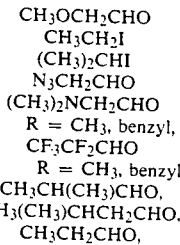

$CF_3CHO$,

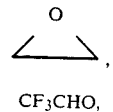

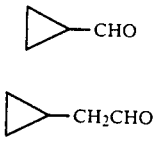

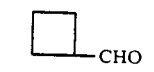

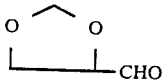

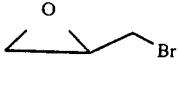

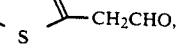

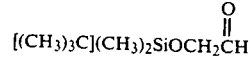

-continued
Alkylating Agents

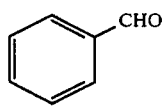

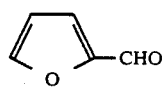

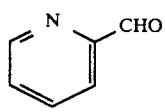

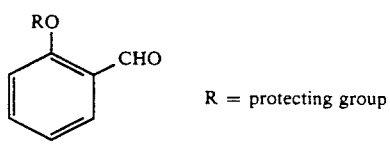

R = protecting group

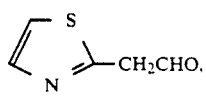

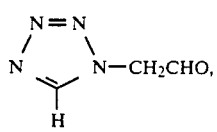

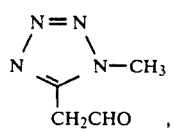

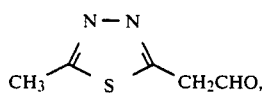

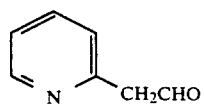

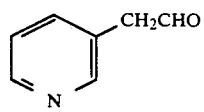

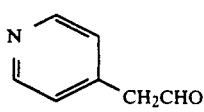

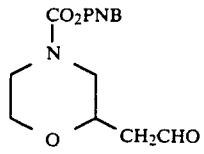

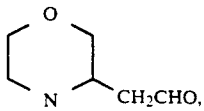

-continued
Alkylating Agents

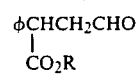

R is removable carboxyl protecting group, such as benzyl.

As mentioned above, the 6-substituents may also be established by acylation. Utilization of such acylating agents may be demonstrated in the following manner with regard to a preferred starting material Ib or Ic:

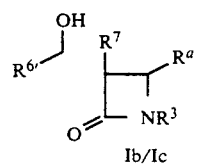

wherein $R^7$, $R^a$ and $R^3$ are as defined above. $R^{6'}$ is defined relative to the definition of $R^6$ and in that sense is the balance of the previously identified group $R^6$. In other words, for purposes of this definition $R^{6'}CH(OH)-=R^6$. An especially preferred material Ib is when $R^7$ is hydrogen and $R^{6'}$ is methyl. Basically, such 1'-hydroxy $R^{6'}$ species Ib are prepared according to the following scheme:

SCHEME II

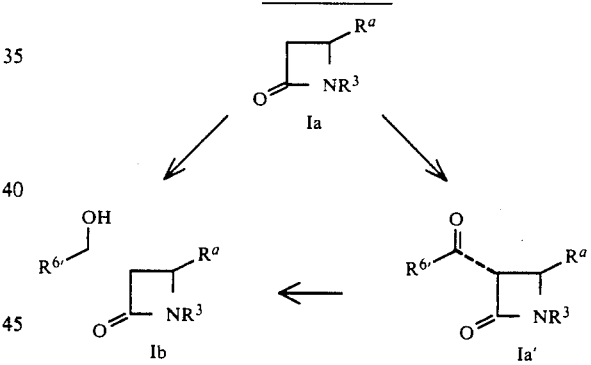

The alkylation Ia→Ib, Scheme II, is accomplished as previously described, by treating Ia in a solvent such as tetrahydrofuran, dimethoxyethane, diethylether, hexamethylphosphoramide, at a temperature of from −100° to 31 20° C. with a strong base such as lithium diisopropylamide, lithium hexamethyldisilazide, lithium 2,2,6,6-tetramethylpiperidide, potassium hydride or the like followed by the addition of an equivalent to 10 fold excess of an aldehyde. This reaction gives a mixture of isomers from which the desired trans-R form Ib can be conveniently separated by chromatography or crystallization.

Intermediate Ia may proceed directly to Ib as indicated above, or it may take the circuitous path via Ia'. The direct acylation, to Ia' is accomplished by treating Ia with two or more equivalents of a base such as lithium diisopropylamide, lithium hexamethyldisilazide, lithium 2,2,6,6-tetramethylpiperidide, in a solvent such as tetrahydrofuran, diethylether, or dimethoxyethane, for example, at a temperature of from −100° to 31 20° C. with an acylating agent such as N-acyl imidazole or the like. Addition of the Ia plus base mixture to the acylating agent is preferred.

Representative acylating agents for this scheme Ia-→Ia'→Ib are listed below.

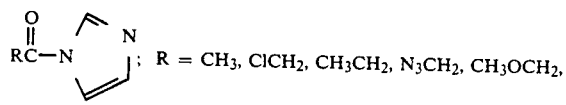

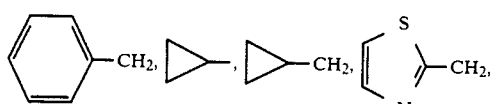

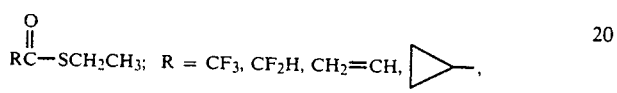

Further with respect to Scheme II, the reduction, Ia'→Ib is accomplished by contacting the ketone with a reducing agent such as potassium tri(sec-butyl)borohydride, lithium tri(sec-butyl)borohydride, sodium borohydride, sodium tris(methoxyethoxy)aluminum hydride, lithium aluminum hydride or the like in a solvent such as diethyether, tetrahydrofuran, toluene, i-propanol or the like at a temperature of from −78° to 25° C. The reaction can conveniently be conducted in the presence of an added complexing salt such as potassium iodide, magnesium bromide or the like.

In a similar manner, unresolved Ib (cis and trans) may be oxidized to Ia' for reduction to Ib as indicated above:

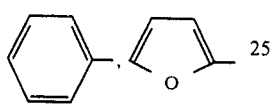

The oxidation is accomplished with an oxidizing agent such as dipyridine chormium (VI) oxide, trifluoroacetic anhydride-dimethylsulfoxide-triethylamine, pyridinium dichromate, acetic anhydride-dimethylsulfoxide in a solvent such as methylene chloride, acetonitrile, or the like at a temperature of from −78° to 25° C. for from 5 minutes to 5 hours.

Finally, relative to 6-substituents $R^6$ and $R^7$, it is to be emphasized that the most preferred class of compounds I is that wherein $R^7$ is hydrogen and $R^6$ is —CH(OH)CH$_3$, and wherein the absolute configuration is 5R, 6S, 6(R 1-hydroxyethyl) about carbon atoms 5 and 6:

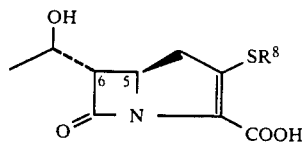

Other preferred values for $R^6$ ($R^7$=H) are: FCH$_2$CH(OH)—, CH$_3$CH$_2$CH(OH)—, CH$_3$CH$_2$—, and (CH$_3$)$_2$C(OH)—.

As noted above, the compounds of the present invention may also generally be represented by the following structural formula:

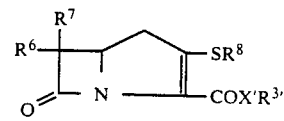

wherein X' is oxygen, sulfur or NR' (R' is hydrogen or loweralkyl having from 1 to 6 carbon atoms); and $R^{3'}$ is hydrogen, or, inter alia, is representatively selected to provide the pharmaceutically acceptable salt, ester, anhydride ($R^{3'}$ is acyl), and amide moieties known in the bicyclic β-lactam antibiotic art; $R^{3'}$ may also be a readily removable blocking group.

Identification of the Radical —COX'R$^{3'}$

In the generic representation of the compounds of the present invention (I, above), the radical represented by —COX'R$^{3'}$ is, inter alia, —COOH (X' is oxygen and $R^{3'}$ is hydrogen) and all radicals known to be effective as pharmaceutically acceptable ester, anhydride ($R^{3'}$ is acyl) and amide radicals in the bicyclic β-lactam antibiotic art, such as the cephalosporins and penicillins and nuclear analogues thereof.

Suitable blocking esters ($R^{3'}$, X=O) include those selected from the following list which is representative:

(i) $R^{3'}$=CR$^a$R$^b$R$^c$ wherein at least one of R$^a$R$^b$ and R$^c$ is an electron-donor, e.g., p-methoxyphenyl. The remaining R$^a$, R$^b$ and R$^c$ groups may be hydrogen or organic substituting groups. Suitable ester groups or this type include p-methoxybenzyloxycarbonyl.

(ii) $R^{3'}$=CR$^a$R$^b$R$^c$ wherein at least one of R$^a$, R$^b$ and R$^c$ is an electron-attracting group, e.g., p-nitrophenyl, trichloromethyl, and o-nitrophenyl. Suitable esters of this type include p-nitrobenzyloxycarbonyl, and 2,2,2-trichloroethoxycarbonyl.

(iii) $R^{3'}$=CR$^a$R$^b$R$^c$ wherein at least two of R$^a$, R$^b$ and R$^c$ are hydrocarbon such as alkyl, e.g., methyl or ethyl, or aryl, e.g., phenyl and the remaining R$^a$, R$^b$ and R$^c$ group, if there is one, is hydrogen. Suitable esters of this type include t-butyloxycarbonyl, diphenylmethoxycarbonyl and triphenylmethoxycarbonyl.

Silyl esters, under this category of blocking groups, may conveniently be prepared from a halosilane of the formula: R$^4$$_3$SiX' wherein X' is a halogen such as chloro or bromo and R$^4$ is alkyl, e.g., methyl, ethyl, t-butyl.

Pharmaceutically acceptable carboxyl derivatives of the present invention are those derived by reacting I with alcohols, acylating reagents and the like. For example, esters and amides of interest are the above-listed starting materials and final products having the —COX'R³' group at the 3-position; wherein X' is oxygen, sulfur or NR' (R' is H or R³'), and R³' is alkyl having 1-6 carbon atoms, straight or branched, such as methyl, ethyl, t-butyl, and the like; carbonylmethyl, including phenacyl; aminoalkyl including 2-methylaminoethyl, 2-diethylaminoethyl; alkanoyloxyalkyl wherein the alkanoyloxy portion is straight or branched and has 1-6 carbon atoms and the alkylportion has 1-6 carbon atoms, such as pivaloyloxymethyl; haloalkyl wherein halo is chloro, and the alkyl portion is straight or branched having 1-6 carbon atoms, e.g., 2,2,2-trichloroethyl; alkenyl having 1-4 carbon atoms such, as 2-propenyl, 3-butenyl, and 4-butenyl; aralkyl and lower alkoxy- and nitro- substituted aralkyl such as benzyl, benzhydryl, o-nitrobenzyl, p-methoxybenzyl, and p-nitrobenzyl; phthalidyl; benzyloxyalkyl having 8-10 carbon atoms such as benzyloxymethyl, and (4-nitro) benzyloxymethyl.

In addition to the esters (and thio esters) listed above, amides are also embraced by the present invention, i.e., wherein X' is the

group. Representative of such amides are those wherein R' is selected from the group consisting of hydrogen and lower alkyl such as methyl and ethyl.

The most preferred —COX'R³' radicals of the present invention are those wherein (relative to Structure I above), X is oxygen and R³' is hydrogen; loweralkyl having 1-4 carbon atoms; lower alkenyl such as 3-methylbutenyl, 4-butenyl and the like; benzyl and substituted benzyl such as p-nitrobenzyl; pivaloyloxymethyl, 3-phthalidyl; and phenacyl.

The compounds of the present invention (I) are valuable atnibiotics active against various gram-positive and gram-negative bacteria and accordingly find utility in human and veterinary medicine. Representative pathogens which are sensitive to antibiotics I include: *Staphylococcus aureus, Escherichia coil, Klebsiella pneumoniae, Bacillus subtilis, Salmonella typhosa Psuedomonas* and *Bacterium proteus.* The antibacterials of the invention are not limited to utility as medicaments; they may be used in all manner of industry, for example: additives to animal feed, preservation of food, disinfectants, and in other industrial systems where control of bacterial growth is desired.

For example, they may be employed in aqueous compositions in concentrations ranging from 0.1 to 100 parts of antibiotic per million parts of solution in order to destroy and inhibit the growth of harmful bacteria on medical and dental equipment and as bactericides in industrial applications, for example in waterbased paints and in the white water or paper mills to inhibit the growth of harmful bacteria.

The products of this invention may be used in any of a variety of pharmaceutical preparations. They may be employed in capsule, powder form, in liquid solution, or in suspension. They may be administered by a variety of means; those of principal interest include: orally, topically or parenterally by injection (intraveneously or intramuscularly).

Such tablets and capsules, designed for oral administration, may be in unit dosage form, and may contain conventional excipients, such as binding agents, for example, syrup, acacia, gelatin, sorbitol, tragacanth, or polyvinylpyrrlidone; fillers, for example, lactose, sugar, cornstarch, calcium phosphate, sorbitol, or glycerine; lubricants, for example, magnesium stearate, talc, polyethylene glycol, silica; disintegrants, for example, potato starch, acceptable wetting agents such as sodium lauryl sulphate. The tablets may be coated according to methods well known in the art. Oral liquid preparations may be in the form of aqueous or oily suspensions, or solutions, or they may be presented as a dry product for reconstitution with water or other suitable vehicle before use. Such liquid preparations may contain conventional additives such as suspending agents, for example, sorbitol, methyl cellulose, glucose/sugar syrup, gelatin, hydroxyethylcellulose, or carboxymethyl cellulose. Suppositories will contain conventional suppository bases, such as cocoa butter-or other glycerides.

Compositions for injection, the preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water.

The compositions may also be prepared in suitable forms for absorption through the mucous membranes of the nose and throat or bronchial tissues and may conveniently take the form of liquid sprays or inhalents, lozenges, or throat paints. For medication of the eyes or ears, the preparations may be presented in liquid or semi-solid form. Topical applications may be formulated in hydrophobic or hydrophilic bases as ointments, creams, lotions, paints, or powders.

The dosage to be administered depends to a large extend upon the condition and size of the subject being treated as well as the route and frequency of administration—the parenteral route by injection being preferred for generalized infections. Such matters, however, are left to the routine discretion of the therapist according to principles of treatment well known in the antibiotic art. In general, a daily dosage consists of from about 5 to about 600 mg of active ingredient per kg. of body weight of the subject in one or more treatments per day. A preferred daily dosage for adult humans lies in the range of from about 10 to 240 mg. of active ingredient per kg. of body weight. Another factor influencing the precise dosage regimen, apart from the nature of the infection and peculiar identity of the individual being treated, is the molecular weight of the chosen species of this invention (I).

The composition for human delivery per unit dosage, whether liquid or solid, may contain from 0.1% to 99% of active material, the preferred range being from about 10-60%. The composition will generally contain from about 15 mg. to about 1500 mg. of the active ingredient;

however, in general, it is preferably to employ a dosage amount in the range of from about 250 mg to 1000 mg. In parenteral administration, the unit dosage is usually the pure compound I in sterile water solution or in the form of a soluble powder intended for solution. For zwitterionic species described under Structure I, the pH of such solutions typically will correspond to the zwitterionic point; however, consideration of individual properties of solubility and stability may require such aqueous solutions to have a pH over than that of the zwitterionic point, for example in the range of 5.5 to 8.2.

In the foregoing word description of the above schematic reaction diagram for the total synthesis of the defined carbapenem antibiotics, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirements for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

Incorporation by Reference

The following paragraphs summarize the previous incorporations.

The compounds of the present invention may also be prepared by the processes disclosed and claimed in the three (3) following, co-pending, commonly assigned, concurrently filed U.S. patent applications of Christensen, Ratcliffe and Salzmann. To the extent that these applications define R⁶, R⁷, and R⁸ of Structure I and to the extent that they described processes for the synthesis of I, they are hereby incorporated by reference.

1. Process for the Preparation of 1-Carbapenems and Intermediates via 4-Allylazetidinone; U.S. patent application Ser. No. 134,408, filed Mar. 27, 1980.
2. Process for the Preparation of 1-Carbapenems and Intermediates via Trithioorthoacetates; U.S. patent application Ser. No. 134,396, filed Mar. 17, 1980.
3. Process for the Preparation of 1-Carbapenems and Intermediates via Silyl-Substituted Dithioacetals; U.S. patent application Ser. No. 134,397, filed Mar. 27, 1980.

Also incorporated is concurrently filed, commonly assigned U.S. patent application Ser. No. 197,865, (filed Oct. 17, 1980) of W. J. Leanza now abandoned.

Also incorporated by reference is Belgian Patent No. 848,545 (which corresponds to co-pending, commonly assigned U.S. Ser. No. 852,425 filed 11-17-77, now U.S. Pat. No. 4,194,047 issued 3-18-80). This patent discloses and claims processes for converting the natural product thienamycin to certain amino derivatives. These "N-derivatives" of thienamycin are not claimed in the instant application. They are:

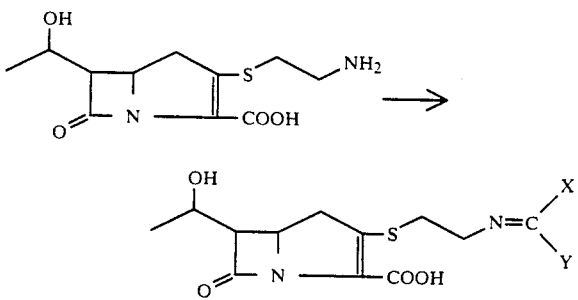

The process disclosed in the cited Belgian Patent is also suitable to prepare preferred, antibiotic embodiments of the present invention (Structure I', see below). The applicability of the process arises from the presence of an amino group on previously defined side chain $-SR^8$ of the compounds of the present invention, Structure I, thus:

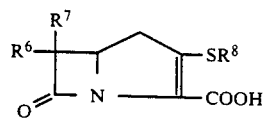

I

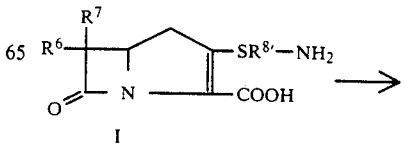

I

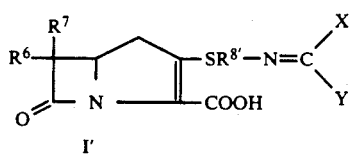

wherein: $-SR^{8'}-NH_2 = -SR^8$; that is, the symbol $-SR^{8'}-NR_2$ indicates, and is specific to $-SR^8$, above-defined, bearing an amino substituent; preferred values for X and Y include: $X=NH_2$; $Y=H$, $CH_3$, $NH_2$.

Thus, to the extent that the Belgian Patent describes the amino derivatization process, the generic definition of X and Y and the preferred, above-indicated, amidine and guanidine embodiments, it is hereby incorporated by reference.

Also incorporated by reference is published European Patent Application No. 0007614 (Application No. 79102615.6, filed 24 July 1979). This application discloses certain dipeptidase inhibitors which, on co-administration to mammalian subjects, enhance the efficacy of certain 1-carbadethiapenem antibiotics. Thus, to the extent that the cited application: (1) defines the manner by which susceptible carbadethiapenems substrates of the present invention may be identified; and (2) discloses suitable inhibitors, compositions, and methods of treatment, it is incorporated herein by reference. A particularly preferred inhibitor is 6-(L-2-Amino-2-carboxyethylthio)-2-(2,2,-DCC)-2-hexenoic acid.

EXAMPLE 1

Preparation of 4-(2-acetoxyvinyl)azetidinone-2-one

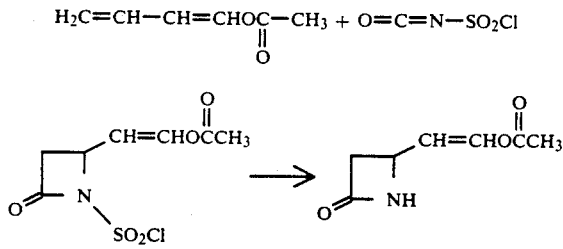

A solution of 1.0 ml distilled chlorosulfonylisocyanate (1.65 g; 11.7 mmoles) in 2.5 ml anhydrous diethyl ether is cooled under $N_2$ in a $-20°$ C. bath.

A solution of 2.5 g 1-acetoxybutadiene (22 mmoles) in 2.5 ml anhydrous ether is similarly cooled under $N_2$ in a $-20°$ C. bath.

The chlorosulfonylisocyanate solution is added dropwise to the acetoybutadiene solution by means of a Teflon tube immersed in the CSI solution and pressurized with $N_2$. The addition takes 10 minutes. Little or no color is seen and the reaction is stirred at $-20°$ C. for 0.5 hour. The solution is clear and has a light yellow color.

A solution of 2 g sodium sulfite and 5 g $K_2HPO_4$ in 20 ml $H_2O$ is prepared during the above 0.5 hour reaction time and is cooled in an ice bath; 20 ml of ether is added and the mixture is vigorously stirred in an ice bath. At the end of the 30 minute reaction time, the reaction mixture is transferred, again using $N_2$ pressure and the Teflon tube, from the reaction flask which is maintained in the $-20°$ C. bath, to the vigorously stirred hydrolysis mixture. Rapid dropwise addition is completed in 5 minutes. The hydrolysis is allowed to continue for 5 additional minutes. The hydrolysis mix has a pH of 6–8, preferably pH 8.

The phases are separated, leaving a yellowish-orange gum with the aqueous phase. The ether phase is dried directly with $MgSO_4$. The aqueous/gum phase is extracted three more times with 50 ml portions of ether, each being added to the initial ether/$MgSO_4$.

The dried extracts are filtered and concentrated under a $N_2$ stream to 5 ml; a portion of the product is crystalline at this stage.

A column of 10 g Baker silica gel, packed in ether is prepared, and the ether concentrate is applied to the top and run in. The flask/solids are rinsed three times with 2 ml ether, each being pipetted off and run into the column. Elution is then begun with ether. The first 25 ml is primarily void volume. The next five 10 ml fractions are collected followed by three 50 ml fractions, and all are reduced in volume under a $N_2$ stream. The product crystallizes from fractions 4–6, with traces in 3 and 7. Fractions 1–3 contain a yellowish sharp-smelling material which resinifies on standing. Yield: 100 mg as a mixture of the cis and trans isomers.

EXAMPLE 2

Preparation of 4- (2-Acetoxyethyl)-2-Azetidinone

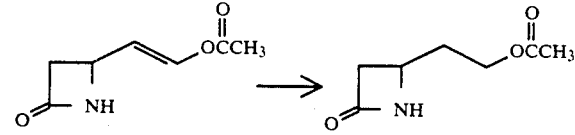

A solution of 4- (2-acetoxyvinyl)-2-azetidinone (10.0 g, 0.065 mole) in 200 ml ethyl acetate containing 100 mg of 10% Pd/C is hydrogenated on a Parr shaker at b 25° C. under 40 psi hydrogen for 15 minutes. The mixture is filtered through a bed of Supercel and washed with additional ethyl acetate. The combined filtrate is evaporated in vacuo to give 4- (2-acetoxyethyl)-2-azetidinone (10.0 g) as a crystalline solid. Recrystallization from ether affords white crystals: M.P. 44°–7°; ir $(CHCl_3)_\mu$ 5.66, 5.74; nmr $(CDCl_3)\tau$ 3.44 (broad s, 1, NH), 5.82 (m, 2, $CH_2OCOCH_3$), 6.29 (m, 1, C-4H), 6.87 (½ AB pattern further split in four by C-4H and NH, 1, $J_{gem}=12.8$ Hz, $J=4.5$ H, $J_{NH}=1.9$ Hz, 7.38 (½ AB pattern further split in four by C-4H and NH, 1, $J_{gem}=12.8$ Hz, $J=2.3$ Hz, $J_{NH}=1.0$ Hz), 7.93 and 8.02 (s, on m, total 5, $OCOCH_3$ and $CH_2CH_2OCOCH_3$, respectively).

EXAMPLE 3

Preparation of 4-(2-Hydroxyethyl)-2-Azetidinone

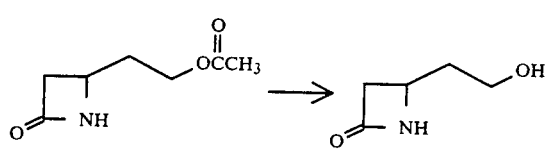

Under nitrogen at 0°, a solution of 4-(2-acetoxyethyl)-2-azetidinone (2.24 g, 0.014 mole) in 25 ml anhydrous methanol is treated with a solution of sodium methoxide (77 mg, 1.4 mmoles) in 5 ml anhydrous methanol. After stirring for 1 hour, the solution is neutralized with glacial acetic acid. Removal of the methanol in vacuo gives crude 4-(2-hydroxyethyl)-2-azetidinone as an oil. The product is purified by chromatography on silica gel eluting with 10% MeOH/CHCl$_3$ to give 1.55 g of the alcohol: m.p. 50°; ir (CHCl$_3$) $\mu$ 5.67; nmr (CDCl$_3$)$\tau$ 3.20 (broad s, 1, NH), 6.214 and 6.28 (m on t, total 3, C-4H and C$\underline{H}_2$OH respectively), 6.90 (broad s on ½ AB pattern further split in four by C-4H and NH, total 2, OH and C-3H respectively, J$_{gem}$=13.0 Hz, J$_{vic}$=4.2 Hz, J$_{NH}$=1.6 Hz), 7.42 (½ AB pattern further split in four by C-4H and NH, 1, C-3H, J$_{gem}$=13.0 HZ, J$_{vic}$=2.2 Hz, J$_{NH}$=1.1 Hz), 8.16 (m, 2, C$\underline{H}_2$CH$_2$OH).

EXAMPLE 4

Preparation of 8-Oxo-2,2-dimethyl-3-oxa-1-azabicyclo[4.2.0]octane

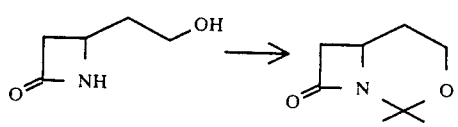

A solution of 4-(2-hydroxyethyl)-2-azetidinone (1.87 g, 0.016 mole) and 2,2-dimethoxypropane (1.69 g, 0.016 mole) in 25 ml anhydrous methylene chloride is treated with boron trifluoride etherate (0.201 ml, 0.002 mole) at 25° C. The resulting solution is stirred for ten minutes. Removal of the solvent under reduced pressure gives an oil (2.5 g). Chromatography of the crude product on silica gel using 2:1 ethyl acetate/benzene as eluting solvent gives 8-oxo-2,2-dimethyl-3-oxa-1-azabicyclo[4.2.0]-octane (1.59 g) as a crystalline solid. Recrystallization from ether/hexane gives product of m.p. 60°-1°.

ir (CHCl$_3$)$\mu$: 5.73 ($\beta$-lactam)

nmr (CDCl$_3$)$\tau$: 6.02-6.28, m, 2H, C-4 methylene 6.22-6.62, m, 1H, C-6 methine 6.90, dd, 1H, J$_{7,7}$=14 Hz, J$_{6,7}$=4.5 Hz C-7 proton cis to C-6H 7.47, dd, 1H, J$_{7,7}$=14 Hz, J$_{6,7}$=2 Hz C-7 proton trans to C-6H 7.82-8.68, m, 2H, C-5 methylene 8.23, s, 3H  
8.57, s, 3H } 0-2 methyls

EXAMPLE 4a

Preparation of 8-oxo-2,2-dimethyl-7α-isopropyl-3-oxa-1-azabicyclo[4.2.0]octane

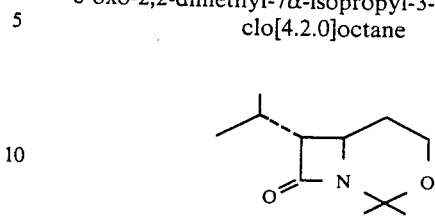

THF, 20 ml is placed under N$_2$, treated with 1.54 ml diisopropylamine and cooled to −78° C. A solution of n-butyl lithium 1.97M in hexane 5.6 ml is added dropwise over 5 min. The reaction mixture is stirred at −78° C. for 10 min. and then treated with 8-oxo-2,2-dimethyl-3-oxa-1-azabicyclo[4.2.0]octane 1.55 g in 15 ml THF added dropwise over 5 min. After another 10 min. hexamethylphosphoramide 1.97 ml is added. The mixture is stirred another 10 min., then treated with 2 ml of isopropyl iodide. The reaction mixture is stirred at −78° C. for 15 min. and allowed to warm to 25° C. and stirred for 15 min. The reaction mixture is diluted with EtOAc, washed once with pH 7 phosphate buffer then dried and evaporated. The residue is chromatographed on silica gel using 25% EtOAc/C$_6$H$_6$ as eluant to give 8-oxo-2,2-dimethyl-7α-isopropyl-3-oxa-1-azabicyclo[4.2.0]-octane. $\mu$ i.r.: 5.7 ($\beta$-lactam).

n.m.r. $\delta$: 0.96 d, 1.06 d

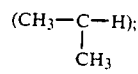

1.4 S 1.76 S (gem dimethyl);
1.9 m (C-5 H); 2.59 d of d (C-7 H); 3.33 m (C-6 H); 3.83 d of d (C-4 H).

EXAMPLE 4b

Preparation of 8-oxo-2,2,7-trimethyl-3-oxa-1-azabicyclo[4.2.0]octane

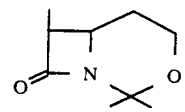

Following the procedure of Example 4a, except substituting an equivalent amount of methyl iodide for the isopropyl iodide, the title compound is obtained.

EXAMPLE 5

Preparation of 8-oxo-2,2,7-trimethyl-7-(hydroxymethyl)-3-oxa-1-azabicyclo[4.2.0]octane

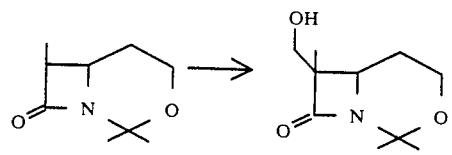

To a solution of 1.1 equivalents of freshly prepared lithium diisopropylamide in anhydrous tetrahydrofuran under a nitrogen atmosphere at −78° is added a solution of 8-oxo-2,2,7-trimethyl-3-oxa-1-azabicyclo-[4.2.0]octane in anhydrous tetrahydrofuran which has been cooled to −78° C. After two minutes, the resulting lithium enolate is treated with excess formaldehyde, introduced as a gas just above the surface of the stirred solution. The solution is stirred for 30 minutes at −78° and then poured into water. The aqueous phase is saturated with sodium chloride and extracted with ethyl acetate. The combined ethyl acetate solutions are dried over magnesium sulfate and filtered. The filtrate is evaporated under reduced pressure to give the crude product. Purification by chromatography on silica gel using ethyl acetate/benzene gives 8-oxo-2,2,7-trimethyl-7-(hydroxymethyl)-3-oxa-1-azabicyclo[4.2.0]octane.

EXAMPLE 6

Preparation of
8-oxo-2,2,7-trimethyl-7-(p-nitrobenzyl-carbonyldioxymethyl)-3-oxa-1-azabicyclo[4.2.0]octane

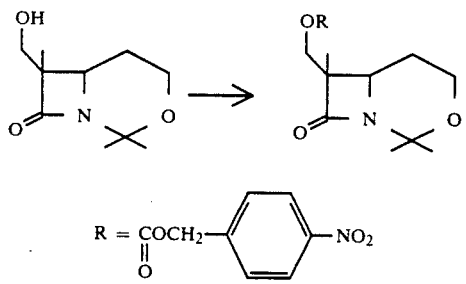

Under anhydrous conditions at 0° C. a solution of 8-oxo-2,2,7-trimethyl-7-(hydroxymethyl)-3-oxa-1-azabicyclo[4.2.0]octane (60 mg., 0.302 mmole) in 0.6 ml ether is treated with powdered potassium hydroxide (19 mg, 0.332 mmole). After a period of 15 minutes, p-nitrobenzyl chloroformate (65 mg, 0.302 mmole) is added to the reaction mixture. Stirring is continued at 25° C. for an additional 15 hours. The mixture is partitioned between 1M pH 7 phosphate buffer and more ether. The ether phase is washed with water and brine, dried over magnesium sulfate and filtered. Evaporation of the filtrate under reduced pressure gives 67 mg of a colorless oil. Purification by preparative thick-layer chromatography on silica gel developing with 1:9 ethyl acetate/benzene gives 8-oxo-2,2,7-trimethyl-7-(p-nitrobenzylcarbonyldioxymethyl)-3-oxa-1-azabicyclo[4.2.0]octane (40 mg) as a mixture of diastereomers.

EXAMPLE 7

Preparation of
3-methyl-3-(p-nitrobenzylcarbonyldioxymethyl)-4-(2-hydoxyethyl)-2-azetidinone

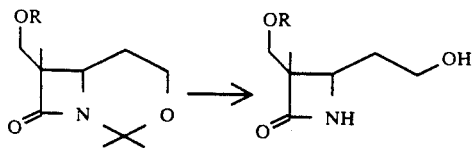

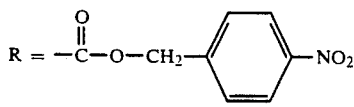

8-Oxo-3-oxa-2,2,7-trimethyl-7-(1-p-nitrobenzylcarbonyldioxymethyl)-1-azabicyclo[4.2.0]octane (1.0 g) is dissolved in 8 ml acetic acid and 2 ml water and heated at 65° C. for 1.25 hours. The acetic acid and water are removed under reduced pressure and the residue is taken up in benzene and evaporated to give 3-methyl-3-(p-nitrobenzylcarbonyldioxymethyl)-4-(2-hydroxyethyl)-2-azetidinone as a mixture of diastereoisomers.

EXAMPLE 8-11

Examples 8, 9, 10 and 11 as alternative to Examples 4, 5, 6 and 7 for the preparation of 3-methyl-3-(p-nitrobenzylcarbonyldioxymethyl)-4-(2-hydroxyethyl)-2-azetidinone

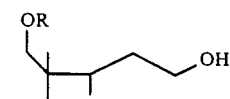

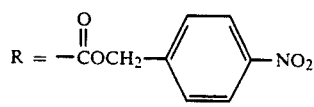

EXAMPLE 8

Preparation of
1-(2-Tetrahydropyranyl)-4-[2-(2-tetrahydropyranyl)oxyethyl]-2-azetidinone

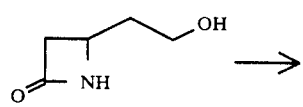

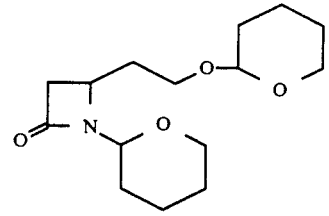

Under nitrogen and at 25° C., a solution of 4-(2-hydroxyethyl)-2-azetidinone (62 mg, 0.539 mmole) in 0.5 ml of anhydrous p-dioxane is treated with 2,3-dihydropyran (0.98 ml, 1.08 mmoles) and p-toluene sulfonic acid monohydrate (19 mg, 0.10 mmole). The resulting solution is stirred for a period of 60 minutes and then partitioned between 10 ml of 0.5M pH 7 phosphate buffer and 10 ml of ethyl acetate. The aqueous phase is extracted a second time with ethyl acetate. The combined ethyl acetate solutions are washed with brine, dried over magnesium sulfate and filtered. The filtrate is evaporated under reduced pressure to give 216 mg of crude product. Purification by preparative thick-layer chromatography developing with ethyl acetate gives 80 mg of 1-(2-tetrahydropyranyl)-4-[2-(2-tetrahydropyranyl)oxyethyl]-2-azetidinone as an oil.

nmr (CDCl₃)τ: 5.13–5.60, m, OCH₂ 5.83–6.85, m, C-4H+OCH₂

6.95, dd, J = 5Hz and 15Hz
7.35, dd, J = 3Hz and 15 Hz  } β-3 methylene 7.62–8.95, m, CHC̲H₂C̲H₂C̲H₂CH₂+CHC̲H₂CH₂O The corresponding 3-methyl-1-(2-tetrahydropyranyl)4-[2-(2-tetrahydropyranyl)oxyethyl]-2-azetidinone is obtained from the product of Example 4a via Examples 7.

EXAMPLE 9

Preparation of 1-(2-tetrahydropyranyl)-3-methyl-3-(1-hydroxymethyl)-4-[2-(2-tetrahydropyranyl)oxyethyl]2-azetidinone

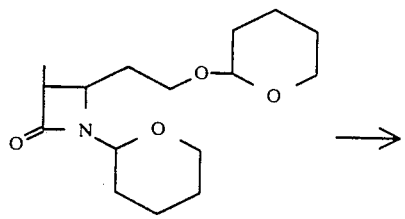

Following the procedure described for the preparation of 8-oxo-2,2,7-trimethyl-7-(hydroxymethyl)-3-oxa-1-azabicyclo[4.2.0]octane from 8-oxo-2,2,7-trimethyl-3-oxa-1-azabicyclo[4.2.0]octane (Example 5, above) and using 3-methyl-1-(2-tetrahydropyranyl)-4-[2-(2-tetrahydropyranyl)-oxyethyl]-2-azetidinone one obtains a diastereomeric mixture of 1-(2-tetrahydropyranyl)-3-methyl-3-(hydroxymethyl)-4-[2-(2-tetrahydropyranyl) oxyethyl]-2-azetidinone.

EXAMPLE 10

Preparation of 3-Methyl-1-(2-tetrahydropyranyl)-3-(1-p-nitrobenzylcarbonyldioxymethyl)-4-[2-(2-tetrahydropyranyl)oxyethyl]-2-azetidinone

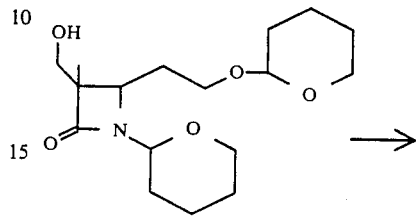

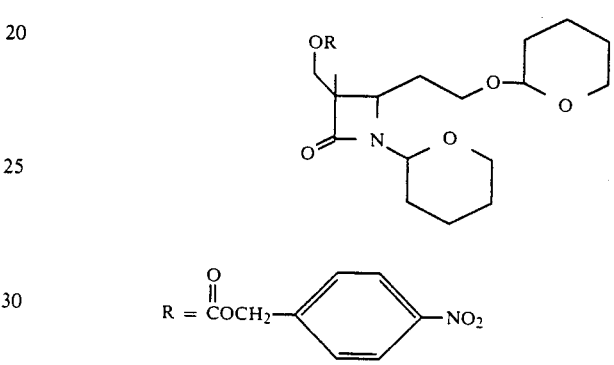

Following the procedure described for the preparation of 8-oxo-2,2,7-trimethyl-7-(1-p-nitrobenzylcarbonyldioxymethyl)-3-oxa-1-azabicyclo[4.2.0]octane from 8-oxo-2,2,7-trimethyl-7-(1-hydroxymethyl)-3-oxa-1-azabicyclo[4.2.0]octane and using 3-methyl-1-(2-tetrahydropyranyl)-3-(hydroxymethyl)-4-[2-(2-tetrahydropyranyl) oxyethyl]-2-azetidinone there is obtained 3-methyl-1-(2-tetrahydropyranyl)-3-(p-nitrobenzylcarbonyldioxymethyl)-4-([2-(2-tetrahydropyranyl)-oxyethyl]-2-azetidinone.

EXAMPLE 11

Preparation of 3-Methyl-3-(p-nitrobenzylcarbonyldioxyethyl)-4-(2-hydroxyethyl)-2-azetidinone

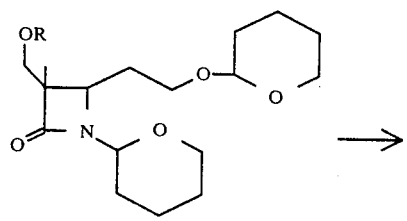

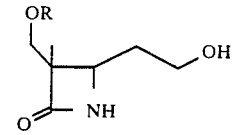

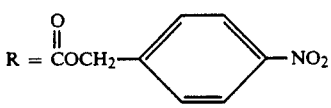

A solution of 3-methyl-1-(2-tetrahydropyranyl)-3-(p-nitrobenzylcarbonyldioxymethyl)-4-[2-(2-tetrahydropyranyl)-oxyethyl]-2-azetidinone in methanol at 25° C. is treated with 0.1 molar equivalent of p-toluenesulfonic acid monohydrate. The solution is stirred for a period of 2 hours and then neutralized with 1M pH 7 phosphate buffer. The product is extracted into ethyl acetate. The ethyl acetate solution is washed with brine, dried over magnesium sulfate and filtered. The filtrate is evaporated under reduced pressure to give 3-methyl-3-(p-nitrobenzylcarbonyldioxymethyl)-4-(2-hydroxyethyl)-2-azetidinone.

EXAMPLE 12

Preparation of 3-(2-aminoethylthio)-6-methyl-6-(hydroxymethyl)-7-oxo-1-azabicyclo[3.2.0]hept-2-ene-2-carboxylic acid

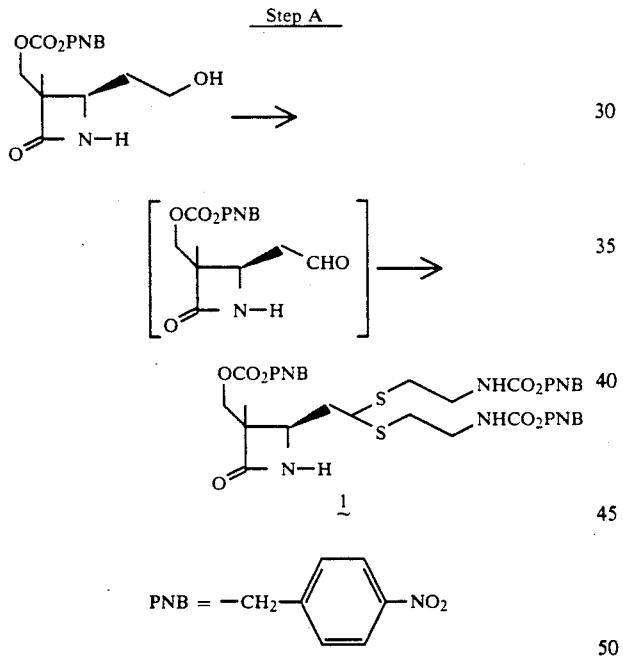

To 6.75 ml anhydrous pyridine (mw=79; ρ=0.982; 83.9 mmole) in 350 ml anhydrous acetonitrile is added 4.05 g anhydrous powdered chromium trixoide (mw=100; 40.5 mmole). After stirring at room temperature (25° C.) for 30 minutes, 9.6 g dried Supercell is added and stirring is continued for 5 additional minutes. A solution of 3.21 g 3-methyl-3-(p-nitrobenzylcarbonyldioxymethyl)-4-(2-hydroxyethyl)-2-azetidinone (mw=338, 9.5 mmole) in 30 ml anhydrous acetonitrile is added all at once. The reaction mixture is stirred under anhydrous conditions at room temperature (25° C.) for one hour. Addition of 9.6 g NaHSO₃ is followed by 5 minutes of stirring after which the reaction mixture is filtered through a mixed packed bed of 40 g silica gel and 40 g anhydrous magnesium sulfate. The bed is washed repeatedly with acetonitrile (total volume of filtrate ~600 ml). The filtrate is concentrated under a N₂ stream to 130 ml total volume. To this solution containing crude aldehyde at 0° C. under N₂ is added 9.64 g p-nitrobenzyloxycarbonylaminoethanethiol (mw=256; 37.7 mmole) as prepared below (Example 12, Step B). To the stirred reaction mixture is added 8.0 ml boron trifluoride etherate (mw=142; ρ=1.125; 63.4 mmole). After 1.5 hours at 0° C., the reaction mixture is poured into a stirred ice-cold mixture of 69 g K₂HPO₄ - 500 ml H₂O and 700 ml ethyl acetate (EA). The layers are separated, and the aqueous one is saturated with NaCl and re-extracted with additional EA. The combined organic layers are washed twice with brine, dried over anhydrous MgSO₄ and filtered. The filtrate is concentrated under a N₂ stream and then pumped on high vacuum to give crude 1.

The material is chromatographed on 450 g silica gel (column height=48 cm; diameter=5.5 cm) packed and applied in CHCl₃ and eluted with increasing percentages of MeOH in CHCl₃ (0-4% MeOH/CHCl₃). Those fractions containing the desired product are combined, concentrated under a N₂ stream; and pumped on high vacuum to give 1.

Step B

Preparation of p-Nitrobenzyloxycarbonylaminoethanethiol

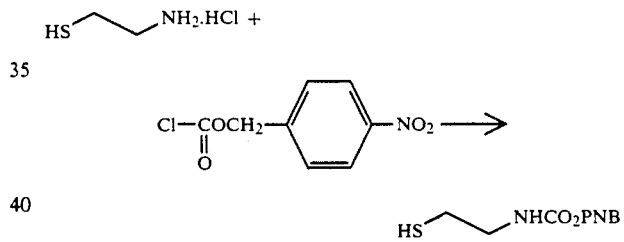

To 600 ml diethyl ether (Et₂O)—75 ml H₂O in an ice bath with stirring is added 3.2 g cysteamine hydrochloride (mw=114; 28.1 mmole). A solution of 7.14 g NaHCO₃ (mw=84; 85 mmole) in 75 ml H₂O is added. The ice bath is removed, and at room temperature a solution of 6.75 g p-nitrobenzylchloroformate (mw=216; 31.3 mmole) in 270 ml Et₂O is added dropwise over a period of one hour. After 10 additional minutes, the layers are separated. The ether layer is extracted with 150 ml 0.25N HCl, and then with 200 ml brine. Each aqueous layer is then backwashed successively with 100 ml Et₂O. The combined Et₂O layers are dried over anhydrous MgSO₄, filtered, and concentrated under a N₂ stream. The crystalline residue is slurried in a small amount of ether, filtered, and the pale yellow crystals are dried under high vacuum to give 4.7 g p-nitrobenzyloxycarbonylaminoethanethiol (65% yield).

NMR (CDCl₃) 8.18 (d, J=8 Hz, aromatic protons ortho to nitro), 7.47 (d, J=8 Hz, aromatic protons meta to nitro), 5.27 (—NH—), 5.20 (s, —CH₂—φ-pNO₂), 3.40 (m, —CH₂—NH—), 2.67 (m, —CH₂—SH), 1.35 (t, J=8.5 Hz, —SH) in ppm downfield from TMS.

IR (CHCl₃ solution) carbonyl—~1725 cm⁻¹

M.S. - molecular ion-256, (M-47) at 209, (M-136) at 120, +CH₂φpNO₂ at 136.

STEP C

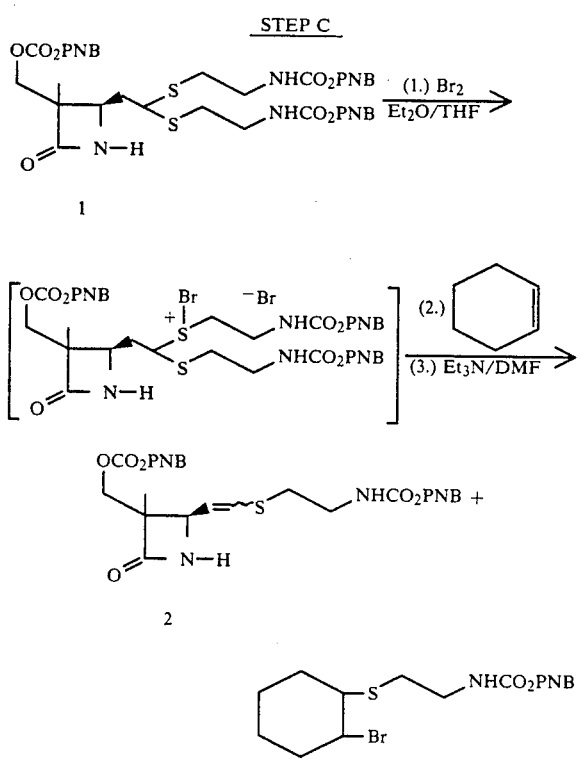

To 14.2 pentane (dried over 4A Linde molecular sieves) is added 0.5 ml Br₂ (mw=160; 9.75 mmole). To 5 g of 1 (mw=830; 6.02 mmole) in 58 ml tetrahydrofuran (THF) (freshly distilled from lithium aluminum hydride) (LAH) and 65 ml Et₂O (dried over 3A 1/16" Linde molecular sieves) at 0° C. under N₂ with stirring is added dropwise 10 ml of the above 0.66M Br₂ solution (6.6 mmole). After 10 minutes at 0° C., 0.67 ml cyclohexene (mw=82; ρ=0.81; 6.6 mmole) is added. After 5 minutes at 0° C., 1.7 ml triethylamine (mw=101; ρ=0.729; 12.3 mmole) is added immediately followed by 40 ml ice-cold dimethylformamide (DMF) (distilled from anhydrous CaSO₄ at 40 mm and stored over 4 A Linde molecular sieves). The ice bath is removed, and stirring is continued for 2¼ hours at room temperature. The reaction mixture is poured into a stirred ice-cold mixture of 12.6 ml 1MKH₂PO₄ 160 ml H₂O—500 ml (EA). After separation of the layers, the aqueous one is saturated with sodium chloride and re-extracted with EA. The combined organic layers are extracted once with brine, dried over anhydrous MgSO₄, filtered and concentrated under a N₂ stream followed by pumping under high vacuum to provide crude 2.

The material is chromotographed on 250 g silica gel (height=45 cm; diameter=4.5 cm) packed and applied in CHCl₃ and eluted with increasing percentages of MeOH in CHCl₃ (0-3% MeOH/CHCl₃). Those fractions containing clean product are combined, concentrated under a N₂ stream, and pumped on high vacuum to give 2. Contaminated fractions are rechromatographed on silica gel using increasing percentages of EA in CHCl₃ (0-25% EA/CHCl₃) to give additional 2.

STEP D

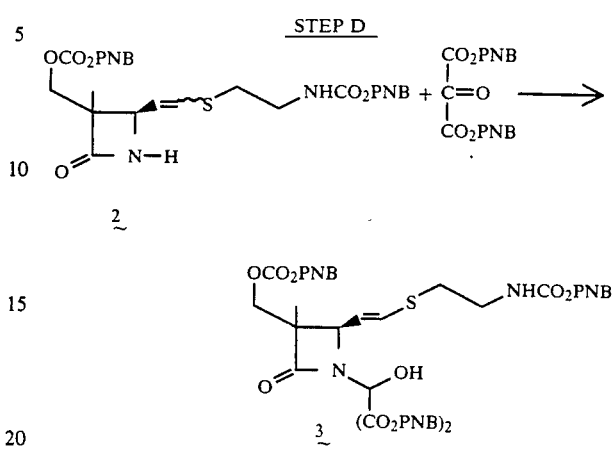

To a stirred solution of 2.48 g di(p-nitrobenzyl) ketomalonate (from Example 12, Step E) (mw=388; 6.39 mmole) in 400 ml hot anhydrous toluene is added a solution of 2.52 g of 2 (mw=574; 4.39 mmole) in 20 ml THF (distilled from LAH) and 40 ml anhydrous toluene. After some of the solvent is boiled off, additional anhydrous toluene is added, and the azeodrying process is repeated three times. The solution is then refluxed under N₂ for 30 minutes. Additional toluene is then allowed to boil off yet the volume is not allowed to diminish so much that precipitation occurs. Total heating time is approximately 2½ hours. The clear yellow reaction mixture is removed from the oil bath and placed under a stream of N₂ which instantaneously causes clouding. After concentration to a yellow oil, the residue is dissolved in CH₂Cl₂, dried over anhydrous MgSO₄, filtered, and concentrated under a N₂ stream to give crude 3.

The material is chromatographed on 250 g silica gel packed and applied in CHCl₃ (height=43 cm; diameter=4.5 cm). Elution with 500 ml 0.5% MeOH/CHCl₃ is followed by continued elution with 1% MeOH/CHCl₃ for the remainder of the chromatography. After the emergence of excess reagent, those fractions containing pure 3 are combined, concentrated under a N₂ stream and then on high vacuum to give 3.

Later fractions containing 3 and the corresponding cis thioenol ether are re-chromatographed on silica gel to give additional 3.

Step E

Preparation of di-p-Nitrobenzyl Ketomalonate

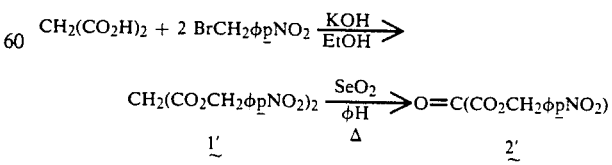

φH = benzene

A mixture of 100 g p-nitrobenzyl bromide (0.46 mole), 28.6 g malonic acid (0.275 mole) and 750 ml ethanol (EtOH) is stirred and warmed on the steam bath until solution is achieved. A solution of 33 g KOH (>85% purity; ~0.6 mole) in 200 ml of water is added carefully with swirling. An additional 200 ml of water is added, and the two-phase system is refluxed for 1.8 hours. The lighter color homogeneous solution is cooled in ice for 1 hour and the crude produce isolated by filtration, washed twice with a minimum of cold EtOH, and dried by pulling dry $N_2$ through the cake; 33.7 g of solid is obtained. If, during the refluxing stage the reaction mixture is slowly concentrating to ca. half volume by allowing refluxing solvent to distill off, the crude product yield rises to 77 g. The material is recrystallized from methanol to give pure di-p-nitrobenzyl malonate 1'.

A mixture of 23.4 of 1', 10 g $SeO_2$, and 30–40 ml of xylene is stirred in a flask immersed in an oil bath. The bath temperature is raised over 1 hour to 130°–135°. A gradual darkening of the reaction mixture is noted, and after a total of 4 hours at 130°–135°, most of the insoluble residue is black Se°. The mixture is cooled, $MgSO_4$ is added to remove the water, and Celite is added to aid in filtration. The mixture is filtered through Celite and the cake washed with xylene and a small portion of EtOAc. Final volume: 60 ml. A 100 g column of Baker Silica Gel is prepared in benzene and 10 of filtrate applied, then eluted with increasing amounts of EtOAc in benzene, 500 ml fractions being collected. After one 2% ethyl acetate (EtOAc)/$\phi$H, and two 10% EtOAc/$\phi$H fractions, the third 10% and first 20% EtOAc/$\phi$H provide the bulk of the product (~1.6 g from 10 ml filtrate) as judged by tlc (20% EtOAc/$CHCl_3$; silica gel GF). Recrystallization from benzene, (1 g in ca. 50 ml concentrated to ~⅓ volume and "spiked" with 1 ml of $H_2O$ saturated benzene): provides 0.24 g 2'; mp (117) 121°–122°.

centrated under a $N_2$ stream, and dried further under high vacuum just prior to the following reaction. To a solution of 3 in 24 ml THF (freshly distilled from LAH) at −20° C. is added 0.206 ml anhydrous pyridine (mw=79; $\rho$=0.982; 2.56 mmole). With stirring under $N_2$, 294 mg of freshly distilled thionyl chloride (mw=119; 2.47 mmole) in 5 ml THF is added dropwise. The reaction mixture is stirred for 10 minutes at −20° C., then ½ hour at 0° C. and finally 1 hour at 25° C. The pyridine hydrochloride is filtered under $N_2$ and washed with 20 ml THF. The filtrate is concentrated under a $N_2$ stream followed by pumping on high vacuum. The resulting yellow foam is swirled in 25 ml anhydrous THF, and a small amount of orange-red insoluble material is filtered off under $N_2$. The filtrate is reconcentrated as above to a yellow foam.

To this freshly prepared chloro compound is added with stirring a freshly shaken suspension of 678 mg tributylphosphine (mw=202; 3.36 mmole) in 36.5 ml 9:1 DMF—$H_2O$ followed by 294 mg $K_2HPO_4$ (mw=174; 1.69 mmole). The reaction mixture is stirred at 25° C., for 35 minutes. After dilution with 120 ml EA and 60 ml brine, the layers are separated, and the aqueous one is extracted two times with EA. The combined organic layers are washed one time with brine, dried over anhydrous $MgSO_4$, filtered and concentrated under a $N_2$ stream followed by pumping on high vacuum to give crude 4.

The material is chromatographed on 100 g silica gel (height=28.5 cm; d=4 cm) packed and applied in $CHCl_3$ and eluted with 0.5% MeOH in $CHCl_3$. Those fractions containing clean product are combined, concentrated under a $N_2$ stream and then on high vacuum to give 4. Contaminated fractions are re-chromatographed on silica gel thin layer plates (eluant=50% acetone/hexane; extraction of desired u.v. band with $CHCl_3$ and EA to provide additional 4.

STEP F

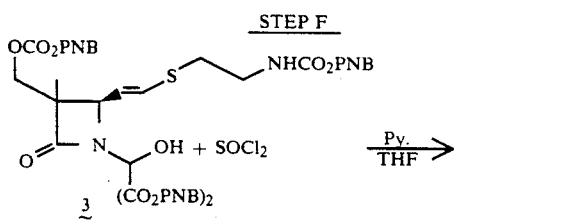

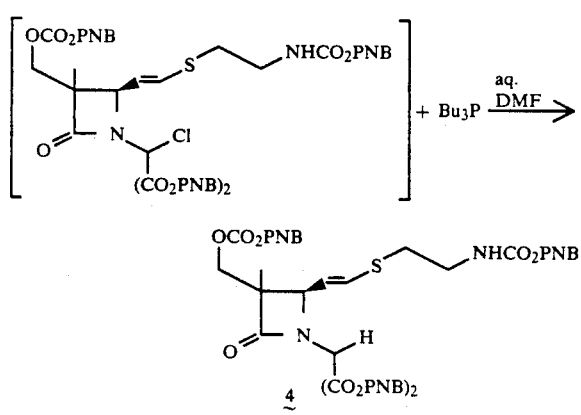

A solution of 1.468 g of 3 (mw=962; 1.53 mmole) in $CH_2Cl_2$ is dried over anhydrous $MgSO_4$, filtered, con- Step G

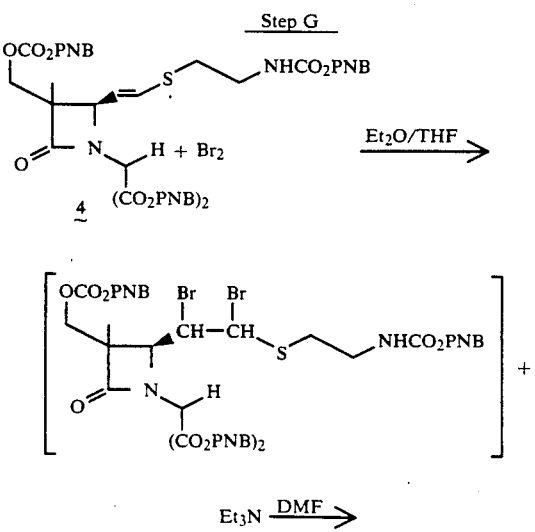

-continued

Step G

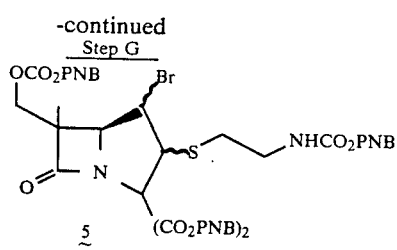

To 8.5 ml pentane (dried over 4A Linde molecular sieves) is added 0.2 ml Br₂ (mw=160; 3.9 mmole). To 0.706 g of 4 (mw=946; 0.746 mmole) in 18 ml THF (freshly distilled from LAH) and 5.7 ml Et₂O (dried over 3A 1/16" Linde molecular sieves) at 0° C. under N₂ with stirring is added dropwise 1.8 ml of the above 0.45M Br₂ solution (0.81 mmole). After 15 minutes at 0° C., 0.42 ml triethyl amine (mw=101; ρ=0.729; 3.03 mmole) is added immediately followed by 10.5 ml ice-cold DMF (distilled from CaSO₄ at 40 mm and stored over 4A Linde molecular sieves). The ice-bath is removed, and stirring at room temperature is continued for 2 hours. The reaction mixture is poured into a stirred ice-cold mixture of 3.1 ml 1M KH₂PO₄—70 ml H₂O—100 ml EA. The layers are separated, and the aqueous one is saturated with NaCl and re-extracted with EA. The combined organic layers are washed once with brine, dried over anhydrous MgSO₄, and filtered. The filtrate is concentrated under a N₂ stream and then pumped on high vacuum to give crude 5.

The material is chromatographed on 60 g silica gel (diameter=2.8 cm) packed and applied in CHCl₃ and is eluted with 100 ml-2% EA/CHCl₃; 100 ml-4% Ea/CHCl₃ and then 5% EA/CHCl₃ for the remainder of the chromatography. The fractions containing pure 5 are combined, concentrated under a N₂ stream, and pumped on high vacuum to give 5.

Step H

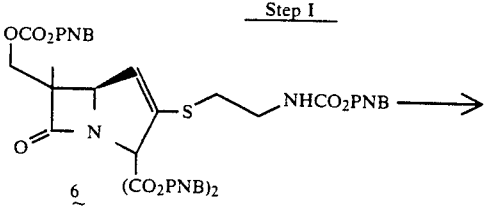

To 29 mg anhydrous silver fluoride (mw=127; 0.23 mmole) is added a solution of 146 mg of 5 (mw=1024; 0.14 mmole) in 3.5 ml anhydrous pyridine. The stoppered reaction mixture is stirred at room temperature in the dark for one hour and then poured into 20 ml cold water—30 ml EA. After separation of the layers, the aqueous one is extracted two times with EA and one time with CHCl₃. Each organic layer is extracted one time with H₂O and one time with brine. The combined organic layers are dried over anhydrous MgSO₄, filtered, and concentrated under a N₂ stream followed by pumping on high vacuum to give crude 6.

Preparative thin layer chromatography (eluant=40% acetone/hexane; repeated extraction of desired u.v. band with a large volume of CHCl₃) yields slightly contaminated 6. Re-chromatographing on silica using EA in CHCl₃ as an eluting system gives 6.

Step I

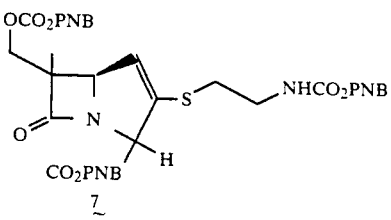

A solution of 77 mg of 6 (mw=944; 0.082 mmole) in 0.9 ml S-collidine (distilled from powdered KOH~30 mm pressure) is added to 13.4 mg anhydrous LiI (dried for few hours at 100° C. over P₂O₅ under vacuum) (mw=134; 0.1 mmole). With stirring under N₂, the reaction mixture is heated in an oil bath at 120° C. After a total of 30 minutes, the reaction mixture is cooled to 25° C., diluted with CH₂Cl₂, and transferred to a round bottom flask for concentration under a N₂ stream and then on high vacuum. Partitioning the residue between EA-H₂O and 1 ml 1M KH₂PO₄ is followed by extraction of the aqueous layer two additional times with EA and one time with CHCl₃. Each organic layer is then backwashed with brine. The combined organic layers are dried over anhydrous MgSO₄, filtered, concentrated under a N₂ stream and then on high vacuum to give crude 7.

Preparative thin layer chromatography on silica gel (plate is eluted two times with 40% acetone/hexane; repeated extraction of the appropriate u.v. bands with large volume of CHCl₃) yields recovered starting material and 7.

Step J

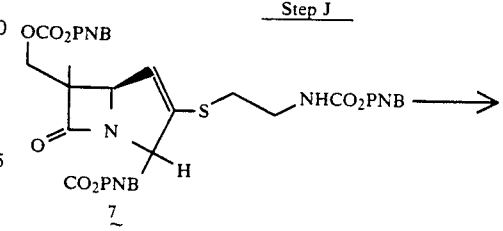

-continued
Step J

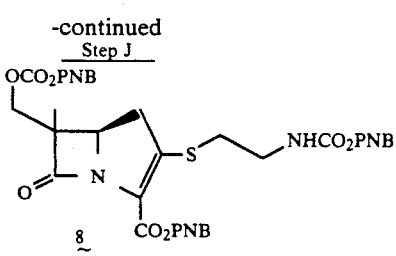

To 49 mg of 7 (mw=765; 0.064 mmole) in 0.7 ml DMSO (distilled from CaH$_2$ at 8 mm and stored over 4A Linde molecular sieves) is added 100 μl diisopropylamine (distilled from NaH under N$_2$ and stored over 4A Linde molecular sieves) (mw=101; ρ=0.722; 0.71 mmole). The stoppered reaction mixture is stirred for a few minutes and then allowed to stand for 2 hours. The amine and most of the DMSO are then concentrated off under high vacuum with no external heating. The residue is passed quickly through a column of silica gel (packed, applied, and eluted with EA) to remove residual DMSO. After concentration under a N$_2$ stream of all fractions having u.v. absorbance, the material is chromatographed on a thin layer silica gel plate (eluant=50% EA/CHCl$_3$; repeated extraction of desired u.v. bands with a large volume of chloroform. Recovered starting material is re-submitted to the reaction conditions and isolation procedure two more times to yield additional 8.

Step K

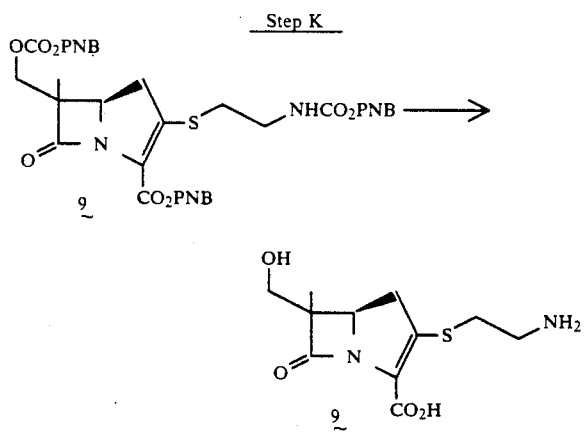

To 5.2 mg 8 is added 0.60 ml dioxane, 0.05 ml ethanol, 0.35 ml deionized water and 0.01 ml of 1.0M K$_2$HPO$_4$. To the resultant clear solution is added 5 mg of 10% Pd/C. The suspension is flushed with N$_2$, then 5–6 times alternately with 50 psi H$_2$ and vacuum. Finally, it is shaken under a 50 psi H$_2$ atmosphere for 30–40 min. After centrifugation, the Pd/C is washed and centrifuged 2–3× with 0.5 ml portions of deionized water. The combined centrifugates are extracted 5×1–2 ml ether. Residual ether is removed under vacuum and the aqueous solution applied to an XAD-2 column (20×140 mm). Fractions of 100 drops (6–7 ml) are collected, with continuous UV monitoring, by elution with deionized water. Emergence of strongly UV absorbing material begins around fractions 3–5 and is usually complete by fractions 25–30. Early fractions are examined by UV to exclude those few deemed too strongly absorbing in the 270–280 mμ region. The remaining fractions are combined and lyophilized. The residue is evaluated by dissolving in 10.0 ml of deionized water and measuring the UV absorption at 298 mμ indicating a 10–30% yield of desired product.

The following Example specifically illustrates a preferred stereo-selective process embodiment of the present invention. As described above in detail, the starting material is a pure optical isomer of 4-vinyl-2-azetidinone (23, above).

EXAMPLE 13

Step A

Preparation of [1-(t-butyldimethylsilyl)-4-vinyl-2-azetidinone)

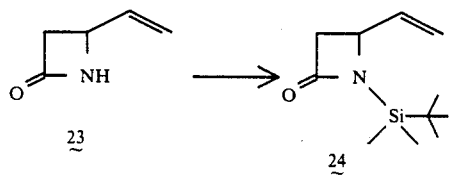

A solution of 23 [4-vinyl-2-azetidinone] (1.153 g, 11.89 mmoles) and triethylamine (1.82 ml, 13.08 mmoles) in anhydrous N,N-dimethylformamide is placed under a nitrogen atmosphere, cooled to 0° C. and treated with t-butyldimethylchlorosilane (1.885 g., 12.48 mmoles) resulting in the immediate appearance of a heavy white precipitate. This mixture is stirred for one hour while gradually warming to room temperature. The mixture is partitioned between 30 ml methylene chloride and 90 ml cold 1M potassium dihydrogen phosphate. The aqueous phase is extracted with 20 ml methylene chloride. The combined organic phases are washed four times with 30 ml portions of water and finally with 50 ml brine. The methylene chloride solution is dried over anhydrous magnesium sulfate and filtered. The filtrate is evaporated under reduced pressure to give 2.25 g of 24 [1-(t-butyldimethylsilyl)-4-vinyl-2-azetidinone] as a colorless liquid.

NMR (CDCl$_3$)δ: 6.23–5.10, m, C$\underline{H}$=CH$_2$ 4.07, 7-line m, J=8,6 and 3 Hz, C-4$\underline{H}$3.35, dd, J=15 and 6 Hz, C-3$\underline{H}$ cis to C-4H 2.73, dd, J=15 and 3 Hz, C-3$\underline{H}$ to C-4$\underline{H}$ 0.98, s, (C$\underline{H}_3$)$_3$ C Si 0.23, s, (C$\underline{H}_3$)$_2$ Si 0.18, s Following the above procedure, but making the indicated substitution, the other isomer is obtained.

Step A'

Preparation of 3-methyl-(t-butyldimethylsilyl)-4-vinyl-2-azetidinone

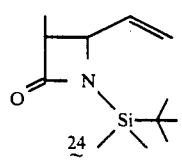

Following the procedure of the preparation of 8-oxo-2,2,7-trimethyl-3-oxa-1-azabicyclo[4.2.0]octane (Example 4b, above), except that an equivalent amount of 1-(t-butyldimethylsilyl)-4-vinyl-2-azetidinone is substituted for the 8-oxo-2,2-dimethyl-3-oxa-1-azabicyclo[4.2.0]octane of Example 4b, the title compound is obtained.

Step B

Preparation of 3-methyl-[1-(t-butyldimethylsilyl)-3-(hydroxymethyl)-4-vinyl-2-azetidinone]

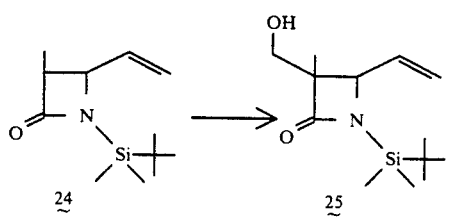

To a solution of freshly prepared lithium diisopropylamide (7.82 mmoles) in 36 ml anhydrous tetrahydrofuran under a nitrogen atmosphere at −75° C. is added a solution of 3-methyl-[1-(t-butyldimethylsilyl)-4-vinyl-2-azetidinone, 24, (1.60 g, 7.11 mmoles) in 10 ml anhydrous THF. The resulting yellow solution of the lithium enolate is, after 16 minutes, treated with excess formaldehyde (see Example 15, below). In 10 minutes, the reaction is quenched by adding 30 ml of a saturated aqueous ammonium chloride solution. This mixture is extracted with 50 ml and 25 ml portions of ethyl acetate. The combined ethyl acetate solutions are washed with 50 ml of brine and dried over anhydrous magnesium sulfate. The drying agent is removed by filtration and the filtrate is evaporated in vacuo to give the crude product as a yellow oil. Purification by chromatography on silica gel eluting with 10% ethyl acetate/chloroform gives 3-methyl-[1-(t-butyldimethylsilyl)-3-hydroxymethyl)-4-vinyl-2-azetidinone, 25.

Step C

Preparation of 3-methyl-1-(t-butyldimethylsilyl)-3-(1-p-nitrobenzylcarbonyldioxymethyl)-4-vinyl-2-azetidinone

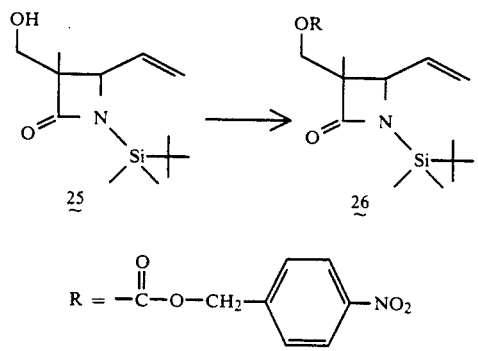

Under nitrogen at −78° C. a solution of 25 (56 mg, 0.220 mmole) in 1 ml of anhydrous tetrahydrofuran is treated with 2.4M n-butyllithium in hexane (101 μl, 0.242 mmole). To this solution is added, in five minutes, a solution of p-nitrobenzyl chloroformate (52 mg, 0.242 mmole) in anhydrous tetrahydrofuran. After stirring at −78° C. for a period of 55 minutes, 10 ml of a saturated aqueous ammonium chloride solution is added and the product extracted into ethyl acetate. The combined ethyl acetate solutions are washed with brine and dried over anhydrous magnesium sulfate. The drying agent is removed by filtration, and the filtrate is evaporated in vacuo to give crude 26. Purification by preparative thick-layer chromatography on silica gel developing with 5% ethyl acetate/chloroform gives 26.

Step D

Desilylation of 26 to provide 27 [3-methyl-3-(p-nitrobenzylcarbonyldioxymethyl)-4-vinyl-2-azetidinone]

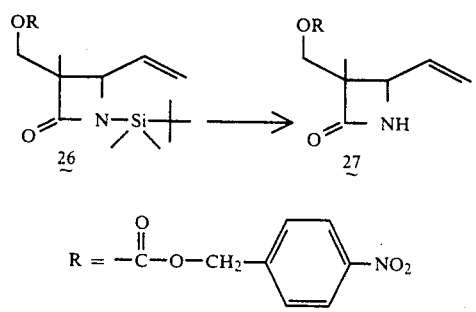

A solution of 26 [1-(t-butyldimethylsilyl)-3-methyl-3-p-nitrobenzylcarbonyldioxymethyl)-4-vinyl-2-azetidinone] (61 mg, 0.141 mmole) in 2 ml of 0.5N HCl/MeOH is stirred at room temperature (25° C.) for a period of 3 hours. The solution is then cooled to 0° C. and neutralized by the addition of 5 ml of 5% aqueous sodium bicarbonate. The product is extracted into ethyl acetate (10 ml, 2×5 ml). The combined ethyl acetate solutions are washed with water (2×5 ml) and 10 ml brine and then dried over anhydrous magnesium sulfate. The drying agent is removed by filtration, and the filtrate is evaporated in vacuo to give an oil. Preparative thick-layer chromatography of this material on silica gel developing with 10% ethyl acetate/chloroform gives 3-methyl-3-(p-nitrobenzylcarbonyldioxymethyl)-4-vinyl-2-azetidinone, 27.

Step E

Preparation of 14 via 28 by sulfenyl halide addition and dehydrohalogenation

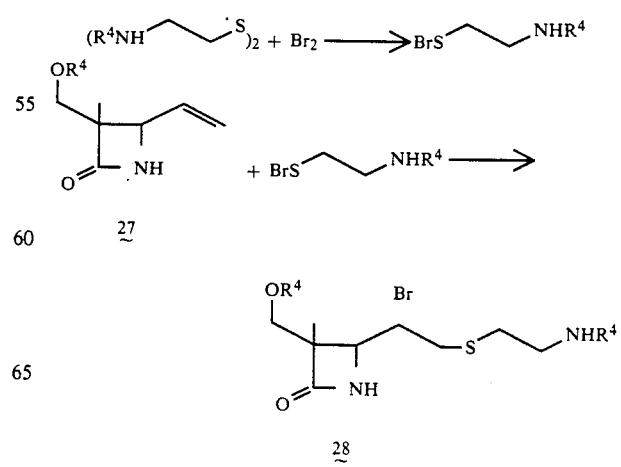

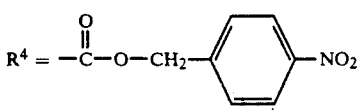

A solution of the N-p-nitroCBZ cysteamine disulfide, 96 mg (0.19 mmoles) in 1.5 THF (freshly distilled from LiAlH$_4$) is cooled to $-25°$ C. and treated dropwise with stirring with 0.5 ml of a solution of 135 mg Br$_2$ in sieve dried CCl$_4$ (2.2 ml final volume; portion added is equivalent to 0.19 mmoles of Br$_2$). The resultant orange solution is stirred at $-20°$ C. for 5 min. then treated with 54.0 mg of the vinyl azetidinone, 27, in 0.5 ml sieve dried CH$_2$Cl$_2$. The color lightens to yellow. The mixture is allowed to come to 0° C. over 5-10 minutes. Examination by tlc (silica 5% MeOH in CH$_2$Cl$_2$ or 20% EtOAc in CH$_2$Cl$_2$) shows a main spot with R$_f$ and Ce$^{IV+}$/H$^+$/heat characteristics different from either disulfide or starting 4-vinyl-2-azetidinone. The reaction mixture is concentrated to 0.5 ml under N$_2$, streaked directly on two 8"×8" 1000μ silica GF plates, and developed with 20% EtOAc in CH$_2$Cl$_2$. The main band under U.V., is scraped off, and extracted with EtOAc to give 28.

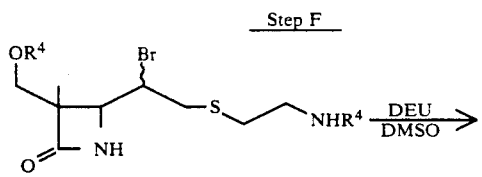

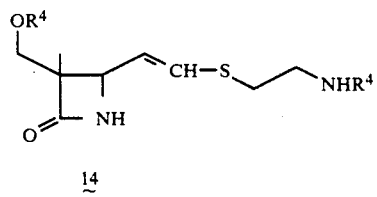

The bromosulfide, 28, 77.0 mg (0.162 mmole) is dissolved in 1.0 ml sieve stored DMSO (distilled from CaH$_2$), and stirred under nitrogen while 25λDBU (0.19 mmole) is added. After 3 hours, the mixture is poured into water/KH$_2$PO$_4$ and extracted repeatedly with EtOAc. The combined extracts are washed twice with water, dried with anhydrous MgSO$_4$ and evaporated under nitrogen. The crude product, is streaked on an 8×8" 1000μ silica GF plate and developed with 20% EtOAc in CH$_2$Cl$_2$ to give 14.

EXAMPLE 14

Preparation of Bis (p-Nitrobenzyloxycarbonylaminoethyl)disulfide

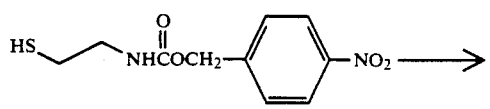

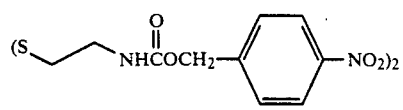

Under nitrogen at $-20°$ C., bromine (1.21 ml, 0.022 mmole) is added to a solution of p-nitrobenzyloxycarbonylaminoethanethiol (11.28 g, 0.044 mole) in 100 ml of anhydrous tetrahydrofuran. The cooling bath is removed, and the cold solution is stirred for 15 minutes. The solution is then diluted with 400 ml ethyl acetate and washed with 200 ml 1M pH 7 phosphate buffer, 200 ml 1M dibasic potassium phosphate, water (2×200 ml, 100 ml) and 200 ml brine. It is dried over anhydrous magnesium sulfate and filtered. The filtrate is evaporated in vacuo giving a yellow solid residue. This material is chromatographed on silica gel eluting with 5% ethyl acetate/chloroform to give 10.5 g of crystalline bis (p-nitrobenzyloxycarbonylaminoethyl)disulfide:

IR (CH$_2$Cl$_2$) μ: 3.04 NH 5.96 carbonyl 6.22, 6.61 nitro

NMR (CDCl$_3$)δ: 8.24 } d, J=8.5Hz, ArH
7.54

5.37, broad s, NH
5.26, s, ArCH$_2$O
3.60, q, J=6 Hz and 6 Hz, NHCH$_2$CH$_2$
2.86, t, J=6 Hz, NHCH$_2$CH$_2$S

EXAMPLE 15

Preparation of 8oxo-2,2-dimethyl-7α and β-hydroxymethyl-3-oxa-1-azabicyclo[4.2.0]octane

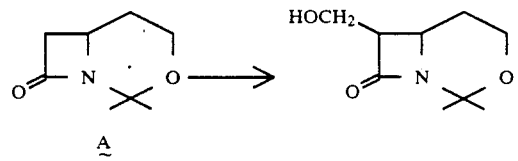

The procedure of Example 5, substituting A for 8-oxo-2,2,6-trimethyl-3-oxa-1-azabicyclo[4.2.0]octane, is carried out. Upon purification by silica gel chromatography, the title compound is obtained.

EXAMPLE 16

Preparation of 3-(2-aminoethylthio)-6-hydroxymethyl-7-oxo-1-azabicyclo[3.2.0]hept-2-ene-2-carboxylic acid

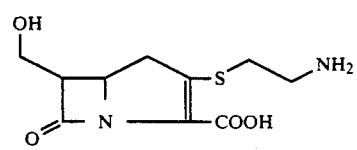

Following the procedure described above for the preparation of 3-(2-aminoethylthio)-6-methyl-6-hydroxymethyl-7-oxo-1-azabicyclo [3.2.0]hept-2-ene-2-carboxylic acid, except that in Example 6 an equivalent amount of 8-oxo-2,2-dimethyl-7-hydroxymethyl-3oxa-1-azabicyclo[4.2.0]octane rather than the 2,2,7-trimethyl species is taken; the title compound is obtained when the procedures of Examples 6,7 and 12 are followed.

EXAMPLE 17

Preparation of 8-oxo-2,2-dimethyl-7α and β-(1-hydroxy-2-phenylethyl)-3-oxa-1-azabicyclo[4.2.-0]octane

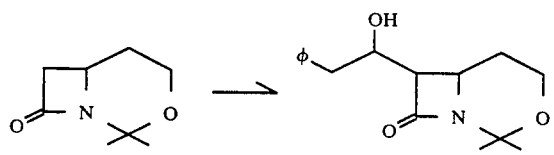

Following the procedure of Example 15, except that instead of formaldehyde, an equivalent amount of phenylacetaldehyde is used, upon purification by silica gel chromatography, the title compound is obtained.

EXAMPLE 18

Preparation of 3-(2-aminoethylthio)-6-(1-hydroxy-2-phenylethyl)-7-oxo-1-azabicyclo[3.2.0]hept-2-ene-2-carboxylic acid

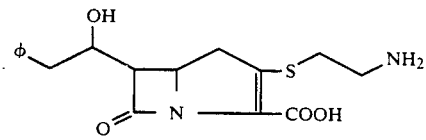

Following the procedure of Example 16 except that 8-oxo-2,2-dimethyl-7(1-hydroxy-2-phenylethyl)-3-oxa-1-azabicyclo[4.2.0]octane is substituted in equivalent amount for its analogous substrate, the title compound is obtained.

EXAMPLE 19

Preparation of 8-oxo-2,2-dimethyl-7α-benzyl-3-oxa-1-azabicyclo [4.2.0]octane

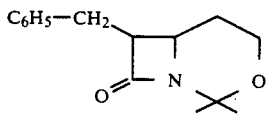

Following the procedure described for the preparation of 8-oxo-3-oxa-2,2-dimethyl-7α-isopropyl-1-azabicyclo [4.2.0]-octane from 8-oxo-3-oxa-2,2-dimethyl-1-azabicyclo[4.2.0]-octane (Example 4a, above) and using benzyl bromide instead of isopropyl iodide there is obtained 8-oxo-2,2-dimethyl-7α-benzyl-3-oxa-1-azabicyclo[4.2.0]octane.

i.r. μ: 5.73 (β-lactam)
n.m.r. δ: 1.33S, 1.75S (gem dimethyl); 1.74 m (C-5H) 3.0 d of d (C₆H₅-CH₂); 3.73 d of d (C-2H) 7.25S (C₆H₅).

EXAMPLE 20

Preparation of 8-oxo-2,2-dimethyl-7α and β-benzyl-7α and α-(1-hydroxyethyl)-3-oxa-1-azabicyclo[4.2.0]octane

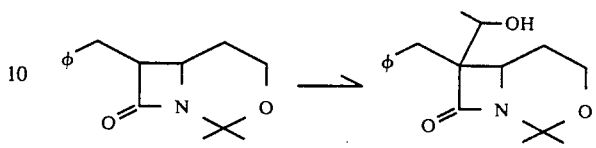

Using the procedure of Example 5 but substituting an equivalent amount of 8-oxo-2,2-dimethyl-7α-benzyl-3-oxa-1-azabicyclo[4.2.0]octane (Example 19) for 8-oxo-2,2,7-trimethyl-3-oxa-1-azabicyclo[4.2.0]octane, and an equivalent amount of acetaldehyde for formaldehyde, there is obtained, upon purification by silica gel chromatography, the title compounds.

EXAMPLE 21

Preparation of 8-oxo2,2-dimethyl-7α(1-mesyloxyethyl)3-oxa-1-azabicyclo[4.2.0]octane

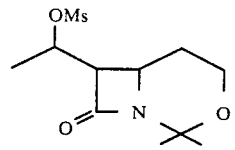

Under nitrogen at 0° a solution of rel-(6S,7R)-8-oxo-2,2-dimethyl-7,(1R-hydroxyethyl)-3-oxa-1-azabicyclo [4.2.0]octane and rel(6S,7R) 8-oxo-2,2-dimethyl-7(1S-hydroxyethyl)-3-oxa-1-azabicyclo-[4.2.0]octane as an approximately 1:2 diastereomeric mixture (128 mg, 0.643 mm) and triethylamine (134 μl or 0.965 mm) in 5 ml of sieve dried methylene chloride is treated with redistilled methane sulfonyl chloride (55 μl or 0.707 mm). The resulting solution is stirred for 30 minutes. It is then washed with 10 ml each of cold water, 1 molar pH 3 phosphate buffer, 5% sodium bicarbonate, water and finally brine. The organic phase is dried over magnesium sulfate and filtered. The filtrate is evaporated in vacuo to give 156 mg of a pale yellow oil. This material is chromatographed on preparative thick layer silica gel plates developed four times with 1:9 acetone/hexane to give a separated diastereomeric mesylate in 68% overall yield.

Diastereomer of R_f 0.13 (25%)
i.r. CH₂Cl₂ μ, 5.73 β-lactam.
n.m.r. C₆D₆ δ5.06–4.61, 8 line multiplet, 1H, J=6.5 and 7.5 Hz, CH₃CH
3.58–3.26 multiplet 3H,C₄-methylene, C₆-methine
2.61,dd, 1H, J=1.8 and 7.5 Hz, C₇-methine.
2.40,s, 3H, CH₃SO₂

1.83,s, 3H ⎫
1.09,s, 3H ⎭ C-2 methyls 1.30,d, 3H, J=6.5 Hz, CH₃CH

Diastereomer of $R_f$ 0.08 (43%)

i.r. $CH_2Cl_2$ $\mu\beta$-lactam 5.71 n.m.r. $C_6D_6$ $\delta$ 5.04–4.64, 8 line multiplet 1H, J=4.5 and 6.5 Hz, $CH_3C\underline{H}$ 3.63–3.10 multiplet, 3H, $C_4$-methylene and $C_6$ methine.

2.67 dd, 1H, J=1.8 and 4.5 Hz, $C_7$-methine 2.46 s; 3H, $C\underline{H}_3SO_2$ 1.81,s, 3H  
1.16,s, 3H  } C-2 methyls 1.34 d, 3H, J=6.5 Hz, $C\underline{H}_3CH$.

EXAMPLE 21a

Preparation of 8-ox-2,2-dimethyl-7α-(1-azidoethyl)-3-oxa-1-azabicyclo[4.2.0]octane

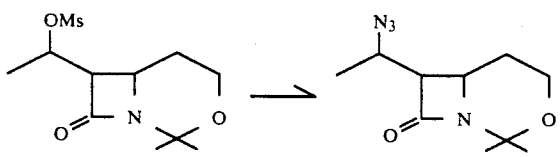

A solution of lithium azide, prepared by stirring over night a mixture of 170 mg sodium azide and 100 mg lithium chloride in 3 ml of anhydrous dimethyl sulfoxide, followed by filtration, is added to 160 mg of 8-oxo-2,2-dimethyl-7α(1-mesyloxyethyl)-3-oxa-1-azabicyclo-[4.2.0]octane and stirred under nitrogen at 25° C. for eight hours or until the reaction is judged complete by tlc. The mixture is then poured into 10 ml ice water and extracted with ethyl acetate, the combined extracts washed once with water, once with saturated sodium chloride solution, dried (MgSO4) and evaporated under a nitrogen stream. The crude product is purified by preparative tlc to afford the title compound.

EXAMPLE 22

Preparation of 8-oxo-2,2-dimethyl-7α-(1-p-nitrobenzyloxycarbonylaminoethyl)-3-oxa-1-azabicyclo[4.2.0]octane

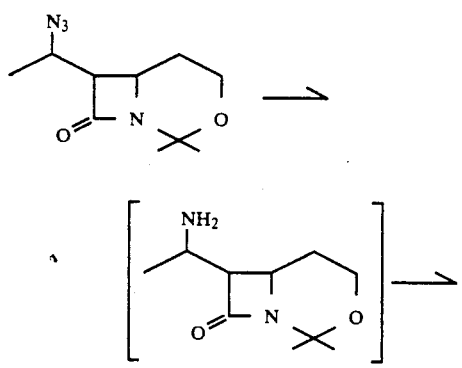

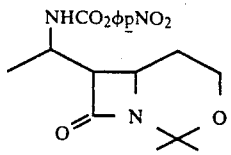

A mixture of 107 mg of 8-oxo-2,2-dimethyl-7α-(1-azidoethyl)-3-oxa-1-azabicyclo[4.2.0]octane and 50 mg of 10% Pd/C in 2 ml of anhydrous dioxane is shaken under 3 atmospheres of hydrogen for 1.5 hours. The mixture is filtered and concentrated to 1 ml under a nitrogen stream, then treated with 1 ml of 1M K2HPO4 and 1 ml methylene chloride. The mixture is stirred vigorously in an ice bath under nitrogen while a solution of 120 mg of p-nitrobenzylchloroformate in 0.5 ml methylene chloride is added dropwise over one minute. The solution is stirred for another 15 minutes, then treated with 0.1 ml pyridine in 2 ml water and stirred vigorously for another 15 minutes. The organic phase is removed and the aqueous phase is extracted several more times with methylene chloride. The combined organic phases are washed twice with water, once with saturated NaCl, dried (MgSO4) and evaporated under reduced pressure. Purification by preparative tlc affords the title compound.

EXAMPLE 23

Preparation of 8-oxo-2,2-dimethyl-7[(1-o-nitrobenzylthioethyl)-3-oxa-1-azabicyclo[4.2.0]octane

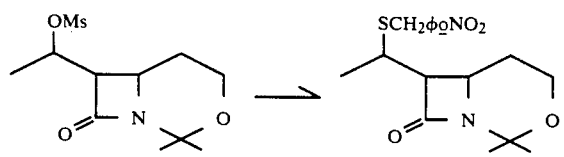

When in Example 21a an equivalent solution of o-nitrobenzyl mercaptan in DMF is substituted for the lithium azide solution, the title compound is obtained.

EXAMPLE 24

Preparation of 4-(2,2-(bisbenzylthio)ethyl)-3-methyl-3-(p-nitrobenzylcarbonyldioxymethyl)-2-azetidinone

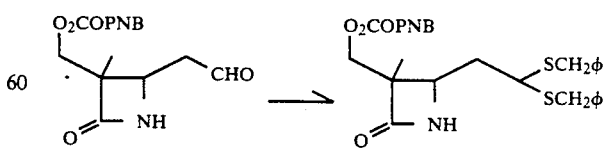

When in Example 12, Step A, an equivalent amount of benzyl mercaptan is substituted for 2-(p-nitrobenzyloxycarbonylamino)ethane thiol, the title compound is obtained.

EXAMPLE 25

Preparation of 3-methyl-4-(2,2-(bis-o-nitrobenzylthio)ethyl)-3-(nitrobenzylcarbonyldioxymethyl)-2-azetidinone

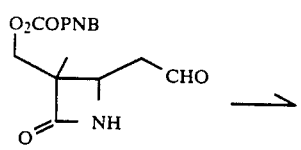

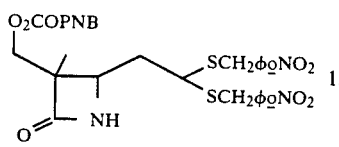

φoNO2 = o-nitrophenyl

When in Example 12, Step A, an equivalent amount of o-nitrobenzylthiol is substituted for 2-(p-nitrobenzyloxycarbonylamino)ethane thiol, the title compound is obtained.

EXAMPLE 26

Preparation of 3-methyl-3-(p-nitrobenzylcarbonyldioxymethyl)-4β-[1-bromo-2-(2-p-nitrobenzyloxycarbonylamino) 1,1-dimethylethylthio)ethyl]-2-azetidinone

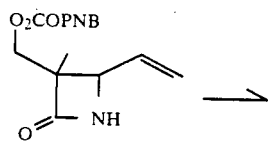

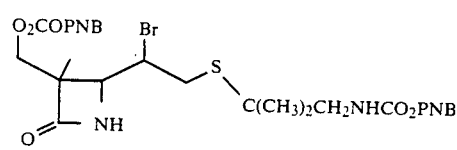

If in Example 13, Step E, an equivalent solution of 2-(p-nitrobenzyloxycarbonylamino)-1,1-dimethylethylsulfenyl bromide, prepared by cleavage of bis(2-(p-nitrobenzyloxycarbonylamino)-1,1-dimethylethylthio)mercury with bromine in THF/ether at 0° C., is substituted for the solution of 2-(p-nitrobenzyloxycarbonylamino)ethylsulfenyl bromide, the title compound is obtained.

EXAMPLE 27

Preparation of 3-benzylthio-6-methyl-6-hydroxymethyl-7-oxo-1-azabicyclo[3.2.0]hept-2-ene-2-carboxylic acid

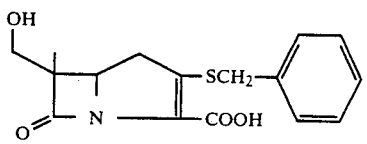

Following the procedure of Example 12, Steps A-K except substituting for the indicated azetidinone the azetidinone of Example 24, the title compound is obtained.

EXAMPLE 28

Preparation of 3-(2-amino-1,1-dimethylethylthio)-6-methyl-6-(1-hydroxymethyl)-7-oxo-1-azabicyclo[3.2.0]hept-2-ene-2-carboxylic acid

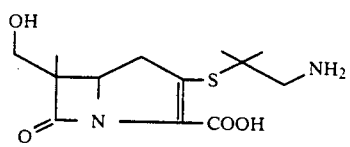

Following the procedure of Example 13, Step F, except substituting for the indicated azetidinone the azetidinone of Example 26, followed by the reactions corresponding to those of Example 12 D-K, the title compound is obtained.

EXAMPLE 29

Preparation of 3-mercapto-6-methyl-6-(p-nitrobenzylcarbonyldioxymethyl)-7-oxo-1-azabicyclo-[3.2.0]hept-2-ene-2-carboxylic acid, p-nitrobenzyl ester

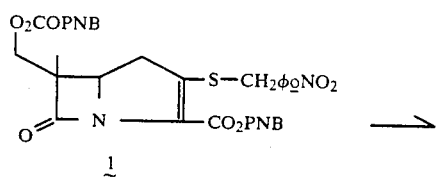

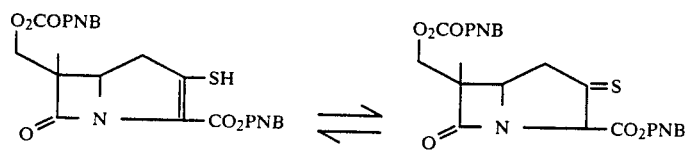

A solution of 5 mg of 1 (prepared from the azetidinones of Example 25 and the procedure of Example 12) in 0.6 ml of dioxane is irradiated for one hour in a quartz vessel under nitrogen with nitrogen being slowly bubbled through (1 bubble per 5 sec.) using 300 nm sources in a Rayonet apparatus, to give the title compound as a mixture of thiol-thione tautomers.

EXAMPLE 30

Preparation of 6-Methyl-6-(hydroxymethyl)-3-mercapto-7-oxo-1-azabicyclo[3.2.0]hept-2-ene-2-carboxylic acid

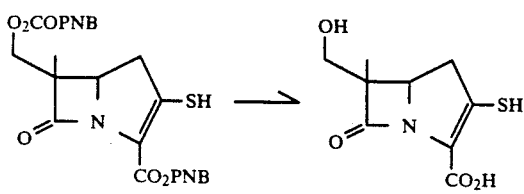

If the solution obtained after irradiation in Example 29 is immediately treated with 0.05 ml of ethanol, 0.35 ml deionized water, 0.01 ml of 1.0M $K_2HPO_4$, and 5 mg of 10% Pd/C and then treated as in Example 12, Step K, except that instead of purification on the XAD-2 column the ether extracted aqueous solution is cooled in ice, carefully acidified to pH 2 and extracted with ethyl acetate, and the combined extracts then washed once with saturated NaCl solution, dried with $MgSo_4$ and concentrated under a stream of $N_2$, the title compound is obtained.

EXAMPLE 31

Preparation of ($\pm$)-9,9-dimethylthienamycin

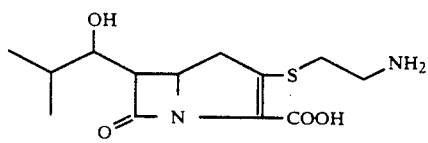

Step A

Preparation of 1-t-butyldimethylsilyl-3α-(1(R²-(-hydroxy-2-methyl-propyl)-4β-vinyl-2-azetidinone

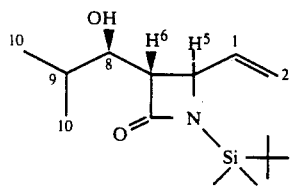

A solution of 1.226 g (5.8 m moles) of 1-t-butyldimethylsilyl-4-vinyl-2-azetidinone in 6 ml of anhydrous THF containing ~1 mg of 2,2'-dipyridyl and 0.075 ml (0.53 m moles) of diisopropyl amine is cooled under nitrogen to −78° C. and treated with 2.5 ml of 2.3M n-butyl lithium (5.75 m moles) with stirring over 5 minutes.

To the resultant orange solution is added 0.8 ml (0.63 g; 8.2 m moles) of freshly distilled isobutyraldehyde over one minute to give a pale yellow solution. The cooling bath is removed and the mixture is allowed to stir for 15 minutes, and is then worked up by pouring into 60 ml of ice/water plus 10 ml 1M $KH_2PO_4$, and extracting 4 times with 15 ml portions of ethyl acetate. The combined extracts are washed once with 0.2M $KH_2PO_4$, once with saturated NaCl, dried with $MgSO_4$, and evaporated evaporated under a $N_2$ stream to give 1.74 g (1.67 g = 100%) of pale yellow oil. Examination by 300 MHz PMR shows three main components, identified as the 3β-(1R*), 3α-(1S*), and the desired 3α-(1R*) isomers in ca. 20, 60, and 20% yield respectively. If desired the product may be obtained at this point by chromatography on silica-gel using $CH_2Cl_2$ with low percentages of EtoAc. Because the product is crystalline, it can be isolated from enriched fractions even though not completely resolved. The 300 MHz PMR ($CDCl_3$) shows (see numbering system above) 5.91 ($H_1$, ddd, $J_{1,2\ cis}=10$ Hz; $J_{1,2\ trans}=17$ Hz; $J_{1,5}=9$ Hz), 5.21 ($H_{2\ cis}$, d, $J_{1,2\ cis}=10$ Hz), 5.33 ($H_{2\ trans}$, d, $J_{1,2\ trans}=17$ Hz), 4.17 ($H_5$, dd, $J_{1,5}=9$ Hz; $J_{5,6}=3$ Hz), 3.86–3.79 ($H_8$, m), 3.17 ($H_6$, dd, $J_{5,6}=3$ Hz; $J_{6,8}=3$ Hz), 1.86–1.74 ($H_9$, m, $J_5 \sim 6$ Hz), 0.96 (Si-t-butyl,s), 0.81 ($H_{10}$,d,$J_{9,10}=6$ Hz), 0.25 and 0.17 (Si-$CH_3$, s) δ.

A preferred procedure entails oxidizing the initial aldol mix to the ketone and reducing with borohydride to give a mixture much enriched in the desired product.

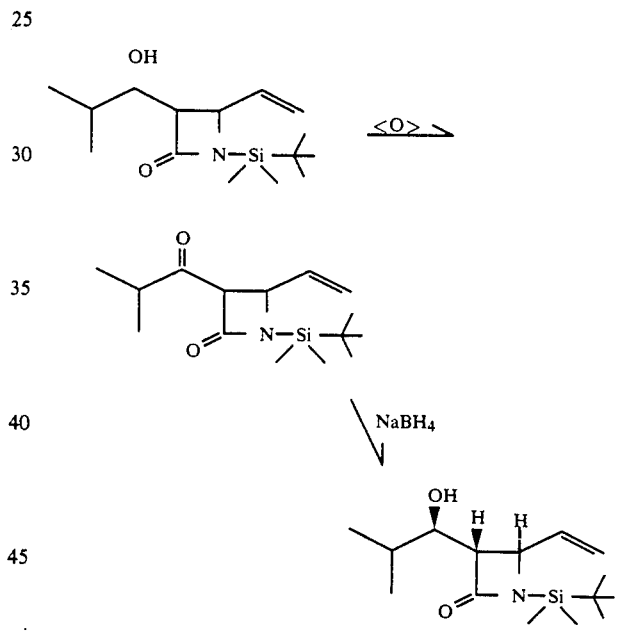

Thus the crude product above is taken up in 10 ml dry $CH_2Cl_2$ and cooled under $N_2$ in a −78° C. bath. To 10 ml dry $CH_2Cl_2$ is added 0.86 ml (945 mg; 12.1 m mole) DMSO and the mix cooled to −65° C. under $N_2$. After 10 minutes, 1.30 ml (1.94 g, 9.2 m moles) of trifluoroacetic anhydride is added and the mixture stirred for 15 minutes at −65° C. To this clear solution is added the chilled aldol solution by siphoning. The mixture is stirred for 1 hour at −65° C., treated with 2.7 ml (1.98 g; 19.5 m moles) of $Et_3N$, the cooling bath is removed and stirring is continued for 1 hour. The mix is then washed four times with water, once with saturated NaCl, and dried with $MgSO_4$; upon removing the solvent under a $N_2$ stream, 1.2 g of an orange oil is obtained. Examination by tlc (silicagel; $CH_2Cl_2$) shows the material to be overwhelmingly one component. If desired, further purification can be effected by chromatography on silica-gel, eluting with $CH_2Cl_2$. A 300 Hz PMR spectrum ($CDCl_3$) shows 5.89 ($H_1$, ddd $J_{1,2cis}=10$ Hz; $J_{1,2trans}=17$ Hz; $J_{1,5}=9$ Hz), 5.26 ($H_{2cis}$, d, $J_{1,2cis}=10$ Hz), 5.39 ($H_{2trans}$, d, $J_{1,2}=17$ Hz), 4.41 ($H_5$, dd, $J_{1,5}=9$ Hz; $J_{5,6}=2$ Hz), 4.18 ($H_6$, d, $J_{5,6}=3$ Hz), 2.75–2.90 ($H_9$, m, $J_{9,10}=7$ Hz), 1.16 ($H_{10}$, d, $J_{9,10}=7$ Hz) 0.97 (Si-t-butyl, s), 0.17 and 0.25 (Si-$CH_3$, s)δ. More commonly, the reduction is carried out on crude ketone which has been freed of the most contaminants by filtration through silica-gel with $CH_2Cl_2$.

Thus, 63.85 g crude ketone is passed through 76 g Baker silica-gel and washed on through with a total of 2 liters of $CH_2Cl_2$ to give, upon evaporation 61.64 g (219 m mole) material which is taken up in 480 ml isopropyl alcohol and cooled with stirring in an ice-/saturated NaCl bath for 30 minutes. To this is added 10.2 g $NaBH_4$ (268 m moles) and the cloudy suspension stirred for 2 hours with continued cooling. It is then (cautiously) poured, with continued swirling, into 2 liters of ice/water containing 150 g $KH_2PO_4$ (1.08 moles). The mix is extracted five times with 100 ml $CH_2Cl_2$, the combined extracts are washed once with water, once with saturated NaCl, dried with $MgSO_4$ and evaporated to an oil. Examination by PMR shows no significant 3β-isomer; the 3α-(1S*) and 3α-(1R*) isomers are present in 45–40% and 55–60% yield respectively. By concentrating in petroleum ether to ~200 ml and seeding, 13 g of crystalline product is obtained directly; a second crop of 10 g is obtained upon further concentration. The mother liquors may be further processed using a preparative HPLC apparatus using 6% EtOAc/$CH_2Cl_2$.

When product can no longer be isolated, the combined mother liquors may be recycled through the oxidation-reduction sequence to generate more.

Step B

Preparation of 1-t-butyldimethylsilyl-3α-(1(R*)-o-nitrobenzylcarbonyldioxy-2-methylpropyl)-4β-vinyl-2-azetidinone

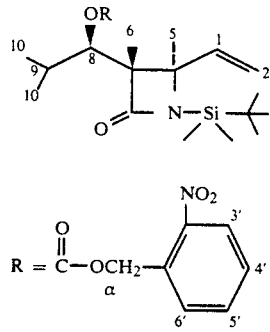

To a mixture of 1.7 g of 1-t-butyldimethylsilyl-3α-(1(R*)-hydroxy-2-methylpropyl)-4β-vinyl-2-azetidinone (6.0 mmoles) and 1.6 g of 4-dimethylaminopyridine (13.1 mmole) in 20 ml of sieve dried $CH_2Cl_2$, stirring in an ice bath under a nitrogen atmosphere, is added 2.9 g of o-nitrobenzyloxycarbonyl chloride (13.4 mmole) in 5 ml of sieve dried $CH_2Cl_2$. The initially slightly milky solution turns within minutes to a thick paste. The bath is removed and the mix allowed to stir over night. The mix is then stirred with 20 ml ice/water for several minutes affording two clear phases. The organic phase is removed and washed twice with water, dried with $MgSO_4$, concentrated to ~5 ml and passed through 5 g of Baker Silica followed by 200 ml of $CH_2Cl_2$. The entire filtrate is blown down with nitrogen to yield 3.1 g gum. Chromatography was carried out with a Waters Prep 500 Preparative HPLC apparatus, using one 500 ml pack and eluting with 3% EtOAc in $CH_2Cl_2$. After two column volumes, product emerges in ca. three column volumes; after another five column volumes, starting aldol begins to emerge and is more quickly eluted by changing to 7.5% EtOAc in $CH_2Cl_2$ and finally straight EtOAc. One obtains 0.97 g recovered starting material and 1.5 g of product which exhibits a 300 MHz PMR($CDCl_3$) with peaks at 8.34($H_3$, d, $J_{3',4'}=8$ Hz), 7.74–7.62 ($H_{5'-6'}$M) 7.52 ($H_{4'}$, dd $J_{3',4'}=8$ Hz, $J_{4',5'}=8$ Hz), 5.88 ($H_1$, ddd, $J_{1,2cis}=9$ Hz; $J_{1,2trans}=17$ Hz; $J_{1,5}=9$ Hz), 5.62 ($H_{60}$,s), 5.29 ($H_{2trans}$,d,$J_{1,2trans}=17$ Hz), 5.21($H_{2cis}$,d,$J_{1,2cis}=9$ Hz), 5.07($H_8$,dd,$J_{6,8}=5$ Hz; $J_{8,9}=5$ Hz), 4.13 ($H_5$,dd,$J_{1,5}=9$ Hz; $J_{5,6}=3$ Hz), 3.28 ($H_6$,dd,$J_{5,6}=3$ Hz;$J_{6,8}=5$ Hz), 2.18–2.02 ($H_9$,m), 0.95–0.85 ($H_{10}$ and Si-t-butyl), 0.24 and 0.15(Si-$CH_3$,s)δ.

On tlc(silica gel GF, 3%EtOAc/$CH_2Cl_2$) product $R_f$ was ~0.4, starting material ~0.15.

Step C

Preparation of 3α-(1(R*)-o-nitrobenzylcarbonyldioxy-2-methylpropyl)-4β-vinyl-2-azetidinone

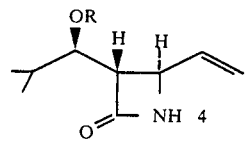

To 50.3 g of 1-t-butyldimethylsilyl-3α-(1(R*)-o-nibrobenzylcarbonyldioxy-2-methylpropyl)-4β-vinyl-2-azetidinone (109 mmoles) in 480 ml of methanol is added 4 ml of concentrated HCl (48 mmoles) and the mix is stirred for four hours, poured into 4 liters of water plus 50 ml of 1M $K_2HOP_4$ and extracted with EtOAc several times. An insoluble interface solid, isolated by filtration, proves to be 9.8 g of product. The combined extracts are washed once with water, once with saturated NaCl solution, dried and evaporated to give 24.7 g of solids. This is combined with the interface solid and recrystallized from acetone/ether to give 29.7 g product in three crops. Pure material has mp. 137.5°–139° C. The 60 MHz PMR ($CDCl_3$) shows 8.15($H_3$,d,d,$J_{3',4'}=7$ Hz), 7.75–7.35($H_{4'-6'}$,m), 6.25–5.00($H_{1-2,8}$,complex), 6.18($H_4$,bs), 5.30($H_\alpha$,s), 4.21 ($H_5$,dd,$J_{1,5}=7$ Hz; $J_{5,6}=2$ Hz), 3.22($H_6$,dd,$J_{5,6}=2$ Hz;$J_{6,8}=6$ Hz), 1.7–2.5($H_9$,m),0.9 & 1.0 ($H_{10's}$),δ.

Step D

Preparation of
3α-(1(R*)-o-nitrobenzylcarbonyldioxy-3-methylpropyl)-4β-[1-bromo-2-(2-p-nitrobenzyloxycarbonylaminoethylthio)ehtyl]-2-azetidinone

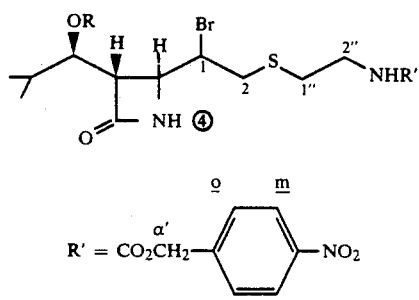

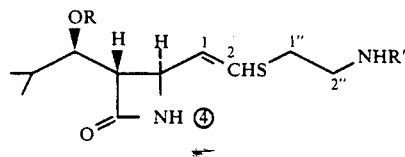

A solution of 254 mg of p-nitrobenzyloxycarbamidoethyldisulfide (0.5 mmole) in 3 ml of THF (freshly distilled from LiAlH$_4$) is cooled under a nitrogen atmosphere to −40° C. and treated dropwise with 80 mg of Br$_2$(0.5 mmole) in 0.5 ml of CCl$_4$. After stirring for ca. 10 minutes, a solution of 349 mg (1.0 mmole) of 3α-(1(R*)-o-nitrobenzylcarbonyldioxy-2-methylpropyl)-4β-vinyl-2-azetidinone in ~3 ml of methanol free CHCl$_3$ (incompletely soluble) is added and rinsed in with additional dry THF. The color of the solution lightens considerably, and it is allowed to stir 2 hours without maintaining the cooling bath. At this point the mix has lightened further and the temperature is ca. −10° C. It is poured into ~50 ml ice/water, shaken vigorously and the phases separated. The aqueous phase is then extracted three more times with CHCl$_3$ the combined extracts washed once with water, once with saturated NaCl solution, dried with MgSO$_4$, and evaporated under a nitrogen stream to give 0.71 g of gum. Examination by tlc (silica; 20%EtOAc/CH$_2$Cl$_2$) shows some unreacted starting materials plus two slower major product spots. The material is separated using the Waters Autoprep 500 with one 500 ml pack and eluting with 20% EtOAc in CH$_2$Cl$_2$. The starting materials emerge with the 3rd and 4th column volumes, the faster bromo-product(105 mg) emerges in the 5th and 6th column volumes and the slower bromo-product (282 mg) emerges in the 8th and 9th column volumes.

The faster bromo isomer has a 300 MHz PMR spectrum (CDCl$_3$) showing 8.25(H$_m$,d,J$_{o,m}$=8 Hz), 8.18(H$_{3'}$, d, J$_{3',4'}$=8 Hz), 7.8-7.5(H$_{4'-6'}$, m), 7.55(H$_2$,d,J$_{o,m}$=8 Hz), 6.26(H$_4$,s), 5.70&5.62(H$_{6α}$, pair of doublets, J$_{αα}$=14 Hz), 5.23(H$_{6α'}$,s), 5.06(H$_8$,dd,J$_{8,9}$=4 Hz; J$_{6,8}$=8 Hz), 4.17(H$_1$, ddd, J$_{1,2x}$=7 Hz; J$_{1,2y}$=7 Hz; J$_{1,5}$=7 Hz), 3.54-3.30(H$_{2''}$,m), 3.10-2.94(H$_2$,m), 2.76(H$_{1'}$,t, J$_{1'',2''}$=6 Hz),2.32-2.14(H$_9$, m), 1.0 and 0.98(H$_{10}$, pair of doublets, J$_{9,10}$=6 Hz), δ. The slower bromo isomer has a 300 MHz PMR spectrum (CDCl$_3$) showing 8.25(H$_m$,d,J$_{o,m}$=8 Hz), 8.17(H$_{3'}$,d,J$_{3'4'}$=8 Hz), 7.8-7.5(H$_{4'-6'}$,m), 7.55(H$_o$,d,J$_{o,m}$=8 Hz) 6.58(H$_4$,s), 5.57(H$_α$,s), 5.19(H$_{α'}$, s), 5.05(H$_8$,dd,J$_{8,9}$=5 Hz; J$_{6,8}$=8.5 Hz), 4.12(H$_1$,ddd,J$_{1,2}$=5 Hz; J$_{1,2y}$=7.5 Hz; J$_{1,5}$=7 Hz), 3.54-3.34(J$_{2''}$,m), 3.18(H$_2$,dd,J$_{2,2y}$=14 Hz; J$_{1,2}$=5 Hz), 3.04(H$_{2y}$,dd,J$_{1,2y}$=7.5 Hz; J$_{2,2y}$=14 Hz). 2.74(H$_{1''}$,t,J$_{1'',2''}$=6 Hz) 2.32-2.18(H$_9$,m), 1.4 & 0.98(H$_{10}$, bs)δ.

In most cases the reaction is more complete than in this example. The ratios of fast to slow isomer appear variable and may even change on handling or standing; however, in the following reaction, the yields and ratios of cis to trans olefins obtained are substantially the same, regardless of which isomer is used.

Step E

Preparation of
3α-(1(R*)-o-nitrobenzylcarbonyldioxy-2-methylpropyl)-4β-[2-(2-p-nitrobenzyloxycarbonylaminoethylthio)vinyl]-2-azetidinone The fast bromo isomer from Step D, 105 mg. (0.154 mmole) in 1 ml. KOH dried pyridine was treated with 49 mg. AgF (0.39 mmole) and stirred for 2 hours under N$_2$, the mix poured into 10 ml. ice/water plus 1-2 ml. EtOAc, shaken vigorously and centrifuged. The organic phase is removed and the aqueous phase extracted three more times with 1-2 ml. EtOAc. The combined extracts are washed twice with water, once with saturated NaCl solution, dried with MgSO$_4$ and evaporated under a nitrogen stream. The residue is flushed twice by evaporating from CHCl$_3$ solution under high vacuum to give 58 mg. dark gum. Preparative tlc on silica with 20% EtOAc/CH$_2$Cl$_2$ gives 27 mg. of trans olefin and 14 mg. of cis olefin. (In larger runs, using somewhat lower ratios of AgF to substrate, the ratio of trans to cis appears somewhat higher.) The pure trans isomer has a 300 Mhz PMR spectrum (CDCl$_3$) which exhibits peaks at 8.22 (H$_m$, d, J$_{o,m}$=8 Hz), 8.19 (H$_3$, d, J$_{3',4'}$=8 Hz), 7.80-7.77 (H$_{3'-5'}$,m) 7.56 (J$_{o,m}$=8 Hz), 6.31 (H$_2$, d,J$_{1,2}$=14 Hz), 5.94 (H$_4$,s), 5.71 (H$_1$, dd, J$_{1,2}$=14 Hz, J$_{1,5}$=8 Hz), 5.58 and 5.66 (H$_α$, two doublets, J$_{αα}$=14), 5.23 (H$_{α'}$, s), 5.10 (H$_8$, dd, J$_{6,8}$=6 Hz; J$_{8,9}$=5 Hz), 4.30 (H$_5$, dd, J$_{1,5}$=8 Hz; J$_{5,6}$=2 Hz), 3.47 (H$_{2''}$, dd, J$_{1'',2''}$=6 Hz; J$_{2'',NH}$=14 Hz), 3.28 (H$_6$, dd, J$_{5,6}$=2 Hz; J$_{6,8}$=6 Hz), 2.90 (H$_{1''}$, t, J$_{1'',2''}$=6 Hz), 2.21-2.03 (H$_9$,m), 0.97 and 0.95 (H$_{10}$, two doublets, J$_{9,10}$=6 Hz)δ. The cis isomer has a 300 MHz PRM spectrum (CDCl$_3$) with peaks at 8.24 (H$_m$, d, J$_{o,m}$=8 Hz), 8.17 (H$_{3'}$, d, J$_{3',4'}$=8 Hz), 7.76-7.49 (H$_{4'-6'}$,m), 7.53 (H$_o$, d,J$_{o,m}$=8 Hz), 6.19 (H$_2$, d, J$_{1,2}$=10 Hz), 5.95 (H$_4$,s), 5.74-5.54 (H$_1$ and H$_α$, complex), 5.20 (H$_α$,s), 5.11 (H$_8$, dd, J$_{6,8}$=6 Hz; J$_{8,9}$=6 Hz), 4.57 (H$_5$,dd, J$_{1,5}$=9 Hz, J$_{5,6}$=2 Hz), 3.49-3.37 (H$_{2''}$,m), 3.33 (H$_6$, dd, J$_{5,6}$=2 Hz; J$_{6,8}$=6 Hz), 2.89-2.81 (H$_{1''}$,m), 2.3-2.1 (H$_9$, m), δ1.0 (H$_{10}$,bs)δ.

Step F

Preparation of 1-bis
carbo-p-nitrobenzyloxyhydroxymethyl-3α(1-(R*)-o-
nitrobenzylcarbonyldioxy-2-methylpropyl)-4β-[2-(2-p-
nitrobenzyloxycarbonylaminoethylthio)vinyl]-2-
azetidinone

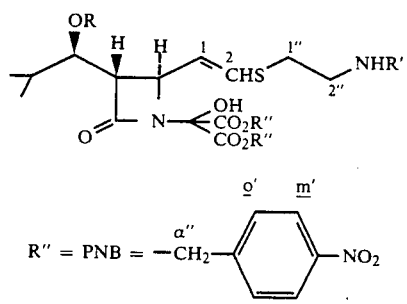

The procedure used in Example 31a, Step F, is followed except that 588 mg. (1.31 mmole) of ketomalonate, 25 ml. toluene, 605 mg. (1.0 mmoles) of 3α-(1-(R*)-o-nitrobenzylcarbonyldioxy-2-methylpropyl)-4β-[2-(2-p-nitrobenzyloxycarbonylaminoethylthio)vinyl]-2-azetidinone in 4 ml. THF, distillation of 18 ml. toluene and 1.5 hours of refluxing are employed. The analytical tlc's are developed three times in 1:2 acetone/hexane for optimum resolution. Chromatography on 30 g. silica gel packed in 1:2 acetone/hexane and collecting 25 ml. fractions after a 150 ml. forerun fraction gives 265 mg. ketomalonic acid (fractions 4-8), 177 mg. starting azetidinone (fractions 9-11), and 706 mg. of product (fractions 12-20). The 60 MHz PMR (CDCl$_3$) shows peaks at 8.24-7.95 (H$_{3',m,m'}$,m), 7.68-7.38 (H$_{o,o',4'-6'}$,m), 6.26 (H$_1$, d,J$_{1,2}$=15 Hz), 5.65 (H$_2$, dd,J$_{1,2}$=15 Hz; J$_{1,5}$=8 Hz), 5.48 (H$_\alpha$,s), 5.30 (H$_{\alpha''}$,s), 5.12 (H$_{\alpha'}$,s), ~5.12-4.9 (H$_8$, partially buried under α'), 4.7 (H$_5$, dd, J$_{1,5}$=8 Hz, J$_{5,6}$=2 Hz), 3.58-3.12 (H$_{2'',6}$,m), 3.0-2.55 (H$_{1''}$,m), 2.3-1.7 (H$_9$, m), 0.95 and 0.83 (H$_{10}$, two bs)δ.

Step G

Preparation of
1-biscarbo-p-nitrobenzyloxymethyl-3α-(1-(R*)-o-
nitrobenzylcarbonylidioxy-2-methylpropyl)-4β-[2-(2-p-
nitrobenzyloxycarbonylaminoethylthio)vinyl]-2-
azetidinone

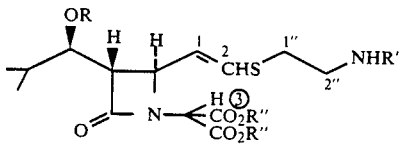

If 706 mg. (0.71 mmole) of 1-biscarbo-p-nitrobenzyloxyhydroxymethyl-3+-(1-R*)-o-nitrobenzylcarbonyldixoy-2-methylpropyl)-4β-[2-p-nitrobenzyloxycarbonylaminoethylthio)vinyl[12-azetidinone in 7 ml. THF containing 100λ pyridine (98 mg.; 1.24 mmole) is treated substantially as in Example 32, Step G, with 86λSOCl$_2$(144 mg.; 1.21 mmole) are subsequently with 353λ(n-but)$_3$P (1.42 mmole) in 7.2 ml. sieve dried DMF with 167 mg. K$_2$HPO$_4$ (0.96 mmole) and worked up as above, the crude title compound is obtained. Chromatography on 50 g. silica gel packed in CH$_2$Cl$_2$ and developed with 5% EtOAc/CH$_2$Cl$_2$, collecting a liter fraction after discarding a 125 ml. forerun; elution with 10% EtOAc/CH$_2$Cl$_2$, collecting 25 ml. fractions, gives product in fractions 10-30. Further purification on preparative tlc with 10% EtOAc/CH$_2$Cl$_2$ gives a 40-50% yield of product which displays a 60 MHz PMR(CDCl$_3$) with peaks at 8.2 (H,$_{3,m,m',bd,J}$=7-8 Hz), 7.75-7.35 (H$_{4'-6',o,o'}$, m),6.3 (H$_2$, d, J$_{1,2}$=15 Hz), 5.6(H$_1$, dd, J$_{1,2}$=15 Hz; J$_{1,5}$=9 Hz), 5.8 (H$_\alpha$, s), 5.44-5.18 (H$_{\alpha,\alpha'',3}$, complex), 5.35-5.0 (H$_8$, m), 4.60 (H$_5$, dd, J$_{5,6}$=2 Hz; J$_{1,3}$=9 Hz), 3.6-3.2 (H$_{2'',6}$, m), 2.65-3.05 (H$_{1''}$,m), 2.4-1.8 (H$_9$,m), 1.02 and 0.95 (H$_{10}$, two singlets)δ.

Step H

Preparation of
2,2-biscarbo-p-mitrobenzyloxy-3-(2-p-nitrobenzylox-
ycarbonylaminoethylthio)-4-bromo-6-exo-(1-(R*)-o-
nitrobenzylcarbonyldioxy-2-methylpropyl)-1-azabicy-
clo[3.2.0]heptan-7-one

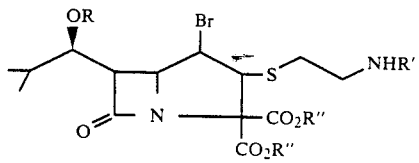

[All numbering and symbolism is the same as before.]

Following the procedure of Example 31a, Step H, and adding 0.20 ml of 132 mg Br/1.3 ml CCl$_4$ (0.125 mmoles) to 98 mg (0.10 mmoles) of 1-biscarbo-p-nitrobenzyloxymethyl-3α-(1(R*)-o-nitrobenzylcarbonyldioxy-2-methylpropyl)-4β-]2-(2-p-nitrobenzyloxycarbonylaminoethylthio)-vinyl]-2azetidinone in 2 ml THF, and then using 40 λEt$_3$N-(0.54 mmoles) and 1.5 ml DMF as in Example 32, Step H, there is obtained, upon work-up, 111 mg crude product. Preparative tlc using 77% EtOAc/CH$_2$Cl$_2$ affords the product, 48 mg, the slowest of the 3-4 major bands observed. The 60 MHz PMR (CDCl$_3$) shows peaks at 8.15-8.0 and 7.7-7.4 (H$_{aromatics}$; clusters of multiplets), 5.60(H$_\alpha$, s), 5.34(H$_{\alpha''}$,s), 5.20(H$_{\alpha'}$, s), 4.8-5.1 (H$_8$, complex), 4.45-4.15 (H$_5$, m), 4.70(H$_1$, dd, J$_{1,2}$=6; J$_{1,5}$=6), 3.7-3.25 (H$_{2,2''}$,m), 2.65-3.00(H$_{2''}$,m), 2.35-1.6 (H$_9$,bm), 0.98 and 1.1 (H$_{10}$, two singlets)δ.

Step I

Preparation of
2,2-biscarbo-p-nitrobenzyloxy-3-(2-p-nitrobenzylox-
ycarbonylaminoethylthio)-6-exo(1-(R*)-o-nitrobenzyl-
carbonyldioxy-2-methylpropyl)-1-azabicyclo[3.2.0-
]hept-3-en-7-one

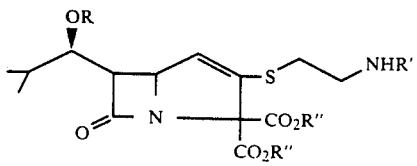

Following the procedure of Example 32, Step I, using 48 mg (0.046 mmole) of 2-biscarbo-p-nitrobenzyloxy-3-

(2-p-nitrobenzxylozycarbonylaminoethylthio)-4-bromo-6-exo-(1-R*)-o-nitrobenzylcarbonyldioxy-2-methylpropyl-1-azabicyclo[3.2.0]heptan-7-one in 10 ml pyridine with 15 mg AgF (0.12 mmole) but working up by pouring into H$_2$O/NaCl and extracting only with EtOAc, crude title compound is obtained. Preparative tlc with 8% EtOAc/CH$_2$Cl$_2$ affords 38 mg clean product with a 60 MHzPMR(CDCl$_3$) spectrum showing peaks at 8.25–8.02(H$_{3',m,m'}$, multiplet), 7.7–7.4(H$_{4'-6'}$, 0,0'm), 6.23(H$_1$,d,J$_{1,5}$=1 Hz) 5.80 and 5.45(H$_α$, two doublets, J$_{αα}$=14 Hz), 5.35(H$_{α''}$,s), 5.20(H$_{α'}$,s), 5.3–5.0(H$_8$,m,partially buried under H$_{α'}$), 4.8(H$_5$,bm), 3.6–3.25(H$_{2'',6}$,m) 3.2–2.9($_{1''}$m), 2.4–1.9(H$_9$, bm), 1.05 and 0.95-(H$_{10}$, two singlets)δ.

Step J

Preparation of 2-carbo-p-nitrobenzyloxy-3-(2-p-nitrobenzyloxycarbonylaminoethylthio)-6-exo-(1(R*)-o-nitrobenzylcarbonyldioxy-2-methylpropyl)-1-azabicyclo[3.2.0]hept-3-en-7-one

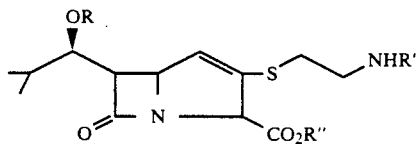

The precedure of Example 31a, Step J, is followed except: 491 mg (0.51 mmoles) of 2-bis carbo-p-nitrobenzyloxy-3-(2-nitrobenzyloxycarbonylaminoethylthio)-6-exo-(1-(R*)-o-nitrobenzylcarbonyldioxy-2-methylpropyl)-1-azabicyclo[3.2.0]-hept-3en-7one, 6 ml collidine, 87 mg (0.65 mmole) LiI and the crude product is purified by tlc with 40% acetone/hexane, the title compound is obtained which gives a 300 MHz PMR spectrum (CDCl$_3$) with peaks at 8.15 (H$_{3',m,m'}$, d.J=8 Hz), 7.66–7.22 (H$_{4'-6',2,2'}$,m), 5.86(H$_1$,s), 5.68 and 5.55H$_α$, two doublets, J$_{αα}$=14 Hz), 5.13(H$_{α''}$,s) 5.05(H$_{α',3}$,bs), 4.96(H$_8$,dd,J$_{8,9}$=4 Hz; J$_{6,8}$=7 Hz), 4.54(H$_5$, 6), 3.3–3.6(H$_{2''}$, m) 3.38(H$_6$, dd,J$_{5,6}$=2 Hz; J$_{6,8}$=7 Hz), 2.90–3.11(H$_{1''}$,m), 1.86–2.04(H$_9$,bm),~1.0(H$_{10}$, off scale)δ.

Step K

Preparation of 2-carbo-p-nitrobenzyloxy-3-(2-p-nitrobenzyloxycarbonylaminoethylthio)-6-exo-(1-(R*)-hydroxyl-2-methylpropyl)1-azabicyclo[3,2,0]hept-3-en-7-one

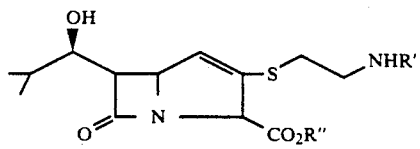

A solution of ca. 130 gm of 2-carbo-p-nitrobenzyloxy-3-(2-p-nitrobenzyloxycarbonylaminoethylthio)-6-exo-(1-(R*)-o-nitrobenzylcarbonyldioxy-2-methylpropyl)-1-azabicyclo[3,2,0]hept-3-en-7-one in 10 ml of CHCl$_3$ is placed in a quartz vessel (~1×1×10 cm) equipped with a 14/20 standard taper mouth and jacketed by a larger quartz vessel through which cold water may be run. A fine stream of nitrogen is blown through the solution for 10 minutes and the system is then closed with a nitrogen line fitted with a pressure-releasing bubbler. The water flow through the jacket is turned on and the vessel placed in a Rayonet Photolysis apparatus equipped with 3500 Å sources. The photolyzer is turned on and the sample is irradiated for 3 hours. Upon evaporation of the solvent and preparative tlc, with an EtOAC/CH$_2$Cl$_2$Stytem, a 5–10% yeild of the title compound is obtained along with a 75–80% recovery of starting material which is resubjected to the photolysis. Overall, a 30–40% conversion is effected. The product has a 300 MHz PMR spectrum (CDCl$_3$) with peaks at 8.23 (H$_{m,m'}$, d, J$_{o,m}$=8 Hz), 7.53 and 7.51(H$_o$ and H$_{o'}$, doublets, J=8 Hz), 6.01(H$_1$,s), 5.20(H$_{α''}$,s), 5.17(H$_{α',3}$,bs), 4.67(H$_5$,bs), 3.92(H$_8$,dd,J$_{6,8}$=6 Hz; J$_{8,9}$=6 Hz), 3.53–3.46 (H$_{2''}$, bm), 3.25(H$_6$,dd,J$_{5,6}$=3 Hz; J$_{6,8}$=6 Hz), 3.12–2.87(H$_{1''}$, bm), 1.94–1.78 (H$_9$, bm), ~0.97 (H$_{10}$, bs)δ.

Step L

Preparation of 2-carbo-p-nitrobenzyloxy-3-(2-p-nitrobenzyloxycaronylaminoethylthio)-6exo-(1-(R*)-hydroxy-2-methylpropyl)-1-azabicyclo[3.2.0]-hept-2-en-7-one

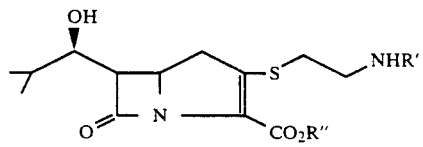

A solution of 9 mg(0.014 mmoles) of 2-carbo-p-nitrobenzyloxy-3-(2-p-nitrobenzyloxycarbonylaminoethylthio)-6-exo-(1-(R*)-hydroxy-2-methyl-propyl)-1-azabicyclo-[3.2.0]hept-3-en-7 one in 0.1 ml DMSO is treated with 0.2–0.3λ(0.0002 mmole) DBU. After standing for 1–2 hours, the solution is diluted with 1 ml of water and extracted several times with EtOAc. The extracts are combined, washed with water, 1M KH$_2$PO$_4$, dried with MgSO$_4$ and concentrated. The concentrate is processed by preparative tlc using 1:1 CH$_2$Cl$_2$/EtOAc to give the starting compound and the title compound. The former may be recycled through

Step M

Preparation of (±)9,9-dimethylthienamycin

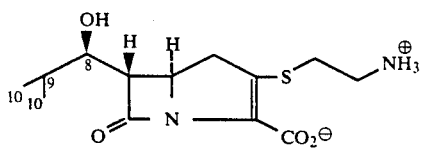

A 5–6 mg sample of 2-carbo-p-nitrobenzyloxy-3-(2-p-nitrobenzyloxycarbonylaminoethylthio)-6-exo-(1)-(R*)-hydroxy-2-methylpropyl)-1-azabicyclo[3,2,0]hept-2en-7-one in a 13×100 mm culture tube is deblocked under precisely the conditions given in Example 12 Step K. The aqueous extract, however, is not applied to an XAD-2 column; instead it is injected in portions onto a Waters Associates Microbondapak $C_{18}$ column (3 ml void volume) and eluted with 5% THF is deionized water. The desired material appears as a major peak (254 photocell) at approximately 6 minutes with a flow rate of 0.7 ml/minture. Collected peaks from multiple injections are combined and carefully concentrated on a rotary evaporator equipped with a DRy Ice/acetone charged cold finger condenser and attached to a high vacuum oil pump to 0.5-1.0 ml. The concentrate is shell frozen and placed in a shelf lyophilizer with $T \leq -10°$ C. overnight. The web-like residue exhibits a 300 mHz PMR Spectrum ($D_2O$) with peaks at 4.27($H_5$,bt,$J_{1,5}$=8-10 Hz) 3.83($H_8$,dd, $J_{8,9}$=5 Hz; $J_{6,8}$=5 Hz), 3.62($H_6$,dd,$J_{5,6}$=3 Hz; $J_{6,8}$=4 Hz), 3.31-2.95($H_{1'',2''}$, bm) 1.87-1.71($H_9$,bm), 0.94 & 0.88 the isomerization process to increase the overall conversion to the latter. The product gives a 300 MHz PMR spectrum ($CDCl_3$) with peaks at 8.24 ($\bar{H}_{m,m'}$, d,J=8 Hz), 7.68($H_{o'}$,d,$J_{o'm'}$=8 Hz), 7.52 ($H_o$,d,$J_{o,m}$=8 Hz), 5.53 and 5.25($H_{\alpha''}$, pair of doublets $J_{\alpha\alpha}$=14 Hz), 5.20($H_{\alpha'}$, s), 4.38-4.28($H_5$m), 3.94-3.88($H_8$,bm), 3.51-3.42($H_2''$,m), 3.41-3.32($H_6$, bdd), 3.20-2.94($H_{1'',1}$,m), 1.95-1.85($H_9$bm),~0.97($H_{10}$, not resolved)$\delta$. ($H_{10}$, two doublets, $J_{9,10}$=6 Hz)$\delta$. There is no significant absortion below the HDO peak at 4.84$\delta$. The PMR sample has a U.V. spectrum with $\lambda$max. 299 mu, quenchable with hydroxylamine.

EXAMPLE 31a

Preparation of (±)-9-benzylthienamycin

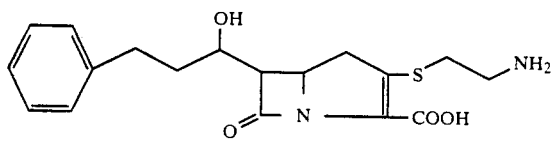

Step A

Preparation of
1-t-butyldimethylsilyl-3α-[(1(R*)-hydroxy-3-phenyl)-propyl]-4β-vinyl-2-azetidinone- and
1-t-butyldimethysilyl-3α-[(1(S*)-hydroxy-3-phenyl)-propyl]-4β-vinyl-2-azetidinone(1 and 2 respectively)

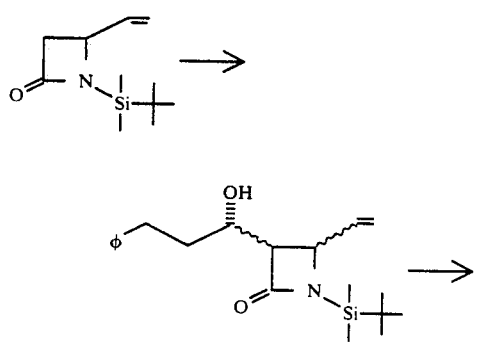

Generation of the anion of 17.8 g of 1-t-butyldimethylsilyl-4-vinyl-2-azetidinone (mw=211; 84.4 mmole), as in Example 31, Step A, is followed by condensation with 12.6 g of hydrocinnamaldehyde (mw=134; 94 mmole) rather than with isobutyraldehyde. Upon work-up, the crude aldol product is quickly chromatographed on silica gel (100 g). Elution with 5% $EA/CH_2Cl_2$ provides 30 g of 1-t-butyldimethylsily-3-[(1-hydroxy-3-phenyl)propyl]-4-vinyl-2-azetidinone as a mixture of diastereomers.

NMR (300 MHz, d6-acetone)$\delta$0.14-0.22 (series of s, $>Si(CH_3)_2$'s), 0.94

$$(s's, -\underset{|}{\overset{|}{Si}}-C(CH_3)_3\text{'s}),$$

1.76-2.10 (m $\phi CH_2C\underline{H}_2$-), 2.59-2.89 (m, $\phi C\underline{H}_2CH_2$-), 3.00-3.06 (2dd, $H_6$ of (8R* & 8S*)-trans-$\beta$-lactams) 3.46 (overlapping dd appearing as a t, $J_{5,6}$=$J_{6,8}$=5 Hz, $H_6$ of cis-$\beta$-lactam), 3.77-3.97 (m's, $H_8$'s), 4.06-4.23 (m's, $H_5$'s), 5.13-5.38 & 5.92-6.29 (m's, $-C\underline{H}=C\underline{H}_2$), 7.14-7.30(m,$\phi$).

A preferred procedure for isolation of the title compounds inquantity involves oxidation of the mixture of diastereomers to the all trans-ketone followed by reducing with $NaBH_4$ to a mixture from which the desired (1R*-hydroxy)diastereomer is more readily isolated.

Using essentially the same oxidation procedure as in Example 31, Step A, 30 g of diastereomeric 1-t-butyldimethylsilyl-3-[(1-hydroxy-3-phenyl)propyl[-4-vinyl-2-azetidinone is oxidized to the corresponding trans-ketone (30 g crude material). Recrystallization from a small volume of $Et_2O$ gives 10.9 of crystalline product in two crops. The mother liquor is chromatographed on silica-gel (100 g; eluting with $CH_2Cl_2$). The fractions containing product are combined and washed with cold petroleum ether to give 2.73 g additional crystalline ketone. A second recrystallization from Et₂O gives an analytical sample: mp=79.5°-82.5° C.; IR(CHCl₃)μ5.76, 5.86; MS m/e 343 (M+), 328,286;

NMR (3000 MHz, CDCl₃)δ0.16 & 0.24 (2a, >Si(CH₃)₂), 0.93

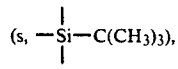

2.74-3.14 (m, φCH₂CH₂), 3.97 (d, J₅,₆=3 Hz, H₆), 4.44 (dd, J=3 Hz & 8 Hz, H5), 5.21-5.39 & 5.77-5.89 (m's, CH=CH₂), 7.19-7.31(m,φ). Anal (C₂₀H₂₉NO₂Si)C, H, N.

With stirring, 3.4 g of crystalline ketone (mw=343, 9.9 mmole) dissolved in 70 ml i-propanol is treated with 471 mg NaBH₄ (mw=38; 12.4 mmole). After stirring under N₂ at room temperature for 0.5 to 2 hours the reaction mixture is poured (cautiously) into a mixture of 60 ml. 1MKH₂PO₄-ice water-CH₂Cl₂. Continuing the work-up as in Example 31, Step A, 3.5 g crude product is isolated. Chromatiography on silica-gel (100 g, eluting with 5% EA/CH₂Cl₂) followed by chromatography on a Waters Associates Prep LC/System 500 instrument (10% acetone/hexane recycle mode) gives 1.0 g of 1-t-butyldimethylsiyl-3α-](1(S*)hydroxy-3-phenyl)propyl]-4β-vinyl-2-azetidinone and 1.1 g of the desired 1-t-butyldimethylsily-3α-[(1(R*)-hydroxy-3-phenyl)propyl)-4β-vinyl-2-azetidinone diastereomer as a crystalline solid. Recrystallization from petroleum ether gives an analytical sample: mp=63°-65° C.; IR(CHCl₃)μ5.79 br; MS m/e 345 (M+), 288, 105, 91;

NMR(300 MHz,d₆-acetone)δ0.14 & 0.21(2s, >Si-(CH₃)₂), 0.93 (s,->Si—C(CH₃)₃), 1.73-1.94(m,φC-H₂—CH₂), 2.62-2.88(m,φCH₂CH₂), 3.02 (dd, J₅,₆=3 Hz, J₆,₈=5 Hz,H6), 3.92-3.98 (m,H₈), 4.21 (dd,J=3 Hz & 9 Hz, H5), 5.14-5.39 & 5.96-6.08 (m's, CH=CH₂), 7.14-7.30 (m,φ).

Anal (C₂₀H₃₁NO₂Si) C,H,N. Data for 1(S*)-hydroxy diastereomer: IR(CHCl₃)μ5.80 br; MS m/e 345(M+), 288, 105, 91; NMR(300 MHz, d₆-acetone)δ0.13 & 0.20

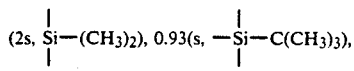

1.80-2.10 (m,φ-CH₂CH₂), 2.62-2.88 (m,φCH₂CH₂), 3.40 (dd, J₅,₆=3 Hz, J₆,₈=4.5 Hz, H₆), 3.83-3.90(m,H₈), 4.08 (dd, J=3 Hz and 6 Hz, H₅), 5.13-5.35 & 5.92-6.06 (m's, CH=CH₂), 7.14-7.30 (m,φ).

Step B

Preparation of 1-t-butyldimethylsilyl-3α-[(1(R*)-o-nitrobenzylcarbonyldioxy-3-phenyl)propyl]-4β-vinyl-2-azetidinone (3)

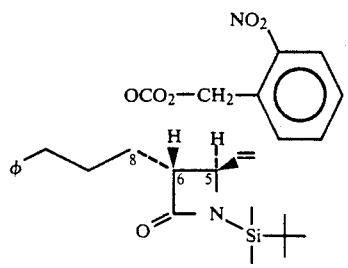

As in Example 31, Step B, 5.7 g of 1-t-butyldimethylsilyl-3α-[(1(R*)-hydroxy-3-phenyl)propyl]-4β-vinyl-2-azetidinone (mw=345; 16.5 mmole) and 4.24 g 4-dimethylaminopyridine (mw=122, 34.8 mmole) in 100 ml CH₂Cl₂ is treated with 7.56 g o-nitrobenzyloxycarbonylchloride (mw=217; 34.8 mmole) in 13 ml CH₂Cl₂. The cooling bath is removed, and stirring is continued under N₂ for 4 hours at room temperature. The reaction mixture is poured into a mixture of 18 ml 1M K₂HPO₄-water. Continuing the work-up as in Example 31, Step B, 11.7 g crude material is obtained. Chromatography on silica gel (350 g, eluting with O→2% EA/CH₂Cl₂) gives 5.76 g of title compound. Chromatography on silica gel (100 g, O→2% EA/CH₂Cl₂) of contaminated column fractions gives 1.36 g. additional product (82% total yield). IR(CHCl₃)μ 5.75br; NMR(300 MHz,CDCl₃)δ0.15 & 0.24 (2s, >Si-(CH₃)₂), 0.93

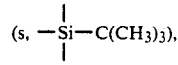

2.06-2.14 (m,φCH₂CH₂), 2.60-2.78(m,φCH₂CH₂), 3.22 (dd, J₅,₆=3 Hz,J₆,₈=7 Hz, H₆), 4.12(dd,J=3 Hz & J=9 Hz, H₅), 5.17-5.32 & 5.81-5.93 (m 's, H₈ & CH=CH₂), 5.60(mid-point of 2d, J=14 Hz, nonequivalent-OCO₂CH₂-arom.)7.16-8.2(m, aromatics).

Step C

Preparation of 3α-[(1(R*)-o-nitrobenzylcarbonyldioxy-3-phenyl)propyl]-4β-vinyl-2-azetidinone (4)

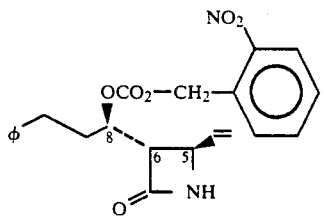

Using essentially the same procedure as in Examples 31, Step C, 150 mg of 1-t-butyldimethylsilyl-3α-[(1(R)-o-nitrobenzylcarbonyldioxy-3-phenyl)propyl]-4β-vinyl-2-azetidinone is converted to 116 mg crude product.

Preparative thin layer chromatography on silica gel (5% EA/CH$_2$Cl$_2$) provides 104 mg of the title compound (87%).

IR(CHCl$_3$)μ 5.69 br.

NMR(300 MHz,CDCl$_3$)δ 2.06–2.23(m,φCH$_2$CH$_2$), 2.62–2.81 (m,φCH$_2$CH$_2$), 3.20(dd, J$_{5,6}$=2 Hz, J$_{6,8}$=7 Hz, H$_6$), 4.23 (dd, J=2 Hz & 7 Hz, H$_5$), 5.18–5.34 & 5.85–5.97(m's, H$_8$ & CH=CH$_2$). 5.59(s,—OCO$_2$CH$_2$-arom.), 7.17–8.19 (m, aromatics).

Larger runs can be purified by chromatography on silica gel eluting with 0→10% EA/CH$_2$Cl$_2$ or 0→4% EA/CHCl$_3$.

Step D

Preparation of 4β-[[1-bromo-2-(2-p-nitrobenzyloxycarbonylamino)ethylthio]ethyl]-3α-[(1(R*)-o-nitrobenzylcarbonyldioxy-3-phenyl)propyl]-2-azetidinone (5)

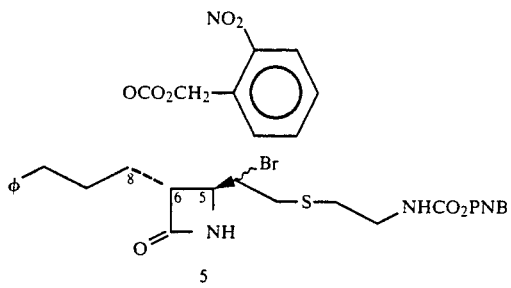

Following the procedure of Example 31, Step D, except that the reaction is allowed to stir for 1.5 hours during which time the temperature is not allowed to rise above +10° C., 100 mg of 3α-[(1(R*)-o-nitrobenzylcarbonyldioxy-3-phenyl)propyl]-4β-vinyl-2-azetidinone is converted to 171 mg of crude product. Chromatography on silica gel (∼10 g, eluting with 0→20% EA/CH$_2$Cl$_2$) provides 139 mg of the more polar product as a mixture of diastereomeric bromides (77%).

IR(CHCl$_3$)μ 5.66, 5.74 sh, 5.82 NMR(300 MHz, CDCl$_3$)δ2.06–2.34(m,φCH$_2$CH$_2$), 2.64–2.85 (m,SCH$_2$CH$_2$N and φCH$_2$CH$_2$), 2.95–3.09 & 3.16–3.23 (m'S,CHBrCH$_2$S), 3.32–3.50(m,SCH$_2$CH$_2$N and H$_6$'s), 3.95 (dd,J$_{5,6}$=2 Hz,J$_{CH_5\text{-}CHBr}$=7 Hz, H$_5$ of minor diastereomer), 4.01(dd,J$_{5,6}$=2 Hz, J$_{CH_5\text{-}CHBr}$=7.5 Hz, H$_5$ of major diastereomer), 4.04–4.16(m,—CHBr—'s), 5.16(Midpt. of m,H$_8$), 5.18(s,NHCO$_2$CH$_2$arom.), 5.52–5.66(m,—OCO$_2$CH$_2$arom.), 6.30, 6.46 & 6.65(3br, s, NH'S), 7.16–8.25(m,aromatics).

Step E

Preparation of 3α-[(1(R*)-o-nitrobenzylcarbonyldioxy-3-phenyl)-propyl[-4β-[2-(2-p-nitrobenzyloxycarbonylamino)ethylthio]vinyl]-2-azetidinone (6)

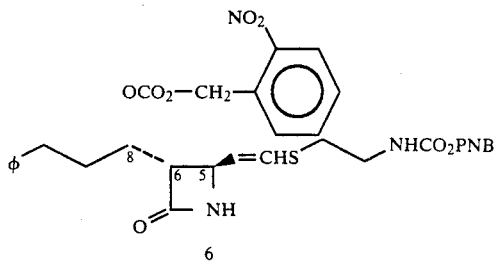

Treatment with 1.01 g. AgF(mw=127; 7.95 mmole) of 3.1 g. crude 4β-[[1-bromo-2-(2-p-nitrobenzyloxycarbonylamino)ethylthio]ethyl]-3α-[(1(R*)-o-nitrobenzylcarbonyldioxy-3-phenyl)propyl]-2-azetidinone (mw=744; 4.2 mmole) in 34 ml. pyridine at room temperature in the dark under N$_2$ for 1 hr. is followed by concentration of the entire reaction mixture under high vacuum and with a water bath at 25°–30° C. to a brown-black residue. After chasing a few times with CHCl$_3$, the residue is slurried in CH$_2$Cl$_2$ and run through a short column of silica gel (eluting with 2% MeOH/CH$_2$Cl$_2$) thus removing most of the silver salts. The fractions containing product are combined. Two additional runs carried out as above give a total of 3.26 g. product (from a total of 9.84 mmole starting material) still containing less polar impurities. Chromatography on silica gel (200 g., 1% MeOH/CH$_2$Cl$_2$) provides 0.63 g. of the desired product. Preparative thin layer chromatography on silica gel of 2.3 g. from column fractions which still contained less polar impurities (2.5% MeOH/CH$_2$Cl$_2$), provides 1.29 g. additional product total yield=30%). Although the product is used as is for completion of the synthesis of (±)-9-benzylthienamycin, for complete characterization, preparative thin layer chromatography (100% Et$_2$O) of 35 mg. of product provides 30 mg. of the faster running trans-olefin and 5 mg. of the cis-olefin.

Data for trans-olefin: IR(CHCl$_3$)μ 5.66, 5.77sh

NMR (300 MHz, CDCl$_3$)δ 2.02–2.22 (m, φCH$_2$CH$_2$), 2.61–2.82 (m, φCH$_2$CH$_2$), 2.85 (t, J=6.5 Hz, SCH$_2$CH$_2$N), 3.18 (dd, J$_{5,6}$=2 Hz, J$_{6,8}$=8 Hz, H$_6$) 3.40–3.47 (m, SCH$_2$CH$_2$N), 4.25 (dd, J=2 Hz & 7.5 Hz, H$_5$), 5.18 (s & m, H$_8$ & NHCO$_2$CH$_2$-arom.), 5.57 (midpt. of 2d, J=15 Hz, nonequivalent-OCO$_2$-CH$_2$-arom.), 5.66 (dd, J=15 Hz & 7.5 Hz, —CH=CHS), 5.92 (s, NH), 6.27 (d, J=15 Hz, CH=CHS), 7.15–8.24 (m, aromatics).

Data for cis-olefin: IR(CHCl$_3$)μ 5.68, 5.79sh;

NMR (300 MHz, CDCl$_3$)δ 2.06–2.20 (m, φCH$_2$CH$_2$), 2.60–2.86 (m, φCH$_2$CH$_2$ & SCH$_2$CH$_2$N), 3.23 (dd, J$_{5,6}$=2 Hz, J$_{6,8}$=7 Hz, H$_6$), 3.32–3.43 (m, SCH$_2$CH$_2$N), 4.54 (dd, J=2 Hz & 9.5 Hz, H$_5$), 5.18 (s & m, H$_8$ & —NHCO$_2$CH$_2$-arom, 5.52–5.69 (m, nonequivalent-OCO$_2$—CH$_2$-arom. and —CH=CHS), 6.00 (s, NH), 6.16 (d, J=9 Hz, CH=CHS), 7.14–8.22 (m, aromatics).

Step F

Preparation of α-hydroxy 3α-[(1-(R*)-o-nitrobenzylcarbonyldioxy-3-phenyl)-propyl]-4β-[2-[2-(p-nitrobenzyloxycarbonylamino)ethylthio]vinyl]-2-oxo-1-azetidinemalonic acid, di-p-nitrobenzyl ester (7).

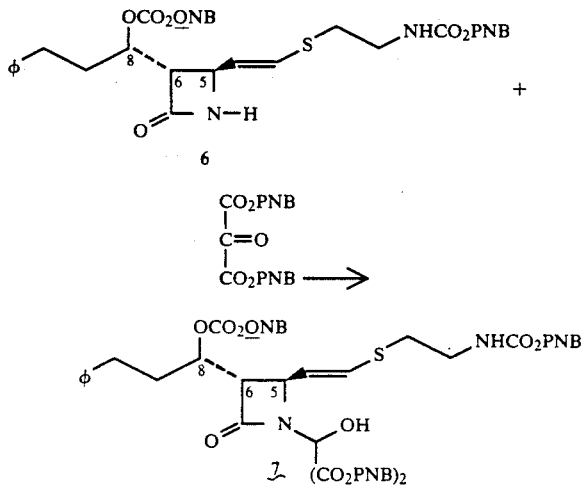

To a stirred solution of 473 mg. di(p-nitrobenzyl) ketomalonate (from Example 12, Step E) (mw=388; 1.22 mmole) in 40 ml. hot anhydrous toluene is added a solution of 516 mg. of mainly trans 6 (mw=664; 0.78 mmole) in 5 ml. THF (distilled from LAH) and 5 ml. anhydrous toluene. After some of the solvent is boiled off, additional anhydrous toluene is added, and the azeodrying process is repeated three times. The solution is then refluxed under $N_2$ for 30 minutes. Additional toluene is then allowed to boil off yet the volume is not allowed to diminish so much that precipitation occurs. Total heating time is approximately 2½ hours. The clear yellow reaction mixture is removed from the oil bath and placed under a stream of $N_2$ which instantaneously causes clouding. After concentration to a yellow oil, the residue is dissolved in $CH_2Cl_2$, dried over anhydrous $MgSO_4$, filtered, and concentrated under a $N_2$ stream to give crude 7.

The material is chromatographed on 120 g. silica gel packed and applied in $CHCl_3$. The column is eluted with $CHCl_3$ until the excess ketomalonate reagent emerges. Continued elution (1→2% MeOH/$CHCl_3$) provides 563 mg. of slightly impure 7. Preparative thin layer chromatography on silica gel (30% EA/$CH_2Cl_2$) provides 450 mg. of pure 7 (55%). IR ($CHCl_3$)μ5.67, 5.80sh NMR (300 MHz, $CDCl_3$)δ 2.02–2.14 (m, φ$CH_2CH_2$), 2.58–2.82 (m, φ$CH_2CH_2$ & $SCH_2CH_2N$), 3.22 (dd, $J_{5,6}$=2 Hz, $J_{6,8}$=7 Hz, $H_6$), 3.26–3.51 (m, $SCH_2CH_2N$), 4.66 (dd, J=2 Hz & 9 Hz, $H_5$), 5.15 (s & m, $H_8$ & $NHCO_2CH_2$-arom.), 5.29 (s, —COH($CO_2CH_2$-arom.)$_2$), 5.52 (midpt. of 2 d, J=14 Hz, nonequivalent-$OCO_2CH_2$-arom), 5.63 (dd, J=9 Hz, & 15 Hz, CH=CHS), 6.21 (d, J=15 Hz, CH=CHS), 7.13–8.22 (m, aromatics). Cis olefin or mixtures of cis and trans olefin may also be carried through the following steps to yield more (±)-9-benzylthienamycin.

Step G

Preparation of 3α-[(1-(R*)-o-nitrobenzylcarbonyldioxy-3-phenyl)-propyl]-4β-[2-[2-p-nitrobenzyloxycarbonylamino)ethylthio]vinyl]-2-oxo-1-azetidinemalonic acid, di-p-nitrobenzylester (8).

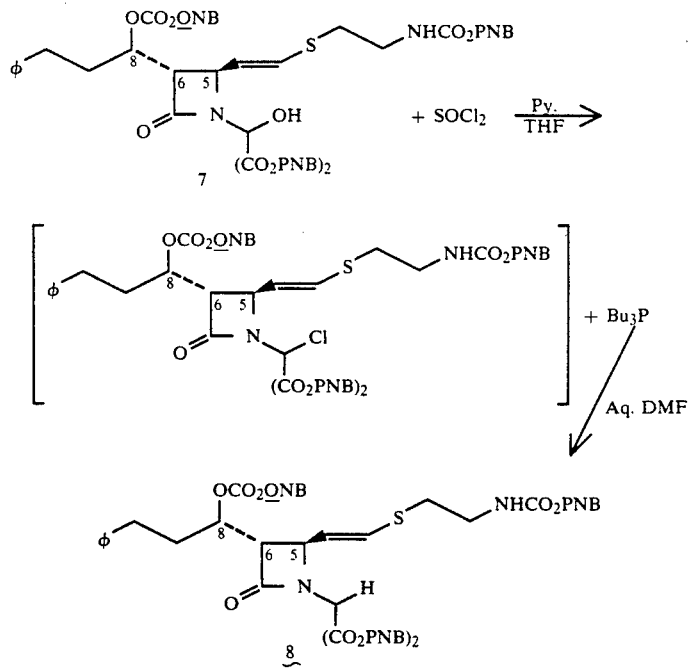

A solution of 431 mg. of 7 (mw=1052; 0.41 mmole) in $CH_2Cl_2$ is dried over anhydrous $MgSO_4$, filtered, concentrated under a $N_2$ stream, and dried further under high vacuum just prior to the following reaction. To a solution of 7 in 77 ml. THF (freshly distilled from LAH) at −20° C. is added 56 μl anhydrous pyridine (mw=79;

ρ=0.982; 0.70 mmole). With stirring under N₂, 80 mg. of freshly distilled thionyl chloride (mw=119; 0.67 mmole) in 0.7 ml. THF is added. The reaction mixture is stirred for 10 minutes at −20° C., then ½ hour at 0° C. and finally 1 hour at 25° C. The pyridine hydrochloride is filtered under N₂ and washed with a few ml. THF. The filtrate and washings are concentrated under a N₂ stream followed by pumping on high vacuum. The resulting yellow foam is swirled in 7 ml. anhydrous THF, and a small amount of orange-red insoluble material is filtered off under N₂. The filtrate is reconcentrated as above as a yellow foam.

φC$\underline{H}$₂CH₂ and SC$\underline{H}$₂CH₂N), 3.27 (dd, J₅,₆=2.5 Hz, J₆,₈=7.5 Hz, H₆), 3.30–3.42 (m, SC$\underline{H}$₂CH₂N), 4.54 (dd, J=2.5 Hz and 9 Hz, H₅), 5.13–5.36 (m, NHCO₂CH₂-arom. and C$\underline{H}$(CO₂C$\underline{H}$₂-arom)₂), 5.44–5.61 (m, —O-CO₂CH₂-arom. and CH=C$\underline{H}$S), 6.23 (d, J=15 Hz, CH=C$\underline{H}$S), 7.13–8.22 (m, aromatics).

Step H

Preparation of 2,2-bis(carbo-p-nitrobenzyloxy)-4-bromo-6-exo-[(1-(R*)-o-nitrobenzylcarbonyldioxy-3-phenyl)propyl]-3-[(2-p-nitrobenzyloxycarbonylamino)ethylthio]-1-azabicyclo[3.2.0]heptan-7-one (9).

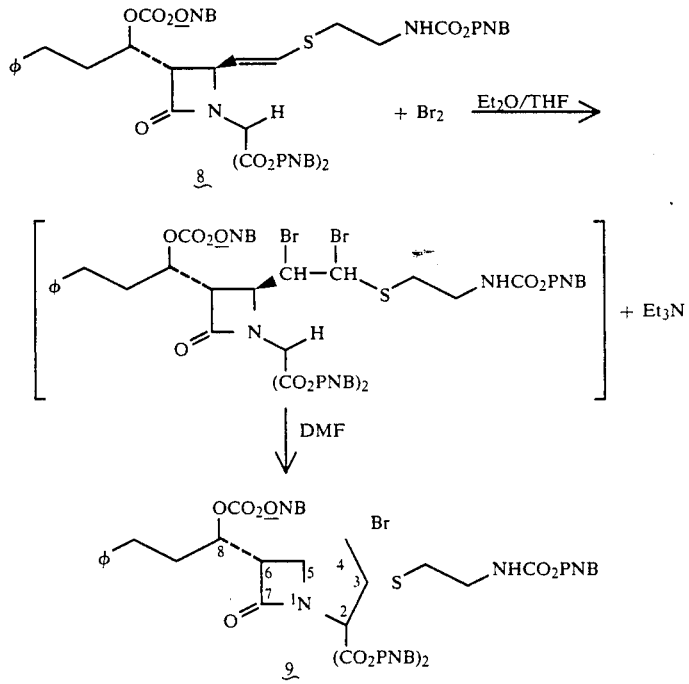

To this freshly prepared chloro compound is added with stirring a freshly shaken suspension of 181 mg. tributylphosphine (mw=202; 0.90 mmole) in 10.4 ml. 9:1 DMF—H₂O followed by 83 mg. K₂HPO₄ (mw=174; 0.48 mmole). The reaction mixture is stirred at 25° C., for 35 minutes. After dilution with EA and brine, the layers are separated, and the aqueous one is extracted two times with EA. The combined organic layers are washed one time with brine, dried over anhydrous MgSO₄, filtered and concentrated under a N₂ stream followed by pumping on high vacuum to give crude 8. The residue is slurried with a small volume of petroleum ether. The supernatant is removed, and the process repeated a few times. The petroleum ether supernatants containing some of the excess n-Bu₃P and n-Bu₃P(O) are discarded.

The residue is chromatographed on 40 g. silica gel packed, applied in, and eluted with CHCl₃. Those fractions containing product are combined, concentrated under a N₂ stream and then on high vacuum to give 286 mg. of slightly impure 8. Preparative thin layer chromatography on silica gel (40% acetone/hexane) then provides 251 mg. of pure 8 (59%).

IR(CHCl₃)μ 5.64 sh, 5.71, 5.81 sh NMR (300 MHz, CDCl₃)δ1.99–2.18 (m, φC$\underline{H}$₂CH₂), 2.58–2.82 (m, To 8.5 ml. CCl₄ (dried over 4A Linde molecular sieves) is added 0.2 ml. Br₂ (mw=160; 3.9 mmole). To 0.244 g. of 8 (mw=1036; 0.236 mmole) in 6 ml. THF (freshly distilled from LAH) and 1.8 ml. Et₂O (dried over 3A 1/16″ Linde molecular sieves) at 0° C. under N₂ with stirring is added dropwise 0.6 ml. of the above 0.45M Br₂ solution (0.27 mmole). After 15 minutes at 0° C., 143 μl triethyl amine (mw=101; ρ=0.729; 1.03 mmole) is added immediately followed by 3.4 ml. ice-cold DMF (distilled from CaSO₄ at 40 mm and stored over 4A Linde molecular sieves). The ice-bath is removed, and stirring at room temperature is continued for 2 hours. The reaction mixture is poured into a stirred ice-cold mixture of 1.1 ml. 1M KH₂PO₄—H₂O-EA. The layers are separated, and the aqueous one is saturated with NaCl and re-extracted with EA. The combined organic layers are washed once with brine, dried over anhydrous MgSO₄, and filtered. The filtrate is concentrated under a N₂ stream and then pumped on high vacuum to hive crude 9.

Preparative thin layer chromatography on silica gel (40% acetone/hexane) provide 250 mg. of 9 (93%). IR (CHCl₃)μ 5.61, 5.74, 5.81 sh; NMR (300 MHz, d₆- acetone)δ peaks related to major diasteriomer: 2.10 (m buried under d6-acetone, φCH2CH2), 2.71–3.16 (m, φCH2CH2 and SCH2CH2N), 3.37–3.53 (m, SCH2CH2N), 3.94 (dd, $J_{5,6}=3$ Hz, $J_{6,8}=5.5$ Hz, H6), 4.41 (dd, $J_{5,6}=3$ Hz, $J_{4,5}=6$ Hz, H5), 4.52 (d, $J_{3,4}=6$ Hz, >CHS), 5.11 (dd appearing as a t, $J_{4,5}=J_{3,4}=6$ Hz, >CHBr), 5.21–5.65 (m, all CH2-arom. and H8), 6.72 (br, NH), 7.2–8.27 (m,aromatics); peaks unique to two minor diastereomers 4.13 (m, H6), 4.24 (m, H5), 4.36 (m, >CHS and >CHBr of one minor diastereomer), 5.02 (d, $J_{3,4}=5$ Hz, >CHS of 2nd minor diastereomer), 5.14 (m, >CHBr of 2nd minor diastereomer.

Step I

Preparation of
2,2-bis(carbo-p-nitrobenzyloxy)-6-exo[(1-(R*)-o-nitrobenzylcarbonyldioxy-3-phenyl)
propyl]-3-[(2-p-nitrobenzyloxycarbonylamino(ethylthio]-1-azabicyclo[3.2.0]hept-3-en-7-one (10).

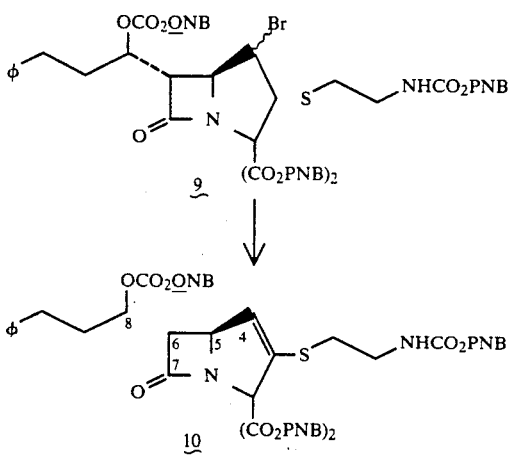

To 80 mg anhydrous silver fluoride (mw=127; 0.63 mmole) is added a solution of 503 mg of 9 (mw=1114; 0.45 mmole) in 13 ml anhydrous pyridine. Under N2, the reaction mixture is stirred at room temperature in the dark for one hour and then poured into cold water and EA. After separation of the layers, the aqueous one is extracted two times with EA and one time with CHCl3. Each organic layer is extracted one time with H2O and one time with brine. The combined organic layers are dried over anhydrous MgSO4, filtered, and concentrated under a N2 stream followed by pumping on high vacuum to give crude 10. Preparative thin layer chromatography on silica gel (40% acetone/hexane)provides 398 mg of 10 which by thin layer chromatography (3% Et2O/CH2Cl2) still contained a slightly faster impurity. Therefore, further preparative thin layer chromatography (3% Et2O/CH2Cl2) provides 255 mg of pure 10 (55%).

IR(CHCl3)μ 5.61, 5.73, 5.81 sh
NMR (300 MHz, CDCl3)δ 2.04–2.14(m,φCH2CH2) 2.61–2.83 (m,φCH2CH2) 2.91–3.08(m,SCH2CH2N), 3.36–3.46 (m,H6 & SCH2CH2N), 4.70(brs*,H5), 5.16(s & m, NHCO2—CH2-aromatics & H8), 5.29 & 5.31 (2s, >CCO2CH2arom.)2), 5.58(midpt. of 2d,J=15 Hz, nonequivalent —OCO2—CH2-arom.), 6.12(br s*, vinyl H4), 7.14–8.22(m,aromatics).

* 60 MHz shows additional couplings not observable with 300 MHz: 4.70(dd, $J_{5,6}=3$ Hz; $J_{4,5}=1.5$ Hz,H5), 6.12(d,$J_{4,5}=1.5$ Hz, vinyl H4).

Step J

Preparation of
2-carbo-p-nitrobenzyloxy-6-exo[(1-(R*)-o-nitrobenzyl-carbonyldioxy-3-phenyl)propyl]-3-[2-p-nitrobenzyloxycarbonylamino)ethylthio]-1-azabicyclo
[3.2.0]hept-3-en-7-one (11).

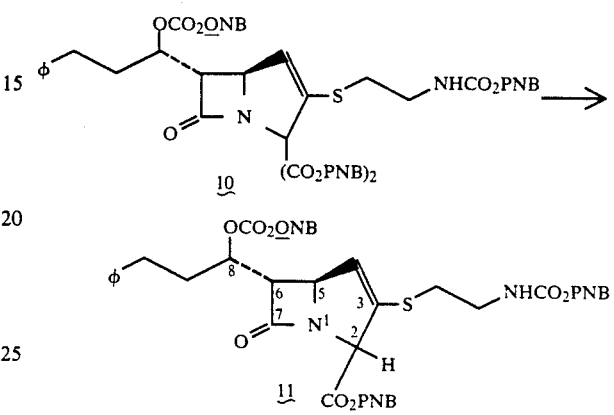

A solution of 144 mg of 10 (mw=1034; 0.014 mmole) in 1.5 ml S-collidine (distilled from powdered KOH~30 mm pressure) is added to 25.1 mg anhydrous LiI (dried for few hours at 100° C. over P2O5 under vacuum) (mw=134; 0.19 mmole). With stirring under N2, the reaction mixture is heated in an oil bath at 120°–130° C. After a total of 30 minutes, the reaction mixture is cooled to 25° C., diluted with CH2Cl2, and transferred to a round bottom flask for concentration under a N2 stream and then on high vacuum. Partitioning the residue between EA-H2O and 2.3 ml 1M KH2PO4 is followed by extraction of the aqueous layer two additional times with EA and one time with CHCl3. Each organic layer is then backwashed with brine. The combined organic layers are dried over anhydrous MgSO4, filtered, concentrated under a N2 stream and then on high vacuum to give crude 11.

Preparative thin layer chromatography on silica gel (40% acetone/hexane) provides 57 mg of slightly impure 11 and 48 mg of slightly impure starting material, travelling just slightly slower.

Two subsequent decarbalkoxylations (starting with 146 mg and 234 mg of 10 followed by preparative thin layer chromatography as above yields a total (for the three runs) of 200 mg slightly impure 11 and 111 mg slightly impure starting material. Further preparative thin layer chromatography on silica gel (5% Et2O/CH2Cl2) provides 164 mg of pure 11(38%). Similar chromatography of the recovered starting material provides 78 mg of pure 10(15%) which may be recycled.

Data for 11:
IR(CHCl3)μ 5.63, 5.72, 5.76
NMR(300 MHz, CDCl3)δ 2.07–2.15(m,φCH2CH2) 2.63–2.85(m,φCH2CH2), 2.89–3.09(m,SCH2CH2N), 3.33 (dd,$J_{5,6}=2.5$ Hz, $J_{6,8}=7.5$ Hz, H6), 3.40–3.49

(m,SCH₂CH₂N), 4.66(brs*,H₅), 5.19(s & m, NHCO₂CH₂-arom., H₈ and H₂), 5.27(midpt. of 2d, J=15 Hz, nonequivalent CO₂CH₂-arom.), 5.60(midpt. of 2d, J=14 Hz, nonequivalent-OCO₂CH₂-arom.), 5.94(brs,* vinyl H₄), 7.15-8.24(m,aromatics).

*60 MHz shows additional couplings not observable with 300 MHz: 4.57-4.70(m,coupling to H₆,vinyl H₄, and homoallylic coupling to H₂ evident, H₅), 5.94 overlapping dd appearing as a t, J₂,₄=J₄,₅=1.5 Hz, vinyl H₄).

Step K

Preparation of 2-carbo-p-nitrobenzyloxy-6-exo-[(1-(R*)-o-nitrobenzylcarbonyldioxy-3-phenyl)propyl]-3-[(2-p-nitrobenzyloxycarbonylamino)ethylthio]-1-azabicyclo[3.2.0]hept-2-en-7-one (12).

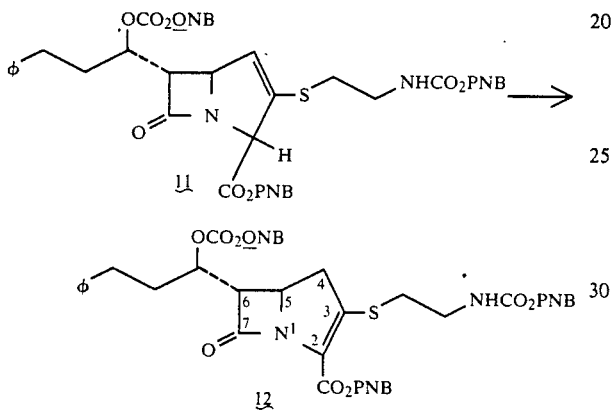

To 52 mg of 11 (mw=855; 0.061 mmole) in 0.75 ml DMSO (distilled from CaH₂ at 8 mm and stored over 4A Linde Molecular Sieves) is added 102 μl diisopropylamine (distilled from NaH under N₂ and stored over 4A Linde molecular sieves) (mw=101; ρ=0.722; 0.73 mmole). The stopped reaction mixture is stirred for a few minutes and then allowed to stand for 2.5 hours. The amine and most of the DMSO are then concentrated off under high vacuum with no external heating. The residue is chased two times with EA and two times with CHCl₃ to give a yellow foam essentially free of DMSO. Preparative thin layer chromatography on silica gel (15% EA/CHCl₃) provides 10 mg of the more polar product 12. Extraction of the starting material band yields 39 mg recovered 11. Resubmitting 11 to the reaction conditions and isolation procedure three more times gives a total of 24 mg of 12. A final preparative thin layer chromatography of 12 on silica gel (50% EA/hexane) removes two very minor less polar impurities and provides 22 mg of pure 12(42%). A similar final purification of recovered starting material (40% EA/hexane) yields 11 mg of recovered 11 (21%).

Data for 12:
IR(CHCl₃)μ5.63, 5.74 sh, 5.81
NMR(300 MHz, CDCl₃)δ2.10-2.22 (m,φCH₂CH₂), 2.64-2.88(m,φCH₂CH₂), 2.92-3.12(m,SCH₂CH₂N, & dd, J₄,₅=8.5 Hz & J₄,₄'=18 Hz, H₄), 3.36(dd, J₄',₅=10 Hz,J₄',₄=18 Hz, H₄'), 3.40-3.50 (m,SCH₂CH₂N and H₆), 4.25-4.32(m,H₅), 5.18(midpt. of m,H₈), 5.19(s,—NHCO₂CH₂-arom.), 5.36(midpt. of 2 widely spaced d, J=14 Hz, nonequivalent —CO₂CH₂-arom.), 5.58(midpt. of 2 widely spaced d,J=14 Hz, nonequivalent, —OCO₂CH₂-arom.), 7.18-8.24(m,aromatics).

When spectrum is run in d₆-acetone, H₆ is no longer buried under SCH₂CH₂N: NMR(300 MHz,d₆-acetone) δ 3.82(dd,J₅,₆=3 Hz, J₆,₈=6 Hz,H₆).

Step L

Preparation of (±)-9-benzylthienamycin (13).

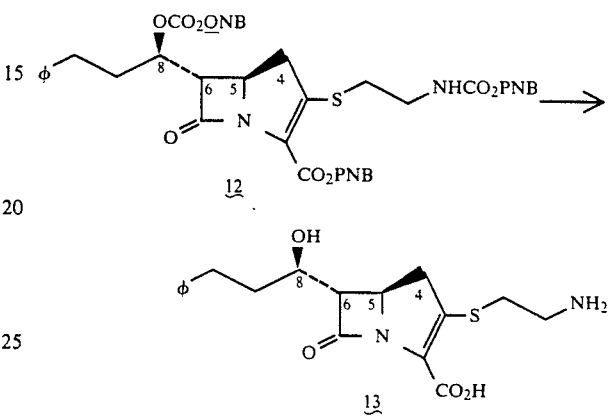

To 5.3 mg 12(mw=855; 0.0062 mmole) is added 350 μl dioxane, 350 μl ethanol, 175 μl deionized water, and 11 μl 1M K₂HPO₄. To the resultant clear solution is added 5.3 mg of 10% Pd/C and a glass bead for efficient mixing. The suspension is flushed with N₂, then 5-6 times alternately with 50 psi H₂ and vacuum. Finally, it is shaken under a 50 psi H₂-atmosphere for 50 minutes. After cooling in an ice bath followed by centrifugation, the supernatant is removed and filtered through a small plug of cotton. The Pd/C is washed and centrifuged 5× with small volumes of cold, deionized water, and the supernatants are filtered as above. The combined, cold filtrates are extracted 3×0.5 ml Et₂O, 2×0.5 ml EA, and then 2×0.5 ml Et₂O. The aqueous layer is then pumped briefly on a water aspirator to remove any residual organic solvents. The remaining solution (ca0.7 ml in volume) is chromatographed (portionwise) by reverse phase HPLC on a Waters analytical μC₁₈-column (eluting with 10% THF in water). The peak having a UV$_{Max.}$ at 299 mμ is collected and is estimated to contain 280-300 ug of 13 (13% yield based upon hydroxylamine quenchable UV). The solution is concentrated on a rotary evaporator under high vacuum and with a water bath no warmer than 25°-30° C. to a final volume of ca 1 ml. The concentrate is then shell-frozen in a lyophilizing vial and lyophilized in a shelf lyophilizer wherein the shelf may be held at −20° C. The product exhibits a 300 MHz NMR spectrum in D₂O with peaks at: δ (no internal standard is used) 1.92-2.04 (m, φCH₂CH₂), 2.70-3.28 (m, φCH₂CH₂, SCH₂CH₂N, and H₄'s), 3.66 (dd, J₅,₆=3 Hz, J₆,₈=6 Hz,H₆), 4.10-4.17 and 4.24-4.30 (m's, H₅ & H₈), 4.90 (HDO), 7.36-7.50 (m,φ).

EXAMPLE 32

Following the procedure of the foregoing Examples and text, the following representative compounds of the present invention (Table I) are obtained by analogy.

TABLE I

| Compound | R⁸ | R⁶ | R⁷ | Remarks |
|---|---|---|---|---|
| (1.) | —(CH₂)₃NH₂ | H | CH₂OH | From BrS(CH₂)₃NHCO₂PNB, Example 13, Step E; or HS(CH₂)₃NHCO₂PNB, Example 12, Step A. |
| (2.) | —(CH₂)₃NHC(=NH)H | H | CH₂OH | From Compound 1. of Example 32 in reaction with methyl formimidate hydrochloride in water at pH 8.5. |
| (3.) | —(CH₂)₃NHC(=NH)CH₃ | H | CH₂OH | From Compound 1. of Example 32 in reaction with ethyl acetimidate hydrochoride in water at pH 8.5. |
| (4.) | —C₆H₄—CH₂NH₂ (para) | H | CH₂OH | From HS—C₆H₄—CH₂NHCO₂PNB, Example 12, Step A. |
| (5.) | —C₆H₄—CH₂NHC(=NH)H (para) | H | CH₂OH | As in 2., above. |
| (6.) | —C₆H₄—CH₂NHC(=NH)CH₃ (para) | H | CH₂OH | As in 3., above. |
| (7.) | —C₆H₄—CH₂NH₂ (meta) | H | CH₂OH | From HS—C₆H₄—CH₂NHCO₂PNB, Example 12, Step A. |
| (8.) | —C₆H₄—CH₂NHC(=NH)H (meta) | H | CH₂OH | As in 2., above. |
| (9.) | —C₆H₄—CH₂NHC(=NH)CH₃ (meta) | H | CH₂OH | As in 3., above. |
| (10.) | thiadiazolyl-CH₃ (S, N—N) | H | CH₂OH | From HS-thiadiazolyl-CH₃, Example 12, Step A. |
| (11.) | —CH(CH₃)—CH₂—NH₂ | H | CH₂OH | From HSCH(CH₃)CH₂NHCO₂PNB, Example 12, Step A; or BrSCH(CH₃)CH₂NHCO₂PNB, Example 13, Step E. |

TABLE I-continued

| | | | | |
|---|---|---|---|---|
| (12.) | —CH₃ | H | CH₂OH | From HSCH₃, Example 12, Step A; or BrSCH₃, Example 13, Step E. |
| (13.) | phenyl | H | CH₂OH | From HSφ, Example 12, Step A; or BrSφ, Example 13, Step E. |
| (14.) | 1-methyl-tetrazol-5-yl | H | CH₂OH | From: HS-(1-methyl-tetrazol-5-yl), Example 12, Step A. |
| (15.) | —CH₂CH(NH₂)CH₃ | H | CH₂OH | From HSCH₂CH(CH₃)NHCO₂PNB, Example 12, Step A; or BrSCH₂CH(CH₃)NHCO₂PNB, Example 13, Step E. |
| (16.) | —CH₂C(NH₂)(CH₃)CH₃ | H | CH₂OH | From HSCH₂C(CH₃)₂NHCO₂PNB, Example 12, Step A; or BrSCH₂C(CH₃)₂NHCO₂PNB, Example 13, Step E. |
| (17.) | pyridin-4-yl | H | CH₂OH | From 4-mercaptopyridine, Example 12, Step A. |
| (18.) | —CH₂CH₂NH₂ | H | CH₃CH(NH₂)— | |
| (19.) | -φ | CH₃ | CH₃CH(NH₂)— | |
| (20.) | —CH₂CH₂CH₂NH₂ | CH₃ | CH₃CH(OH)— | |
| (21.) | -φ | CH₃ | CH₂OH | |
| (22.) | CH₂CH₂NH₂ | H | (CH₃)₂CHCH₂CH(OH)— | |
| (23.) | CH₂CH₂NH—C(=NH)—H | H | (CH₃)₂CHCH₂CH(OH)— | |
| (24.) | CH₂CH₂NH—C(=NH)—CH₃ | H | (CH₃)₂CHCH₂CH(OH)— | |
| (25.) | CH₂CH₂NH₂ | CH₃ | (CH₃)₂CHCH₂CH(OH)— | |
| (26.) | CH₂CH₂NH—C(=NH)—H | CH₃ | (CH₃)₂CHCH₂CH(OH)— | |
| (27.) | CH₂CH₂NH—C(=NH)—CH₃ | CH₃ | " | |
| (28.) | CH₂CH(CH₃)NH₂ | CH₃ | " | |
| (29.) | CH₂CH₂NH₂ | H | cyclopropyl-CH(OH)— | |

TABLE I-continued

| | | | |
|---|---|---|---|
| (30.) | " | CH₃ | " |
| (31.) | CH₂CH₂NH.C(=NH)—H | H | " |
| (32.) | CH₂CH₂NH—C(=NH)—CH₃ | H | " |
| (33.) | CH₂CH₂NHC(=NH)—H | H | φCH₂CH₂C(OH)— |
| (34.) | CH₂CH₂NHC(=NH)CH₃ | H | " |
| (35.) | CH(CH₃)₂CH₂NH₂ | H | " |
| (36.) | φ | H | CF₃CH(OH)— |
| (37.) | 1-methyl-tetrazol-5-yl | H | cyclopropyl-CH₂CH(OH)— |
| (38.) | CH₂CH₂NH₂ | H | CH₃CH₂CH(OH)— |
| (39.) | CF₃ | H | " |
| (40.) | CH₂CH₂N(morpholino) | H | 1,3-dioxolan-2-yl-CH(OH)— |
| (41.) | CH₂CH₂NH₂ | H | HOCH₂—CH₂— |
| (42.) | CH₂CO₂CH₃ | H | CH₃CH(OH)— |
| (43.) | 4-(H₂NCH₂)C₆H₄— | H | CH₃CH₂CH(OH)— |
| (44.) | 4-methyl-thiazol-2-yl | H | 2-methylcyclopentan-1-ol |
| (45.) | pyridin-4-yl | H | HOCH₂CH₂— |
| (46.) | pyridin-4-yl | H | MeON=CH.CH₂— |
| (47.) | 1-(aminomethyl)-tetrazol-5-yl | H | HOCH₂—CH₂— |

TABLE I-continued

| | | | |
|---|---|---|---|
| (48.) | 3-phenyl-5-methylisoxazol-4-yl | H | $(CH_3)_2CHCH_2CH(OH)-$ |
| (49.) | 3-methyl-5-(aminomethyl)-1,2,4-thiadiazol-... (N=N, S, CH₂NH₂) | $CH_3$ | " |
| (50.) | $CH_2CH_2OH$ | H | $\phi CH_2CH_2\overset{OH}{\underset{\vert}{C}}-$ |
| (51.) | $CH_2CH_2NH_2$ | H | $\phi CH_2CH_2\overset{OH}{\underset{\underset{CO_2H}{\vert}}{CH}}-$ |
| (52.) | $CH_2CH_2NH_2$ | H | 1-methyl-5-(tetrazolyl)-$N-CH_2\overset{OH}{\underset{\vert}{CH}}-$ (with CH₃) |
| (53.) | $CH_2CH_2NH_2$ | H | 3-(aminomethyl)phenyl-$CH_2\overset{OH}{\underset{\vert}{CH}}-$ |
| (54.) | phenyl | H | " |
| (55.) | 4-pyridyl | H | " |
| (56.) | $CH_2CH_2NH\overset{NH}{\underset{\Vert}{C}}-CH_3$ | H | cyclopropyl-$\overset{OH}{\underset{\vert}{CH}}-$ |
| (57.) | $CH_2CH_2NH\overset{NH}{\underset{\Vert}{C}}CH_3$ | H | cyclopropyl-$CH_2\overset{OH}{\underset{\vert}{CH}}-$ |
| (58.) | $CH_2CH_2NH\overset{NH}{\underset{\Vert}{C}}H$ | H | cyclopropyl-$CH_2\overset{OH}{\underset{\vert}{CH}}-$ |
| (59.) | $CH_2CH_2NH_2$ | H | " |
| (60.) | " | $CH_3$ | " |
| (61.) | $CH_2CH_2NH\overset{NH}{\underset{\Vert}{C}}H$ | $CH_3$ | " |
| (62.) | $CH_2CH_2NH\overset{NH}{\underset{\Vert}{C}}CH_3$ | $CH_3$ | " |

TABLE I-continued

| | | | |
|---|---|---|---|
| (63.) | CH₂CH₂NHCH(=NH) | H | CH₃CH₂CH(OH)— |
| (64.) | CH₂CH₂NHCCH₃(=NH) | H | " |
| (65.) | CH₂CH₂NH₂ | CH₃ | " |
| (66.) | CH₂CH₂NHCCH₃(=NH) | CH₃ | " |
| (67.) | CH₂CH₂NHCH(=NH) | CH₃ | " |
| (68.) | CH₂CH₂NHCCH₃(=NH) | H | φCH₂CH₂CH(OH)— |
| (69.) | CH₂CH₂NHCH(=NH) | H | " |
| (70.) | " | H | φCH(CO₂H)CH₂CH(OH)— |
| (71.) | 4-pyridyl | CH₃ | φCH(CO₂H)CH₂CH(CH)— |
| (72.) | " | " | φCH₂CH₂CH(OH)— |
| (73.) | " | " | (CH₃)₂CHCH(OH)— |
| (74.) | " | " | (CH₃)₂CH—CH₂CH(OH)— |
| (75.) | " | " | CH₃CH₂CH(OH)— |
| (76.) | CF₃ | " | HOCH₂CH₂— |
| (77.) | " | " | (CH₃)₂CHCH₂CH(OH)— |
| (78.) | " | " | (CH₃)₂CHCH(OH)— |
| (79.) | " | " | φCH₂CH₂CH(OH)— |
| (80.) | " | " | φCH(CO₂H)CH₂CH(OH)— |
| (81.) | " | " | cyclopropyl-CH(OH)— |
| (82.) | " | " | cyclopropyl-CH₂CH(OH)— |

TABLE I-continued

| | | | |
|---|---|---|---|
| (83.) | " | " | CF$_3$CH(OH)— |
| (84.) | " | H | " |
| (85.) | " | " | HOCH$_2$CH$_2$— |
| (86.) | CF$_3$ | H | cyclopropyl-CH(OH)— |
| (87.) | " | " | φ-CH(CO$_2$H)CH$_2$CH(OH)— |
| (88.) | " | " | φCH$_2$CH$_2$CH(OH)— |
| (89.) | " | " | (CH$_3$)$_2$CHCH(OH)— |
| (90.) | " | " | (CH$_3$)$_2$CHCH$_2$CH(OH)— |
| (91.) | 1-methyl-tetrazol-5-yl | " | " |
| (92.) | " | " | CH$_3$CH$_2$CH(OH)— |
| (93.) | " | " | (CH$_3$)$_2$CHCH(OH)— |
| (94.) | " | " | φCH$_2$CH$_2$CH(OH)— |
| (95.) | " | " | φCH$_2$CH$_2$CH(OH)— with CO$_2$H |
| (96.) | " | " | cyclopropyl-CH(OH)— |
| (97.) | " | " | CF$_3$CH(OH)— |
| (98.) | " | " | HOCH$_2$CH$_2$— |
| (99.) | 4-(CH$_2$NH$_2$)phenyl | H | CF$_3$CH(OH) |
| (100.) | " | CH$_3$ | " |
| (101.) | 3-methyl-1,2,4-thiadiazol-5-yl | H | " |

TABLE I-continued

| | | | |
|---|---|---|---|
| (102.) | " | " | ![cyclopropyl-CH(OH)-CH2-] |
| (103.) | " | " | ![cyclopropyl-CH(OH)-] |
| (104.) | " | " | (CH₃)₂CH—CH(OH)— |
| (105.) | " | " | HOCH₂CH₂— |
| (106.) | " | CH₃ | (CH₃)₂CH—CH(OH)— |
| (107.) | " | " | HOCH₂CH₂— |
| (108.) | " | " | ![cyclopropyl-CH(OH)-] |
| (109.) | " | " | ![cyclopropyl-CH(OH)-CH2-] |
| (110.) | " | " | φCHCH₂CH(OH)— with CO₂H |
| (111.) | " | " | φCH₂CH₂CH(OH)— |
| (112.) | " | " | (CH₃)₂CHCH(OH)— |
| (113.) | " | " | (CH₃)₂CHCH₂CH(OH)— |
| (114.) | 4-pyridyl | H | " |
| (115.) | 4-pyridyl | H | (CH₃)₂CHCH(OH)— |
| (116.) | " | " | φCH₂CH₂CH(OH)— |
| (117.) | " | " | φCHCH₂CH(OH)— with CO₂H |
| (118.) | " | " | ![cyclopropyl-CH(OH)-] |

TABLE I-continued

| | | | |
|---|---|---|---|
| (119.) | " | " | △-CH₂CH(OH)- |
| (120.) | " | " | CH₃CH(OH)- |
| (121.) | " | " | CH₃CH₂CH(OH)- |
| (122.) | " | CH₃ | CH₃CH(OH)- |
| (123.) | " | " | △-CH₂CH(OH)- |
| (124.) | " | " | △-CH(OH)CH₃ |
| (125.) | CH₂CH₂NHC(=NH)CH₃ | " | " |
| (126.) | " | CH₃ | " |
| (127.) | CH₂CH₂NHC(=NH)—H | " | " |
| (128.) | CH₂CH₂NH₂ | " | " |
| (129.) | CH₂CH₂NH₂ | H | CF₃CH(OH)- |
| (130.) | CH₂CH₂NH—C(=NH)CH₃ | " | " |
| (131.) | CH₂CH₂NHC(=NH)H | " | " |
| (132.) | " | CH₃ | " |
| (133.) | CH₂CH₂NHC(=NH)CH₃ | " | " |
| (134.) | CH₂CH₂NH₂ | " | " |
| (135.) | " | " | HO-CHCH₂- |
| (136.) | CH₂CH₂NHC(=NH)CH₃ | " | " |
| (137.) | CH₂CH₂NHC(=NH)H | " | " |
| (138.) | " | H | " |
| (139.) | CH₂CH₂NHC(=NH)CH₃ | " | " |

TABLE I-continued

| | | | |
|---|---|---|---|
| (140.) | 4-(CH₂NH₂)-C₆H₄- | " | " |
| (141.) | " | CH₃ | " |
| (142.) | 4-(CH₂NH-C(=NH)-CH₃)-C₆H₄- | CH₃ | HOCH₂CH₂- |
| (143.) | 4-(CH₂NHCH=NH)-C₆H₄- | " | " |
| (144.) | 4-(CH₂NH₂)-C₆H₄- | H | CF₃CH(OH)- |
| (145.) | 1-methyl-tetrazol-5-yl | CH₃ | CH₃CH(OH)CH- |
| (146.) | " | " | cyclopropyl-CH₂CH(OH)- |
| (147.) | " | " | cyclopropyl-CH(OH)- |
| (148.) | " | " | CF₃CH(OH)- |
| (149.) | " | " | φCH₂CH₂CH(OH)- |
| (150.) | " | " | φCH(CO₂H)CH₂CH(OH)- |
| (151.) | " | " | (CH₃)₂CHCH(OH)- |
| (152.) | " | " | (CH₃)₂CHCH₂CH(OH)- |
| (153.) | 1-methyl-tetrazol-5-yl | CH₃ | HOCH₂CH₂- |
| (154.) | 4-methyl-thiadiazol-2-yl | H | CH₃CH₂CH(OH)- |
| (155.) | " | " | φCH₂CH₂CH(OH)- |

TABLE I-continued (156.) " " $\phi CHCH_2CH-$ with OH above CH and $CO_2H$ below

| Compound | |
|---|---|
| 157–313 | Compounds 157–313 correspond sequentially to compounds 1–156, above, except that the value for $R^7$ is taken as $CH_3CH(OH)$ rather than the values shown for compounds 1–156. |
| 314–470 | Compounds 314–470 correspond sequentially to compounds 1–156, above, except that the value for $R^7$ is taken as $CH_3CH_2$ rather than the values shown for compounds 1–156. |
| 471–627 | Compounds 471–627 correspond sequentially to compounds 1–156, above, except that the value for $R^7$ is taken as $Cl_2CHCH(OH)$ rather than the values shown for compounds 1–156. |
| 628–784 | Compounds 628–784 correspond sequentially to compounds 1–156, above, except that the value for $R^7$ is taken as $CF_3CH(OH)$ rather than the values shown for compounds 1–156. |
| 785–941 | Compounds 785–941 correspond sequentially to compounds 1–156, above, except that the value for $R^7$ is taken as $HOCH_2CH(OH)$ rather than the values shown for compounds 1–156. |
| 942–1098 | Compounds 942–1098 correspond sequentially to compounds 1–156, above, except that the value for $R^7$ is taken as $ClCH_2CH(OH)$ rather than the values shown for compounds 1–156. |
| 1099–1255 | Compounds 1099–1255 correspond sequentially to compounds 1–156, above, except that the value for $R^7$ is taken as $CH_3CH_2CH(OH)$ rather than the values shown for compounds 1–156. |
| 1256–1412 | Compounds 1256–1412 correspond sequentially to compounds 1–156, above, except that the value for $R^7$ is taken as cyclopropyl–CH(OH) rather than the values shown for compounds 1–156. |
| 1413–1569 | Compounds 1413–1569 correspond sequentially to compounds 1–156, above, except that the value for $R^7$ is taken as $H_2NCH_2CH(OH)$ rather than the values shown for compounds 1–156. |
| 1570–1726 | Compounds 1570–1726 correspond sequentially to compounds 1–156, above, except that the value for $R^7$ is taken as $CF_2HCH(OH)$ rather than the values shown for compounds 1–156. |
| 1727–1883 | Compounds 1727–1883 correspond sequentially to compounds 1–156, above, except that the value for $R^7$ is taken as $HOCH_2$ rather than the value shown for compounds 1–156. |
| 1884–2040 | Compounds 1884–2040 correspond sequentially to compounds 1–156, above, except that the values for $R^7$ is taken as $CH_3OCH_2CH(OH)$ rather than the values shown for compounds 1–156. |
| 2041–2197 | Compounds 2041–2197 correspond sequentially to compounds 1–156, above, except that the values for $R^7$ is taken as $(CH_3)_3CCH_2CH(OH)$ rather than the values shown for compounds 1–156. |
| 2198–2354 | Compounds 2198–2354 correspond sequentially to compounds 1–156, above, except that the values for $R^7$ is taken as $HO_2CCH_2$ rather than the values shown for compounds 1–156. |
| 2355–2511 | Compounds 2355–2511 correspond sequentially to compounds 1–156, above, except that the values for $R^7$ is taken as $FCH_2CH(OH)$ rather than the values shown for compounds 1–156. |

NOTES FOR TABLE I EXAMPLE 32, COMPOUNDS 18–156

(18.) Same as Example 7 substituting the produce from Example 22 and then carrying on following procedures of Example 12.

NOTES FOR TABLE I EXAMPLE 32, COMPOUNDS 18–156 -continued (19.) Same as Examples 21–22, except substituting the product from Example 5 in which acetaldehyde has been substituted for formaldehyde. The resultant

NOTES FOR TABLE I EXAMPLE 32, COMPOUNDS 18-156 product is exposed to the conditions of Example 7 and 12 except that in Step 12a, thiophenol is substituted for the blocked cysteamine.

(20.) Same as in Example 5 except substituting acetaldehyde for formaldehyde. The product is treated as in Examples 6, 7 and 12, except that in 12a the blocked homocysteamine is substituted for the blocked cysteamine.

(21.) From Example 12 by substituting in Step A thiophenol for the blocked cysteamine.

(22.) Following Example 31 except substituting isovaleraldehyde in Step A for isobutyraldehyde.

(23.) By treating compound 22, Example 32 with methylformimidate hydrochloride in water at pH 8.5

(24.) By treating compound 22 Example 32 with methyl acetimidate hydrochloride in water at pH 8.5

(25.) By following the procedure of Example 13, except substituting the product from Example 13, Step A' for the simple blocked vinylazetidinone.

(26.) By treating compound 25 Example 32 with methylformimidate hydrochloride in water at pH 8.5.

(27.) By treating compound 25 Example 32 with methylacetimidate hydrochloride in water at pH 8.5.

(28.) As in preparation of compound 25 Example 32 except that 2-amino-2-mercaptopropane is substituted for cysteamine.

(29.) As in Example 31 except substituting cyclopropane carboxaldehyde for isobutyraldehyde in Step A.

(30.) As in preparing compound 29 Example 32, except substituting the product from Example 13 Step A' for the simple blocked vinyl azetidinone.

(31.) From compound 29 Example 32 by treatment with methylformimidate hydrochloride in water at pH 8.5

(32.) From compound 29 Example 32 by treatment with methylacetimidate hydrochloride in water at pH 8.5.

(33.) From the product of Example 31a by treatment with methylformimidate hydrochloride in water at pH 8.5

(34.) From the product of Example 31a by treatment methylacetimidate hydrochloride in water at pH 8.5.

(35.) As in Example 31a except substituting 1-aminopropane-2-thiol for cysteamine.

(36.) If in Example 15, trifluoroacetaldehyde is substituted for acetaldehyde and the product is carried through the steps of Example 16 except that thiophenol is substituted for the p-nitroCbz blocked cysteamine, the indicated compound is obtained.

(37.) If the procedure for the preparation of compound 57, Example 32 is carried out except that 5-mercapto-1-methyltetrazole is substituted for the p-nitroCbz blocked cysteamine, the indicated compound is obtained.

(38.) If the procedure in Example 31a is followed except that propionaldehyde is substituted for dihydrocinnamaldehyde, the indicated compound is obtained.

(39.) If the procedure for preparing compound 38 Example 32 is followed except that trifluoromethylmercaptan is substituted for the p-nitroCbz blocked cysteamine, the indicated compound is obtained.

(40.) If the procedure used in Example 15 is followed substituting the acetonide of dihydroxy-propionaldehyde for formaldehydr, and the product is exposed to the conditions of Example 16, except substituting N-2-mercapto ethyl-morpholine for the p-nitroCbz blocked cysteamine, the indicated product is obtained.

(41.) Following the procedure of Examples 15 and 16 except substituting ethylene oxide for the formaldehyde in the former, the indicated product is obtained.

(42.) Following the procedure of Examples 15 and 16 except substituting acetaldehyde for formaldehyde in the former and substituting methylmercapto-acetate for p-nitroCbz blocked cysteamine, the indicated compounds are obtained.

(43.) Following the procedure for the preparation of compound 38 Example 32, except substituting 4-(4-nitrobenzyloxycarbonylaminomethyl)-thiophenol for the p-nitroCbz blocked cysteamine in Step D, the indicated compound is obtained.

(44.) Following the procedure for the preparation of compound 41 example 32, except substituting cyclopentene oxide for ethylene oxide and 2-mercapto-5-methyl-1,3,4-thiadiazole for the p-nitroCbz blocked cysteamine, the indicated compound is obtained.

(45.) Following the procedure or the preparation of compound 41, Example 32 except substituting 4-mercaptopyridine for the p-nitroCbz blocked cysteamine the indicated compound is obtained.

(46.) If Compound 45 Example 32 is converted to the o-nitrobenzyl ester, isomerized to the $\Delta^1$ compound oxidized with Moffats reagent to the aldehyde, treated with methoxyamine to form the methoxime, re-isomerized to the $\Delta^2$ compound and photolytically deblocked, the indicated compound is obtained.

(47.) Following the procedure for Compound 45, Example 32, except substituting 5-mercapto-4-(4-nitrobenzyloxycarbonylaminomethyl)tetrazole for the 4-mercaptopyridine, the indicated compound is obtained.

(48.) Following the procedure for Compound 22, Example 32, except substituting 3-phenyl-5-methyl-4-mercapto-1,2-oxazole for the p-nitroCbz blocked cysteamine, the indicated compound is obtained.

(49.) Following the procedure for Compound 25 Example 32 except substituting 5-mercapto-2-(4-nitrobenzyloxycarbonylaminomethyl)-1,3,4-thiadiazole for the p-nitroCbz blocked cysteamine, the indicated compound is obtained.

(50.) Following the procedure of Example 31a, if the p-nitroCbz blocked cysteamine is replaced with 2-(4-nitrobenzylcarbonyldioxy)ethyl mercaptain the indicated compound is obtained (51.) Following the procedure of Example 31a, but replacing the dihydrocinnamaldehyde with 4-nitrobenzyl 2-phenyl-4-oxobutyrate, the indicated compound is obtained.

(52.) Following the procedure of Example 31 but substituting 2-(5-methyl-2-tetrazolyl)-acetaldehyde for the isobutyraldehyde, the indicated compound is obtained.

(53.) Following the procedure of Example 31, but substituting 3-(4-nitrobenzyloxycarbonylamino-methyl)phenylacetaldehyde for the isobutyraldehyde the indicated compound is obtained (54.) Following the procedure for Compound 53, Example 32, except substituting thiophenol for the p-nitroCbz blocked cysteamine, the indicated compound is obtained.

(55.) Following the procedure for Compound 53, Example 32 except substituting 4-mercapto-pyridine for the p-nitroCbz blocked cysteamine, the indicated compound is obtained.

(56.) If compound 29 Example 32 is treated with methylacetimidate hydrochloride in water at pH 8.5 the indicated compound is obtained.

(57.) If Compound 59, Example 32 is treated with methylacetimidate hydrochloride in water at pH 8.5 the indicated compound is obtained.

(58.) If Compound 59, Example 32 is treated with methylformimidate hydrochloride in water at pH 8.5 the indicated compound is formed.

(59.) If the procedure of Example 31 is used except that cyclopropylacetaldehyde is substituted for isobutyraldehyde, the indicated compound is obtained.

(60.) If the procedure used to prepare Compound 59 Example 32 is carried out, with the substitution of the product from Example 13, Step $A^1$ for the simple blocked vinyl azetidinone.

(61.) By treating compound 60, Example 32 with methylformimidate hydrochloride in water

NOTES FOR TABLE I EXAMPLE 32, COMPOUNDS 18-156

(62.) By treating product 60 Example 32 with methylacetimidate hydrochloride in water at pH 8.5.
(63.) By treating product 38 Example 32 with methylformimidate hydrochloride in water at pH 8.5
(64.) By treating product 38 Example 32 with methylacetimidate hydrochloride in water at pH 8.5.
(65.) If the compound obtained from Example 13, Step A$^1$, is used in place of the simple blocked vinyl azetidinone in the procedure for preparing compound 38 Example 32, the indicated compound is obtained.
(66.) By treating product 65 Example 32 with methylacetimidate hydrochloride in water at pH 8.5.
(67.) By treating product 65, Example 32 with methylformimidate hydrochloride in water at pH 8.5.
(68.) By treating the product from Example 31a with methylacetimidate hydrochloride in water at pH 8.5.
(69.) By treating the product from Example 31a with methylformimidate hydrochloride in water at pH 8.5.
(70.) By treating product 51 Example 32 with methylformimidate hydrochloride in water at pH 8.5.
(71.) If the procedure for preparing compound 55, Example 32 is followed except that 4-nitrobenzyl 2-phenyl-4-oxobutyrate is substituted for isovaleraldehyde and 4-mercaptopyridine is substituted for thiophenol, the indicated compound is formed.
(72.) As in 71 except substituting dihydrocinnamaldehyde for isovaleraldehyde.
(73.) As in 71 except substituting isobutyraldehyde for the isovaleraldehyde.
(74.) As in 71 except that isovaleraldehyde is kept and only the 4-mercaptopyridine for thiophenol change is made.
(75.) As in 71 except substituting propionaldehyde for the isovaleraldehyde.
(76.) The procedure for Compound 39 Example 32, is followed substituting the product from procedure 13 Step A$^1$ for the simple blocked vinyl azetidinone and ethylene oxide for propionaldehyde.
(77.) As in 76 except isovaleraldehyde is substituted for propionaldehyde.
(78.) As in 76 except isobutyraldehyde is substituted for propionaldehyde.
(79.) As in 76 except dihydrocinnamaldehyde is substituted for propionaldehyde.
(80.) As in 76 except 4-nitrobenzyl 2-phenyl-4-oxobutyrate is substituted for propionaldehyde.
(81.) As in 76 except cyclopropylcarboxaldehyde is substituted for propionaldehyde.
(82.) As in 76 except cyclopropylacetaldehyde is substituted for propionaldehyde.
(83.) As in 76 except trifluoroacetaldehyde is substituted for propionaldehyde.
(84.) The procedure for compound 39 Example 32 is followed substituting trifluoroacetaldehyde for propionaldehyde.
(85.) As in 84 except ethylene oxide is substituted for propionaldehyde
(86.) As in 84 except cyclopropylcarboxaldehyde is substituted for propionaldehyde.
(87.) As in 84 except 4-nitrobenzyl 2-phenyl-4-oxobutyrate is substituted for propionaldehyde.
(88.) As in 84 except dihydrocinnamaldehyde is substituted for propionaldehyde.
(89.) As in 84 except isobutyraldehyde is substituted for propionaldehyde.
(90.) As in 84 except isovaleraldehyde is substituted for propionaldehyde.
(91.) The procedure for Compound 37 Example 32 is followed except that isovaleraldehyde is substituted for cyclopropylacetaldehyde.
(92.) As in 91 except propionaldehyde is substituted for cyclopropylacetaldehyde.
(93.) As in 91 except isobutyraldehyde is substituted for cyclopropylacetaldehyde.
(94.) As in 91 except dihydrocinnamaldehyde is substituted for cyclorpopylacetaldehyde.
(95.) As in 91 except 4-nitro 2-phenyl-4-oxobutyrate is substituted for cyclopropylacetaldehyde.
(96.) As in 91 except cyclopropylcarboxaldehyde is substituted for cyclopropylacetaldehyde.
(97.) As in 91 except trifluoroacetaldehyde is substituted for cyclopropylacetaldehyde.
(98.) As in 91 except ethylene oxide is substituted for cyclopropylacetaldehyde.
(99.) If the procedure for Compound 43 Example 32 is followed, substituting trifluoroacetaldehyde for propionaldehyde, the indicated compound is obtained.
(100.) If the procedure for Compound 99 Example 32 is followed, substituting the product from Example 13 Step A$^1$ for the simple blocked vinyl azetidinone, the indicated product is obtained.
(101.) If the procedure for Compound 44 Example 32 is followed, substituting trifluoroacetaldehyde for cyclopentene oxide, the indicated compound is obtained.
(102.) As in 101 except cyclopropylacetaldehyde is substituted for cyclopentene oxide.
(103.) As in 101 except cyclopropylcarboxaldehyde is substituted for cyclopentene oxide.
(104.) As in 101 except isobutyraldehyde is substituted for cyclopentene oxide.
(105.) As in 101 except ethylene oxide is substituted for cyclopentene oxide.
(106.) If the procedure of compound 104 is followed, substituting the product from Example 13, Step A' for the simple blocked vinyl azetidinone, the indicated product is obtained.
(107.) As in 106 except ethylene oxide is substituted for cyclopentene oxide.
(108.) As in 106 except cyclopropylcarboxaldehyde is substituted for cyclopentene oxide.
(109.) As in 106 except cyclopropylacetaldehyde is substituted for cyclopentene oxide.
(110.) As in 106 except 4-nitrobenzyl 2-phenyl-4-oxobutyrate is substituted for cyclopentene oxide.
(111.) As in 106 except dihydrocinnamaldehyde is substituted for cyclopentene oxide.
(112.) As in 106 except isobutyraldehyde is substituted for cyclopentene oxide.
(113.) As in 106 except isovaleraldehyde is substituted for cyclopentene oxide.
(114.) If the procedure for Compound 45 Example 32 is followed, using isovaleraldehyde in place of ethylene oxide, the indicated compound is obtained.
(115.) As in 114 ecept isobutyraldehyde is substituted for ethylene oxide.
(116.) As in 114 except dihydrocinnamaldehyde is substituted for ethylene oxide.
(117.) As in 114 except 4-nitrobenzyl 2-phenyl-4-oxobutyrate issubstituted for ethylene oxide.
(118.) As in 114 except cyclopropylcarboxaldehyde is substituted for ethylene oxide.
(119.) As in 114 except cyclorpropylacetaldehyde is substituted for ethylene oxide.
(120.) As in 114 except acetaldehyde is substituted for ethylene oxide.
(121.) As in 114 except propionaldehyde is substituted for ethylene oxide.
(122.) As in 75 except acetaldehyde is substituted for propionaldehyde.
(123.) As in 75 except cyclopropylcarboxaldehyde is substituted for propionaldehyde.
(124.) As in 75 except cyclopropylacetaldehyde is substituted for propionaldehyde.
(125.) Use methyl acetimidate hydrochloride in water at pH 8.5
(126.) Use methyl acetimidate hydrochloride in water at pH 8.5.
(127.) Use methyl formimidate hydrochloride in water at pH 8.5.
(128.) As in compound 124, using HSCH$_2$CH$_2$NHCO$_2$PNB.

-continued

NOTES FOR TABLE I EXAMPLE 32, COMPOUNDS 18–156

(129.) Following the procedures of Example 15 and 16, except substituting trifluoroacetaldehyde for formaldehyde in the former, gives the indicated product.

(130.) By treating product 129 Example 32 with methyl acetimidate hydrochloride in water at pH 8.5

(131.) By treated product 129 Example 32 with methyl formimidate hydrochloride in water at pH 8.5

(132.) By treating product 134 Example 32 with methyl formimidate hydrochloride in water at pH 8.5.

(133.) By treating product 134 Example 32 with methyl acetimidate hydrochloride in water at pH 8.5.

(134.) If the reactions of Examples 5, 6, 7 and 12 are carried out substituted trifluoroacetaldehyde for formaldehyde in Example 5, the indicated product is obtained.

(135.) If the reactions of Example 5,6,7 and 12 are carried out substituted ethylene oxide for formaldehyde in Example 5, the indicated product is obtained.

(136.) By treating product 135 Example 32 with methyl acetimidate hydrochloride in water at pH 8.5.

(137.) By treating product 135 Example 32 with methyl formimidate hydrochloride in water at pH 8.5.

(138.) By treating product 41 Example 32 with methyl formimidate hydrochloride in water at pH 8.5.

(139.) By treating product 41 Example 32 with methyl acetimidate hydrochloride in water at pH 8.5.

(140.) Following the procedure for compound 43 Example 32 but substituting ethylene oxide for propionaldehyde, the indicated compound is obtained.

(141.) As in 140 but using the product from Example 13 Step $A^1$ in place of the simple blocked vinyl azetidinone.

(142.) By treating the product from 141 with methyl acetimidate hydrochloride in water at pH 8.5.

(143.) By treating the product from 141 with methyl formimidate hydrochloride in water at pH 8.5

(144.) Following the procedure for compound 43 Example 32 but substituting trifluoroacetaldehyde for propionaldehyde, the indicated compound is obtained.

(145.) If in the preparation of compound 92 Example 32, the product from Example 13 Step A'is substituted for the simple blocked vinyl azetidinone, the indicated compound is obtained.

(146.) As in compound 145 Example 32, substituting cyclopropylacetaldehyde for propionaldehyde.

(147.) As in compound 145 Example 32, substituting cyclopropylcarboxaldehyde for propionaldehyde.

(148.) As in compound 145 Example 32, sustituting trifluoroacetaldehyde for propionaldehyde.

(149.) As in compound 145 Example 32, substituting dihydrocinnamaldehyde for propionaldehyde.

(150.) As in compound 145 Example 32, substituting 4-nitrobenzyl 2-phenyl-4-oxobutyrate for propionaldehyde.

(151.) As in compound 145 Example 32, substituting isobutyraldehdye for propionaldehyde.

(152.) As in compound 145 Example 32, substituting isovalerylaldehyde for propionaldehyde.

(153.) As in compound 145 Example 32, substituting ethylene oxide for propionaldehyde.

(154.) As in compound 101 except propionaldehyde is substituted for cyclopentene oxide.

(155.) As in 101 except dihydrocinnamaldehyde is substituted for cyclopentene oxide.

(156.) As in 101 except 4-nitrobenzyl 2-phenyl-4-oxobutyrate is substituted for cyclopene oxide.

EXAMPLE 33

Preparation of the N-Formimidoyl derivative of 3-(2-aminoethylthio)-6-methyl-6-(hydroxymethyl)-7-oxo-1-azabicyclo[3.2.0]hept-2-ene-2-carboxylic acid

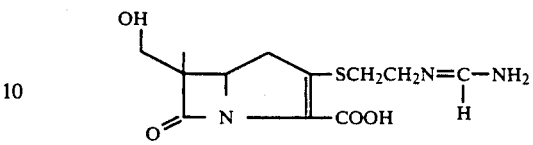

Compound 9 from Example 12 - Step K (517 mg) is dissolved in pH 7 0.1N phosphate buffer (25 ml) and cooled in an ice bath with magnetic stirring. The solution is adjusted to pH 8.5 using 2.5N sodium hydroxide solution dispensed from an automatic burette. While maintaining a pH of 8.5, methyl formimidate hydrochloride (711 mg) is added portionwise over 2–3 minutes. After an additional 10 minutes, the pH of the solution is brought to 7.0 using 2.5N hydrochloric acid. The solution is chromatographed on a column of XAD-2 resin (150 cc) which is eluted with water. The N-formimidoyl derivative is eluted and lyophilized.

Following the procedure of Example 33, enhanced product isolation is achieved when the XAD-2 column is replaced by an otherwise equivalent column of Dowex 50-X4 Na+ cycle, 200–400 mesh.

Amidine embodiments of the present invention, such as that illustrated in Example 33, represent a preferred class. With reference to the generic representation of the compounds of the present invention (Structure I, above), such embodiments are possible when the radical —$SR^8$ bears an amino functional group. The preparation of amidine and amidine-like species is fully described in copending, commonly assigned U.S. patent application Ser. No. 852,425, filed 11-17-77 (now U.S. Pat. No. 4,194,047) which application is incorporated herein by reference to the extent that it describes the preparation of amidine and amidine-like derivatives from species of the present invention which carry an amino group on —$SR^8$.

EXAMPLE 34

Preparation of the N-Acetimidoyl derivative of 3-(2-aminoethylthio)-6-methyl-6-(hydroxymethyl)-7-oxo-1-azabicyclo[3.2.0]hept-2-ene-2-2-carboxylic acid

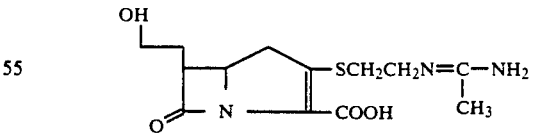

Compound 9 from Example 12, Step K (190 mg) is dissolved in pH 7 0.1N phosphate buffer (13 ml) and cooled in an ice bath with magnetic stirring. The solution of adjusted to pH 8.5 using 2.5N sodium hydroxide solution dispensed from an automatic burette. While maintaining a pH of 8.5, ethyl acetimidate hydrochloride (400 mg) is added portionwise over a few minutes. After an additional 40 minutes the solution is adjusted to pH 7.0 with 2.5N hydrochloric acid. The solution is

EXAMPLE 35

Preparation of Silylated 3-(2-aminoethylthio)-6-methyl-6-(hydroxymethyl)-7-oxo-1-azabicyclo[3.2.0]hept-2-ene-2-carboxylic acid

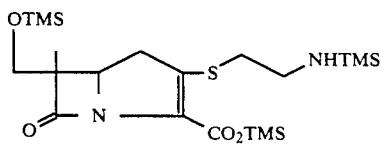

Compound 9 from Example 12, Step K (80.0 mg) is suspended in 40 ml tetrahydrofuran (THF) under a $N_2$ atmosphere and is concentrated to 10 ml; hexamethyldisilazane (1.0 ml) and trimethylchlorosilane (300 µl) is added. The mixture is reacted for 20 mins. at 25° C. with vigorous stirring. The suspension is then centrifuged to remove ammonium chloride. The supernatant is evaporated to provide the title compound under a nitrogen stream for future reaction.

EXAMPLE 36

Preparation of the N-Piperidin-1-yl Methylene Derivative of 3-(2-aminoethylthio)-6-methyl-6-(hydroxymethyl)-7-oxo-1-azabicyclo[3.2.0]hept-2-ene-2-carboxylic acid

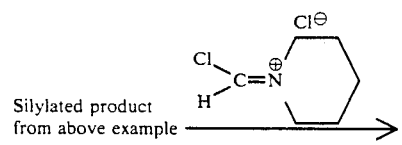

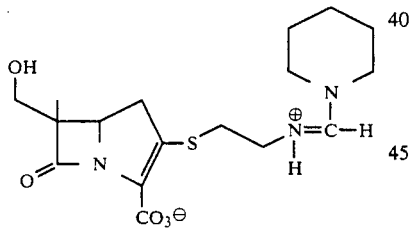

Compound 9 from Example 12, Step K (57 mg., 162 µmol) is silylated according to the procedure previously described. The silylated antibiotic is dissolved in methylene chloride (6 cc) in a septum stoppered flask under positive nitrogen pressure and cooled in a dry ice-acetone bath. To the magnetically stirred solution is added a solution (180 µl) of triethylamine (644 µmol) in methylene chloride. This is followed by the addition of a solution of chloropiperidinomethylium chloride (67 mg, 405 µmol) in methylene chloride (465 µl). After 1 hour in the dry ice bath, the reaction solution is rapidly addedto a tetrahydrofuran -pH 7, 0.1N phosphate buffer (1:1) solution (50 ml). The mixture is then concentrated under vacuum to 10 ml to give a homogeneous solution. The solution is washed twice with ethyl acetate (2×5 ml) and ether (2×5 ml) and briefly pumped under vacuum. This aqueous solution is then chromatographed on an XAD-2 resin column (60 ml bed). The product is eluted in 10% aqueous tetrahydrofuran (following water elution) to give the captioned product.

EXAMPLE 37

Preparation of the N'-Tert-Butyl-N-Formimidoyl derivative of 3-(2-aminoethylthio)-6-methyl-6-(hydroxymethyl)-7-oxo-1-azabicyclo[3.2.0]hept-2-ene-2-carboxylic acid

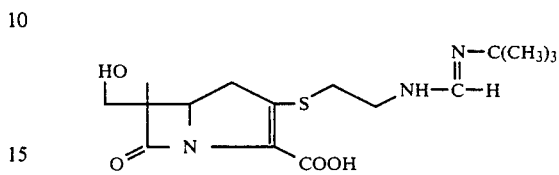

Compound 9 from Example 12, Step K (105 mg) is dissolved in pH 7 0.1N phosphate buffer (5 ml) and to this is added a solution of ethyl N-tert-butyl formimidate (290 mg) in tetrahydrofuran (1 ml). The pH of the solution is adjusted to and maintained at 8.5 using an autoburette dispensing 1N NaOH. After 30 minutes, the pH is adjusted to 7.0 with 2.5N HCl. The solution is chromatographed on an ice water jacketed column of Dowex 50-X4 resin (53 cc, Na+ cycle, 200-400 mesh) and eluted with deionized water. The fractions containing the title produce are combined and lyophilized.

EXAMPLE 38

Preparation of 8-oxo-2,2-dimethyl-7-ethyl-3-oxa-1-azabicyclo[4.2.0]-octane

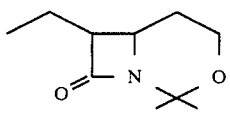

Following the procedure described for the preparation of 8-oxo-3-oxa-2,2-dimethyl-7α-isopropyl-1-azabicyclo[4.2.0]octane from 8-oxo-3-oxa-2,2-dimethyl-1-azabicyclo[4.2.0]octane (Example 4a, above) and using ethyl iodide instead of isopropyl iodide there is obtained 8-oxo-2,2-dimethyl-7-ethyl-3-oxa-1-azabicyclo [4.2.0]octane

EXAMPLE 39

Preparation of 3-(2-aminoethylthio)-6-ethyl-7-oxo-1-azabicyclo[3.2.0-]hept-2-ene-2-carboxylic acid

Following the procedures described in Example 7 followed by Example 12—Steps A-K except that in Example 7 an equivalent amount of 8-oxo-2,2-dimethyl-7-ethyl-3-oxa-1-azabicyclo[4.2.0]octane rather than the 2,2,7-trimethyl species is taken, the title compound is obtained.

EXAMPLE 40

Preparation of the N-formimidoyl derivative of 3-(2-aminoethylthio)-6-ethyl-7-oxo-1-azabicyclo[3.2.0-]hept-2-ene-2-carboxylic acid

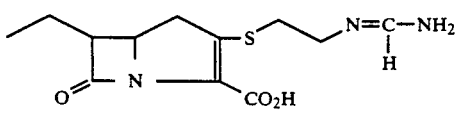

Following the procedure described in Example 33 except that the equivalent amount of 3-(2-aminoethylthio)-6-ethyl-7-oxo-1-azabicyclo[3.2.0]hept-2-ene-2-carboxylic acid rather than Compound 9 is taken, the title compound is obtained.

EXAMPLE 41

Preparation of 3-ethyl-1-(t-butyldimethylsilyl)-4-vinyl-2-azetidinone

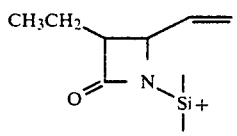

Following the procedure for the preparation of 8-oxo-2,2-dimethyl-7α-isopropyl-3-oxa-1-azabicyclo[4.2.0]octane (Example 4a, above), except that an equivalent amount of 1-(t-butyl-dimethylsilyl)-4-vinyl-2-azetidinone is substituted for the 8-oxo-2,2-dimethyl-3-oxa-1-azabicyclo [4.2.0]octane of Example 4a and using ethyl iodide instead of isopropyl iodide, the title compound is obtained.

EXAMPLE 42

Preparation of 3-ethyl-4-[2-(2-p-nitrobenzyloxycarbonylamino)ethylthio)vinyl]-2-azetidinone

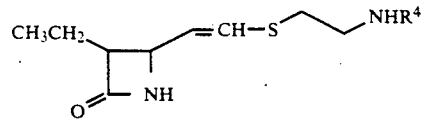

Following the procedures in Example 13—Steps D-F except that an equivalent amount of 3-ethyl-1-(t-butyl-dimethylsilyl)-4-vinyl-2-azetidinone is used in place of Compound 26 of Example 13—Step D, the title compound is obtained.

EXAMPLE 43

Following the foregoing Examples and text, the following additionally preferred antibiotic compounds of the present invention are prepared in further representative demonstration of the disclosed process (Table II). The column labelled "Remarks and Reagents" annotates the established procedure where necessary to obtain the indicated compound. In most instances the compounds are deblocked according to the previously described procedure. However, when the $SR^8$ side chain does not contain a basic function, the final product I is more conveniently isolated as the sodium salt (M=Na); which result is facilitated by conducting the deblocking in a slight excess of $NaHCO_3$. In any event, when either $R^6$ or $R^7$ bears a basic group, the final product I is most conveniently isolated as the free acid (M=H), rather than the sodium salt. It should be noted that compounds designated as "free acids" in reality are isolated as inner salts as a consequence of their zwitterionic nature.

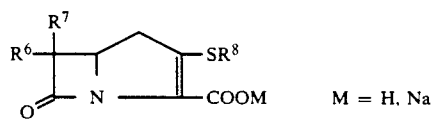

$M = H, Na$

Also entered in Table II, under the

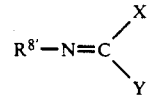

column, are certain preferred amidine and guanidine derivatives of I. Such derivatives are formed from compounds of Table II which carry an $R^8$ side chain bearing an amino group (—$NH_2$). As mentioned earlier such side chains may be symbolized by $R^{8'}$-$NH_2$ and thus such amidine and guanidine derivatives may depicted generically by the structure:

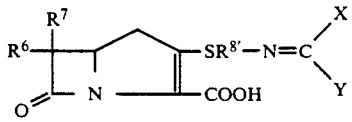

TABLE II $$R^8N=C\begin{matrix}X\\Y\end{matrix}$$

| Compound | $R^6$ | $R^7$ | $R^8$ | Remarks, Reagents |
|---|---|---|---|---|
| (1.) | $(CH_3)_2CH$ | H | φ | As in Example 12, but substitute HSφ for $HSCH_2CH_2NHCO_2PNB$. Deblock and isolate product as Na salt. M = Na. |
| (2.) | $CH_3$ | H | $CH_2φ$ | $HSCH_2φ$; M = Na |
| (3a–d.) | $HOCH_2$ | $CH_3$ | $CH_2CH_2CH_2NH_2$ | $HSCH_2CH_2CH_2NHCO_2PNB$; M = H. X = $NH_2$; Y = H, $CH_3$, $NH_2$ |
| (4a–d.) | $\overset{OH}{\underset{φCH_2CH}{|}}$ | H, φ = phenyl | $CH_2C(CH_3)_2NH_2$ | $HSCH_2C(CH_3)_2NHCO_2PNB$; M = H. X = $NH_2$; Y = H, $CH_3$, $NH_2$ |
| (5a–d.) | $\overset{OH}{\underset{CH_3CH}{|}}$ | $CH_3$ | $CH_2CH_2NH_2$ | M = H. X = $NH_2$; Y = H, $CH_3$, $NH_2$ |
| (6a–d.) | $\overset{OH}{\underset{CH_3CH}{|}}$ | $\overset{OH}{\underset{CH_3CH}{|}}$ | $CH_2CH_2NH_2$ | M = H. X = $NH_2$; Y = H, $CH_3$, $NH_2$ |
| (7.) | $\overset{OH}{\underset{CH_3CH}{|}}$ | $φCH_2$ | $CH_2CH_2N(CH_3)_2$ | $HSCH_2CH_2N(CH_3)_2$; M = H |
| (8a–d.) | $\overset{NH_2}{\underset{CH_3CH}{|}}$ | H | $CH_2CH_2NH_2$ | M = H. X = $NH_2$; Y = H, $CH_3$, $NH_2$ |
| (9.) | $\overset{OH}{\underset{(CH_3)_2CHCH}{|}}$ | H | imidazolyl-CH₂ | HSCH₂-imidazole; M = H |
| (10.) | $\overset{OH}{\underset{(CH_3)_2CHCH_2CH_2CH}{|}}$ | H | pyridin-3-yl-CH₂ | HS-pyridine; M = H |
| (11.) | $\overset{OH}{\underset{CH}{|}}$-cyclopropyl | H | pyridin-2-yl-CH₂ | HSCH₂-pyridine; M = H |

TABLE II-continued

| | | | | |
|---|---|---|---|---|
| (12a–d.) | OH<br>\|<br>CF$_3$CH | H | CH$_2$CH$_2$NH$_2$ | CH$_2$CH$_2$NH$_2$; M = H<br>X = NH$_2$<br>Y = H, CH$_3$, NH$_2$ |
| (13a–d.) | OH<br>\|<br>HOCH$_2$CH | H | CH$_2$CH$_2$NH$_2$ | CH$_2$CH$_2$NH$_2$; M = H<br>X = NH$_2$<br>Y = H, CH$_3$, NH$_2$ |
| (14.) | HOCH$_2$CH$_2$ | H | CH$_2$CH$_2$–N⟨piperazine⟩NCH$_3$ | HSCH$_2$CH$_2$–N⟨piperazine⟩NCH$_3$; M = H |
| (15.) | OH<br>\|<br>CH$_3$CH$_2$CH | H | CH$_2$–(2-pyridyl) | HSCH$_2$–(2-pyridyl); M = H |
| (16a–d.) | OH<br>\|<br>CH$_3$CH$_2$CH | H | CH$_2$NH$_2$ (o-tolyl) | HS-phenyl-CH$_2$NHCO$_2$PNB; M = H<br>X = NH$_2$<br>Y = H, CH$_3$, NH$_2$ |
| (17a–d.) | OH<br>\|<br>FCH$_2$CH | H | CH$_2$CH$_2$NH$_2$ | CH$_2$CH$_2$NH$_2$; M = H<br>X = NH$_2$<br>Y = H, CH$_3$, NH$_2$ |
| (18.) | cyclopropyl-CH$_2$CH(OH) | H | CH$_2$CH$_2$CO$_2$H | HSCH$_2$CH$_2$CO$_2$PNB;<br>Product isolated as disodium salt. |
| (19a–d.) | CH$_3$CH$_2$ | H | CH$_2$CH$_2$NH$_2$ | CH$_2$CH$_2$NH$_2$; M = H<br>X = NH$_2$<br>Y = H, CH$_3$, NH$_2$ |
| (20.) | CH$_3$ | CH$_3$ | methylthiazoline–SH | N=N, N–CH$_3$, HS ring; M = Na |
| (21.) | cyclopropyl-CH$_2$ | H | CH$_2$CH$_2$OH | HSCH$_2$CH$_2$OCO$_2$PNB<br>M = Na |
| (22a–d.) | HOCH$_2$CH$_2$ | CH$_3$ | CH$_2$CH$_2$CH$_2$NH$_2$ | HSCH$_2$CH$_2$CH$_2$CO$_2$PNB;<br>M = H<br>X = NH$_2$<br>Y = H, CH$_3$, NH$_2$ |

TABLE II-continued

| # | Col1 | Col2 | Col3 | Col4 | Col5 |
|---|---|---|---|---|---|
| (23a–d.) | cyclopentyl-OH | H | CH₂C(CH₃)₂CH₂NH₂ | X = NH₂; Y = H, CH₃, NH₂ | HSCH₂C(CH₃)₂CH₂NHCO₂PNB; M = H |
| (24a–d.) | 3-methylcyclopentyl-OH | H | CH₂CH₂NH₂ | X = NH₂; Y = H, CH₃, NH₂ | M = H |
| (25a–d.) | 2-methylcyclopentyl-OH | H | CH₂CH₂NH₂ | X = NH₂; Y = H, CH₃, NH₂ | M = H |
| (26.) | CH₃CH(OH)– | H | S–CH₂CH₂CH₂–CH₃ | | HS–CH₂CH₂CH₂–CH₃; M = Na |
| (27.) | " | H | S–CH₂CH₂CH₂–OH | | HS–CH₂CH₂CH₂–CO₂PNB; M = Na |
| (28a–d.) | " | H | S–CH₂CH₂CH₂CH₂–NH₂ | X = NH₂; Y = H, CH₃, NH₂ | HS–CH₂CH₂CH₂CH₂–NHCO₂PNB; M = H |
| (29.) | " | H | S–CH₂CH₂CH₂–NHC(O)CH₃ | | HS–CH₂CH₂CH₂–NHC(O)CH₃; M = Na |
| (30a–d.) | CH₃CH(OH)– | H | S–CH₂CH(NH₂)–CH₃ | X = NH₂; Y = H, CH₃, NH₂ | HS–CH₂CH(NHCO₂PNB)–CH₃; M = H |
| (31a–d.) | " | H | S–CH₂C(NH₂)(CH₃)–CH₃ | X = NH₂; Y = H, CH₃, NH₂ | HS–CH₂C(NHCO₂PNB)(CH₃)–CH₃; M = H |
| (32a–d.) | " | H | S–CH₂CH(CH₃)–NH₂ | X = NH₂; Y = H, CH₃, NH₂ | HS–CH₂CH(CH₃)–NHCO₂PNB; M = H |
| (33a–d.) | " | H | S–CH₂C(CH₃)₂–NH₂ | X = NH₂; Y = H, CH₃, NH₂ | HS–CH₂C(CH₃)₂–NHCO₂PNB; M = H |

TABLE II-continued

| | | | |
|---|---|---|---|
| (34a–d.) | " | H | ![structure: S-CH2-C(CH3)2-CH2-NH2] | X = NH2<br>Y = H, CH3, NH2 | ![structure: HS-CH2-C(CH3)2-CH2-NHCO2PNB]; M = H |
| (35.) | " | H | ![pyrrolidine N-CH2CH2-S] | X = NH2<br>Y = H, CH3, NH2 | ![pyrrolidine N-CH2CH2-SH]; M = H |
| (36.) | CH3CH(OH)– | H | ![S-CH2CH2-N(CH3)2] | X = NH2<br>Y = H, CH3, NH2 | ![HS-CH2CH2-N(CH3)2]; M = H |
| (37a–d.) | " | H | ![S-CH2-CH(OH)-CH2-NH2] | X = NH2<br>Y = H, CH3, NH2 | ![HS-CH2-CH(OCO2PNB)-CH2-NHCO2PNB]; M = H |
| (38a–d.) | " | H | ![S-CH2-CH(COOH)-NH2] | X = NH2<br>Y = H, CH3, NH2 | ![HS-CH2-CH(CO2PNB)-NHCO2PNB]; M = H |
| (39a–d.) | " | H | ![S-CH2CH2-C(=NH)-NH2] | X = NH2<br>Y = H, CH3, NH2 | ![HS-CH2CH2-C(=NH)-NHCO2PNB]; M = H |
| (40a–d.) | " | H | ![S-CH2-CH(NH2)-CH2-OH] | X = NH2<br>Y = H, CH3, NH2 | ![HS-CH2-CH(NHCO2PNB)-CH2-OCO2PNB] M = H |
| (41a–d.) | CH3CH(OH)– | H | ![S-CH2CH2CH2-NHφ] | X = NH2<br>Y = H, CH3, NH2 | M = H |
| (42a–d.) | " | H | ![S-CH2CH2-NC(CH3)3 H] | X = NH2<br>Y = H, CH3, NH2 | ![HS-CH2CH2-N+(C(CH3)3)-CO2PNB] M = H |
| (43.) | " | H | ![S-φ] | | M = Na |
| (44a–d.) | " | H | ![o-aminothiophenol S-C6H4-NH2] | X = NH2<br>Y = H, CH3, NH2 | ![o-HS-C6H4-NHCO2PNB] M = H |

TABLE II-continued

| | | | |
|---|---|---|---|
| (45.) | " | [pyridyl-S-] | [pyridyl-SH]; M = H |
| (46.) | CH₃CH(OH)— | [1-methyl-tetrazol-5-yl-S-] | M = Na |
| (47.) | " | [benzyl-S-] | M = Na |
| (48.) | " | [(pyridin-2-yl)methyl-S-] | M = H |
| (49.) | " | [(pyridin-3-yl)methyl-S-] | M = H |
| (50a–d.) | " | [(2-amino-thiazol-5-yl)methyl-S-] | X = NH₂<br>Y = H, CH₃, NH₂ | M = H |
| (51.) | " | [4,5-dihydro-imidazol-2-yl-SCH₂-] | M = H |
| (52a–d.) | " | [(2-amino-thiazol-5-yl)methyl-S-, thiol form with NHCO₂PNB] | X = NH₂<br>Y = H, CH₃, NH₂ | NHCO₂PNB<br>M = H |

TABLE II-continued

| | | | |
|---|---|---|---|
| (53.) | CH$_3$CH(OH)– | H | [structure with piperazine-NCH$_3$ and S-CH$_2$CH$_2$-]; M = H |
| (54.) | " | H | [structure with N-methylpiperidine and S]; M = H |
| (55.) | " | H | [imidazole-CH$_2$CH$_2$-S structure]; [imidazole-N-CO$_2$PNB, CH$_2$CH$_2$-S structure]; M = H |
| (56a–d.) | " | H | S–CH$_2$CH$_2$–O–CH$_2$CH$_2$–NH$_2$, X = NH$_2$, Y = H, CH$_3$, NH$_2$ ; S–CH$_2$CH$_2$–O–CH$_2$CH$_2$–NHCO$_2$PNB, M = H |
| (57a–d.) | " | H | S–CH$_2$CH$_2$–N(CH$_3$)–CH$_2$CH$_2$–NH$_2$, X = NH$_2$, Y = H, CH$_3$, NH$_2$ ; S–CH$_2$CH$_2$–N(CH$_3$)–CH$_2$CH$_2$–NHCO$_2$PNB; M = H |

| Compounds | |
|---|---|
| 58–89 | Compounds 58–89 correspond sequentially to compounds 26–57 (including listed amidine and guanidine derivatives, above), except that the value for R$^6$ is taken as CH$_3$CH$_2$ rather than the CH$_3$C(OH)H of Compounds 26–57. |
| 90–121 | Compounds 90–121 correspond sequentially to compounds 26–57 (including listed amidine and guanidine derivatives, above), except that the value for R$^6$ is taken as Cl$_2$CHCH rather than the CH$_3$C(OH)H of Compounds 26–57. $\overset{|}{OH}$ |
| 122–153 | Compounds 122–153 correspond sequentially to compounds 26–57 (including listed amidine and guanidine derivatives, above), except that the value for R$^6$ is taken as CF$_3$CH rather than the CH$_3$C(OH)H of Compounds 26–57. $\overset{|}{OH}$ |
| 154–185 | Compounds 154–185 correspond sequentially to compounds 26–57 (including listed amidine and guanidine derivatives, above), except that the value for R$^6$ is taken as HOCH$_2$CH rather than the CH$_3$C(OH)H of Compounds 26–57. $\overset{|}{OH}$ |
| 186–217 | Compounds 186–217 correspond sequentially to compounds 26–57 (including listed amidine and guanidine derivatives, above), except that the value for R$^6$ is taken as ClCH$_2$CH rather than the CH$_3$C(OH)H of Compounds 26–57. $\overset{|}{OH}$ |
| 218–249 | Compounds 218–249 correspond sequentially to compounds 26–57 (including listed amidine and guanidine derivatives, above), except that the value for R$^6$ is taken as CH$_3$CH$_2$CH rather than the CH$_3$C(OH)H of Compounds 26–57. $\overset{|}{OH}$ |
| 250–281 | Compounds 250–281 correspond sequentially to compounds 26–57 (including listed amidine and guanidine derivatives, above), |

TABLE II-continued

| | |
|---|---|
| | except that the value for $R^6$ is taken as $\overset{OH}{\underset{|}{\triangle\!\!\!-\!\!\!CH}}$ rather than the CH$_3$C(OH)H of Compounds 26–57. |
| 282–313 | Compounds 282–313 correspond sequentially to compounds 26–57 (including listed amidine and guanidine derivatives, above), except that the value for $R^6$ is taken as H$_2$NCH$_2$CH rather than the CH$_2$C(OH)H of Compounds 26–57. |
| 314–345 | Compounds 314–345 correspond sequentially to compounds 26–57 (including listed amidine and guanidine derivatives, above), except that the value for $R^6$ is taken as CF$_2$HCH rather than the CH$_3$C(OH)H of Compounds 26–57. |
| 346–377 | Compounds 346–377 correspond sequentially to compounds 26–57 (including listed amidine and guanidine derivatives, above), except that the value for $R^6$ is taken as HOCH$_2$ rather than the CH$_3$C(OH)H of Compounds 26–57. |
| 378–409 | Compounds 378–409 correspond sequentially to compounds 26–57 (including listed amidine and guanidine derivatives, above), except that the value for $R^6$ is taken as HO$_2$CCH$_2$ rather than the CH$_3$C(OH)H of Compounds 26–57. |
| 410–441 | Compounds 410–441 correspond sequentially to compounds 26–57 (including listed amidine and guanidine derivatives, above), except that the value for $R^6$ is taken as CH$_3$OCH$_2$CH rather than the CH$_3$C(OH)H of Compounds 26–57. |
| 442–473 | Compounds 442–473 correspond sequentially to compounds 26–57 (including listed amidine and guanidine derivatives, above), except that the value for $R^6$ is taken as (CH$_3$)$_3$CCH$_2$CH rather than the CH$_3$C(OH)H of Compounds 26–57. |
| 474–505 | Compounds 474–505 correspond sequentially to compounds 26–57 (including listed amidine and guanidine derivatives, above), except that the value for $R^6$ is taken as FCH$_2$CH(OH) rather than the CH$_3$C(OH)H of Compounds 26–57. |

EXAMPLE 44

This example, and those depending from it, demonstrate the so called "guanidino" embodiments of I. Such embodiments have been defined above (see general description of the invention under the 2-substituent $R^8$, above; and see text, above, under category No. 9 of reagents $HSR^8$: "9.) Guanidino mercaptans $HSR^8$"). As defined above, such guanidino embodiments are characterized by the following generic representation:

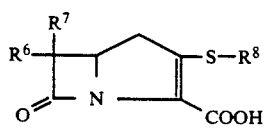

wherein $R^8$, characterized by the presence of the guanidino group, is defined above.

The following diagram summarizes the foregoing text (see Diagram III) and is illustrative of the preferred procedure for making the guanidino embodiments. In the diagram the guanidino group is illustrated as unsubstituted to demonstrate best the general case:

wherein: all symbols and conditions of reaction are as defined above; for example: $X^a$ is a leaving group such as mesylate, tosylate, nosylate or a phosphate such as

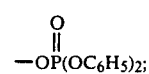

$R^5$ is a protecting group such as p-nitrobenzyl (PNB) and $R^{5'}$ is a protecting group such as —$CO_2PNB$; $R^6$, $R^7$, $R^8$, and $R^1$ are as defined above. Examples 44a, et seq., specifically demonstrate the process of Example 44.

EXAMPLE 44a (5R,6S)-2-(3-Guanidinopropyl-1-thio)-6-(1-P-hydroxyethyl)carbapen-2-em-3-carboxylic Acid Step A: P-Nitrobenzyl (5R, 6S)-2-(3-p-Nitrobenzyloxycarbonylguanidino)propyl-1-thio-6-(1-R-hydroxyethyl)carbapen-2-em-3-carboxylic Acid

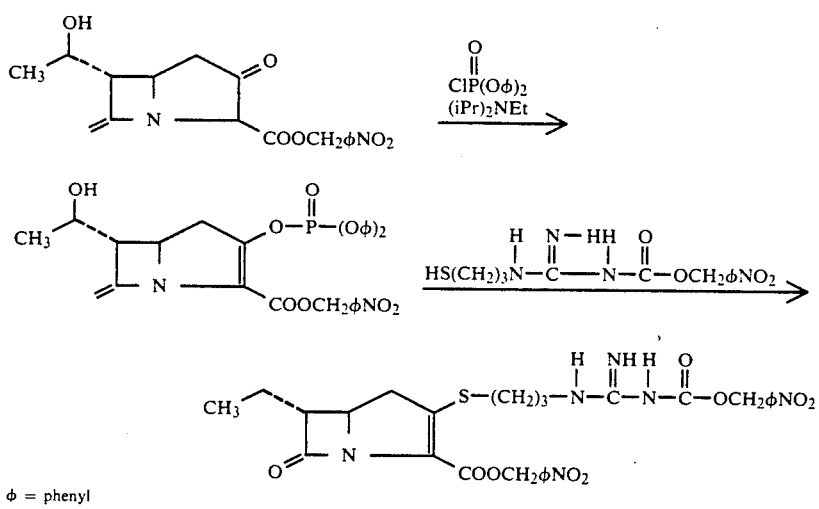

Cool to 0° C. under nitrogen a solution of 49 mg of (5R, 6S)-p-nitrobenzyl-6(1-R-hydroxyethyl)-1-azabicyclo[3.2.0]heptan-3,7-dione-2-carboxylate in 1 ml of acetonitrile. Add with stirring 29.2 ml of diisopropylethylamine and 30.6 ml of diphenylchlorophosphate. After 15

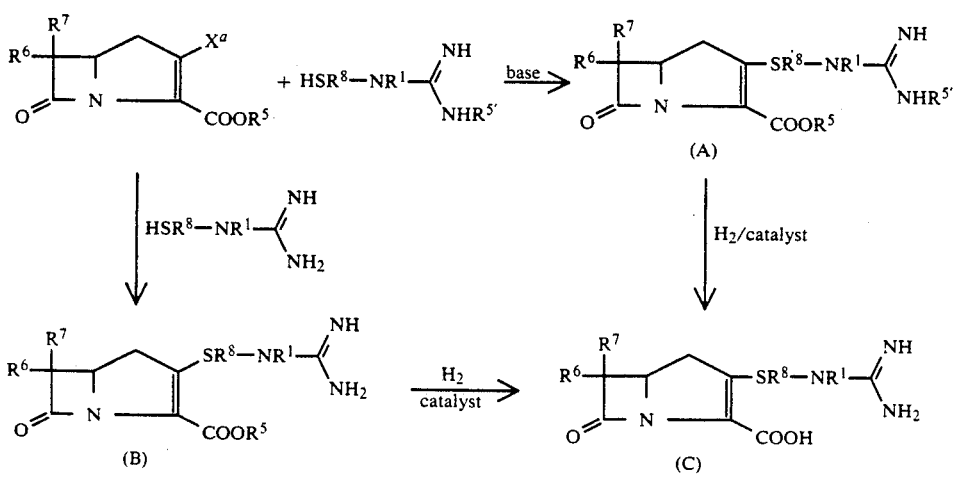

minutes, add an additional 24.4 ml of diisopropylethylamine and 50 mg of 3-(N'-p-nitrobenzyloxycarbonylguanidino)propanol in 0.4 ml of dimethylformamide. Store the reaction mixture at 4° C. for 18 hours. Dilute with 50 ml of cold ethylacetate and extract twice with 50 ml portions of cold pH 7 phosphate buffer followed by 50 ml of brine. Dry the organic phase over anhydrous magnesium sulfate and evaporate to dryness. Chromatograph the residue on a 8"×8"1000μ silica gel plate developing with 15% isopropanol in methylene chloride. Isolate the band at $R_f$ 0.28 (yield 0.5 mg.)

Step B: (5R, 6S)-2-(3-Guanidinopropyl-1-thio)-6-(1-R-hydroxyethyl)carapen-2em-3-carboxylic Acid

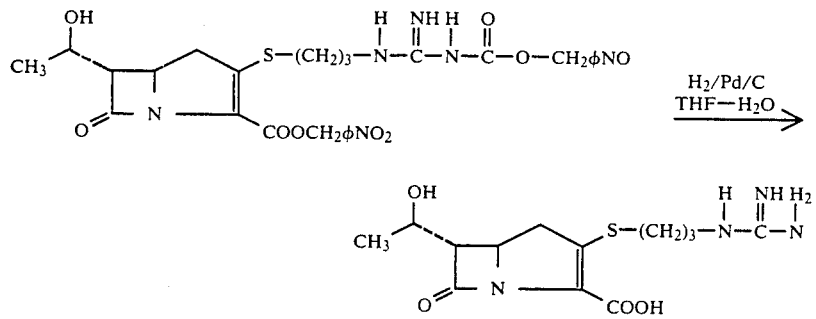

Hydrogenate the p-nitrobenzoyl ester of Step A in a mixture of 3.3 ml of tetrahydrofuran, 1 ml of water and 60 μl of M $K_2HPO_4$ buffer (pH 7) in the presence of 10 mg of 10% Pd/C catalyst at 45 psig for 1 hour. Remove the catalyst by filtration, wash the filtrate, twice with water and extract with ether. The aqueous solution contains the title product (U.V. λmax 303 mμ, 79 ODU).

Preparation of 3-(N'-p-Nitrobenzyloxycarbonylguanidino)propane thiol

Step A:
3-(N'-p-Nitrobenzyloxycarbonylguanidino)-propyldisulfide

Suspend 100 mg of 3-guanidinopropyldisulfide disulfate in 2 ml of dioxane. Add 0.4 ml of 2.5N sodium hydroxide and cool the mixture in an ice-bath. Add dropwise a solution of 207 mg of p-nitrocarbobenzoylchloride in 3 ml of dioxane stirring alternately with 0.4 ml of additional sodium hydroxide solution during 5 minutes. Stir for 1 hour at room temperature. Add 7 ml of water and store at 4° C. overnight. Separate the precipitate by filtration, wash with water; triturate in the funnel with methanol and air dry (yield 100 mg). (TLC on silica gel in 5% methanol/chloroform —$R_f$ 0.21)

Step B:
3-(N'-p-Nitrobenzyloxycarbonylguanidino)-propanethiol

Dissolve the product of Step A in 3.3 ml of dimethylformamide and add 67 mg of dithiothreitol. After standing at room temperature for 40 minutes, remove the dimethylformamide under vacuum. Dissolve the residue in chloroform and chromatograph on two 8"×8" 1000μ silica gel plates developing with ethyl acetate. Isolate the band at $R_f$ 0.48, elute with ethylacetate and evaporate the ethyl acetate solution (yield 63 mg).

EXAMPLE 44b (5R, 6S)-2-(2-Guanidino-2,2-dimethylethyl-1-thio)-6-(1-R-hydroxyethyl)carbapen-2em-3-carboxylic Acid To the enol phosphate ester prepared from 34.8 mg of from (5R, 6S)-p-nitrobenzyl-6-(1-R-hydroxyethyl)-1-azabicyclo[3 2 0]heptan-3,7-dione-2-carboxylate according to Step A of EXAMPLE 44a in 0.7 ml of acetonitrile, add with stirring and cooling a solution of 2-guanidino-2,2-dimethylethylthiol (40 mg) in 0.7 ml of dimethylsulfoxide over a 5 minute period. Stir the mixture at 0° C. under nitrogen for 1 hour. Add 12 ml of ether and separate the precipitate by decantation. Triturate the insoluble residue with ether. Dissolve the ether insoluble residue in 6 ml of 1:1 $THF/H_2O$ and adjust the pH to 8.2 by addition of dipotassium hydrogen phosphate. Hydrogenate at 50 psig in the present of 15 mg of 10% Pd/C catalyst for 1 hour. Separate the catalyst by filtration and extract the filtrate three times with 7 ml portions of ether. Concentrate the aqueous phase to 1.5 ml and pour onto a column (1×12 cm) of neutral polystyrene resin (XAD-2). Wash the column with 30 ml of water and elute with 20 ml of 5% $THF/H_2O$. Concentrate the eluate and freeze-dry (yield 6.4 mg) (U.V. $\lambda_{max}$ 300 nm E % 181, 95% $NH_2OH$ ext.).

Preparation of 2-Guanidino-2,2-dimethylethanethiol

Step A: 2-Amino-2,2-dimethylisothiouroniumditosylate

Dissolve 6.78 g of thiourea and 30.82 g of p-toluenesulfonic acid hydrate in 300 ml of warm ethanol. Cool to room temperature. Add dropwise with vigorous stirring 1.78 g. of 2,2-dimethylaziridine over a period of 2 minutes. Stir for 20 minutes at room temperature and separate the precipitate by filtration. Wash the precipitate with ethanol and air-dry (yield 31.6 g, mp dec. 250° C.).

Step B: 2-Guanidino-2,2-dimethylethanethiol

Dissolve 4.3 g of the product of Step A in 100 ml of water and add with stirring DOWEX 1×8 resin (OH⁻ cycle) in portions until the pH (initially 4.2) remains steady at 7.5. Stir at room temperature for 30 minutes. Pass through a column (1.5×9 cm) of DOWEX 1×8 resin (OH⁻ cycle). Wash the column with 100 ml of water and concentrate the total eluate to 30 ml. Freeze-dry (yield 0.63 g).

EXAMPLE 44C

N-Guanylthienamycin

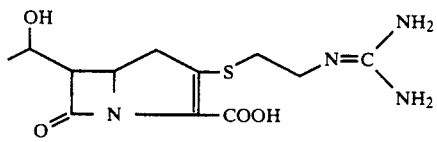

Step A:
N-(p-nitrobenzyloxycarbonylguanyl)-thienamycin p-Nitrobenzyl ester

Dissolve 45.4 mg of (5R, 6S)-p-nitrobenzyl-6-(1-R-hydroxyethyl)-1-azabicyclo[3.2.0]heptan-3,7-dione-2-carboxylate in 0.5 ml of acetonitrile with stirring and cool in an ice-bath under nitrogen. Add 53 mg of p-nitrobenzenesulfonic anhydride and 26 µl of diisopropylethylamine. After 20 minutes, the reaction is complete as shown by thin layer chromatography (5% methanol/methylene chloride-R$_f$ 0.48). Blow off excess acetonitrile in a stream of nitrogen. Dissolve the residue in 0.7 ml of dimethylformamide and cool to −15° C. Add 32 µl of diisopropylethylamine and 54.2 mg of p-nitrobenzyloxycarbonylguanidinoethyl mercaptan DMF complex. Stir under nitrogen for 3 hours allowing the temperature slowly to rise to −8° C. Thin layer chromatography (TLC) on silica gel (5% methanol/methylene chloride) shows a new spot at R$_f$ 0.18. Add 35 ml of ethylacetate and extract three times with M pH 7 phosphate buffer (70 ml) and with brine. Dry the organic layer over magnesium sulfate and evaporate to dryness. Chromatograph the residue on an 8″×8″ 1000µ silica gel plate developing with 15% isopropanol/methylene chloride. Elute the band at 5–10 cm with 20 ml of tetrahydrofuran. The solution assayed by U.V. shows 1420 ODU at λ$_{max}$ 273 mµ and 811 ODU at λ$_{max}$ 315 mµ corresponding approximately to 40 mg (48%) of the desired N-(p-nitrobenzyloxycarbonylguanyl)-thienamycin ester.

Step B: N-Guanylthienamycin

Concentrate the solution from Step A to 10 ml and add 3 ml of water, 0.7 ml of ethanol, 132 µl of 1M K$_2$HPO$_4$ and 50 mg 10% Pd/C catalyst. Shake the mixture under a hydrogen atmosphere (50 psig) for 1 hour. Separate the catalyst by filtration and wash with 10 ml of water. Extract the combined filtrate and washings with 100 ml of ether and concentrate to 4 ml in vacuo. Adjust the pH to 6.7 and pour the solution onto a 1 cm×17 cm ice-water jacketed column of XAD-2 resin (neutral polystyrene). Elute with water at a flow rate of 0.75 cc/min. and monitor the effluent by a U.V. detector. Collect the fraction peaking at 1.3 CV. Concentrate to a small volume and freeze-dry (15.8 mg) (U.V. H$_2$O, λ$_{max}$ 301 E % 160, E 5024, 89% NH$_2$OH extinguished, indicates approximately 60% purity). NMR D$_2$O shows doublet CH$_3$ at δ1.29 and multiplets at δ2.9–4.2.

Preparation of
N-p-Nitrobenzyloxycarbonylguanidinoethylmercaptan
DMF • Complex

Step A:
N,N'-bis-(p-Nitrobenzyloxycarbonyl)guanidinoethyl Disulfide

Cool a solution of guanidinoethyl disulfide dihydrogenbromide (2 g) on 10 ml of dioxane in an ice-bath. Add 5 ml of 2.5N sodium hydroxide, followed by a solution of 3.22 g. of p-nitrobenzyloxychloride in 10 ml of dioxane in portions with stirring. Maintain the pH at approximately 12 during the addition over a 10 minute period with additional sodium hydroxide solution (0.7 ml). Stir the mixture for 50 minutes and refrigerate overnight. Separate the precipitate by filtration and wash with water. Air dry. Extract with 50 ml of warm methylene chloride and filter (yield 1.55 g - mp 165° C.). A sample recrystallized from aqueous dioxane melts at 170° C.

Analysis Calculated (C$_{11}$H$_{13}$N$_4$O$_4$S): C44.44; H4.44, N18.85, S10.78. Found: 44.22; 4.14, 18.11, 10.69.

Step B:
N'-p-Nitrobenzyloxycarbonylguanidinoethylmercaptan
• DMF Complex

Stir a mixture of 1.2 g of the product of Step A and 0.33 g of dithiothreitol in 5 ml of dimethylformamide (DMF) under nitrogen for 30 minutes. Dilute with 25 ml of ethyl acetate and store in ice for 1 hour. Separate the precipitate by filtration and wash with ethylacetate and with ether. Dry under nitrogen (yield 750 ml). TLC on silica gel, 5% methanol/chloroform, R$_f$ 0.35 with streaking from origin. Yellow color when sprayed with Ellman's reagent (5,5'-dithio-bis-(2-nitrobenzoic acid). NMR in CDCl$_3$ (60 MHz) δ2.71 (t) J6 Hz CH$_2$, 5.2 CH$_2$φ, 7.57(d) 8.9(d) aromatic, also 2.9, 2.97 and 8.27 (DMF).

Example 44d

Guanyl N-Methylthienamycin

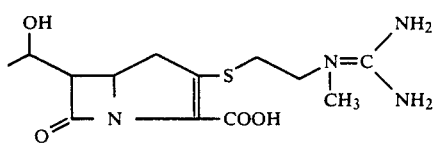

Following the procedure of EXAMPLE 1, add a solution of 48 mg of 2-(N-methyl-N'-p-nitrobenzyloxycarbonylguanidino)ethanethiol in 0.5 ml of dimethylformamide to the enol phosphate ester prepared from 49 mg of (5R, 6S)-p-nitrobenzyl-6-(1-R-hydroxyethyl)-1-azabicyclo-[3.2.0]heptan-3,7-dione-2-carboxylate and hydrogenate the resulting product as described in Step B (yield 18 mg). (U.V.$\lambda_{max}$ 300$_{nm}$, E % 78 (95% NH$_2$OH ext.) Electrophoresis at pH 7, 60 V/cm, followed by bioautography gave a zone of inhibition at −1.5 cm.

EXAMPLE 5

(5R, 6S)-2-(1-S-guanidinopropyl-2-thiol)-6-(1-R-hydroxyethyl)carbapen-2-em-3-carboxylic Acid To the enol phosphate ester prepared from 34.8 mg of (5R, 6S)-1-nitrobenzyl-6-(1-R-hydroxyethyl)-1-azabicyclo[3.2.0]heptan-3,7-dione-2-carboxylate according to Step A of EXAMPLE 1 in 0.7 ml of acetonitrile, add with stirring and cooling a solution of (S)-1-guanidinopropane-2-thiol hydrochloride simultaneously with 21 ml of diisopropylethylamine over a 5 minute period. Stir the mixture at 0° C. under nitrogen for 1 hour. Pour the mixture into 40 ml of ether and centrifuge. Decant the supernatant solution and dissolve the ether insoluble residue in 8 ml of 1:1 THF/H$_2$O and 4 ml of 0.1M phosphate buffer (pH 7). Hydrogenate at 40 psig in the presence of 35 mg of 10% Pd/C catalyst by filtration and extract the filtrate twice with 10 ml portions of ether. Concentrate the aqueous phase under vaccum to 3 ml and pour onto a column containing 32 mg of XAD-2 resin (neutral polystyrene). Wash the column 90 ml of water and elute with 45 ml of 5% THF/H$_2$O. Concentrate the eluate and freeze-dry (yield 17 mg). (U.V.$\lambda_{max}$ 300 m$\mu$, E % 118, 90% NH$_2$OH ext.).

EXAMPLE 44e

Following the procedure of the foregoing examples and text, the following "guanidino" embodiments of the present invention are obtained.

TABLE 44e

| Compound | R⁶ | R⁷ | —SR⁸ | Remarks |
|---|---|---|---|---|
| (1.) | H | OH-isopropyl | —S—(phenyl)—CH₂CH₂—N=C(NH₂)(NH₂) | Throughout Table 45e, the symbol for R⁷ as CH₃CH(OH)— is isopropyl-OH |
| (2.) | H | OH-isopropyl | —S—CH₂CH(CH₃)—N=C(NH₂)(NH₂) | |
| (3.) | H | OH-isopropyl | —S—(cyclopropyl)—CH₂—N=C(NH₂)(NH₂) | |
| (4.) | H | OH-isopropyl | —S—(cyclopropyl)—CH₂—N(CH₂CH₃)—C(NH₂)(NH₂) | |
| (5.) | H | OH-isopropyl | —S—CH(CH₃)—N=C(NH₂)(NH₂) | |

TABLE 44e-continued

[Structure: β-lactam ring with R6, R7 on C adjacent to N, and SR8 substituent on C=C-COOH]

| | R6 | R7 | SR8 |
|---|---|---|---|
| (6.) | H | OH (isopropyl) | —S—CH(CH3)—CH2—N=C(NH2)NH2 |
| (7.) | H | OH (isopropyl) | —S—C(CH2CH3)(CH3)—N=C(NH2)NH2 (wavy bond) |
| (8.) | H | OH (isopropyl) | —S—CH(CH3)—N(CH3)—C(NH2)=NH... —C(NH2)NH2 |
| (9.) | H | OH (isopropyl) | —S—CH2—CH(CH3)—N=C(NH2)NH2 |
| (10.) | H | OH (isopropyl) | —S—CH2—CH(CH3)—N=C(NH2)NH2 |
| (11.) | H | OH (isopropyl) | —S—CH2—CH(COOH)—NH—C(NH2)=NH |
| (12.) | H | OH (isopropyl) | —S—CH(CH3)—CH(CH3)—N=C(NH2)NH2 |
| (13.) | H | OH (isopropyl) | —S—CH(CH3)—CH(CH3)—NH—C(NH2)=NH |
| (14.) | H | OH (isopropyl) | —S—CH2—CH(CH3)—N(CH3)—C(NH2)=NH |
| (15.) | H | OH (isopropyl) | —S—CH(C2H5)—CH2—NH—C(=NH)NH2 |
| (16.) | H | OH (isopropyl) | —S—CH(CH3)—CH2—NH—C(NH2)=NCH3 |

TABLE 44e-continued
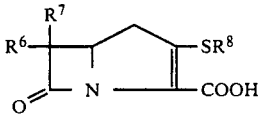

TABLE 44e-continued

![structure: R6, R7 on β-lactam with SR8 and COOH]

| | | | |
|---|---|---|---|
| (28.) | H | OH (isopropyl) | -S-phenyl-NH-C(=NH)-NH2 |
| (29.) | H | OH (isopropyl) | -S-CH2CH2-N(OCH3)-C(=NH)-NH2 |
| (30.) | H | OH (isopropyl) | -S-CH(CH3)CH2-N(N(CH3)2)-C(=NH)-NH2 |
| (31.) | H | OH (isopropyl) | -S-CH2CH2-N(N(CH3)2)-C(=NH)-NH2 |
| (32.) | H | OH (isopropyl) | -S-CH2CH2-N(OCH3)-C(=NH)-NHCH3 |
| (33.) | H | OH (isopropyl) | -S-CH2-CH(OCH3)-CH2-NH-C(=NH)-NH2 |

| Compounds | |
|---|---|
| 34–67 | Compounds 34–67 correspond sequentially to Compounds 1–32 of Table 44e except that the value for $R^7$ is CH3CH(OH) is replaced by FCH3CH(OH). |
| 68–101 | Compounds 68–101 correspond sequentially to Compounds 1–32 of Table 44e except that the value for $R^7$ is CH3CH2CH(OH) is replaced by FCH3CH(OH). |
| 102–135 | Compounds 102–135 correspond sequentially to Compounds 1–32 of Table 44e except that the value for $R^7$ is CH3CH2 is replaced by FCH3CH(OH). |
| 136–169 | Compounds 136–169 correspond sequentially to Compounds 1–32 of Table 44e except that the value for $R^7$ is (CH3)2C(OH) is replaced by FCH3CH(OH). |

EXAMPLE 45

This example and those depending from it demonstrate the so called "amidino" embodiments of I. Such embodiments have been defined above (see general description of the invention under the 2-substituent $R^8$, above; and see text above, under category No. 8 of reagents $HSR^8$: "8.) Amidino Mercaptans $HSR^8$"). As defined above, such amidino embodiments are characterized by the following generic representation:

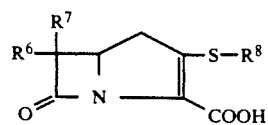

I wherein: $R^8$, characterized by the presence of the amidino group, is defined above.

The following diagram summarizes the foregoing text (see Diagram III, and U.S. Pat. No. 4,194,047). and is illustrative of the preferred procedure for making the amidino embodiments. In the following scheme, the synthesis of simplest amidine, the formimidoyl, is demonstrated since it is representative. Other species members of the amidino genus are prepared by analogy.

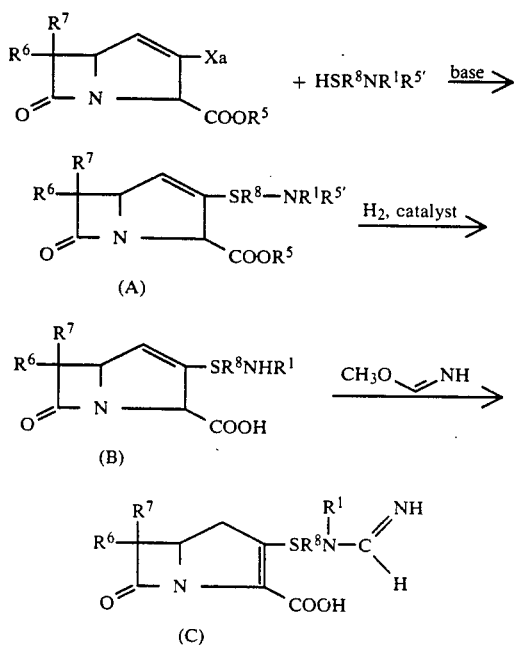

wherein: all symbols and conditions of reaction are as defined above; for example $X^a$ is a leaving group such as mesylate, tosylate, mosylate, or a phosphate such as

$R^5$ is a protecting group such as p-nitrobenzyl (pNB) and $R^{5'}$ is a protecting group such as —$CO_2pNB$; $R^6, R^7, R^8$, and $R^1$ is as defined above.

Examples 45a, et seq., specifically demonstrate the process of Example 45.

EXAMPLE 45a

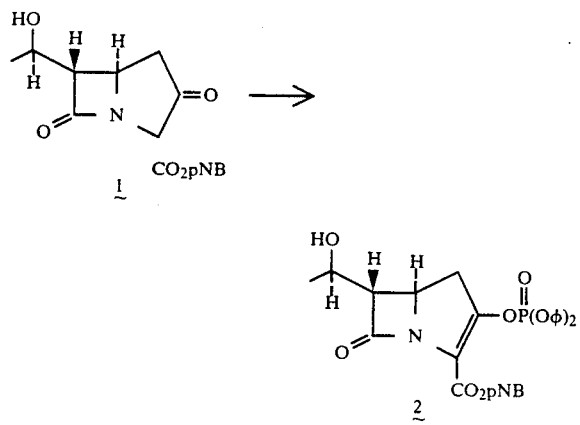

Preparation of p-nitrobenzyl (5R,6S)-3-diphenylphosphoryl-6-[(R)-1-hydroxyethyl]-1-azabicyclo [3,2,0]hept-2-en-7-one-2-carboxylate (2).

A solution of bicyclic keto ester (1) (17.4 mg, 0.105 mmol) in MeCN (0.5 ml) was cooled in an ice-bath and treated with iPr$_2$NEt (10.4 μl, 0.06 mmol) and diphenyl chlorophosphate (10.9 μl, 0.053 mmol). The resulting solution was stirred in the cold for 2 hrs., then diluted to 10 ml with EtOAc, washed with H$_2$O (2 ml), 5% NaHCO$_3$ (2 ml) and brine, dried with MgSO$_4$, and filtered. Evaporation of the solvent under vacuum afforded the crude vinyl phosphate (2) (27 mg, 93%) as a pale yellow oil: IR(CDCl$_3$) 1775, 1720, 1630, 1585, 1520, 1485, 1345 cm$^{-1}$; NMR(CDCl$_3$)δ1.30 (d, 3, J=6.3 Hz, CHCH$_3$), 3.22 (m, 3, H4a, H4b, H6), 4.18 (m, 2, CHCH$_3$, H5), 5.32 (ABq, 2, J=13.9 Hz, CO$_2$CH$_2$), 7.28 (m, 10, phenyl), 7.55 (d, 2, J=9.0 Hz, aryl), 8.15 (d, 2, J=9.0 Hz, aryl).

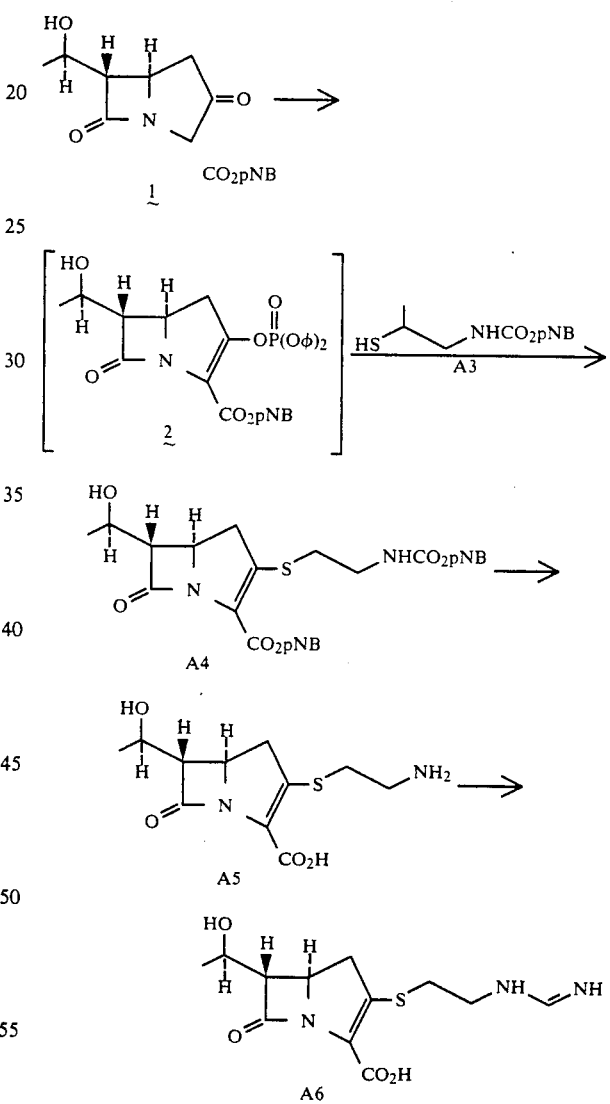

Step 1. Preparation of N-(p-nitrobenzyloxycarbonyl)-1-amino-2-propanethiol (A3)

A solution of p-nitrobenzyl chloroformate (0.95 g, 4.41 mmol) in Et$_2$O (30 ml) was added dropwise over 45 min. to an ice-cold, stirring mixture of 1-amino-2-propanethiol (0.504 g, 3.94 mmol) in Et$_2$O (100 ml), H$_2$O (11 ml), and 10% aqueous NaHCO$_3$ (10 ml). The resulting mixture was stirred an additional 80 min. at 0°–5°, and then separated into two phases. The organic portion was washed with cold 0.025N HCl (30 ml) and brine (20 ml), dried with MgSO4, filtered, and concentrated under vacuum to a yellow oil (1.28 g). The crude product was purified by preparative TLC on silica gel GF using 20:1 CH2Cl2-EtOAc as developing solvent to afford an off-white solid (1.00 g). Recrystallization of the chromatographed product from Et2O-petroleum ether gave compound (A3) (0.183 g) as a cream colored solid: mp 54°–56.5°.

Step 2. Preparation of p-nitrobenzyl (5R,6S)-3-[(RS)-N-(p-nitrobenzyloxycarbonyl)-1-aminopropyl-2-thio]-6-[(R)-1-hydroxyethyl]-1-azabicyclo[3.2.0]hept-2-en-7-one-2-carboxylate (A4).

N,N-Diisopropylethylamine (79 μl, 0.46 mmol) and diphenyl chlorophosphate (88 μl, 0.42 mmol) were added to an ice-cold solution of bicyclic keto ester (1) (146 mg, 0.42 mmol) in MeCN (3.0 ml). The resulting solution was stirred in the cold and under a N2 atmosphere for 40 min. to effect conversion to the vinyl phosphate (2). The solution was treated with more iPr2-NEt (79 μl, 0.46 mmol) and with a solution of mercaptan (A3) in MeCN (1.1 ml). The resulting mixture was kept in the cold for 19 hrs., then diluted with EtOAc, washed with brine, dried over Na2SO4, filtered, and evaporated under vacuum to a yellow oil (675 mg). The crude product was purified by chromatography on a column of silica gel (1.5×15.2 cm) using 5:1 EtOAc-CH2Cl2 as eluting solution; 7 ml fractions were collected. Fractions 12–21 provide compound (A4) (111 mg) as an off-white solid: IR(CHCl3) 3400, 2940, 1770, 1725, 1605, 1510, 1350, 1230 (br), 1140, 1053 cm$^{-1}$; NMR((CD3)2CO)δ1.06 (d, J=6.5 Hz), 1.27 (d, J=6.5 Hz), 1.32 (d, J=6.5 Hz), 1.37 (d, J=6.5 Hz), 3.16–3.84 (m), 4.13 (m), 4.27 (m), 5.27 (s), 5.32 (d, J=14 Hz), 5.55 (d, J=14 Hz), 6.98 (brs), 7.69 (d, J=9 Hz), 7.86 (d, J=9 Hz), 8.28 (d, J=9 Hz), 8.29 (d, J=9 Hz).

Compound (4) obtained by this method is a mixture of two diastereomers which are isomeric at the chiral center of the thia side chain.

Step 3. Preparation of (5R,6S)-3-[(RS)-1-aminopropyl-2-thio]-6-[(R)-1-hydroxyethyl]-1-azabicyclo[3.2.0]hept-2-en-7-one-2-carboxylic acid (A5).

(a) A mixture of diprotected derivative (A4) (51 mg), PtO2 (29 mg), THF (10 ml), H2O (5 ml), and 0.1 M pH7 MOPS buffer (1 ml) was stirred under a H2 atmosphere at room temperature for 45 min. Additional PtO2 (50 mg) was added and the mixture was hydrogenated an additional 30 min. The catalyst was removed by filtration through a pad of moist cellite and the filtrate was diluted with H2O (20 ml) and EtOAc (25 ml) and shaken. The aqueous phase was separated, washed with EtOAc and Et2O, concentrated under vacuum, and filtered through a plug of glass wool. UV analysis of the aqueous phase indicated that there was 4.7 mg of product (A5) in 6.5 ml of solution.

(b) A mixture of diprotected derivative (A4) (28.7 mg), THF (12.2 ml), 0.1M pH7 phosphate buffer (15.3 ml) and PtO2 (21.4 mg) was hydrogenated at 45 psi for 1 hr. The mixture was filtered through a cellite pad to remove the catalyst which was washed with ~50 ml H2O. The filtrate was washed with EtOAc (2×50 ml, 30 ml), concentrated under vacuum to 3 ml volume, and loaded onto an XAD-2 column (6 ml). The column was eluted with H2O (30 ml) followed by 5% THF/H2O; 4.5 ml fractions were collected. Fractions 3–7 were combined, concentrated, and lyophilized to provide compound (A5) as a white powder:

Step 4. Preparation of (5R,6S)-3-[(RS)-N-formimidoyl-1-aminopropyl-2-thio]-6-[(R)-1-hydroxyethyl]-1-azabicyclo[3.2.0]hept-2-en-7-one-2-carboxylic acid (A6)

A solution of crude amine (A5) (11 mg, 0.038 mmol) in H2O (~2 ml) containing MOPS buffer was cooled in an ice-bath and stirred. The pH of the solution was brought to 8.5 with 0.025N NaOH prior to addition of methyl formimidate hydrochloride (55 mg, 0.58 mmol). The pH was readjusted to 8.5 and the solution was stirred in the cold for 10 min. After that time, the solution was acidified to pH7, diluted with H2O, extracted with EtOAc and Et2O, filtered through a glass wool plug, concentrated under vacuum to ca. 2 ml colume, and loaded onto an XAD-2 column (50 ml). The column was eluted with H2O (15 column volumes) followed by 5% THF/H2O (2 column volumes). The chromatography was performed in a cold room at 5°. Column volumes 2–5 were combined, concentrated under vacuum to ca. 7.5 ml volume, and lyophilized to provide compound (A6) (2.1 mg by UV assay) as a fluffy, white solid:

EXAMPLE 45a

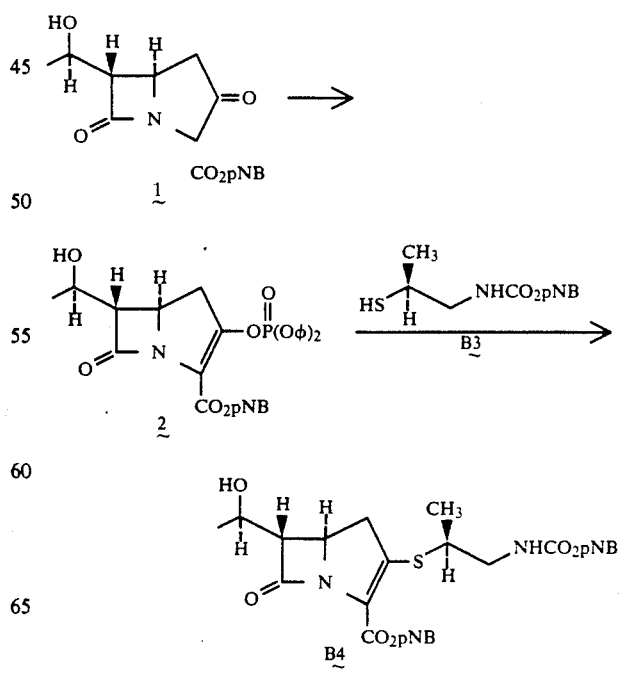

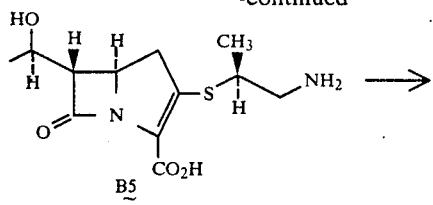

B5

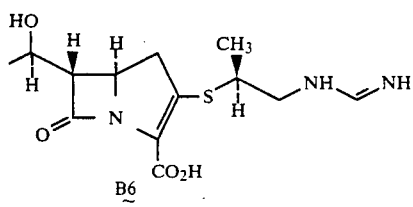

B6

Step 1. Preparation of (S)-N-(p-nitrobenzyloxycarbonyl)-1-amino-2-propanethiol (B3)

Saturated aqueous NaHCO$_3$ (8 ml) was added dropwise to an ice-cold, stirring mixture of (S)-(+)-1-amino-2-propanethiol hydrochloride (363 mg, 2.85 mmol) in Et$_2$O (75 ml) and H$_2$O (8 ml) and the resulting slurry was stirred in the cold for 30 min. A solution of p-nitrobenzyl chloroformate (693 mg, 3.21 mmol) in Et$_2$O (25 ml) was then added dropwise over 35 min. After having been stirred in the cold an additional 50 min., the reaction mixture was transferred to a separately funnel and the layers were separated. The organic portion was washed with ice-cold 0.025N HCl and brine, dried with MgSO$_4$, filtered, and evaporated under a vacuum to a yellow oil (886 mg) which solidified on standing. The crude product was purified by preparative TLC on four 0.1×20×40 cm silica gel GF plates using 30:1 CH$_2$Cl$_2$-EtOAc as developing solvent. The product band provided a yellow oil (667 mg) which crystallized on scratching. Recrystallization from Et$_2$O-petroleum ether offorded the title compound B3) in two crops; crop 1 consisted of tiny, white crystals (216 mg) having mp 55.5°-60.5° and crop 2 afforded larger, off-white crystals (284 mg) having mp 55.5°-62°, [α]$_D$+21.5° (C1.32 in CHCl$_3$).

Step 2. Preparation of p-nitrobenzyl (5R,6S)-3-[(S)-N-(p-nitrobenzyloxycarbonyl-1-aminopropyl-2-thio]-6-[(R)-1-hydroxyethyl]-1-azabicyclo[3.2.0]hept-2-en-7-one-2-carboxylate (B4)

N,N-Disopropylethylamine (75 μl, 0.45 mmol) and diphenyl chlorophosphate (88 μl, 0.42 mmol) were added to an ice-cold solution of bicyclic keto ester (1) in anhydrous MeCN (3.1 ml). The resulting solution was stirred for 35 min. at 0° in order to effect formation of the vinyl phosphate (2). More N,N-iPr$_2$NEt (79 μl, 0.45 mmol) and a solution of (+)-thiol (B3) (339 mg, 1.25 mmol) in MeCN (1.1 ml) were added to the reaction mixture. After stirring in the cold for 75 min., a heavy white precipitate had formed. The mixture was kept in a refrigerator at 4° for 16 hrs., then diluted with EtOAc (50 ml) and washed with brine. The organic phase was dried with Na$_2$SO$_4$, filtered and evaporated under vacuum to a residue which was purified by chromatography on a silica gel column (1.5×16.5 cm). The column was eluted with 5:1 EtOAc-CH$_2$Cl$_2$; 3.5 ml fractions being collected. Fractions 22-32 gave compound (B4) (39 mg) as a while solid. Fractions 11-21 gave slightly impure (B4) (77 mg) which was rechromatographed to give additional, pure (B4) (46 mg): IR(THF) 1770, 1720, 1600, 1525 cm$^{-1}$; NMR((CD$_3$)$_2$CO)δ1.06 (d, J=6.5 Hz, OH), 1.28 (d, J=6.5 Hz, CH$_3$CH—O), 1.32 (d, J=6.5 Hz, CH$_3$CHS, 3.12-3.76 (m, CH$_2$N, CHS, H4a, H4b, H6), 4.13 (m, H5), 4.28 (m, CH$_3$CHO), 5.28 (s, NCO$_2$CH$_2$), 5.31 and 5.56 (two d's, J=14 Hz, CO$_2$CH$_2$) 7.05 (brs, NH), 7.69, 7.85, and 8.29 (three d's, J=9 Hz, aryl).

Step 3. Preparation of (5R,6S)-3-[(S)-1-aminopropyl-2-thio]-6-[(R)-1-hydroxyethyl]-1-azabicyclo [3.2.0]hept-2-en-7-one-2-carboxylic acid (B5)

A mixture of diprotected derivative (B4) (100 mg, 0.167 mmol), PtO$_2$ (90 mg), THF (20 ml), H$_2$O (20 ml), and 0.1M pH7 MOPS (5 ml) was shaken under 40 psi of hydrogen for 75 min. The mixture was filtered through a cellite pad and the filtrate was diluted with H$_2$O and washed with EtOAc (3×30 ml) and Et$_2$O (2×25 ml). The aqueous phase, which assayed for 18.5 mg product by UV, was concentrated under vacuum to 6.5 ml volume and loaded onto an XAD-2 column (74 ml). The column was eluted with water (335 ml) followed by 5% THF/H$_2$O in 10 ml fractions. The chromatography was performed in a cold room at 4°-5°. Fractions 3-9 of the 5% THF/H$_2$O eluant were combined to give a solution assaying for 16 mg of (B5). An aliquot of the solution was concentrated under vacuum and lyophilized to afford (B5) as a white powder:

Step 4. Preparation of (5R,6S)-3-[(S)-N-formimidoyl-1-aminopropyl-2thio]-6-[(R)-1-hydroxyethyl]-1-azabicyclo[3.2.0]hept-2-en-7-one-2-carboxylic acid (B6)

A solution of amino acid (B5) (8 mg, 0.0279 mmol) in H$_2$O (2 ml) and 0.5M pH7 MOPS (0.1 ml) was cooled in an ice-bath, stirred, and brought to pH8.7 with 0.025N NaOH. Methyl formimidate hydrochloride (41 mg, 0.434 mmol) was added to the solution followed by 0.025N NaOH to bring the pH back to 8.6 and the resulting solution was stirred in the cold for 13 min. After acidifying pH7 with 0.025N HCl, the solution was diluted with H$_2$O (20 ml), washed with EtOAc (2×25 ml) and Et$_2$O (2×25 ml), concentrated under vacuum to 2.5 ml volume, and loaded onto a column of XAD-2 resin (40 ml). The column was eluted with H$_2$O (38×8 ml fractions) followed by 5% THF/H$_2$O (8 ml fractions), the separation being performed in a cold room at 4°-5. Fractions 32-56 were combined and concentrated under vacuum to 3.4 ml volume. This solution contained 3.2 mg of product (B6) as shown by UV. Fractions 21-31, which contained additional product (1.6 mg) as shown by UV, were concentrated and lyophilized to a white powder.

EXAMPLE 45c

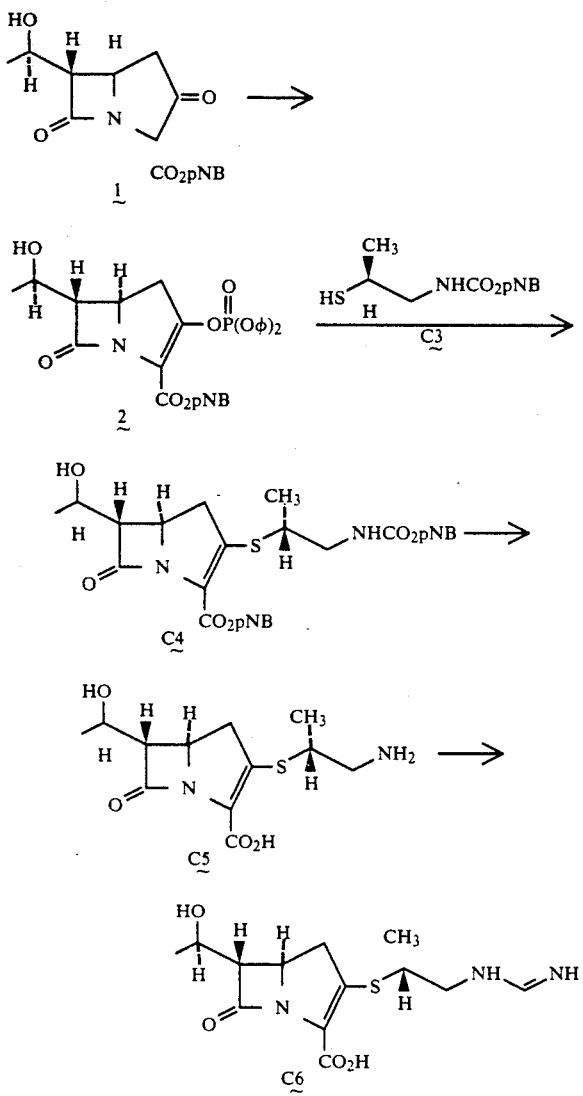

Step 1. Preparation of (R)-N-(p-nitrobenzyloxycarbonyl)-1-amino-2-propanethiol (C3)

The title compound (C3) is prepared from (R)-(−)-1-amino-2-propanethiol by the procedure of Example 45b, step 1.

Step 2. Preparation of p-nitrobenzyl (5R,6S)-3-[(R)-N-(p-nitrobenzyloxycarbonyl)-1-aminopropyl-2-thio]-6-[(R)-1-hydroxyethyl]-1-azabicyclo[3.2.0]hept-2-en-7-one-2-carboxylate (C4)

Compound (C4) was prepared from (1) and (C3) according to the procedure of Example B, step 2. Compound (C4) exhibited the following spectral properties: IR(THF) 1770, 1720, 1600, 1525 cm$^1$; NMR((CD$_3$)$_2$CO) δ 1.07 (d, J=6 Hz, OH), 1.27 (d, J=6.5 Hz, CH$_3$CHO), 1.36 (d, J=6.5 Hz, CH$_3$CHS), 3.31 (m, H4a, H4b), 3.43 (m, CH$_2$N, CH$_3$CHS, H6), 4.14 (m, H5), 4.27 (m, CH$_3$CHO), 5.27 (s, NCO$_2$CH$_2$), 5.32 and 5.55 9two d's, J=14 Hz, CO$_2$CH$_2$), 6.99 (brs, NH), 7.68, 7.85, 8.27, and 8.28 (four d's, J=9 Hz, aryl).

Step 3. Preparation of (5R,6S)-3-[(R)-1-aminopropyl-2-thio]-6-[(R)-1-hydroxyethyl]-1-azabicyclo[3.2.0]hept-2-en-7-one-2-carboxylic acid (C5)

Compound (C4) is deblocked by the procedure of Example 45b step 3 to provide the amino acid (C5).

Step 4. Preparation of (5R,6S)-3-[(R)-N-formimidoyl-1-aminopropyl-2-thio]-6-[(R)-1-hydroxyethyl]-1-azabicyclo[3.2.0]hept-2-en-7-one-2-carboxylic acid (C6)

Compound (C5) is converted to the formamidine (C6) by the procedure of Example 45b, Step 4.

EXAMPLE 45d

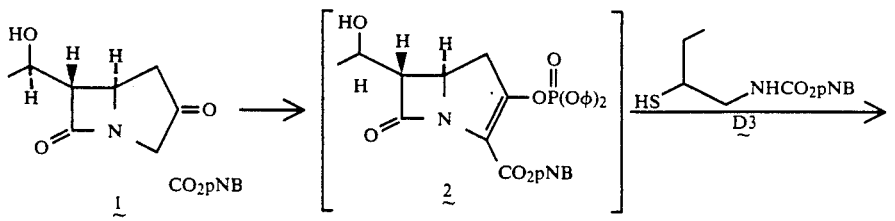

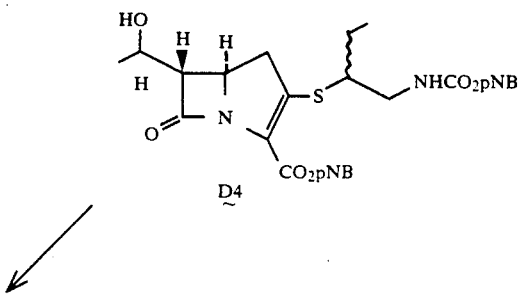

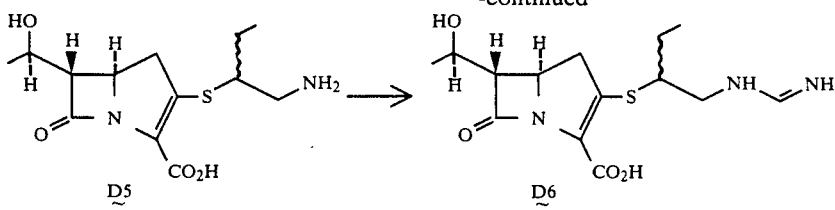

Step 1. Preparation of N-(p-nitrobenzyloxycarbonyl)-1-amino-2-butanethiol (D3)

N,N-Diisopropylethylamine (8.50 ml, 0.0488 mol) and Me$_3$SiCl (3.50 ml, 0.0239 mol) were added to an ice-cold, stirring solution of 1-amino-2-butanethiol (3.00 g, 0.0212 mol) in MeCN (16.0 ml). The solution was stirred 10 minutes at 0°, then treated with more N,N-diisopropylethylamine (3.70 ml, 0.0212 mol) and with a solution of p-nitrobenzyl chloroformate (4.57 g, 0.0212 mol) in MeCN (5.0 ml). The resulting mixture was stirred for 30 minutes at 0° and 90 minutes at room temperature. The mixture was poured into ice-water (50 ml) and extracted with EtOAc (75 ml). The organic phase was separated, washed with 1.25N HCl, 5% NaHCO$_3$, and brine, dried with MgSO$_4$, filtered and evaporated under vacuum to an oil (5.79 g).

The crude product was chromatographed on a Waters Prep LC (250 ml/min, 30% EtOAc/petroleum ether, silica gel pack) and the fractions containing the product were evaporated under vacuum to provide (D3) (4.80 g, 80%) as a light yellow, viscous oil: IR (film) 3350, 1710, 1515 cm$^1$; NMR (CHCl$_3$) δ 1.06 (t, 3, J=7 Hz, CH$_3$), 1.3-2.1 (m, 3, CH$_2$ and SH), 2.81 (p, 1, J=7 Hz, SCH), 3.1 (m, 2, CH$_2$N), 5.23 (s, 2, CO$_2$CH$_2$), 5.88 (br s, 1, NH), 7.48 (d, 2, J=9 Hz, aryl), 8.11 (d, 2, J=9 Hz, aryl); mass spectrum m/e 284 (M), 251 (M-SH), 197 (M-C$_4$H$_7$S).

Step 2. Preparation of p-nitrobenzyl (5R,6S)-3-[(RS)-N-p-nitrobenzyloxycarbonyl)-1-aminobutyl-2-thio]-6-[(R)-1-hydroxyethyl]-1-azabicyclo[3.2.0]hept-2-en-7-one-2-carboxylate (D4)

A solution of bicyclic keto ester (1) (400 mg, 1.14 mmol) in MeCN (8.0 ml) was cooled in an ice-bath and treated with iPr$_2$NEt (220 µl, 1.26 mmol) and diphenyl chlorophosphate (2.50 µl, 1.20 mmol). The resulting solution was stirred at 0° for 45 minutes to effect formation of the p-nitrobenzyl (5R,6S)-3-diphenylphosphonyl-6-[(R)-1-hydroxyethyl]-1-azabicyclo[3.2.0]hept-2-en-7-one-2-carboxylate intermediate (2). The solution was treated with more iPr$_2$NEt (220 µl, 1.26 mmol) and thiol (D3) (8.02 µl, 3.45 mmol), stirred ca. 30 minutes at 0°, and then placed in a freezer at −10° for ca. 2.5 days. The solution was diluted with CH$_2$Cl$_2$ (50 ml), washed with H$_2$O (2×50 ml), dried over MgSO$_4$, filtered, and evaporated to an oil (1.609 g). The crude product was chromatographed on a column of EM silica gel 60 (100 g) using 3:2 CH$_2$Cl$_2$-EtOAc as eluting solvent; 15 ml fractions were collected every 1 minute. Fractions 46-85 were combined and evaporated to afford (D4) (0.367 g, 52%) as a foam: IR (CH$_2$Cl$_2$) 1770, 1720, 1510 cm$^1$; NMR (CDCl$_3$δ 1.08 (t, 3, J=7 Hz, CH$_2$CH$_3$), 1.37 (d, J=6.7 Hz, CHCH$_3$), 1.5-1.9 (m, CH$_2$CH$_3$), 3.0-3.55 (m, SCH, CH$_2$N, H4a, H4b, H6), 4.1-4.3 (m, H5, CH$_3$CH), 5.16-5.56 (m, CO$_2$CH$_2$, NCO$_2$CH$_2$), 7.53, 7.69, 8.26, 8.27 (four d's, J=9 Hz, aryl); mass spectrum m/e 528 (M-C$_4$H$_6$O$_2$); UV (dioxane)max. 268, 320 (sh) nm.

Compound (4) was obtained as a mixture of two diastereomers which are epimeric at the thia side chain chiral center.

Step 3. Preparation of (5R,6S)-3-[(RS)-1-amino-butyl-2-thio]-6-[(R)-1-hydroxyethyl]-1-azabicyclo[3.2.0]hept-2-en-7-one-2-carboxylate (D5)

A solution of diprotected derivative (D4) (350 mg, 0.57 mmol) in THF (42 ml) was added to a prereduced mixture of PtO$_2$ (350 mg) in H$_2$O (28 ml), EtOH (42 ml), and 0.5M pH 7 MOPS (2.8 ml) and the resulting mixture was stirred rapidly under an atmosphere of H$_2$. After 2 hrs, the mixture was filtered through a cellite pad which was washed with H$_2$O. The filtrate was diluted with H$_2$O (100 ml), extracted with EtOAc (3×150 ml), concentrated under vacuum to 20 ml, and loaded onto a column of XAD-2 resin (3.2×30 cm, 240 ml). The XAD chromatography was performed in a cold room at 5°. The column was eluted with H$_2$O (1000 ml) followed by 3% THF/H$_2$O; ca. 20 ml fractions were collected every 1 min. Fractions 62-85 of the THF/H$_2$O eluant were combined, concentrated under vacuum to ca. 20 ml volume, and lyophilized to provide compound (D5) (55 mg) as a white, amorphous powder: UV (H$_2$O) λ max 298 (E 5, 310, 95% NH$_2$OH extinguished) nm.

Step 4. Preparation of (5R,6S)-3-[(RS)-N-formimidoyl-1-aminobutyl-2-thio]-6-[(R)-1-hydroxyethyl]-1-azabicyclo[3.2.0]hept-2-en-7-one-2-carboxylate (D6)

A solution of amino acid (D5) (15 mg, 0.05 mmol) in H$_2$O (3.0 ml) was treated with 0.5 M MOPS (0.3 ml, 0.15 mmol) and stirred in an ice-bath. The pH was adjusted to ~8.5 prior to addition of methyl formimidate hydrochloride (~20 mg, 0.2 mmol). Additional portions (~20 mg) of the formimidate were added after 10 and 20 minutes. The pH was maintained near 8.5 throughout the reaction by addition of 1N NaOH. After 30 minutes, the solution was brought to pH 7 with 1N HCl and charged onto a column of XAD-2 resin (50 ml, 1.8×19 cm) which was maintained in cold room at 5°. The column was eluted with H$_2$O (30 fractions) followed by 3% THF/H$_2$O; ca. 5 ml. fractions being collected every 1 minute. Fractions 40-55 were concentrated under vacuum and lyophilized to provide (D6) as a white, amorphous powder: UV (H₂O) λ max. 300 (E 5, 290; 96% H₂NOH quenched) nm.

EXAMPLE 45e

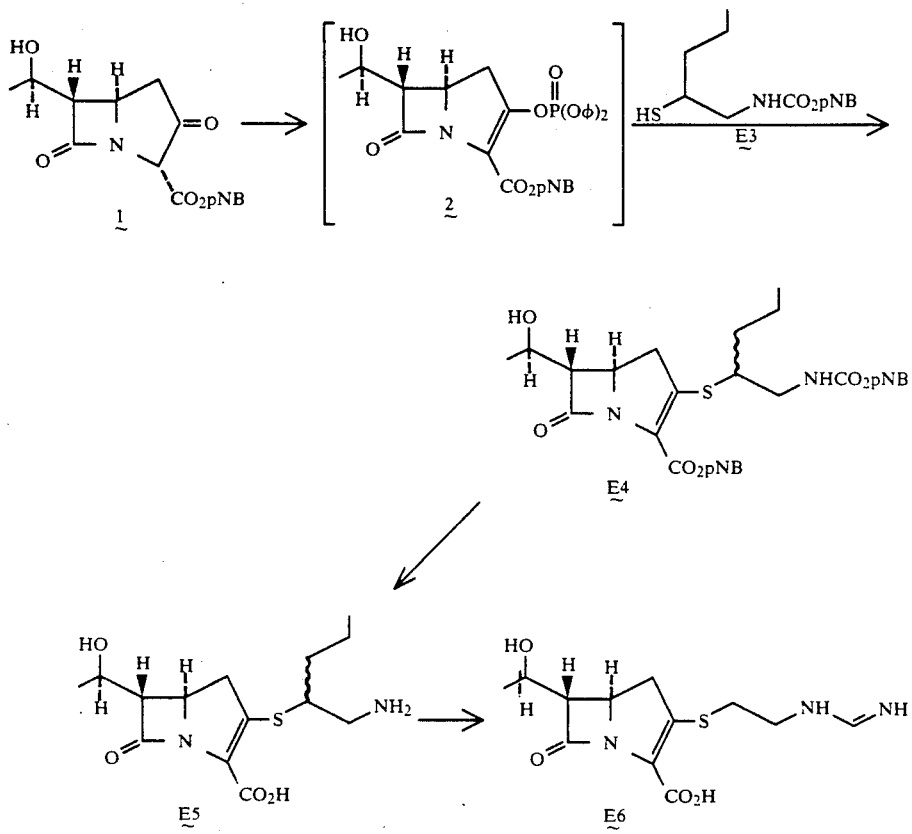

Step 1

Preparation of N-(p-nitrobenzyloxycarbonyl)-1-amino-2-pentanethiol (E3)

1-Amino-2-pentanethiol is converted to the N-(p-nitrobenzyloxycarbonyl) derivatives (E3) by the procedure of Example 45d, Step 1. Compound (E3) has the following spectral properties:

IR (neat) 3300, 1715, 1515 cm$^{-1}$; NMR (CDCl₃) δ 0.92 (m, 3, CH₃), 1.53(m, 4, CH₂CH₂), 3.00 (m, 1, SCH), 3.47(m, 2, CH₂N), 5.28(s, 2, CO₂CH₂), 5.55(brS, 1, NH), 7.57 and 8.27 (two d's, 4, J=9 Hz, aryl); mass spectrum m/e 298 (M), 265 (M-SH).

Step 2

Preparation of p-nitrobenzyl (5R,6S)-3-[(RS)-N-p-nitrobenzyloxycarbonyl)-1-aminobutyl-2-thio]-6-[(R)-1-hydroxyethyl]-1-azabicyclo[3.2.0]hept-2-en-7-one-2-carboxylate (E4)

Derivative (E4) is prepared from thiol (E3) and bicyclic keto ester (1) by the procedure described in Example 45d, Step 2. The product is obtained as a mixture of two diastereomers which are isomeric at the thia side-chain chiral center. Compound (E4) displays the following spectral characteristics: IR (CH₂Cl₂) 1781, 1730, 1525 cm$^{-1}$; NMR (CDCl₃) δ 0.93 (m, CH₂CH₃), 1.37 (d, J=6.9 Hz, CH₃CH), 1.48 (m, CH₂CH₂), 3.00-3.55 (m, H4a, H4b, H6), 4.24 (m, H5, CH₃CH), 5.16-5.56 (m, NCO₂CH₂, CO₂CH₂, NH), 7.52, 7.68, 8.24, 8.25 (four doublets, J=9 Hz, aryl); mass spectrum m/e 582(M-C₂H₄O), 542 (M-C₄H₆O₂).

Step 3

Preparation of (5R,6S)-3-[(RS)-1-aminobutyl-2-thio]-6-[(R)-1-hydroxyethyl]-1-azabicyclo[3.2.0]hept-2-en-7-one-2-carboxylate (E5)

Diprotected intermediate (E4) is deblocked to amino acid (E5) by the procedure described in Example 45d, Step 3.

Step 4

Preparation of (5R,6S)-3-[(RS)-N-formimidoyl-1-aminopentyl-2-thio]-6-[(R)-1-hydroxyethyl]-1-azabicyclo[3.2.0]hept-2-en-7-one-2-carboxylic (E6)

Amino acid (E5) is formimidoylated as described in Example 45d, Step 4, to provide compound (E6).

EXAMPLE 45f

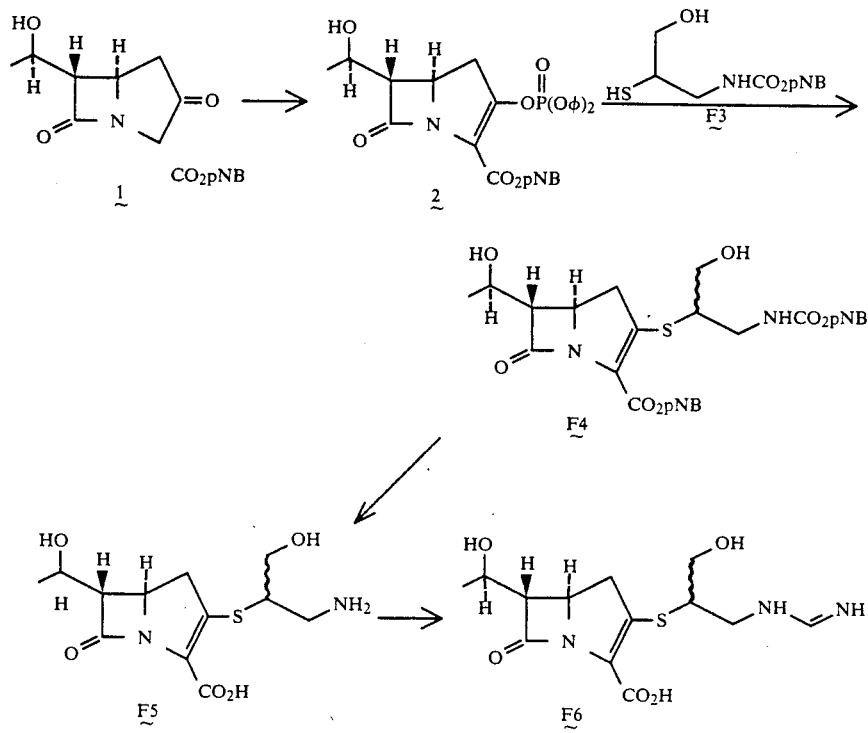

Step 1
Preparation of N-(p-nitrobenzyloxycarbonyl)-1-amino-3-hydroxy-2-propanethiol (F3)

1,2-Propanediol (10.0 ml) was dissolved in H$_2$O (26.4 ml) containing NaOH (5.27 g) and the solution was added dropwise to rapidly stirring solution of ethyl chloroformate (12.6 ml) in toluene (25.2 ml). The temperature of the reaction mixture was kept below 15° C. by ice-bath cooling. The mixture was stirred for 10 more-minutes following the addition. The organic layer was separated, dried with MgSO$_4$, fitlered, and evaporated under vacuum to an oil which was distilled under vacuum to provide 2,3-epthio-1-propanol (5.3 g).

The epithio compound was added dropwise to an ice-cold vigorously stirring solution of silver nitrate (3.30 g) in H$_2$O (4.5 ml) and concentrated aqueous NH$_4$OH (10.4 ml). The cooling bath was removed and the mixture was stirred at room temperature for 2.5 hrs. The yellow precipitate was collected, washed with H$_2$O until the filtrate was neutral, and then suspended in H$_2$O (50 ml). Hydrogen sulfide was parred through the rapidly stirring suspension for 30 mins. The resulting mixture was filtered to remove silver sulfide. The filtrate was adjusted to pH 8.5 with 10% NaOH, diluted with an equal volume of dioxane, cooled in an ice-bath, and treated with p-nitrobenzyl chloroformate while maintaining the pH at 8.5-9.0. After stirring for 30 mins at 0°, the mixture was neutralized with dilute hydrochloric acid and extracted with EtOAc. The EtOAc extracts were dried with Na$_2$SO$_4$, filtered, and evaporated under vacuum to a solid residue. Chromatography of the crude product on a silica gel column using 40% EtOAc/cyclohexane as eluting solvent provided N-(p-nitrobenzyloxycarbonyl)-1-amino-3-hydroxy-2-propanedisulfide.

A mixture of the disulfide (2.00 g), dithiothreotol (541. mg), dioxane (10.3 ml) and 1M K$_2$HPO$_4$ (5.8 ml) was stirred under a N$_2$ atmosphere and at room temperature for 45 mins. The mixture was evaporated under vacuum to a residue which was taken up in EtOAc and washed with H$_2$O and brine. The organic phase was dried over Na$_2$SO$_4$, filtered, and evaporated under vacuum to a residue (1.85 g) which was chromatographed silica gel (185 g) using 1:1 EtOAc - petroleum ether as eluting solvent. The appropriate fractions were combined and evaporated under vacuum to a residue which was triturated with EtOAc - hexanes to provide thiol (F3) (603 mg) as a white, crystalline solid: m.p. 65°-67°; NMR (CDCl$_3$) δ 1.48 (d, J=9.5 Hz, SH), 3.00 (m, CH$_5$), 3.22 (t, J=7 Hz, OH), 3.34-3.56 (m, CH$_2$N), 3.59-3.80 (m, CH$_2$O), 5.22(S, CO$_2$CH$_2$), 5.32 (br m, NH), 7.53 and 8.25 (two d's, J=8 Hz, aryl); IR(CH$_2$Cl$_2$) 3400, 1715, 1510, 1345 cm$^{-1}$.

Step 2
Preparation of p-nitrobenzyl (5R, 6S)-3-[(RS)-N-(p-nitrobenzyloxycarbonyl)-1-amino-3-hydroxypropyl-2thio]-6-[(R)-1-hydroxyethyl]-1-azabicyclo[3.2.0]-hept-2-en-7-one-2-carboxylate (F4)

N,N-Diisopropylethylamine (156 μl, 0.896 mmol) and diphenyl chlorophosphate (164 μl, 0.791 mmol) were added to an ice-cold, stirring solution of bicyclic keto ester (1) (261 mg, 0.75 mmol) in MeCN (2.4 ml). After stirring for 35 mins at 0° the reaction mixture was treated with more iPr$_2$NEt (144 l, 0.827 mmol) and with a solution of thiol (F3) (2.36 mg, 0.823 mmol) in MeCN (0.6 ml.) The mixture was stirred at 0° for 65 mins, then diluted with EtOAc, washed with H$_2$O (3×) and brine, dried with Na₂SO₄, filtered, and evaporated under vacuum to an oil (522 mg). The crude product was chromatographed on a column of EM silica gel 60 (53 g) which was eluted with EtOAc. Twenty 50 ml fractions were collected every 2 mins followed by fifteen 85 ml fractions every 4 mins. Fractions 20-34 were combined and evaporated to a residue which crystallized from EtOAc-hexanes at dry ice temperature to afford compound (F4) (185 mg, 40%) as an off-white solid. Compound (F4) is a mixture of two diastereomers which are epimeric at the thia side chain chiral center: IR(CH₂Cl₂) 1776, 1710, 1520, 1345 cm¹; UV (dioxane) λmax 269, 321 (sh)nm; NMR (CD₃)₂CO) δ 1.26 (d, J=6 Hz, CH₃CH), 3.26-3.68 (m, CHS, CH₂N, H4a, H4b, H6), 3.80 (m, CH₂OH), 4.08-4.36 (m, H5 and CH₃CH), 5.27 (s, NCO₂CH₂), 5.31 and 5.36 (d's, J=14 Hz, CO₂CH₂), 6.99 (br s, NH), 7.07, 7.23, 8.26 (d's, J=9 Hz, aryl).

Step 3

Preparation of (5R, 6S)-3-[(RS)-1-amino-3-hydroxypropyl-2thio]-6-[(R)-1-hydroxyethyl]-1-azabicyclo[3.2.0]-hept-2-en-7-one-2-carboxylate (F5)

A solution of diportected intermediate (F4) (89 mg, 0.145 mmol) in THF (10.7 ml), EtOH (5.35 ml), H₂O (7.13 ml) and 0.5 pH 7 MOPS (0.89 ml) was added to a prereduced mixture of PtO₂ (89 mg) in EtOH (5.35 ml). The resulting mixture was stirred vigorously under a H₂ atmosphere for 75 mins and then filtered to remove the catalyst. The filtrate was diluted with H₂O and washed repeatedly with EtOAc and Et₂O. UV analysis of the aqueous phase revealed that it contained ca. 21 mg of product. One-third of the aqueous phase was concentrated under vacuum and loaded onto an XAD-2 column (11 ml) which was eluted with H₂O (30 ml) and 3% THF/H₂O at a rate of 4.4 ml fractions every 2 mins. The chromatography was performed in a cold room at 4°-5°. Fractions 2-7 contained the amino acid (F5) (2.6 mg) as shown by UV: UV (H₂O) λmax 297 nm.

Step 4

Preparation of (5R, 6S)-3-[(RS)-N-formimidoyl-1-amino-3-hydroxypropyl-2thio]-6-[(R)-1-hydroxyethyl]-1-azabicyclo[3.2.0]-hept-2-en-7-one-2-carboxylate (F6)

A solution of crude amino acid (F5) (11 mg, 0.036 mmol) in H₂O (2.1 ml) containing MOPS buffer was cooled in an ice-bath and brought to a pH of 8.5 with 1N NaOH. The solution was rapidly stirred at 0° while methyl formimidate hydrochloride (105 mg, 1.094 mmol) was added in 7 portions over a period of 30 mins. The pH of the solution was maintained at 8.2-8.5 by addition of 1N NaOH. After an additional 10 mins, the mixture was acidified to pH 7 with 1N HCl, washed with EtOAc, and charged onto an XAD-2 column (50 ml). The column was eluted with H₂O (150 ml) and 3% THF/H₂O at a rate of 10 ml fractions every 3 mins. The chromatograph was performed in a cold room at 4°-5°. Fractions 7-14 were combined and concentrated under vacuum to give a solution containing 5.6 mg of (F6) by UV. Half of the solution was lyophilized to provide compound (F6) as a solid residue: UV (H₂O) λmax 298 nm; NMR (D₂O) δ 1.29 (d, J=6 Hz, CH₃CH), 4.23 (M, H5 and CH₃CH), 7.84 and 7.88 (two singlets, CH=N).

EXAMPLE 45g

Following the procedure of the foregoing examples and text, the following "amidino" embodiments of the presetn invention are obtained. In the following table the amino precursor ("—SR⁸—NR¹H") to the amidino embodiment is also entered.

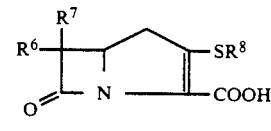

EXAMPLE 45g

| Compound | R⁶ | R⁷ | —SR⁸—NHR¹ | —SR⁸ |
|---|---|---|---|---|
| 1 | H | OH<br>CH₃—CH | —S~~~NH₂<br>≡<br>CH₃ | S~~~NH≡NH<br>CH₃ |
| 2 | H | OH<br>CH₃—CH | —S~~~NH₂<br>▲<br>CH₃ | S~~~NH≡NH<br>CH₃ |
| 3 | H | OH<br>CH₃—CH | —S~~~NH₂<br>H₃C CH₃ | S~~~NH≡NH<br>H₃C CH₃ |
| 4 | H | OH<br>CH₃—CH | —S~~~NH₂<br>≡<br>CO₂H | —S~~~NH≡NH<br>CO₂H |
| 5 | H | OH<br>CH₃—CH | CH₃<br>▼<br>—S~~~NH₂<br>≡<br>CH₃ | CH₃<br>▼<br>—S~~~NH≡NH<br>CH₃ |

-continued

| # | | | | |
|---|---|---|---|---|
| 6 | H | CH₃—CH(OH) | CH₃-CH(-S-)-CH(NH₂)-CH₃ | CH₃-CH(-S-)-CH(CH₃)-NH-CH=NH |
| 7 | H | CH₃—CH(OH) | -S-CH₂CH₂-NH-CH₂CH₃ | -S-CH₂CH₂-N(CH₂CH₃)-CH=NH |
| 8 | H | CH₃—CH(OH) | -S-CH(CH₃)-CH₂-NHCH₃ | -S-CH(CH₃)-CH₂-N(CH₃)-CH=NH |
| 9 | H | CH₃—CH(OH) | -S-CH(CH₃)-CH₂-NHCH₃ | -S-CH(CH₃)-CH₂-N(CH₃)-CH=NH |
| 10 | H | CH₃—CH(OH) | -S-CH₂-CH(CH₃)-NHCH₃ | -S-CH₂-CH(CH₃)-N(CH₃)-CH=NH |
| 11 | H | CH₃—CH(OH) | -S-CH₂CH₂CH₂-NH₂ | -S-CH₂CH₂CH₂-NH-CH=NH |
| 12 | H | CH₃—CH(OH) | -S-CH₂-C(CH₃)₂-CH₂-NH₂ | -S-CH₂-C(CH₃)₂-CH₂-NH-CH=NH |
| 13 | H | CH₃—CH(OH) | -S-CH(CH₂CH₃)-CH₂-NH | -S-CH(CH₂CH₃)-CH₂-NH-CH=NH |
| 14 | H | CH₃—CH(OH) | -S-CH(CH₂CH₃)-CH₂-NH | -S-CH(CH₂CH₃)-CH₂-NH-C(CH₃)=NH |
| 15 | H | CH₃—CH(OH) | -S-CH(CH₃)-CH₂-NH₂ | -S-CH(CH₃)-CH₂-NH-C(CH₃)=NH |
| 16 | H | CH₃—CH(OH) | -S-CH(CH₃)-CH₂-NH₂ | -S-CH(CH₃)-CH₂-NH-C(CH₃)=NH |
| 17 | H | CH₃—CH(OH) | -S-CH(CH₃)-CH₂-NH₂ | -S-CH(CH₃)-CH₂-NH-CH=NHCH₃ |
| 18 | H | CH₃—CH(OH) | -S-CH(CH₃)-CH₂-NH₂ | -S-CH(CH₃)-CH₂-NH-CH=NHCH₂CH₃ |
| 19 | H | CH₃—CH(OH) | -S-CH(CH₃)-CH₂-NH₂ | -S-CH(CH₃)-CH₂-NH-(2-pyrrolin-2-yl) |
| 20 | H | CH₃—CH(OH) | -S-CH(CH₃)-CH₂-NH₂ | -S-CH(CH₃)-CH₂-N=CH-N(CH₃)₂ |
| 21 | H | CH₃—CH(OH) | -S-CH(CH₃)-CH₂-NH₂ | -S-CH(CH₃)-CH₂-NH-CH=NH-OCH₃ |

-continued

| # | | | | |
|---|---|---|---|---|
| 22 | H | CH₃—CH(OH) | CH₃-CH(S-)-CH₂-NH₂ | CH₃-CH(S-)-N=CH-N(pyrrolidine) |
| 23 | H | CH₃—CH(OH) | CH₃-CH(S-)-CH₂-NH₂ | CH₃-CH(S-)-N=CH-N(morpholine-like, oxazolidine) |
| 24 | H | CH₃—CH(OH) | CH₃-CH(S-)-CH₂-N(CH₃)H | CH₃-CH(S-)-CH₂-N(CH₃)-C(CH₃)=NH |
| 25 | H | CH₃—CH(OH) | CH₃-CH(S-)-CH₂-N(CH₃)H | CH₃-CH(S-)-CH₂-N(CH₃)-CH=NCH₃ |
| 26 | H | CH₃—CH(OH) | CH₃-CH(S-)-CH₂-N(CH₃)H | CH₃-CH(S-)-CH₂-N⁺(CH₃)=CH-N(CH₃)₂ |
| 27 | H | CH₃—CH(OH) | -S-C(CH₃)₂-CH₂-NH₂ | -S-C(CH₃)₂-CH₂-NH-CH=NH |
| 28 | H | CH₃—CH(OH) | -S-CH(CH₂OH)-CH₂-NH₂ | -S-CH(CH₂OH)-CH₂-NH-CH=NH |
| 29 | H | CH₃—CH(OH) | -S-CH(CH₂F)-CH₂-NH₂ | -S-CH(CH₂F)-CH₂-NH-CH=NH |
| 30 | H | CH₃—CH(OH) | -S-CH(CF₃)-CH₂-NH₂ | -S-CH(CF₃)-CH₂-NH-CH=NH |
| 31 | H | CH₃—CH(OH) | -S-CH(CH₃)-CH₂-N(OCH₃)H | -S-CH(CH₃)-CH₂-N(OCH₃)-CH=NH |
| 32 | H | CH₃—CH(OH) | -S-CH(φ)-CH₂-NH₂ | -S-CH(φ)-CH₂-NH-CH=NH |
| 33 | H | CH₃—CH(OH) | -S-CH(OCH₃)-CH₂-NH₂ | -S-CH(OCH₃)-CH₂-NH-CH=NH |
| 34 | H | CH₃—CH(OH) | -S-CH(CH(CH₃)₂)-CH₂-NH₂ | -S-CH(CH(CH₃)₂)-CH₂-NH-CH=NH |
| 35 | H | CH₃—CH(OH) | -S-CH₂CH₂CH₂-NH₂ | -S-CH₂CH₂CH₂-NH-CH=NH |
| 36 | H | CH₃—CH(OH) | -S-CH₂-CH(OCH₃)-CH₂-NH₂ | -S-CH₂-CH(OCH₃)-CH₂-NH-CH=NH |
| 37 | H | CH₃—CH(OH) | -S-CH(CH₂NH₂)-CH₂-NH₂ | -S-CH(CH₂-N=CH-NH-CH₂)- (cyclic dihydropyrimidine) |
| 38 | H | CH₃—CH(OH) | S-pyrrolidine-NH | S-pyrrolidine-N-CH=NH |

-continued

| # | | | | |
|---|---|---|---|---|
| 39 | H | CH₃—CH(OH) | [cyclopentyl-S- with NH₂] | [cyclopentyl-S- with NH-CH=NH] |
| 40 | H | CH₃—CH(OH) | -S-[cyclopropyl]-NH₂ | -S-[cyclopropyl]-NH-CH=NH |
| 41 | H | CH₃—CH(OH) | -S-CH₂-CH(NH₂)-CH₂-NH₂ | -S-CH₂-CH(N=CH-)-CH₂-NH |
| 42 | H | CH₃—CH(OH) | -S-[phenyl]-N(CH₃)H | -S-[phenyl]-N(CH₃)-CH=NCH₃ |
| 43 | H | CH₃—CH(OH) | -S-[phenyl]-CH₂NH₂ | -S-[phenyl]-CH₂-NH-CH=NH |
| 44 | H | CH₃—CH(OH) | -S-CH(CH₃)-[phenyl]-NH₂ | -S-CH(CH₃)-[phenyl]-NH-CH=NH |
| 45 | H | CH₃—CH(OH) | -S-[phenyl]-C(CH₃)₂-O-N(CH₃)H | -S-[phenyl]-C(CH₃)₂-O-N(CH₃)-CH=NH |

| Compound | |
|---|---|
| 46–91 | Compounds 46–91 correspond sequentially to Compounds 1–45 of Example 45g except that the value of R⁷ is CH₃CH₂CH(OH)— rather than CH₃CH(OH). |
| 92–137 | Compounds 92–137 correspond sequentially to Compounds 1–45 of Example 45g except that the value of R⁷ is FCH₂CH(OH) rather than CH₃CH(OH). |
| 138–183 | Compounds 138–183 correspond sequentially to Compounds 1–45 of Example 45g except that the value of R⁷ is (CH₃)₂C(OH) rather than CH₃CH(OH). |
| 184–229 | Compounds 184–229 correspond sequentially to Compounds 1–45 of Example 45g except that the value of R⁷ is CH₃CH₂ rather than CH₃CH₂. |

EXAMPLE 46

This example and those depending from it demonstrate the so called "carbamimidoyl" embodiments of I. Such embodiments have been defined above (see general description of the invention under 2-substituent $R^8$, above: and see text, above, under category No. 10 of reagents $HSR^8$: "Carbamimidoyl Mercaptans $HSR^8$"). As defined above, such carbamimidoyl embodiments are characterized by the following generic representation:

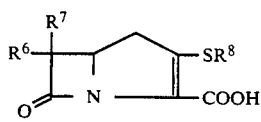

I wherein:

$R^8$, characterized by the carbamimidoyl group, is defined above.

The following diagram summarizes the foregoing text (see Diagram III) and is illustrative of a preferred procedure for making the carbamimidoyl embodiments. In the following scheme, the synthesis shows a subgeneric objective, since it is representative of the entire carbamimidoyl genus. Other subgeneric expressions and species members of the carbamimidoyls are obtained by analogy:

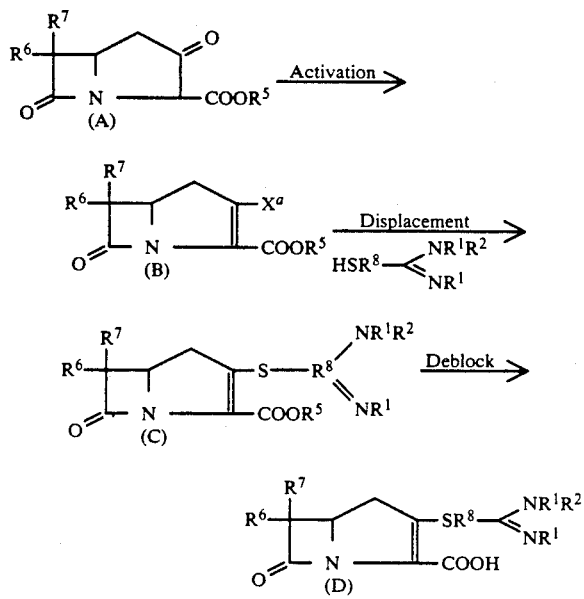

wherein: all symbols are as previously defined.

The activation step, A→B, which establishes the leaving group $X^a$ is accomplished by acylating the keto ester A with an acylating agent such as, for example, p-toluenesulfonic acid anhydride, trifluorometanesulfonic acid anhydride, p-nitrophenylsulfonic acid anhydride, 2,4,6-triisopropylphenylsulfonic acid anhydride, methanesulfonic acid anhydride, diphenylchlorophosphate, toluenesulfonyl chloride, p-bromophenylsulfonyl chloride, or the like. The leaving group $X^a$ thus is established as the corresponding p-toluenesulfonyloxy, p-nitrophenylsulfonyloxy, methanesulfonyloxy, p-bromophenylsulfonyloxy, diphenylphosphate, for example. Typically, the activation is carried out in a suitable organic solvent such as methylene chloride, chloroform, acetonitrile, dimethylformamide, dichloromethane, tetrahydrofuran, and the like, in the presence of a base such as diisopropylethylamine, triethylamine, 4-dimethylaminopyridine, pyridine, and the like at a temperature of from −20° to 40° C. The reaction usually is complete in from 0.5 to 5 hours.

The carboxyl protecting group $R^5$ in the keto ester, A may be any of the well-known, readily removable carboxyl protecting groups such as, benzyl, p-nitrobenzyl, o-nitrobenzyl, methoxymethyl and the like.

The carbamimidoylthio side chain, B→C, is established by treating the activated keto ester, B, in a solvent such as dioxane, dimethylformamide, dimethylsulfoxide, acetonitrite, dichloromethane, tetrahydrofuran, hexamethylphosphoramide, and the like, in the presence of an approximately equivalent to excess quantity of the mercaptan reagent of choice in the presence of a base, such as diisopropylamine, triethylamine, pyridine, sodium hydrogen, carbonate, potassoium carbonate, and the like. The reaction is run at −40° to 50° C. and usually is complete in 1-72 hours. Such mercaptan reagents are either known or readily prepared by known techniques.

The mercaptan reagent may be employed in the form of the free base (as described above), a salt such as the hydrochloride, the hydrobromide, the sulfate and the toluenesulfonate, or a nitrogen atom may be protected with a conventional N-blocking group such as p-nitrobenzyloxycarbonyl. When the mercaptan reagent is in the free base form, the displacement reaction does not require the presence of additional base.

The final deblocking step, C→D, preferably is carried out by catalytic hydrogenation. Catalysts suitable for the reaction include platinum metals, for example, platinum oxide, Pd/C, Pd(OH)$_2$, Pt/C, and the like which are employed with a hydrogen pressure of from 1 to 10 atmospheres at a temperature of from 0 to 10 atmospheres at a temperature of from 0° to 25° C. in the presence of a solvent such as tetrahydrofuran, dioxane, water, and the like. The reaction usually is complete in from 0.5 to 12 hours.

Examples 46a, et seq., specifically demonstrate the process of Example 46.

EXAMPLE 46a (5R, 6S)-2-(Carbamimidoylmethyl-1-thio)-6-(-1-R-hydroxyethyl)carbapen-2-em-3-carboxylic acid

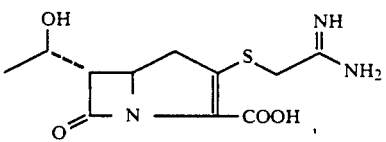

To a solution of (5R,6S)-P-nitrobenzyl 6-[(R)-1-hydroxyethyl]-1-azabicyclo[3.2.0]heptan-3,7-dione-2-carboxylate (34.8 mg) in dry acetonitrile (0.7 ml) at 0° is added simultaneously diphenylchlorophosphoridate (21.8 μl) and diisopropyl ethylamine (20.8 μl). The solution is stirred in an ice bath for 1 hr then a solution of 2 mercaptoacetamidine hydrochloride (15 mg) in dry dimethylsulfoxide (0.7 ml) is added dropwise simultaneously with diisopropylethylamine (25 μl) during a period of 8 minutes. After stirring 20 minutes at 0° the solution is poured into 40 ml of ether and centrifuged. The gummy precipitate is shaken twice with 10 ml portions of ether which are decanted. The residue of p-nitrobenzyl (5R,6S)-2-(carbamimidoyl-methyl-1-thio)-6-(1-R-hydroxyethyl)carbapen-2-em 3-carboxylate is dissolved in 8 ml of tetrahydrofuran-water 1:1, pH 7 phosphate buffer (4 ml, 0.1M) is added and the solution is hydrogenated at 40 PSIG in the presence of 25 mg of 10% Pd/C for 1 hour. The catalyst is removed by filtration and washed with 10 ml of water. The combined filtrates are extracted with ether (30 ml). The aqueous layer is concentrated to 5 ml and applied to a column of Dowex 50×4, (K+ cycle) resin (30 ml). The column is eluted with water taking 9 ml portions. The products obtained in fractions 10-13 is combined, concentrated to 4 ml in vacuo at a bath temperature of 35and freeze dried. Yield 11.3 mg (38%) U.V. λmax 295 mμ, E %291 (97% NH$_2$OH ext).

EXAMPLE 46b (5R,6S)-2-(N-Methylcarbamimidoylmethyl-1-thio)-6-(1-R-hydroxyethyl)carbapen-2-em Carboxylic Acid

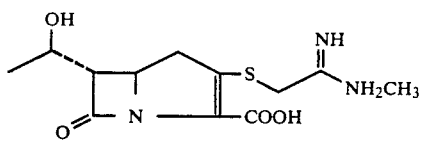

(5R,6S)-p-nitrobenzyl-6-[(R)-1-hydroxyethyl]-1-azabicyclo[3.2.0]heptan-3,7-dione-2-carboxylate (0.7 g) is dissolved in acetonitrile (14 ml). The solution is cooled in an ice-bath under nitrogen. Diphenylphosphorochloridate (0.44 ml) and diisopropylethylamine (0.42 ml) are added all at once. The reaction is complete in 20 minutes. To the solution of p-nitrobenzyl (5R,6S)-3-diphenylphosphoryl-6-[(R)-1-hydroxyethyl] 1-azabicyclo[3.2.0]hept-2-en-7-one-2-carboxylate thus obtained are added diisopropylethylamine (0.42 ml) and a solution of N-methyl-2-mercaptoacetamidine hydrochloride (0.35 g) in dimethylsulfoxide (8 ml) during a period of 5 minutes. The solution is poured into a flask containing 300 ml of ether with swirling, as the major portion of the product precipitates as a gum. The cloudy supernatant solution is filtered through a layer of "cellite" and the flask and filter pad are rinsed with ether. The gum on the filter is dissolved in 100 ml of THF-$H_2O$, 3:2 and the filtrate is added to the residue in the flask. pH 7 Phosphate Buffer (80 ml 0.1M) is added and the solution is hydrogenated at 50 PSIG in the presence of 10% palladium-charcoal catalyst (0.7 g) for 1 hour 20 minutes. The catalyst is filtered and the filtrate is extracted with ether (100 ml). The aqueous layer is concentrated to 20 ml under vacuum and applied to a column (4 cm×36 cm) of Dowex 50×2 (K+ cycle) resin in a cold room.

The column is eluted with water taking 28 ml fractions every 6 minutes. Fractions 25-55 are concentrated and freeze dried. Yield 210 mg. U.V. λmax. 295 mμ, E% 169, 95% $NH_2OH$ ext. Crystals from $H_2O$ give λmax. 295, E% 241, 95% ext.

EXAMPLE 46C (5R,6S)-2-(N,N-Dimethylcarbaminidoylmethyl-1-thio)6-(1-R-hydroxyethyl)carbapen-2-em-3-carboxylic acid

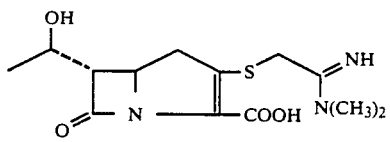

To a stirred solution of (5R,6S)-p-nitrobenzyl-6-[(R)-1-hydroxethyl]-1-azabicyclo[3.2.0]heptan-3,7-dione-2-carboxylate (1.45 g) in acetonitrile (20 ml) in an ice-bath under nitrogen is added diphenylchlorophosphate (0.88 ml) and diisopropylethylamine (0.84 ml) dropwise during 5 minutes. After 30 minutes, diisopropylethylamine (0.7 ml) and a solution of N,N-dimethyl-mercaptoacetamidine hydrochloride (0.82 g) in dimethylsulfoxide (12 ml) are added dropwise during 15 minutes. The solution is poured into ether (0.6 L) and the resulting gum is immediately taken up in a mixture of tetrahydrofuran 120 ml, water 40 ml, and 0.1M phosphate (pH 7, 140 ml) and hydrogenated for 2 hours at 50 PSIG in the presence of 1.4 g. of 10% Pd/C catalyst. The catalyst is filtered and the filtrate is extracted with ether (250 ml). The aqueous layer is concentrated to 125 ml under vacuum and chromatographed on 600 ml of Dowex 50×2 (K+ cycle) resin, eluted with water. The fractions obtained between 1.1 L and 1.6 L of eluate are combined, concentrated and freeze dried. Yield 0.58 g (33%) U.V. λmax 295 nμ, E% 205, 94% $NH_2OH$ ext.

Following the above procedure, the following compound is obtained when the corresponding 9-fluoro starting material is substituted in equivalent amount:

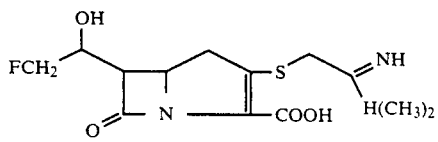

EXAMPLE 46d

N,N-Dimethyl-2-chloroacetamidine Hydrochloride

Sodium (23 mg) is dissolved in methanol (40 ml) under an atmosphere of nitrogen. To the solution is added chloroacetonitrile (6.32 ml) followed after 30 minutes by dimethylamine hydrochloride (8.16 g). After stirring an additional hour the solution is concentrated to a small volume. Ether is added and the product which crystallizes the filtered and washed with ether, yielding 14.5 g of N,N-dimethylchloroacetamidine hydrochloride. NMR, 60 MHZ, $D_2O$, 94 3.23 and 3.37N $(CH_3)_2$; 4.06 (S) $CH_2Cl$. This process is found in J. Med. Chem, 1979, Vol. 22, p 295; William A. Bolhofer, Charles W. Habeckes, Adolph M. Pretruszkiewicz.

EXAMPLE 46E

N,N-Dimethyl-2-mercaptoacetamidine Hydrochloride

A solution of N,N-dimethyl 2-chloroacetamidine hydrochloride (1.8 g), and trisodium phosphorothioate (2.2 g) in 15 ml of water is stirred at room temperature for one hour. Hydrochloric acid (12 ml, 1N) is added and the solution is heated at 90° for 30 minutes under an atmosphere of nitrogen. The solution is concentrated to a slurry of crystals and isopropanol is added. The mixture is filtered and the filtrate is evaporated to an oil. The residue is triturated several times with ether and finally residual solvents are removed on a vacuum pump leaving a gummy residue. This is recrystallized from ethanol ether. m.p. 157°–159°, 60 MHz, NMR, $D_2O$, δ3.15 and 3.28 $(CH_3)_2$; 3.65 $CH_2SH$. See Bolhofer, et al., J. Med. Chem., 1979, Vol. 22, p. 295.

EXAMPLE 46F

Following the procedure in Examples 46d and 46e, but using ethylamine hydrochloride there is obtained N-ethyl-2-mercaptoacetamidinium chloride 60 MHZ, NMR, $D_2O$, δ1.3(t) $CH_2CH_3$; 3.42 $CH_2CH_3$; 3.62, (S),$CH_2SH$. Substituting 2-chloropropionitrile in gives R,S-2-mercapto propionamidine hydrochloride, NMR, δ, 1.64, (d,) CH₃; 3.93, (q) CH, and R,S-N-methyl-2-mercaptopropionamidine hydrochloride, NMR, δ, 1.61, d, CH₃; 3.0, NCH₃; 3.97, (g),CHCH₃.

EXAMPLE 46G

Following the procedure of Example 46A, p-nitrobenzyl (5R,6S)-3-diphenylphosphoryl-6-[(R)-1-hydroxyethyl]-1-azabicyclo[3.2.0]hept-2-en-7-one-2-carboxylate is reacted with the following mercapto carbamimidoes to yield the corresponding carbamimidoes I:

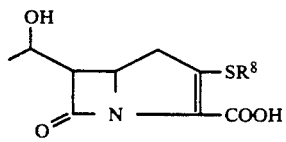

| Compound | —SR⁸ | HSR⁸ | % Yield | λmax. | E% | NH₂OH ext |
|---|---|---|---|---|---|---|
| 1 | S-C(=NH)-NH₂ | HS-C(=NH)-NH₂ | 26 | 294 mμ | 257 | 94% |
| 2 | S-C(=NH)-NHCH₃ | HS-C(=NH)-NHCH₃ | 32 | 296 mμ | 232 | 95% |
| 3 | S-C(=NH)-NHC₂H₅ | HS-C(=NH)-NHC₂H₅ | 23 | 294 mμ | 215 | 96% |
| 4 | S-CH₂CH₂-C(=NH)-NH₂ | HS-CH₂CH₂-C(=NH)-NH₂ | 54 | 299 mμ | 271 | 96% |

EXAMPLE 46h

Following the procedure of Examples 46–46g, the following compounds I are obtained when an equivalent amount of the appropriately substituted bicyclic keto ester (A) is taken:

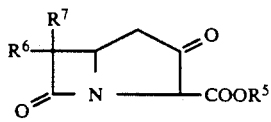

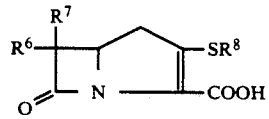

| Compound | R⁶ | R⁷ | R⁸ |
|---|---|---|---|
| 1 | H | FCH₂CH(OH) | —CH₂C(=NH)—NH₂ |
| 2 | H | FCH₂CH(OH) | —CH₂C(=NH)—NCH₃ H |
| 3 | H | FCH₂CH(OH) | —CH₂C(=NH)—N(CH₃)₂ |
| 4 | H | FCH₂CH(OH) | —CH(CH₃)—C(=NH)—NH₂ |
| 5 | H | FCH₂CH(OH) | —C(CH₃)(H)—C(=NH)—NCH₃ H |
| 6 | H | FCH₂CH(OH) | —CH₂C(=NH)—NCH₂CH₃ H |
| 7 | H | FCH₂CH(OH) | —CH₂CH₂C(=NH)—NH₂ |
| 8–15 | | | Compounds 8–15 correspond sequentially to Compound 1–7 of Table 46h when the value of R⁷ = FCH₂CH(OH) is changed to CH₃CH₂CH(OH). |
| 16–23 | | | Compounds 16–23 correspond sequentially to Compound 1–7 of Table 46h when the value of R⁷ = FCH₂CH(OH) is changed to CH₃CH₂. |
| 24–31 | | | Compounds 24–31 correspond sequentially to Compound 1–7 of Table 46h when the value of R⁷ = FCH₂CH(OH) is changed to (CH₃)₂C(OH)—. |

EXAMPLE 46i

Following the procedure of the foregoing text and examples, the following "carbamimidoyl" embodiments of the present invention are obtained.

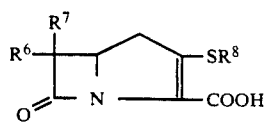

| Compound | R⁶ | R⁷ | —SR⁸ |
|---|---|---|---|
| 1 | H | CH₃CH(OH)— | —SCH₂—C(=NCH₃)—NHCH₃ |
| 2 | H | CH₃CH(OH)— | —SCH₂—C(=NCH₃)—N(CH₃)₂ |
| 3 | H | CH₃CH(OH)— | —SCH₂—C(=N(CH₃)₂)—N(CH₃)₂ |
| 4 | H | CH₃CH(OH)— | —SCH₂—C(=NH)—N(C₂H₅)(CH₃) |
| 5 | H | CH₃CH(OH)— | —S—CH₂C(=NH)—N(C₂H₅)₂ |
| 6 | H | CH₃CH(OH)— | —SCH₂—C(=NH)—NCH(CH₃)₂ |
| 7 | H | CH₂—CH(OH)— | —SCH₂—C(=NH)—NC(CH₃)₃ |
| 8 | H | CH₂—CH(OH) | —SCH(CH₃)—C(=NH)—N(CH₃)₂ |
| 9 | H | CH₂—CH(OH)— | —SCH(φ)—C(=NH)—NH₂ |
| 10 | H | CH₂—CH(OH)— | —S—C(=CH₂)—C(=NH)—NH₂ |
| 11 | H | CH₂—CH(OH)— | —S—CH(CH=CH₂)—C(=NH)—NH₂ |
| 12 | H | CH₂CH(OH)— | —S—CH₂CH(OCH₃)—C(=NH)—NH₂ |
| 13 | H | CH₂—CH(OH)— | —SCH₂—CH(OH)—C(=NH)—NH₂ |
| 14 | H | CH₂—CH(OH)— | —S—CH₂—C(=N—OCH₃)—C(=NH)—NH₂ |
| 15 | H | CH₂—CH(OH)— | —SCH₂—CH(N(CH₃)₂)—C(=NH)—NH₂ |

-continued

| | | | |
|---|---|---|---|
| 16 | H | CH$_2$—CH(OH)— N(CH$_3$)$_2$ Cl$^\ominus$ ⊕ position on CH | —SCH$_2$—CH(—C(=NH)NH$_2$)— with N(CH$_3$)$_2$ Cl$^\ominus$ on CH |
| 17 | H | CH$_2$—CH(OH)— | —S—CH$_2$—C(=NH)—NH$_2$ with SCH$_3$ on CH$_2$ |
| 18 | H | CH$_2$—CH(OH)— | —S—CH$_2$—C(=NH)—NHφ |
| 19 | H | CH$_3$CH(OH)— | SCH$_2$—C(=N—OCH$_3$)=NH |
| 20 | H | CH$_3$CH(OH)— | S—CH$_2$CH$_2$CH$_2$—C(=NH)—NH$_2$ |
| 21 | H | CH$_3$CH(OH)— | SCH$_2$—C(CH$_3$)$_2$—C(=NH)—NH$_2$ |
| 22 | H | CH$_3$CH(OH)— | SCH$_2$CH$_2$—C(=NH)—N(CH$_3$)$_2$ |
| 23 | H | CH$_3$CH(OH)— | —SCH$_2$—C(=NH)—N(pyrrolidine) |
| 24 | H | CH$_3$CH(OH)— | SCH$_2$—C(=NH)—N(morpholine) |
| 25 | H | CH$_3$CH(OH)— | SCH$_2$—C(=NH)—N(piperidine) |
| 26 | H | CH$_3$CH(OH)— | SCH$_2$—C(=NH)—N(4-methylpiperazine) |
| 27 | H | CH$_3$CH(OH)— | —SCH$_2$—C(=NH)—NHCH$_2$φ |
| 28 | H | CH$_3$CH(OH)— | —SCH$_2$—C(=NH)—NHCH$_2$-(2-pyridyl) |
| 29 | H | CH$_3$CH(OH)— | SCH$_2$—C(=NH)—NH—CH$_2$-(3-pyridyl) |
| 30 | H | CH$_3$CH(OH)— | —S—CH$_2$—C(=NH)—NH—CH$_2$-(4-pyridyl) |

-continued

| # | R | R' | R group |
|---|---|---|---|
| 31 | H | CH₃—CH(OH)— | —S—CH₂—(2-(N-methylindolyl)) |
| 32 | " | " | —S—CH₂—C(=NH)—NH—(2-pyridyl) |
| 33 | " | " | —S—CH₂—C(=NH)—NHN(CH₃)₂ |
| 34 | " | " | —S—CH₂—C(=NH)—N(CH₃)—N(CH₃)₂ |
| 35 | " | " | —S—CH₃—C(=NH)—N(CH₃)—NHCH₃ |
| 36 | " | " | —SCH₂—C(CH₃)(=NH)... |

Table:

| No. | R | R' | Substituent |
|---|---|---|---|
| 31 | H | CH₃—CH(OH)— | $-S-CH_2-\text{(1-methylindol-2-yl)}$ |
| 32 | " | " | $-S-CH_2-C(=NH)-NH-\text{(2-pyridyl)}$ |
| 33 | " | " | $-S-CH_2-C(=NH)-NHN(CH_3)_2$ |
| 34 | " | " | $-S-CH_2-C(=NH)-N(CH_3)-N(CH_3)_2$ |
| 35 | " | " | $-S-CH_3-C(=NH)-N(CH_3)-NHCH_3$ |
| 36 | " | " | $-SCH_2-C(CH_3)(=NH)-N(CH_3)-N(CH_3)_2$ |
| 37 | " | " | $-S-CH_2-C(=NH)-N(CH_3)-O-CH_3$ |
| 38 | " | " | $-S-CH(C_2H_5)-C(=NH)-NH_2$ |
| 39 | H | CH₃—CH(OH)— | $-S-CH(C_2H_5)-C(=NH)-N(CH_3)_2$ |
| 40 | " | " | $-S-CH(CH_3)-CH_2-C(=NH)-NH_2$ |
| 41 | " | " | $-S-CH_2-CH(CH_3)-C(=NH)-NH_2$ |
| 42 | H | CH₃CH(OH) | $-SCH=CH-C(=NH)-NH_2$ |
| 43 | H | CH₃CH(OH)— | $-SCH=CH-C(=NH)-N(CH_3)_2$ |
| 44 | H | CH₃CH(OH)— | $-SC(CH_3)=CH-C(=NH)-NH_2$ |

45–89    Compounds 45–89 correspond to Compounds 1–44 of Example 46i except that the value of $R^7$ as CH₃CH(OH) is FCH₂CH(OH)—.

90–134    Compounds 90–134 correspond to Compound 1–44 of Example 46i except that the value of $R^7$ as CH₃CH(OH) is CH₃CH₂CH(OH).

135–179    Compounds 135–179 correspond to Compounds 1–44 of Example 46i except that the value of $R^7$ -continued

| | |
|---|---|
| | as $CH_3CH_2$. |
| 180–224 | Compounds 180–224 correspond to Compounds 1–44 of Example 46i except that the value of $R^7$ as $CH_3CH(OH)$ is $(CH_3)_2C(OH)—$. |

EXAMPLE 47

Preparation of Pharmaceutical Compositions

One such unit dosage form is prepared by mixing 120 mg of 3-(2-aminoethylthio)-6-(2-hydroxyethyl)-7-oxo-1-azabicyclo-[3.2.0]hept-2-ene-2-carboxylic acid with 20 mg of lactose and 5 mg of magnesium stearate and placing the 145 mg mixture into a No. 3 gelatin capsule. Similarly, by employing more of the active ingredient and less lactose, other dosage forms can be put up in No. 3 gelatin capsules, and, should it be necessary to mix more than 145 mg of ingredients together, larger capsules such as compressed tablets and pills can be prepared. The following examples are illustrative of the preparation of pharmaceutical formulations:

| TABLET | PER TABLET |
|---|---|
| 3-(2-aminoethylthio)-6-(2-hydroxyethyl)-7-oxo-1-azabicyclo[3.2.0]hept-2-ene-2-carboxylic acid | 125 mg. |
| Cornstarch, U.S.P. | 6 mg. |
| Dicalcium Phosphate | 192 mg. |
| Lactose, U.S.P. | 190 mg. |
| Magnesium Stearate | Balance/800 mg. |

The active ingredient is blended with the dicalcium phosphate, lactose and about half of the cornstarch. The mixture is then granulated with 15% cornstarch paste (6 mg) and rough-screened. It is dried at 45° C. and screened again through No. 16 screens. The balance of the cornstarch and magnesium stearate is added and the mixture is compressed into tablets, approximately 0.5 inch in diameter each weighing 800 mg.

| PARENTERAL SOLUTION | PER TABLET |
|---|---|
| Ampoule: | |
| 3-(2-aminoethylthio)-6-(2-hydroxyethyl)-7-oxo-1-azabicyclo[3.2.0]hept-2-ene-2-carboxylic acid | 500 mg. |
| Diluent: Sterile Water for Injection | 2 cc. |
| OPTHALMIC SOLUTION | |
| 3-(2-aminoethylthio)-6-(2-hydroxyethyl)-7-oxo-1-azabicyclo[3.2.0]hept-2-ene-2-carboxylic acid | 100 mg. |
| Hydropropylmethyl Cellulose | 5 mg. |
| Sterile Water to | 1 ml. |
| OTIC SOLUTION | |
| 3-(2-aminoethylthio)-6-(2-hydroxyethyl)-7-oxo-1-azabicyclo[3.2.0]hept-2-ene-2-carboxylic acid | 100 mg. |
| Benzalkonium chloride | 0.1 mg. |
| Sterile Water to | 1 ml. |
| TOPICAL OINTMENT | |
| 3-(2-aminoethylthio)-6-(2-hydroxyethyl)-7-oxo-1-azabicyclo[3.2.0]hept-2-ene-2-carboxylic acid | 100 mg. |
| Polyethylene Glycol 4000 U.S.P. | 400 mg. |
| Polyethylene Glycol 400 U.S.P. | 1.0 gram |

What is claimed is:

1. A compound having the structural formula:

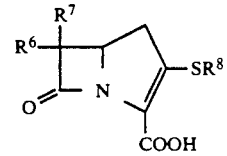

and pharmaceutically acceptable salt and ester derivatives thereof; wherein $R^6 = H$; and

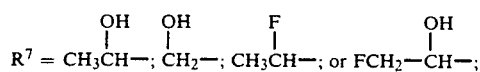

and $R^8$ is independently selected from the group consisting of:

(a) hydrogen;

SUBSTITUTED, MONO- AND DI- SUBSTITUTED:

(b) $C_1$–$C_6$ alkyl;

(c) $C_3$–$C_6$ cycloalkyl;

(d) phenyl, phenyl $C_1$–$C_3$ alkyl;

(e) heteroaryl selected from the group consisting of:

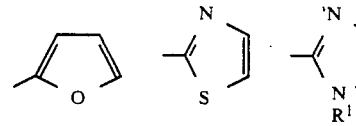

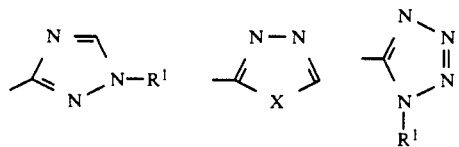

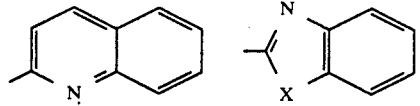

wherein:

$X = S$ or $NR^1$, where $R^1$ is as defined further below;

(f) heteroaralkyl selected from the group consisting essentially of:

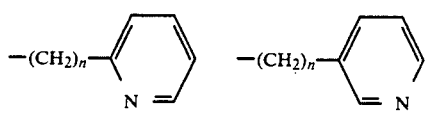

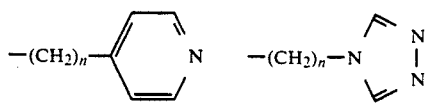

-continued

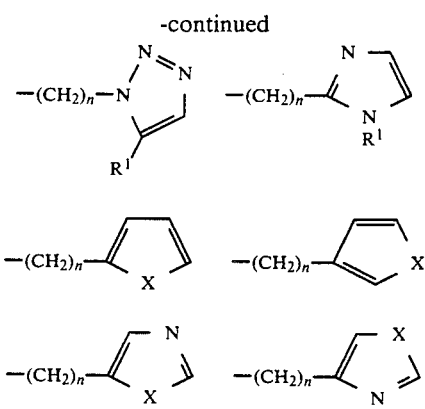

n=1, 2; and
X=O, S, or NR$^1$, where R$^1$ is as defined further below;

(g) heterocyclylalkyl selected from the group consisting essentially of:

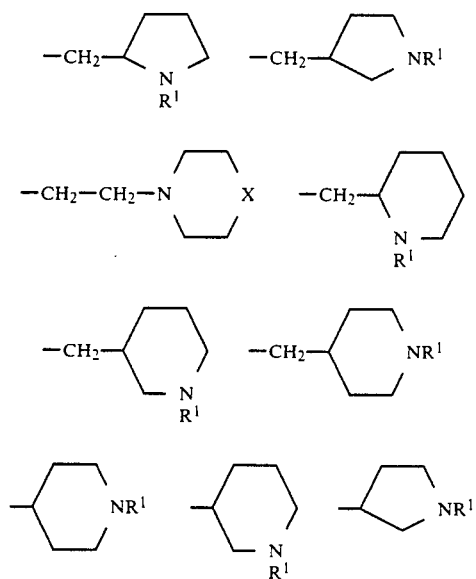

wherein:
X=O or NR$^1$, where R$^1$ is as defined further below; wherein the substituent or substituents relative to the above-named radicals are selected from the group consisting of: chloro, bromo, fluoro,

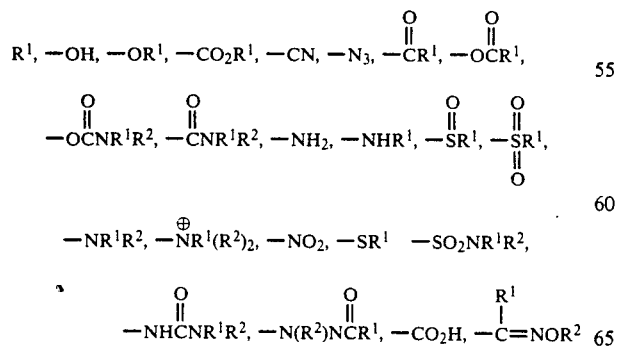

and C$_1$-C$_3$ alkyl mono-substituted by any of the above groups;

and amidines of the formula:

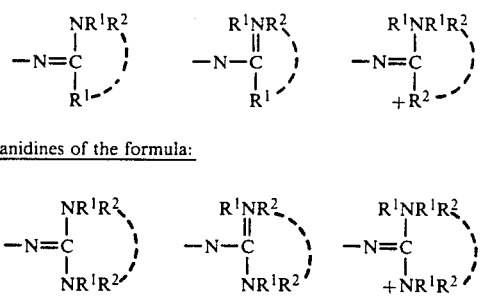

or guanidines of the formula:

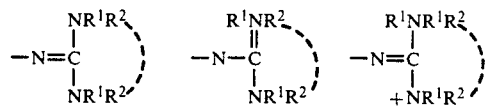

wherein the dotted line indicates additionally that the substituents may be joined to form a ring; and wherein, R$^1$ and R$^2$=H, C$_{1-6}$ alkyl, optionally substituted by OH, NH$_2$ or by up to three fluoro atoms, PROVIDED, THAT when R$^7$ is CH$_3$CH(OH), R$^8$ is not —SCH$_2$CH$_2$NH$_2$ or N-derivative thereof.

2. A compound according to claim 1 selected from the group:

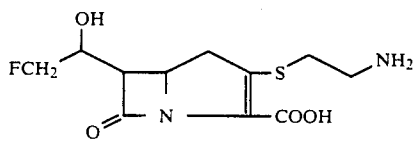

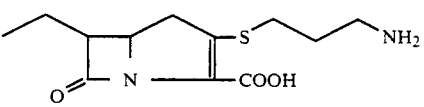

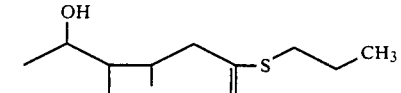

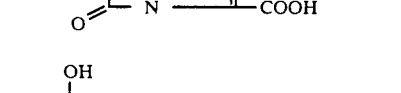

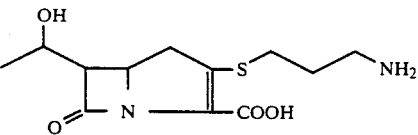

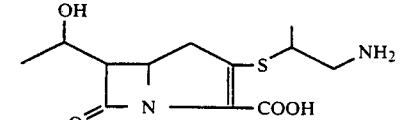

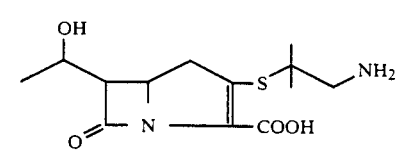

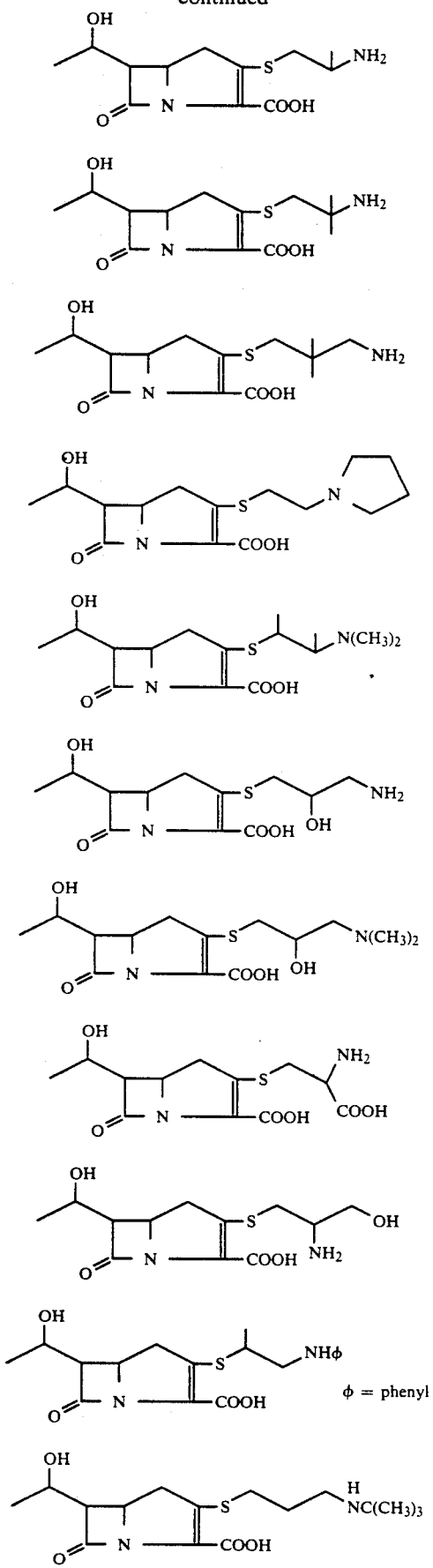
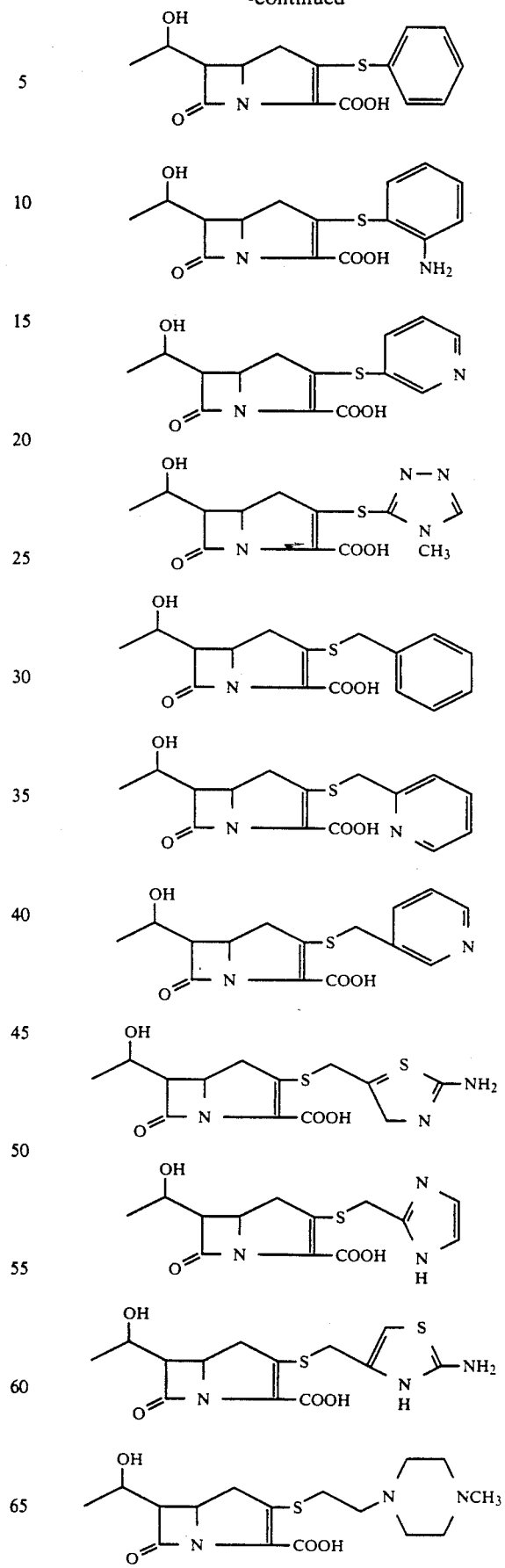

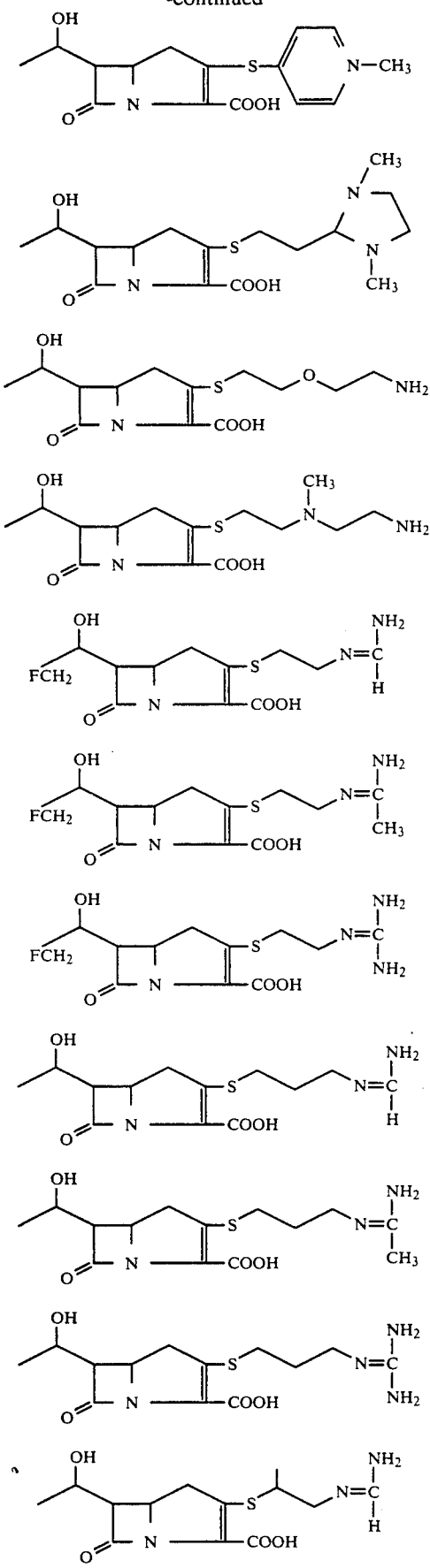
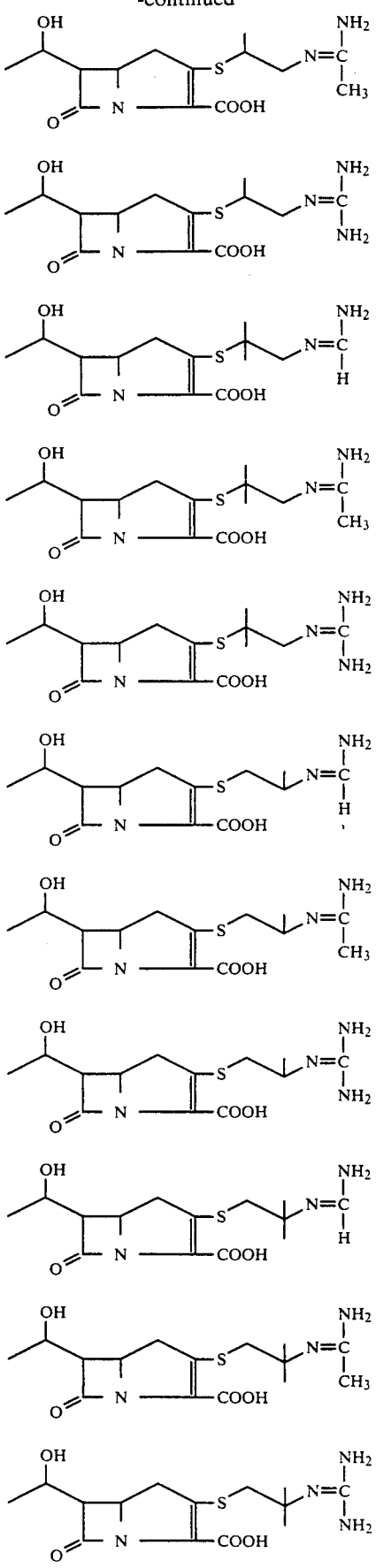

-continued
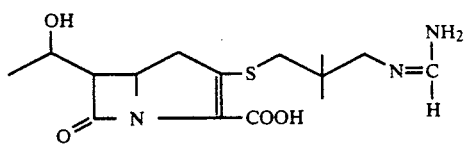
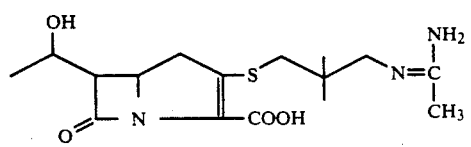
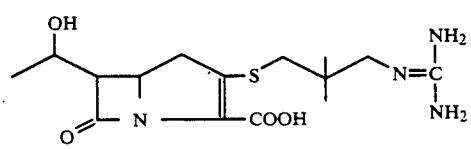
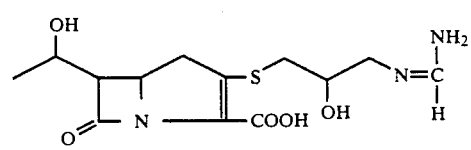
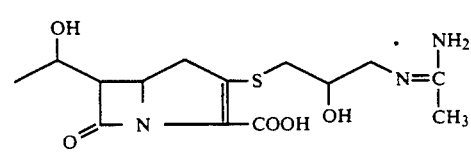
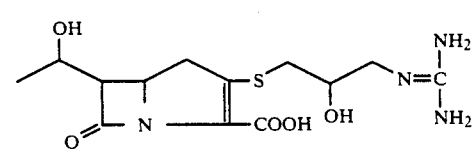
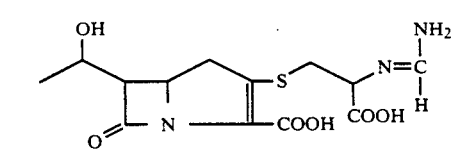
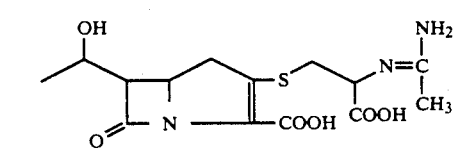
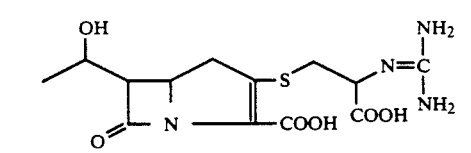
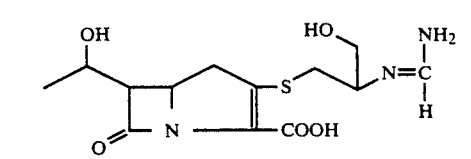
-continued
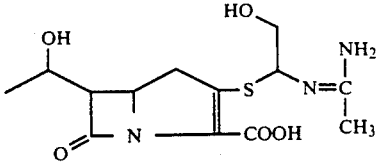
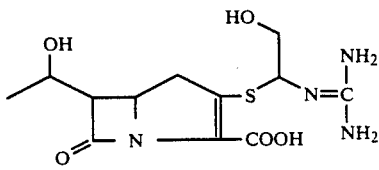
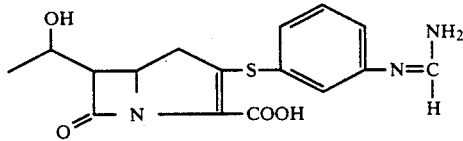
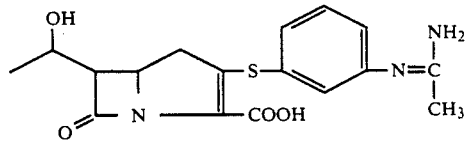
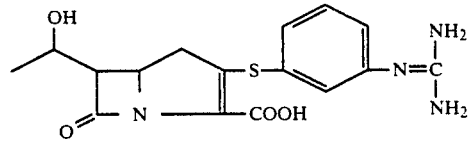
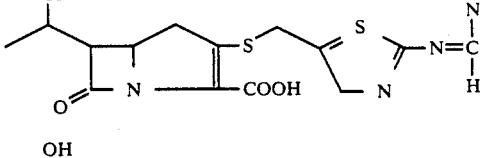
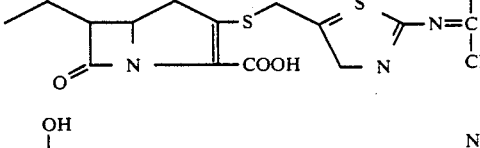
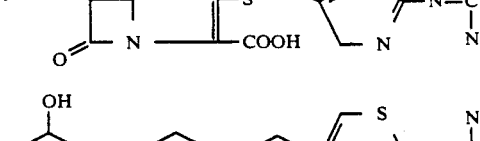
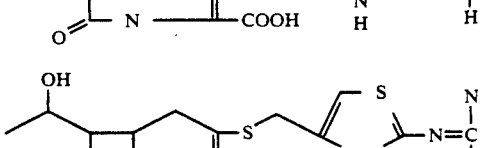
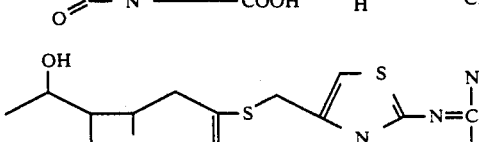
* * * * *